US007776336B2

(12) United States Patent
Grandi et al.

(10) Patent No.: US 7,776,336 B2
(45) Date of Patent: Aug. 17, 2010

(54) **COMPOSITIONS COMPRISING *YERSINIA PESTIS* ANTIGENS**

(75) Inventors: Guido Grandi, Segrate (IT); John Telford, Monteriggioni (IT); Renata Maria Grifantini, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 0 days.

(21) Appl. No.: 12/091,604

(22) PCT Filed: Oct. 25, 2006

(86) PCT No.: PCT/IB2006/003843

§ 371 (c)(1),
(2), (4) Date: Sep. 11, 2008

(87) PCT Pub. No.: WO2007/049155

PCT Pub. Date: May 3, 2007

(65) Prior Publication Data

US 2009/0047293 A1 Feb. 19, 2009

Related U.S. Application Data

(60) Provisional application No. 60/817,838, filed on Jun. 30, 2006, provisional application No. 60/730,182, filed on Oct. 25, 2005.

(51) Int. Cl.
*A61K 39/02* (2006.01)
*C07H 21/04* (2006.01)
*C07K 14/00* (2006.01)
*C12P 21/06* (2006.01)

(52) U.S. Cl. .............. 424/190.1; 424/192.1; 424/234.1; 435/69.1; 435/69.5; 435/69.7; 530/300; 530/350; 536/23.5; 536/23.7

(58) Field of Classification Search ........................ None
See application file for complete search history.

(56) References Cited

FOREIGN PATENT DOCUMENTS

WO    WO 2007/068902    6/2007

OTHER PUBLICATIONS

Meyer KF 1970, Bull World Health Organ.;42(5):653-66.*
Torres-Ramos, The journal of Biological Chemistry 1997, vol. 272, pp. 25445-25448.*
Lindler et al ; Journal of Clinical Microbiology, vol. 39.(10) 3649-3655.2001.*
Abath et al ; J Med Microbiol 37 (1992), 420-424.*
Anisimov, et al., "Intraspecific Diversity of *Yersinia pestis*," *Clinical Microbiology Reviews* 17:434-464 (2004).
Capecchi, et al., "The Genome Revolution in Vaccine Research," *Curr Issues Mol Biol* 6:17-28 (2004).
Chain, et al., "Insights Into the Evolution of *Yersinia pestis* Through Whole-Genome Comparison With *Yersinia pseudotuberculosis*," *PNAS* 101:13826-13831 (2004).
Deng, et al., "Genome Sequence of *Yersinia pestis* Kim," Journal of Bacteriology 184:4601-4611 (2002).
Flashner, et al., "Generation of *Yersinia pestis* Attenuated Strains by Signature-Tagged Mutagenesis in Search of Novel Vaccine Candidates," *Infection and Immunity* 72:908-915 (2004).
Grandi, et al., "The Impact of Genomics in Vaccine Discovery: Achievements and Lessons," *Expert Rev Vaccines* 3:621-623 (2004).
Li, et al., "Protein Microarray for Profiling Antibody Responses to *Yersinia pestis* Live Vaccine," *Infection and Immunity* 73:3734-3739 (2005).
Parkhill, et al., "Genome Sequence of *Yersinia pestis*, The Causative Agent of Plague," *Nature* 413:523-527 (2001).
Serruto, et al., "Biotechnology and Vaccines: Application of Functional Genomics to *Neisseria meningitidis* and Other Bacterial Pathogens," *Journal of Biotechnology* 113:15-32 (2004).
Song, et al., "Complete Genome Sequence *Yersinia pestis* Strain 91001, an Isolate Avirulent to Humans," *DNA Research* 11:179-197 (2004).
Titball, et al., "*Yersinia pestis* (Plague) Vaccines," *Expert Opin Biol Ther* 4:965-973 (2004).
Zhou, et al., "Transcriptome Analysis of the $MG^{2+}$-Responsive PhoP Regulator in *Yersinia pestis*," *FEMS Microbiology Letters* 250:85-95 (2005).
Capecchi et al., "The genome revolution in vaccine research," Current Issues in Molecular Biology, vol. 6, 2004, pp. 17-27.
Flashner et al., "Generation of *Yersinia pestis* attenuated strains by signature-tagged mutagenesis in search of novel vaccine candidates," Infection and Immunity, vol. 72, No. 2, Feb. 2004, pp. 908-915.
Li, B et al., "Protein microarray for profiling antibody responses to *Yersinia pestis* live vaccine," Infection and Immunity, vol. 73, No. 6, Jun. 2005, pp. 3734-3739.
Titball et al., "*Yersinia pestis* (Plague) Vaccines," Expert Opinion on Biological Therapy, vol. 4, No. 6, Jun. 2004, pp. 965-973.
Zhou et al., "Transcriptome analysis of the $Mg^{<+2>}$-responsive PhoP regulator in *Yersinia pestis*," FEMS Microbiloby Letters, vol. 250, No. 1, Sep. 1, 2005, pp. 85-95.
Chain et al., "Insights into the evolution of *Yersinia pestis* through whole-genome comparison with *Yersinia pseudotuberculosis*," Proceedings of the National Academy of Sciences of the United States of America, vol. 101, No. 38, Sep. 21, 2004, pp. 13826-13831.
Deng et al., "Genome Sequence of *Yersinia pestis* Kim," Journal of Bacteriology, vol. 184, No. 16, Aug. 2002, pp. 4601-4611.
Parkhill et al., "Genome of *Yersinia pestis*, the causative agent of plague," Nature, vol. 413, No. 6855, Oct. 4, 2001, pp. 523-527.
Song et al., "Complete genome sequence of *Yersinia pestis* strain 91001, an isolate avirulent to humans," DNA Research 2004 Japan, vol. 11, No. 3, 2004, pp. 179-197.
Grandi et al., "The impact of genomics in vaccine discovery: achievements and lessons," Expert Review of Vaccines Dec. 2004, vol. 3, No. 6, Dec. 2004, pp. 621-623, XP009086130.

(Continued)

*Primary Examiner*—Robert B Mondesi
*Assistant Examiner*—Padma V Baskar
(74) *Attorney, Agent, or Firm*—Robins & Pasternak LLP

(57) ABSTRACT

Disclosed are several *Y. pestis* antigens that are particularly suitable for immunisation purposes, particularly when used in combinations.

5 Claims, 8 Drawing Sheets

OTHER PUBLICATIONS

Anisimov et al., "Intraspecific diversity of *Yersinia pestis*," Clinical Microbiology Reviews, vol. 17, No. 2, Apr. 2004, pp. 434-464.

Serruto et al., "Biotechnology and vaccines: application of functional genomics to *Neisseria meningitidis* and other bacterial pathogens," Journal of Biotechnology, vol. 113, No. 1-3, Sep. 30, 2004, pp. 15-32.

Tanabe et al., "The ABC Transporter Protein OppA Provides Protection Against Experimental *Yersinia pestis* Infection," *Infection and Immunity* 74:3687-3691 (2006).

Hammerl, et al., "Antigenic Competition in the Immune Response Against Protein Mixtures: Strain-Specific Non-Immunogenicity of *Escherichia coli* Antigens," *Molecular Immunology* 25(3):313-320 (1988).

* cited by examiner

SEQUENCE LISTING

<160> NUMBER OF SEQ ID NOS: 91

<210> SEQ ID NO 1
<211> LENGTH: 163
<212> TYPE: PRT
<213> ORGANISM: Yersinia pestis

<400> SEQUENCE: 1

```
Met Arg Ser Leu Phe Arg Val Leu Pro Ile Phe Ile Leu Thr Gly Cys
1               5                   10                  15

Val Leu Leu Ser Gly Cys Ser Trp Phe Ser Ser Ser Glu Ala Ala
            20                  25                  30

Leu Gln Lys Arg Arg Ile Asp Leu Gln Val Val Ala Ala Pro Leu Ile
        35                  40                  45

Asn Pro Gly Pro Asn Gly Gln Ala Gln Pro Leu Lys Val Cys Ile Ile
    50                  55                  60

Glu Leu Asn Lys Glu Gly Trp Ser Pro Pro Gly Leu Tyr Gln Gly Thr
65                  70                  75                  80

Leu Cys Ser Gly Ile Ser Val Gly Gly Glu Val Val Ser Val Thr Glu
                85                  90                  95

Tyr Ile Leu Ala Pro Thr Glu Val Arg Gln Tyr Ser Arg Asp Val Pro
            100                 105                 110

Phe Glu Gln Glu Arg Trp Trp Ala Ile Ala Ala Glu Phe Gln Glu Met
        115                 120                 125

Ser Asn Gly Lys Ser Leu Leu Thr Leu Lys Ser Asp Ala Arg Ala Asp
    130                 135                 140
```

```
Phe Asn Arg Val Val Leu Val Asp Gly Lys Ala Leu Ser Leu Lys Ala
145                 150                 155                 160

Ser Thr Lys

<210> SEQ ID NO 2
<211> LENGTH: 211
<212> TYPE: PRT
<213> ORGANISM: Yersinia pestis

<400> SEQUENCE: 2

Met Arg Lys Glu Ile Val Ser Met Arg Ile Ile Leu Leu Leu Ala Ala
1               5                   10                  15

Leu Leu Leu Ile Thr Phe Met Leu Ile Thr Thr Ile Asn His Ala His
                20                  25                  30

Ala Asp Pro Thr Asn Asp Ser Ser Pro Pro Lys Glu Gly Ala Pro Pro
            35                  40                  45

Ile Ala Pro Tyr Leu Leu Phe Asn Ala Pro Thr Phe Asp Leu Thr Leu
        50                  55                  60

Val Lys Phe Arg Glu Ser Tyr Asn Arg Ala Asn Pro Thr Leu Pro Ile
65                  70                  75                  80

Asn Glu Phe His Ala Ile Thr Val Lys Glu Asp Ser Pro Pro Leu Thr
                85                  90                  95

Arg Ala Ala Ser Lys Ile Asn Glu Asn Leu Tyr Ala Ser Thr Ala Leu
            100                 105                 110

Glu Lys Gly Thr Gly Lys Ile Lys Thr Leu Gln Ile Thr Tyr Leu Pro
        115                 120                 125

Ile Lys Gly Asn Glu Glu Lys Thr Ala Lys Leu Leu Ala Ile Asn Tyr
130                 135                 140

Met Ala Ala Leu Met Arg Gln Phe Glu Pro Thr Leu Ser Val Ala Gln
145                 150                 155                 160

Ser Leu Ala Asn Val Gln Lys Leu Leu Thr Glu Gly Lys Gly Ser Pro
                165                 170                 175

Phe Tyr Ala His Thr Ile Gly Ala Ile Arg Tyr Val Val Ala Asp Asn
            180                 185                 190

Gly Glu Lys Gly Leu Thr Phe Ala Val Glu Pro Ile Lys Leu Ser Leu
        195                 200                 205

Ser Glu Ala
    210

<210> SEQ ID NO 3
<211> LENGTH: 177
<212> TYPE: PRT
<213> ORGANISM: Yersinia pestis

<400> SEQUENCE: 3

Met Ile Gly Ile Leu Asn Arg Trp Arg Gln Phe Gly Arg Arg Tyr Phe
1               5                   10                  15

Trp Pro His Leu Leu Gly Met Val Ala Ala Ser Leu Gly Val Pro
                20                  25                  30

Leu Asn Leu Ser Gly Val Pro Asp His Ala Ala Leu Ala Asn Thr Ser
            35                  40                  45

Ser Ser Gln Ser Arg Gln Asn His Gly Thr Thr Asn Phe Asn Ser Leu
        50                  55                  60

Ala Leu Leu His Asp Ile His Arg Arg Leu Ser Phe Ser Val Asp Tyr
65                  70                  75                  80
```

```
Trp Gln Gln His Ala Leu Arg Thr Val Ile Arg His Leu Ser Phe Ala
                85                  90                  95

Leu Ala Pro Gln Ala Ala Tyr Ala Arg Val Gln Glu Val Ala Glu Thr
            100                 105                 110

Glu Arg Val Ala Pro Ser Lys Ile Gln Gln Leu Ala Leu Leu Asp Thr
        115                 120                 125

Leu Asn Ala Leu Leu Thr His Glu Phe Lys Pro Pro Ala Ile Ile Arg
130                 135                 140

Tyr Thr Glu Gln Val Glu Arg Pro Val Leu Ser Pro Tyr Lys Pro Gly
145                 150                 155                 160

Leu Trp Leu Ala Gln Val Gln Gly Ile Arg Ala Gly Pro Ala Asn Leu
                165                 170                 175

Ser

<210> SEQ ID NO 4
<211> LENGTH: 318
<212> TYPE: PRT
<213> ORGANISM: Yersinia pestis

<400> SEQUENCE: 4

Met Asn Gln Asn Gly Ile Ala Leu Leu Met Val Leu Cys Ala Leu Phe
1               5                   10                  15

Leu Met Ser Thr Met Val Met Ala Ser Tyr Asn Tyr Trp Phe Asp Ile
            20                  25                  30

Tyr Tyr Leu Ala Lys Asn Ser Gln Gln Arg Gln Lys Glu Lys Trp Ile
        35                  40                  45

Leu Leu Gly Ala Glu Lys Phe Val Ser Lys Leu Ile Lys Asn Thr
    50                  55                  60

Ser Glu Asp Arg Phe Asn Asp Asn Glu Phe Arg Arg Leu Leu Ser Gly
65                  70                  75                  80

Gly Arg Val Thr Val Gly Thr Trp Asn Val Asn Phe Lys Ser Ile Asp
                85                  90                  95

Asn Thr Asn Cys Phe Asn Ile Asn Ala Leu Lys Thr Lys Ile Ser Asn
            100                 105                 110

Pro Glu Glu Ile Ile Glu Thr Tyr Ser Trp Gln Val Phe Lys Tyr Leu
        115                 120                 125

Leu Leu Ile Ser Gly Val Gly Val Lys Glu Thr Gln Asp Thr Leu Glu
    130                 135                 140

Arg Val Val Glu Leu Tyr Arg Ser Asn Leu Val Ile Glu Gln Ser Ile
145                 150                 155                 160

Asn Gly Leu Ser Thr Leu Lys Glu Ile Pro Tyr Glu Ala Asp Glu Ile
                165                 170                 175

Asn Ile Ser Ser Lys Met Asn Arg Ala Asp Phe Leu Lys Ile Ala Pro
            180                 185                 190

Val Leu Cys Ile Arg Gly Asp Arg Lys Leu Leu Val Asn Ile Asn Met
        195                 200                 205

Leu Asp Ala Gly Asn Ser Gln Tyr Leu Gln Ala Ala Leu Leu Asn Lys
    210                 215                 220

Val Ser Ala Arg Asp Ile Tyr Asp Val Ile Ser Ala Lys Pro Asn Asn
225                 230                 235                 240

Gly Trp Asp Asn Ile Phe Ile Phe Tyr Asp Leu Leu Ser Ser His Ser
                245                 250                 255

Pro Met Ser Ala Arg Asn Val Asn Lys Asn Ile Leu Asp Lys Leu Thr
            260                 265                 270
```

```
Val Asp Glu Tyr Phe Ile Asn Tyr Ile Phe Arg Ile Asp His Glu Asp
        275                 280                 285

Ser Tyr Tyr Gln Leu Ile Thr Phe Ile His Ala Val Gly Lys Ser Ile
        290                 295                 300

Ala Ile Leu Asn Arg Arg Tyr Ser Phe Ser Glu Gln His His
305                 310                 315

<210> SEQ ID NO 5
<211> LENGTH: 333
<212> TYPE: PRT
<213> ORGANISM: Yersinia pestis

<400> SEQUENCE: 5

Met Lys Lys Thr Met Leu Gln Thr Leu Leu Ala Ala Thr Leu Ile Leu
1               5                   10                  15

Ser Phe Ala Ala Ser Val Gln Ala Ala Pro Val Lys Ile Ala Ile Leu
            20                  25                  30

Met Tyr Gly Met Lys Ala Glu Phe Val Gln Leu Met Gly Lys Ser Ala
        35                  40                  45

Lys Glu His Pro Ala Val Thr Gln Gly Leu Thr Thr Leu Thr Leu Phe
50                  55                  60

Asp Gly Arg Tyr Asp Pro Leu Val Gln Asn Asn Gln Ala Glu Thr Ala
65                  70                  75                  80

Ile Arg Thr Arg Tyr Asp Ala Ile Ile Ile Val Pro Ile Asp Phe Glu
                85                  90                  95

Ala Asn Val Asp Val Val Thr Met Ala Asn Lys Ala Asn Ile Pro Val
            100                 105                 110

Ile Val Ala Asn Ala Arg Leu Asn Thr Asp Lys Ala Thr Ser Gly Ile
        115                 120                 125

Phe Ser Asp Asp Val Gln Gly Gly Tyr Leu Glu Ala Lys Ala Val Leu
130                 135                 140

Asp Lys Met Gln Cys Gln Gly Asn Val Val Val Ile Glu Gly Pro Ile
145                 150                 155                 160

Gly Gln Ser Ala Gln Ile Gln Arg Gly Gln Gly Asn Asp Lys Ala Ile
                165                 170                 175

Ala Glu Cys Gly Pro Gly Lys Ile Asn Val Leu Glu Arg Lys Thr Ala
            180                 185                 190

Asn Trp Ser Arg Ala Glu Ala Met Pro Leu Met Glu Asn Trp Leu Gln
        195                 200                 205

Lys His Arg Gly Lys Ile Asn Gly Val Ile Gly Gln Asn Asp Glu Met
210                 215                 220

Ala Leu Gly Ala Ile Glu Ala Ile Lys Ser Ala Gly Leu Asn Val Gln
225                 230                 235                 240

Asp Phe Ala Ile Ala Gly Ile Asp Gly Val Ser Asp Ala Ile Arg Ala
                245                 250                 255

Val Lys Gln Gly Glu Met Met Ser Ile Leu Gln Asp Gly Gln Ala Gln
            260                 265                 270

Ile Gln Gly Ala Ile Asp Ile Ala Met Arg Ser Val Gln Gly Glu Arg
        275                 280                 285

Tyr Gln Pro Met Ser Thr Ile Trp Gln Tyr Gln Gly Lys Met Asp
290                 295                 300

Trp Gln Gln Gly Thr Ala Lys Met Tyr Glu Val Pro Trp Thr Glu Val
305                 310                 315                 320

Thr Pro Gln Asn Ala Asp Glu Leu Leu Lys Met Arg Gln
                325                 330
```

<210> SEQ ID NO 6
<211> LENGTH: 135
<212> TYPE: PRT
<213> ORGANISM: Yersinia pestis

<400> SEQUENCE: 6

Met Arg Ala Leu Pro Leu Cys Leu Leu Ala Leu Ser Leu Thr Gly Cys
1               5                   10                  15

Thr Leu Leu Pro Ser Lys Pro Ser Thr Asp Asn Pro Ile Lys Gln
            20                  25                  30

Pro Pro Pro Val Ile Glu Arg Ser Pro Thr Ala Ala Pro Arg Pro Ala
        35                  40                  45

Pro Val Lys Leu Tyr Lys Ser Ala Glu Leu Val Gly Lys Pro Phe
    50                  55                  60

Arg Asp Leu Gly Glu Val Ser Gly Glu Ser Cys Gln Ser Thr Val Gln
65                  70                  75                  80

Asp Ser Pro Pro Ser Ile Ser Thr Ala Arg Lys Arg Met Gln Ile Arg
                85                  90                  95

Ala Ser Tyr Met Lys Ala Asn Ala Val Leu Leu His Glu Cys Glu Ile
            100                 105                 110

Gln Ser Gly Val Pro Gly Cys Tyr Gln Gln Ala Val Cys Gln Gly Ser
        115                 120                 125

Ala Leu Asn Val Ser Ser Lys
    130             135

<210> SEQ ID NO 7
<211> LENGTH: 388
<212> TYPE: PRT
<213> ORGANISM: Yersinia pestis

<400> SEQUENCE: 7

Met Gly Lys Ala Thr Glu Gln Asn Asp Lys Leu Asn Arg Ala Val Ile
1               5                   10                  15

Val Ser Val Val Leu His Ile Ile Leu Ile Ala Leu Leu Ile Trp Gly
            20                  25                  30

Ser Leu Thr Gln Thr Thr Glu Met Gly Gly Gly Ala Gly Gly Glu
        35                  40                  45

Val Ile Asp Ala Val Met Val Asp Pro Gly Ala Val Thr Glu Gln Tyr
    50                  55                  60

Asn Arg Gln Gln Gln Gln Thr Asp Ala Lys Arg Ala Glu Gln Gln
65                  70                  75                  80

Arg Gln Lys Lys Ala Glu Gln Ala Glu Glu Leu Gln Gln Lys Gln
            85                  90                  95

Ala Ala Glu Gln Gln Arg Leu Lys Glu Leu Glu Lys Glu Arg Leu Gln
        100                 105                 110

Ala Gln Glu Asp Ala Lys Leu Ala Ala Glu Gln Lys Gln Val
    115                 120                 125

Ala Glu Gln Gln Lys Gln Ile Ala Glu Gln Lys Gln Ala Ala Glu
    130                 135                 140

Gln Gln Lys Ile Ala Ala Ala Val Ala Lys Ala Lys Glu Glu Gln
145                 150                 155                 160

Lys Gln Ala Glu Thr Ala Ala Ala Gln Ala Lys Ala Glu Ala Asp Lys
            165                 170                 175

Ile Val Lys Ala Gln Ala Glu Ala Gln Lys Lys Ala Glu Ala Glu Ala
        180                 185                 190

-continued

```
Lys Lys Glu Ala Ala Val Ala Ala Ala Lys Lys Gln Ala Asp Ala
            195                 200                 205

Asp Ala Lys Lys Ala Val Glu Val Ala Glu Lys Ala Ala Asp Ala
        210                 215                 220

Ala Glu Lys Lys Ala Ala Asp Ala Glu Lys Lys Ala Ala Ala Ala
225                 230                 235                 240

Lys Lys Val Ala Ala Ala Glu Ala Lys Lys Ala Ala Ala Ala Glu
                245                 250                 255

Ala Ala Ala Ser Thr Asp Val Asp Leu Phe Gly Gly Leu Ala Asn
            260                 265                 270

Ala Lys Asn Ala Pro Lys Ser Gly Ser Gly Ala Gly Ala Ala Ala
        275                 280                 285

Gly Lys Gly Gly Gly Lys Lys Ser Gly Ala Ser Gly Ala Asp Ile Ser
                290                 295                 300

Gly Tyr Leu Gly Gln Ile Thr Gly Ala Ile Gln Ser Lys Phe Tyr Asp
305                 310                 315                 320

Ala Asp Leu Tyr Lys Gly Arg Thr Cys Asp Leu Arg Ile Lys Leu Ala
                325                 330                 335

Pro Asp Gly Leu Leu Ile Asp Val Lys Ala Glu Gly Gly Asp Pro Ala
            340                 345                 350

Leu Cys Gln Ala Ala Ile Ala Ala Ala Lys Gln Ala Lys Ile Pro Lys
        355                 360                 365

Pro Pro Ser Thr Asp Val Tyr Glu Gln Phe Lys Asn Ala Pro Leu Val
370                 375                 380

Phe Lys Pro Gln
385

<210> SEQ ID NO 8
<211> LENGTH: 360
<212> TYPE: PRT
<213> ORGANISM: Yersinia pestis

<400> SEQUENCE: 8

Met Met Lys Arg Asn Ile Leu Ala Val Val Ile Pro Ala Leu Leu Ala
1               5                   10                  15

Ala Gly Ala Ala Asn Ala Ala Glu Ile Tyr Asn Lys Asp Gly Asn Lys
                20                  25                  30

Leu Asp Leu Tyr Gly Lys Val Asp Ala Arg His Ser Phe Ser Asp Asn
            35                  40                  45

Asn Lys Gln Asp Gly Asp Lys Ser Tyr Val Arg Phe Gly Phe Lys Gly
        50                  55                  60

Glu Thr Gln Ile Thr Asp Gln Leu Thr Gly Tyr Gly Gln Trp Glu Tyr
65                  70                  75                  80

Asn Ile Gln Ala Asn Asn Ala Glu Asp Thr Gly Ala Gln Asp Gly Asn
                85                  90                  95

Ala Thr Arg Leu Gly Phe Ala Gly Leu Lys Phe Ala Glu Phe Gly Ser
            100                 105                 110

Phe Asp Tyr Gly Arg Asn Tyr Gly Val Ile Tyr Asp Val Asn Ala Trp
        115                 120                 125

Thr Asp Met Leu Pro Val Phe Gly Gly Asp Ser Ile Ser Asn Ser Asp
    130                 135                 140

Asn Phe Met Ala Gly Arg Ser Thr Gly Leu Ala Thr Tyr Arg Asn Asn
145                 150                 155                 160

Asn Phe Phe Gly Leu Val Asp Gly Leu Asn Phe Ala Leu Gln Tyr Gln
```

-continued

```
                165                 170                 175
Gly Lys Asn Asp Arg Ser Glu Val Lys Glu Ala Asn Gly Asp Gly Phe
            180                 185                 190

Gly Ile Gly Ser Thr Tyr Asp Ile Gly Asn Gly Ile Asn Phe Gly Ala
            195                 200                 205

Gly Phe Ser Ser Ser Asn Arg Thr Leu Asp Gln Lys Tyr Gly Ser Thr
            210                 215                 220

Ala Glu Gly Asp Lys Ala Gln Ala Trp Asn Val Gly Ala Lys Tyr Asp
225                 230                 235                 240

Ala Asn Asn Val Tyr Leu Ala Val Met Tyr Ala Glu Thr Gln Asn Leu
                245                 250                 255

Thr Pro Tyr Gly Ser Phe Ser Asp Thr Ile Ala Asn Lys Thr Arg Asp
            260                 265                 270

Ile Glu Ile Thr Ala Gln Tyr Gln Phe Asp Phe Gly Leu Arg Pro Ser
            275                 280                 285

Leu Gly Tyr Val Gln Ser Lys Gly Lys Asp Leu Asn Asp Val Asp Ala
            290                 295                 300

Asn His Asp Leu Leu Lys Tyr Val Ser Val Gly Thr Tyr Tyr Tyr Phe
305                 310                 315                 320

Asn Lys Asn Met Ser Thr Tyr Val Asp Tyr Lys Ile Asn Leu Leu Asp
                325                 330                 335

Glu Asp Glu Phe Thr Ile Ala Asn Gly Leu Asn Thr Asp Asn Val Val
            340                 345                 350

Ala Val Gly Leu Val Tyr Gln Phe
            355                 360

<210> SEQ ID NO 9
<211> LENGTH: 341
<212> TYPE: PRT
<213> ORGANISM: Yersinia pestis

<400> SEQUENCE: 9

Met Lys Arg Lys Ser Thr Lys Ala Leu Ile Leu Phe Val Val Ile Cys
1               5                   10                  15

Leu Gly Leu Leu Leu Gly Tyr Gln Lys Val Gln Asp Phe Ala Arg
            20                  25                  30

Gln Pro Leu Ala Ile Lys Gln Glu Thr Tyr Phe Thr Leu Pro Ala Gly
            35                  40                  45

Thr Gly Arg Val Ala Leu Glu Asn Leu Leu Arg Asp His Val Ile
            50                  55                  60

Ala Asn Thr Gly Leu Phe Pro Trp Leu Leu Arg Ile Glu Pro Glu Leu
65                  70                  75                  80

Ala Asn Phe Lys Ala Gly Thr Tyr Arg Phe Thr Pro Gly Met Thr Val
                85                  90                  95

Arg Glu Met Leu Glu Leu Leu Val Ser Gly Lys Glu Ala Gln Phe Thr
            100                 105                 110

Val Arg Phe Ile Glu Gly Lys Arg Leu Arg Asp Trp Leu Asp Glu Leu
            115                 120                 125

Gln Gln Ser Lys Tyr Ile Lys His Val Leu Glu Gly Lys Thr Asp Ala
            130                 135                 140

Glu Ile Ala Gln Leu Leu Gly Leu Lys Glu Ser Glu His Pro Glu Gly
145                 150                 155                 160

Trp Leu Tyr Pro Asp Thr Tyr Ser Tyr Thr Ala Gly Thr Thr Asp Leu
                165                 170                 175
```

```
Thr Leu Leu Lys Arg Ala His Gln Arg Met Glu Glu Thr Val Ala Glu
            180                 185                 190

Ile Trp Gln Gly Arg Asp Asp Gly Leu Pro Tyr Lys Thr Pro Ser Asp
        195                 200                 205

Leu Val Thr Met Ala Ser Ile Ile Glu Lys Glu Thr Ala Val Asn Glu
    210                 215                 220

Glu Arg Asp Lys Val Ala Ser Val Phe Ile Asn Arg Leu Arg Leu Gly
225                 230                 235                 240

Met Arg Leu Gln Thr Asp Pro Thr Val Ile Tyr Gly Met Gly Glu Lys
                245                 250                 255

Tyr Asn Gly Asn Ile Thr Arg Lys Asp Leu Asp Thr Pro Thr Pro Tyr
            260                 265                 270

Asn Thr Tyr Val Ile Ser Gly Leu Pro Pro Thr Pro Ile Ala Met Pro
        275                 280                 285

Gly Leu Ala Ser Leu Thr Ala Ala His Pro Ala Gln Thr Pro Tyr
    290                 295                 300

Leu Tyr Phe Val Ala Asp Gly Lys Gly Gly His Thr Phe Thr Thr Asn
305                 310                 315                 320

Leu Ala Ser His Asn Gln Ala Val Arg Val Tyr Arg Gln Ser Leu Lys
                325                 330                 335

Asp Lys Asn Glu Gln
            340

<210> SEQ ID NO 10
<211> LENGTH: 249
<212> TYPE: PRT
<213> ORGANISM: Yersinia pestis

<400> SEQUENCE: 10

Met Lys Leu Thr Lys Leu Trp Arg Val Cys Leu Val Ser Val Leu
1               5                   10                  15

Thr Gly Cys Ser Gly Thr Pro Pro Glu Asn Thr Ser Gln Ala Val Ala
                20                  25                  30

Gly Gln Thr Arg Leu Gln Leu Gly Leu Ala Tyr Leu Ala Gln Gly Asp
            35                  40                  45

Leu Thr Ala Ala Arg Lys Asn Leu Glu Lys Ala Val Glu Ala Asp Pro
50                  55                  60

Gln Asp Tyr Arg Thr Gln Leu Gly Met Ala Phe Tyr Ala Gln Arg Ile
65                  70                  75                  80

Gly Glu Asn Ser Ala Ala Glu Gln Arg Tyr Gln Gln Ala Met Lys Leu
                85                  90                  95

Ala Pro Gly Asn Gly Thr Val Leu Asn Asn Tyr Gly Ala Phe Leu Cys
            100                 105                 110

Ser Leu Gly Gln Tyr Val Ser Ala Gln Gln Phe Ser Ala Ala Ala
        115                 120                 125

Leu Leu Pro Asp Tyr Gly Gln Val Ala Asp Ser Leu Glu Asn Ala Gly
    130                 135                 140

Tyr Cys Phe Leu Arg Ala Asn Gln Asp Lys Gln Ala Arg Val Leu Leu
145                 150                 155                 160

Ser Arg Ala Leu Lys Tyr Asp Pro Asp Lys Gly Glu Pro Leu Leu Ala
                165                 170                 175

Glu Ala Gln Arg His Phe Gly Glu Gly Asn Arg Ala Gln Ala Gln Leu
            180                 185                 190

Leu Leu Asp Val Tyr Gln His Thr Leu Pro Ala Ser Ala Glu Ser Leu
        195                 200                 205
```

```
Trp Leu Gln Ile Arg Phe Ala Ala Leu Ala Gly Arg Gln Asp Ser Val
    210                 215                 220
Gln Arg Tyr Gly Lys Gln Leu Ala Arg Ser Phe Pro Gln Ser Lys Gln
225                 230                 235                 240
Tyr Gln His Phe Leu Ala Asn Glu Tyr
                245

<210> SEQ ID NO 11
<211> LENGTH: 352
<212> TYPE: PRT
<213> ORGANISM: Yersinia pestis

<400> SEQUENCE: 11

Met Ala Ile Ser Leu Gln Lys Ser Thr Val Lys Val Gly Val
1               5                   10                  15

Ser Leu Val Met Leu Leu Ala Ala Cys Ser Thr Asp Gln Arg Tyr Lys
            20                  25                  30

Arg Gln Val Ser Gly Asp Glu Ser Tyr Leu Thr Ala Pro Gly Leu Lys
        35                  40                  45

Pro Leu Asn Ala Pro Ser Gly Met Ile Leu Pro Val Gln Asn Gly Glu
    50                  55                  60

Phe Asp Val Arg Thr Val Asn Ser Gln Gly Ala Val Gly Lys Gln Leu
65                  70                  75                  80

Asp Ile Arg Pro Pro Val Gln Pro Leu Thr Leu Leu Ser Gly Ser Arg
                85                  90                  95

Ala Glu Asn Ala Thr Asp Thr Ser Lys Leu Leu Leu Glu Asn Ser Pro
            100                 105                 110

Gln Asn Arg Asp Leu Trp Ala Gln Val Thr Arg Val Leu Gln Asp His
        115                 120                 125

Asn Trp Pro Ile Ala Ser Arg Gln Asp Ala Ser Gln Thr Leu Thr Thr
130                 135                 140

Asp Trp Ile Lys Trp Asn Arg Ala Asp Glu Asp Val Gln Phe Glu Gly
145                 150                 155                 160

Arg Tyr Gln Ile Ser Val Gln Glu Gln Gly Tyr Gln Leu Ala Leu Val
                165                 170                 175

Val Lys Ser Leu Glu Leu Gln Gln Gly Gly Lys Thr Ile Thr Gln Tyr
            180                 185                 190

Ser Glu Ile Gln Arg Tyr Asn Ser Ala Met Leu Asn Ala Ile Ile Glu
        195                 200                 205

Gly Leu Asp Lys Val Arg Ala Asp Ser Glu Ser Ser Gln Ala Ser Arg
    210                 215                 220

Lys Val Gly Thr Leu Asp Val Gln Ser Gly Ser Asp Asp Thr Gly Leu
225                 230                 235                 240

Pro Leu Leu Ile Val Arg Ala Pro Tyr Ala Val Val Trp Glu Arg Leu
                245                 250                 255

Pro Ala Ala Leu Glu Lys Val Gly Met Lys Val Thr Asp Arg Ser Arg
            260                 265                 270

Pro Gln Gly Thr Val Ser Val Thr Ser Lys Ser Leu Ser Ser Ser Ser
        275                 280                 285

Trp Asp Ala Leu Gly Ala Lys Asp Pro Glu Leu Pro Glu Gly Asp Tyr
    290                 295                 300

Lys Leu Gln Val Gly Asp Leu Asp Asn Arg Ser Ser Leu Gln Phe Ile
305                 310                 315                 320

Gly Pro Lys Gly His Thr Leu Thr Gln Ala Gln Asn Asp Ala Leu Val
```

```
                    325                 330                 335
Ala Val Phe Gln Ala Ala Phe Ser Gln Thr Ser Ala Thr Ala Ile Lys
            340                 345                 350

<210> SEQ ID NO 12
<211> LENGTH: 139
<212> TYPE: PRT
<213> ORGANISM: Yersinia pestis

<400> SEQUENCE: 12

Met Lys Ile Leu Lys Arg Leu Ile Phe Ile Cys Leu Val Ile Ile Ile
1               5                   10                  15

Ile Phe Phe Leu Ile Asp Cys Ser Met Gln Lys Val Ala Glu Gly Arg
            20                  25                  30

Asp Gly Tyr Thr Arg Ser Asn Ile Trp Ala Tyr Tyr Leu Tyr Thr Asp
        35                  40                  45

Lys Asp Ile Arg Ser Ala Pro Arg Ala Ala Glu Ser Tyr Tyr Phe Ile
    50                  55                  60

Phe Thr Ala Gln Asp Gly Ser Gln Pro Arg Glu Ser Ser Ile Val Tyr
65                  70                  75                  80

Arg Asp Asp Val Cys Leu Ser Asp Val Lys Asn His Leu Thr Thr Leu
                85                  90                  95

Gly Tyr Arg Val Ser Asp His Asp Gly Leu Ser Glu Lys Trp Ile Lys
            100                 105                 110

Lys Asp Glu Val Ile Pro Tyr Phe Tyr Ile Ser Ile Asp Lys Tyr Thr
        115                 120                 125

His Thr Val Thr Leu Ser Lys Val Ser Leu Arg
    130                 135

<210> SEQ ID NO 13
<211> LENGTH: 256
<212> TYPE: PRT
<213> ORGANISM: Yersinia pestis

<400> SEQUENCE: 13

Met Gln Met Lys Lys Leu Ser Leu Gly Ile Met Val Leu Ala Leu Ile
1               5                   10                  15

Ser Ser Gln His Val Leu Ala Lys Asn Trp Gln Glu Ile Lys Gln Ser
            20                  25                  30

Gly Glu Leu Arg Ile Gly Val Pro Gly Asp Tyr Ala Pro Leu Ala Phe
        35                  40                  45

His Asp Lys Gln Gly Gln Leu Ile Gly Tyr Asp Val Asp Met Ala Asn
    50                  55                  60

Ala Phe Gly Glu Asp Leu Lys Leu Lys Val Asn Phe Val Ser Thr Ser
65                  70                  75                  80

Trp Pro Thr Leu Ser Asp Asp Leu Ala Ala Asp Lys Phe Asp Ile Ala
                85                  90                  95

Met Gly Gly Val Thr Ala Thr Pro Gly Arg Glu Ala Gln Phe Ala Leu
            100                 105                 110

Ser His Ala Val Val Lys Asn Gly Lys Ile Ala Leu Thr His Cys Gln
        115                 120                 125

Lys Val Asn Lys Phe Pro Thr Leu Asp Ala Ile Asp Arg Gln Asn Val
    130                 135                 140

Lys Val Ile Val Asn Pro Gly Gly Thr Asn Gln Ser Phe Val Asp Ala
145                 150                 155                 160

Asn Ile Lys Gln Ala Gln Ile Ile Arg Thr Lys Asp Asn Val Ala Asn
```

```
                165                 170                 175
Leu Gln Gly Ile Arg Asn Lys Ser Ala Asp Ile Met Phe Thr Asp Leu
            180                 185                 190

Ile Glu Gly Asp Tyr Tyr Gln Ser Lys Glu Pro Gly Val Phe Cys Val
        195                 200                 205

Ala Thr Pro Glu Val Leu Ala Gly Thr Gly Ser Tyr Lys Val Tyr Met
    210                 215                 220

Met Ala Lys Asp Asn Gln Pro Leu Leu Glu Glu Val Asn Gln Trp Leu
225                 230                 235                 240

Ala Gly Lys Thr Lys Thr Leu Leu Ala Gln Lys Trp Asn Ile Ser Glu
                245                 250                 255

<210> SEQ ID NO 14
<211> LENGTH: 241
<212> TYPE: PRT
<213> ORGANISM: Yersinia pestis

<400> SEQUENCE: 14

Met Ser Asn Phe Ala Val Ser Leu Pro Glu Val Ile Ala Val Leu Pro
1               5                   10                  15

Ala Ala Gly Ile Gly Ser Arg Met Leu Val Asp Cys Pro Lys Gln Tyr
            20                  25                  30

Leu Thr Val Gly Gly Lys Thr Ile Ile Glu His Ala Ile Phe Ser Leu
        35                  40                  45

Leu His His Pro Arg Ile Gln Arg Val Ile Val Ile His Pro Gln
    50                  55                  60

Asp Thr Gln Phe Ser Arg Leu Ser Val Ala Gln Asp Pro Arg Ile Ser
65                  70                  75                  80

Thr Val Tyr Gly Gly Asp Gln Arg Ala Asn Ser Val Met Ala Gly Leu
                85                  90                  95

Gln Leu Ala Gly Gln Ala Glu Trp Val Leu Val His Asp Ala Ala Arg
            100                 105                 110

Pro Cys Leu His Leu Asp Asp Leu Ser Arg Leu Leu Ser Ile Thr Glu
        115                 120                 125

Cys Ser Gln Val Gly Gly Ile Leu Ala Ala Pro Val Arg Asp Thr Met
    130                 135                 140

Lys Arg Ala Glu Pro Gly Ile Gln Ala Ile Ala His Thr Val Asp Arg
145                 150                 155                 160

Gln Asp Leu Trp His Ala Leu Thr Pro Gln Leu Phe Pro Leu Glu Leu
                165                 170                 175

Leu Lys Leu Cys Leu Ser Arg Ala Leu Arg Glu Gly Val Ala Val Thr
            180                 185                 190

Asp Glu Ala Ser Ala Leu Glu His Cys Gly Tyr His Pro Ile Leu Val
        195                 200                 205

Thr Gly Arg Ser Asp Asn Ile Lys Val Thr Arg Pro Glu Asp Leu Ala
    210                 215                 220

Leu Ala Glu Phe Tyr Leu Thr Gln Arg Gln Ser Leu Asn Asn Asp Ser
225                 230                 235                 240

Leu

<210> SEQ ID NO 15
<211> LENGTH: 481
<212> TYPE: PRT
<213> ORGANISM: Yersinia pestis

<400> SEQUENCE: 15
```

-continued

```
Met Lys Lys Thr Thr Leu Val Leu Ser Ala Leu Ala Leu Ser Ile Gly
1               5                   10                  15

Phe Ala Met Gly Pro Val Ser Ser Val Val Ala Ala Glu Thr Ala Ala
            20                  25                  30

Ser Ser Ser Gln Gln Leu Pro Ser Leu Ala Pro Met Leu Glu Lys Val
        35                  40                  45

Met Pro Ser Val Val Ser Ile Asn Val Glu Gly Ser Ala Pro Val Ser
50                  55                  60

Ser Ala Gly Ala Arg Gly Met Pro Pro Gln Phe Gln Gln Phe Phe Gly
65                  70                  75                  80

Asp Asn Ser Pro Phe Cys Gln Asp Gly Ser Pro Phe Gln Gly Ser Pro
                85                  90                  95

Met Cys Gln Gly Asp Leu Gly Gly Leu Gly Gln Gly Met Pro Ser Lys
            100                 105                 110

Arg Glu Phe Arg Ser Leu Gly Ser Gly Val Ile Ile Asp Ala Gly Lys
        115                 120                 125

Gly Tyr Val Val Thr Asn Asn His Val Val Asp Asn Ala Asn Lys Ile
    130                 135                 140

Ser Val Lys Leu Ser Asp Gly Arg Ser Phe Asp Ala Lys Val Ile Gly
145                 150                 155                 160

Lys Asp Pro Arg Thr Asp Ile Ala Leu Leu Gln Leu Lys Asp Ala Lys
                165                 170                 175

Asn Leu Thr Ala Ile Lys Ile Ala Asn Ser Asp Gln Leu Arg Val Gly
            180                 185                 190

Asp Tyr Thr Val Ala Ile Gly Asn Pro Tyr Gly Leu Gly Glu Thr Val
        195                 200                 205

Thr Ser Gly Ile Val Ser Ala Leu Gly Arg Ser Gly Leu Asn Val Glu
    210                 215                 220

Asn Tyr Glu Asn Phe Ile Gln Thr Asp Ala Ala Ile Asn Arg Gly Asn
225                 230                 235                 240

Ser Gly Gly Ala Leu Ile Asn Leu Asn Gly Glu Leu Ile Gly Ile Asn
                245                 250                 255

Thr Ala Ile Leu Ala Pro Asp Gly Gly Asn Ile Gly Ile Gly Phe Ala
            260                 265                 270

Ile Pro Ser Asn Met Val Lys Asn Leu Thr Ser Gln Met Val Glu Phe
        275                 280                 285

Gly Gln Val Lys Arg Gly Glu Leu Gly Ile Met Gly Thr Glu Leu Asn
    290                 295                 300

Ser Glu Leu Ala Lys Ala Met Lys Val Asp Ala Gln Lys Gly Ala Phe
305                 310                 315                 320

Ile Ser Gln Val Val Pro Lys Ser Ala Ala Lys Ala Gly Ile Lys
                325                 330                 335

Ala Gly Asp Ile Ile Val Ser Met Asn Gly Lys Ala Ile Asn Ser Phe
            340                 345                 350

Ala Gly Phe Arg Ala Glu Ile Gly Thr Leu Pro Val Gly Ser Lys Met
        355                 360                 365

Thr Leu Gly Leu Leu Arg Asp Gly Lys Pro Ile Asn Val Asp Val Val
    370                 375                 380

Leu Glu Gln Ser Ser His Ser Gln Val Glu Ser Gly Asn Leu Tyr Thr
385                 390                 395                 400

Gly Ile Glu Gly Ala Glu Leu Ser Asn Ser Asp Val Ser Gly Lys Lys
                405                 410                 415
```

```
Gly Val Lys Val Asp Ser Val Lys Pro Gly Thr Ala Ala Arg Ile
            420             425             430

Gly Leu Lys Lys Gly Asp Ile Ile Met Gly Ile Asn Gln Gln Pro Val
        435             440             445

Gln Asn Leu Gly Glu Leu Arg Lys Ile Leu Asp Ala Lys Pro Pro Val
    450             455             460

Leu Ala Leu Asn Ile Gln Arg Gly Asp Thr Ser Leu Tyr Leu Leu Met
465             470             475             480

Gln
```

<210> SEQ ID NO 16
<211> LENGTH: 206
<212> TYPE: PRT
<213> ORGANISM: Yersinia pestis

<400> SEQUENCE: 16

```
Met Thr Tyr Ile Val Ala Leu Thr Gly Gly Ile Gly Ser Gly Lys Ser
1               5                   10                  15

Thr Val Ala Asn Ala Phe Ala Asn Leu Gly Val Pro Leu Val Asp Ala
                20                  25                  30

Asp Ile Ile Ala Arg Gln Val Val Glu Pro Gly Thr Ser Ala Leu Ala
            35                  40                  45

Ala Ile Ala Ser Arg Tyr Gly Glu Asn Ile Leu Gln Gln Asp Gly Ser
        50                  55                  60

Leu Asn Arg Ala Ala Leu Arg Gln Lys Ile Phe Ser Glu Gln Gln Glu
65                  70                  75                  80

Lys Ala Trp Leu Asn Ser Leu Leu His Pro Leu Ile Gln Gln Glu Thr
                85                  90                  95

Gln Arg Gln Leu Ala Gly Ile Asp Gln Pro Tyr Ala Leu Trp Val Val
            100                 105                 110

Pro Leu Leu Val Glu Asn Gly Leu His His Arg Ala Asp Arg Val Leu
        115                 120                 125

Val Val Asp Val Thr Pro Asp Ile Gln Leu Ala Arg Thr Met Ala Arg
    130                 135                 140

Asp Gly Ile Thr Arg Gln Gln Ala Glu Asn Ile Leu Ala Ser Gln Val
145                 150                 155                 160

Ser Arg Gln Gln Arg Leu Ala Cys Ala Asp Asp Ile Ile Asp Asn Ser
                165                 170                 175

Gly Asp Pro Leu Met Ile Ala Gln His Val Ala Ser Leu His His Arg
            180                 185                 190

Tyr Leu Lys Leu Ala Thr Ala Ala Gln Gln Asp Leu His Gln
        195                 200                 205
```

<210> SEQ ID NO 17
<211> LENGTH: 294
<212> TYPE: PRT
<213> ORGANISM: Yersinia pestis

<400> SEQUENCE: 17

```
Met Lys Pro Phe Leu Arg Trp Cys Tyr Val Ala Thr Ala Leu Met Leu
1               5                   10                  15

Ala Gly Cys Ser Asn His Asp Trp Arg Lys Asp Glu Val Leu Ala Ile
                20                  25                  30

Pro Leu Gln Pro Thr Leu Gln Gln Glu Val Ile Leu Ala Arg Met Glu
            35                  40                  45

Gln Ile Leu Ala Ser Arg Ala Leu Thr Asp Asp Glu Arg Ala Gln Leu
```

```
                50                  55                  60
Leu Tyr Glu Arg Gly Val Leu Tyr Asp Ser Leu Gly Leu Arg Ala Leu
 65                  70                  75                  80

Ala Arg Asn Asp Phe Ser Gln Ala Leu Ala Ile Arg Pro Asp Met Pro
                 85                  90                  95

Glu Val Phe Asn Tyr Leu Gly Ile Tyr Leu Thr Gln Ala Gly Asn Phe
                100                 105                 110

Asp Ala Ala Tyr Glu Ala Phe Asp Ser Val Leu Glu Leu Asp Pro Thr
                115                 120                 125

Tyr Asn Tyr Ala Arg Leu Asn Arg Gly Ile Ala Leu Tyr Tyr Gly Gly
            130                 135                 140

Arg Phe Pro Leu Ala Gln Asp Asp Leu Gln Ala Phe Tyr Gln Asp Asp
145                 150                 155                 160

Pro Asn Asp Pro Phe Arg Ser Leu Trp Leu Tyr Val Glu Arg Glu
                165                 170                 175

Ile Asp Pro Lys Ala Ala Val Val Ala Leu Gln Gln Arg Tyr Glu Lys
                180                 185                 190

Ser Asp Arg Gly Gln Trp Gly Trp Asn Ile Val Glu Phe Tyr Leu Gly
            195                 200                 205

Lys Ile Ser Glu Lys Ser Leu Met Glu Arg Leu Lys Ala Asp Ala Thr
    210                 215                 220

Asp Asn Thr Ser Leu Ala Glu His Leu Ser Glu Thr Asp Phe Tyr Leu
225                 230                 235                 240

Gly Lys His Tyr Leu Ser Leu Gly Asp Lys Asn Thr Ala Ser Val Leu
                245                 250                 255

Phe Lys Leu Thr Val Ala Asn Asn Val His Asn Phe Val Glu His Arg
                260                 265                 270

Tyr Ala Leu Leu Glu Leu Ala Leu Gly Gln Glu Gln Asp Asp Leu
            275                 280                 285

Ser Glu Ser Asp Gln Gln
    290

<210> SEQ ID NO 18
<211> LENGTH: 161
<212> TYPE: PRT
<213> ORGANISM: Yersinia pestis

<400> SEQUENCE: 18

Met Lys Phe His Leu Pro Phe Ile Val Gly Gly Leu Leu Ala Met Ser
 1               5                  10                  15

Ser Ser Ala Phe Ala Met Ser Leu Asn Tyr Gln Glu Val Gly Tyr Asn
                20                  25                  30

Ile Glu Ala Arg Gly Ala Arg Ala Val Val Ala Glu Leu Glu Lys Ser
            35                  40                  45

Gly Gln Leu Pro Ala Val Glu Asn Asn Ile Lys Leu Gly Asp Asp Asn
        50                  55                  60

Trp Ile Ala Met Ala Pro Lys Leu Ala Ser Ala Gly Asn Pro Lys Phe
 65                 70                  75                  80

Thr Glu Gly Val Lys Ser Ala Leu Ser Ser Ala Leu Thr Tyr Asn Pro
                85                  90                  95

Ala Ala Val Leu Lys Ala Val Ser Gly Ser Lys Ile Leu Thr Leu Ser
                100                 105                 110

Asp Val Cys Thr Ala Pro Ile Asp Val Lys Asp Ser Glu Ala Lys Ala
            115                 120                 125
```

```
Asn Phe Gln Gln Arg Ala Ser Arg Thr Leu Leu Thr Ile Lys Asn Ser
    130                 135                 140

Asp Met Ala Gly Pro Arg Asp Ser Cys Leu Ala Glu Leu Lys Lys Leu
145                 150                 155                 160

Ser

<210> SEQ ID NO 19
<211> LENGTH: 395
<212> TYPE: PRT
<213> ORGANISM: Yersinia pestis

<400> SEQUENCE: 19

Met Lys Ser Leu Ile Leu Leu Ala Leu Leu Ile Pro Ala Ser Val
1               5                   10                  15

Thr Ala Asn Thr Leu Ser Val Glu Pro Lys Asp Thr Lys Pro Ala Leu
            20                  25                  30

Ile Asp Ser Leu Ser Ala Thr Phe Ala Ile Asp Lys Ile Ala Met Leu
        35                  40                  45

Lys Lys Glu Lys Gly Ala Asn Glu Ser Asn Leu Tyr Leu Pro Phe Glu
50                  55                  60

Gln Thr Lys Asp Gly Leu Ala Ile Leu Phe Gly Asp Ile Asn Gln Asp
65                  70                  75                  80

Gly Lys Ile Asp Ala Leu Val Pro Phe Thr Trp Glu Gly Leu Asn Gly
                85                  90                  95

Leu Asp Gln Glu Ile Pro Ser Asn Asp Trp Tyr Ser Tyr Tyr Ala Ile
            100                 105                 110

Tyr Leu Gln Asp Asp Gln Gly Trp Lys Gln Val Gly Gln Ile Pro Thr
        115                 120                 125

Gly Thr Phe Thr Thr Asp Asn Gln Thr Leu Leu Thr Asn Ile Glu Asp
    130                 135                 140

Gly Val Ile Tyr Gly Glu Ile Met Pro Arg Met Thr Asp Asp Pro
145                 150                 155                 160

Gln Pro Gln Gln Trp Val Leu Arg Ala His Pro Glu Lys Asp Asn Leu
                165                 170                 175

Leu Val Pro Ile Pro Thr Pro Gln Pro Leu Ala Asn Ala Leu Thr Leu
            180                 185                 190

Asn Leu Ser Lys Lys Arg Pro Leu Thr Arg Asn Ala Leu Val Thr Ala
        195                 200                 205

Phe Gly Glu Pro Ile Asn Ile Gly Asp Asn Tyr Phe Leu Val Asp Gly
210                 215                 220

Asp Cys Val Gly His Pro Asp Trp Lys Tyr Tyr Gln Tyr Pro Gly Ala
225                 230                 235                 240

Ala Phe Asn Val Ser Gln Asn Asp Asn Ser Val Gly Val Ser His Phe
                245                 250                 255

Ile Gly Ile Pro Asp Asn Leu Ser Leu Val Leu Gly Asp Leu Thr Ile
            260                 265                 270

Thr Gln Lys Thr Ser Ala His Gln Leu Ile Lys Ala Leu Ser Gln Asn
        275                 280                 285

Asp Ser Phe Thr Val Ser Arg Thr Ser Thr Asp Leu Arg Thr Asp Leu
290                 295                 300

Gly Gln Ser Ser Pro Tyr Phe Asp Asp Ala Asn Asp Ile Phe Ala Leu
305                 310                 315                 320

Arg Leu Pro Tyr Tyr Ile Ala Gly Phe Glu Ala Trp Ala Lys Lys Asn
                325                 330                 335
```

```
Glu Ala Arg Glu Val Pro Asn Asp Glu Ala Asp Thr Phe Thr Arg
            340                 345                 350

Gln Phe Tyr Phe Thr Thr Ile Gly Val Ala Pro Ile Gln Asn Ser
            355                 360                 365

Pro Thr Arg Leu Met Phe Tyr Phe Leu Gly Asp Lys Met Val Ala Leu
            370                 375                 380

Ser Val Ile Tyr Asp Asp Gly Gln Val Cys Ile
385                 390                 395

<210> SEQ ID NO 20
<211> LENGTH: 154
<212> TYPE: PRT
<213> ORGANISM: Yersinia pestis

<400> SEQUENCE: 20

Met Lys Val Lys Ser Lys Lys Asn Leu Trp Ala Leu Leu Leu Thr Gly
1               5                   10                  15

Ser Ala Leu Leu Gly Tyr Val Phe Trp Leu Leu Leu His Pro Val Glu
            20                  25                  30

Ile Val Ser Val His Gln Arg Asn Asp Tyr Ser Asp Val Leu Val Arg
        35                  40                  45

Asn Phe Pro Leu Thr Asp Lys Ser Lys Ile Asn Trp Trp Leu Glu Asn
    50                  55                  60

Arg Asp Met Leu Lys Asp Lys Tyr Ser Ile Pro Lys Pro Ala Ser Asp
65                  70                  75                  80

Gly Phe Tyr Thr Val Ile Phe Trp Asp Phe Asp Gly Tyr Lys Glu
                85                  90                  95

Glu Gly Lys Tyr Asp Arg Arg Cys Phe Asp Asp Met Lys Thr Ser Lys
            100                 105                 110

Asn Cys Ile Asp Lys Asn Lys Val Phe Ser Val Glu Asn Asp Arg Asp
        115                 120                 125

Lys Asp Ile Leu Phe Ser Val Tyr Asp Gly Met Tyr Arg Leu Glu Lys
    130                 135                 140

Asn Gly Lys Ile Val Lys Met Lys Arg Glu
145                 150

<210> SEQ ID NO 21
<211> LENGTH: 535
<212> TYPE: PRT
<213> ORGANISM: Yersinia pestis

<400> SEQUENCE: 21

Met Thr Ile Ser Leu Arg Arg Thr Gly Ile Leu Lys Phe Gly Ile Gly
1               5                   10                  15

Leu Val Ala Leu Thr Ile Ala Ala Ser Val Gln Ala Lys Thr Leu Val
            20                  25                  30

Tyr Cys Ser Glu Gly Ser Pro Glu Gly Phe Asn Pro Gln Leu Phe Thr
        35                  40                  45

Ser Gly Thr Thr Tyr Asp Ala Ser Ser Val Pro Ile Tyr Asn Arg Leu
    50                  55                  60

Val Glu Phe Lys Ile Gly Thr Thr Glu Ile Glu Pro Ser Leu Ala Glu
65                  70                  75                  80

Arg Trp Glu Val Ser Glu Asp Gly Lys Thr Tyr Thr Phe Tyr Leu Arg
                85                  90                  95

Lys Gly Val Lys Trp Gln Asp Asn Lys Asp Phe Lys Pro Thr Arg Asp
            100                 105                 110
```

```
Phe Asn Ala Asp Asp Val Ile Tyr Ser Phe Met Arg Gln Lys Asp Asp
            115                 120                 125
Lys Asn Pro Tyr His Lys Val Ser Gly Gly Ser Tyr Glu Tyr Phe Gln
        130                 135                 140
Gly Met Gly Met Gly Asp Leu Ile Thr Asn Val Val Lys Val Asp Asp
145                 150                 155                 160
Asn Thr Val Arg Phe Glu Leu Thr Arg Pro Glu Ser Pro Phe Leu Ala
                165                 170                 175
Asp Leu Ala Met Asp Phe Ala Ser Ile Leu Ser Ala Glu Tyr Ala Asp
            180                 185                 190
Asn Met Leu Lys Ala Gly Thr Pro Glu Lys Val Asp Leu Asn Pro Ile
        195                 200                 205
Gly Thr Gly Pro Phe Gln Leu Gln Gln Tyr Gln Lys Asp Ser Arg Ile
210                 215                 220
Leu Tyr Lys Ala Phe Pro Gly Phe Trp Gly Thr Lys Pro Lys Ile Asp
225                 230                 235                 240
Arg Leu Val Phe Ser Ile Thr Pro Asp Ala Ser Val Arg Tyr Ala Lys
                245                 250                 255
Leu Gln Lys Asn Glu Cys Gln Ile Met Pro Tyr Pro Asn Pro Ala Asp
            260                 265                 270
Ile Ala Arg Met Lys Glu Asp Lys Thr Ile Asn Leu Met Glu Gln Pro
        275                 280                 285
Gly Leu Asn Val Gly Tyr Leu Ser Phe Asn Ile Glu Lys Lys Pro Leu
290                 295                 300
Asp Asn Leu Lys Val Arg Gln Ala Leu Thr Met Ala Val Asn Lys Asp
305                 310                 315                 320
Ala Ile Ile Asp Ala Val Tyr Gln Gly Ala Gly Gln Ala Ala Lys Asn
                325                 330                 335
Leu Ile Pro Pro Thr Met Trp Gly Tyr Asn Asp Asp Val Lys Asp Tyr
            340                 345                 350
Ala Tyr Asp Pro Ala Lys Ala Lys Glu Leu Leu Lys Glu Ala Gly Leu
        355                 360                 365
Pro Asp Gly Phe Ser Ile Asp Leu Trp Ala Met Pro Val Gln Arg Pro
370                 375                 380
Tyr Asn Pro Asn Ala Arg Arg Met Ala Glu Met Ile Gln Ser Asp Trp
385                 390                 395                 400
Ala Lys Ile Gly Val Lys Ala Lys Ile Val Thr Tyr Glu Trp Gly Glu
                405                 410                 415
Tyr Leu Lys Arg Ala Lys Asp Gly Glu His Glu Thr Val Met Met Gly
            420                 425                 430
Trp Thr Gly Asp Asn Gly Asp Pro Asp Asn Phe Phe Ala Thr Leu Phe
        435                 440                 445
Ser Cys Asp Ala Ala Lys Gln Gly Ser Asn Tyr Ser Lys Trp Cys Tyr
450                 455                 460
Lys Pro Phe Glu Asp Leu Ile Gln Pro Ala Arg Ala Glu Ala Asp His
465                 470                 475                 480
Asp Lys Arg Val Ala Leu Tyr Lys Gln Ala Gln Val Val Met Asn Glu
                485                 490                 495
Gln Ala Pro Ala Leu Ile Ile Ala His Ser Thr Val Tyr Glu Pro Val
            500                 505                 510
Arg Lys Glu Val Lys Gly Tyr Val Val Asp Pro Leu Gly Lys His His
        515                 520                 525
Phe Asp Asn Val Ser Leu Asp
```

-continued

```
            530                 535

<210> SEQ ID NO 22
<211> LENGTH: 70
<212> TYPE: PRT
<213> ORGANISM: Yersinia pestis

<400> SEQUENCE: 22

Met Ser Asn Lys Met Thr Gly Leu Val Lys Trp Phe Asp Ala Gly Lys
1               5                   10                  15

Gly Phe Gly Phe Ile Thr Pro Ala Asp Gly Ser Lys Asp Val Phe Val
            20                  25                  30

His Phe Ser Ala Ile Gln Ser Asn Asp Phe Lys Thr Leu Asp Glu Gly
        35                  40                  45

Gln Asn Val Glu Phe Ser Ile Glu Asn Gly Ala Lys Gly Pro Ser Ala
    50                  55                  60

Val Asn Val Ile Ala Leu
65                  70

<210> SEQ ID NO 23
<211> LENGTH: 70
<212> TYPE: PRT
<213> ORGANISM: Yersinia pestis

<400> SEQUENCE: 23

Met Ser Asn Lys Met Thr Gly Leu Val Lys Trp Phe Asp Ala Gly Lys
1               5                   10                  15

Gly Phe Gly Phe Ile Thr Pro Ala Asp Gly Ser Lys Asp Val Phe Val
            20                  25                  30

His Phe Ser Ala Ile Gln Ser Asn Asp Phe Lys Thr Leu Asp Glu Gly
        35                  40                  45

Gln Asn Val Glu Phe Ser Ile Glu Asn Gly Ala Lys Gly Pro Ala Ala
    50                  55                  60

Val Asn Val Ile Ala Leu
65                  70

<210> SEQ ID NO 24
<211> LENGTH: 150
<212> TYPE: PRT
<213> ORGANISM: Yersinia pestis

<400> SEQUENCE: 24

Met Gln Val Ile Leu Leu Asp Lys Val Ala Asn Leu Gly Ser Leu Gly
1               5                   10                  15

Asp Gln Val Asn Val Lys Ala Gly Tyr Ala Arg Asn Phe Leu Val Pro
            20                  25                  30

Gln Gly Lys Ala Val Pro Ala Thr Lys Lys Asn Val Glu Phe Phe Glu
        35                  40                  45

Ala Arg Arg Ala Glu Leu Glu Ala Lys Leu Ala Asp Val Leu Ala Ala
    50                  55                  60

Ala Glu Ala Arg Ala Thr Lys Ile Asn Glu Leu Val Ser Val Thr Ile
65                  70                  75                  80

Ser Ser Lys Ala Gly Asp Glu Gly Lys Leu Phe Gly Ser Ile Gly Thr
                85                  90                  95

Arg Asp Ile Ala Asp Ala Val Thr Ala Ala Gly Val Glu Val Ala Lys
            100                 105                 110

Ser Glu Val Arg Leu Pro Asn Gly Val Leu Arg Thr Ala Gly Glu His
            115                 120                 125
```

```
Glu Val His Phe Gln Val His Ser Asp Val Phe Ala Lys Leu Asn Val
            130                 135                 140

Val Val Val Pro Glu Ala
145                 150

<210> SEQ ID NO 25
<211> LENGTH: 362
<212> TYPE: PRT
<213> ORGANISM: Yersinia pestis

<400> SEQUENCE: 25

Met Leu Met Lys Ile Lys Val Phe Met Phe Ala Met Ala Ala Leu Thr
1               5                   10                  15

Thr Leu Pro Ala Phe Ala Gln Leu Pro Ser Tyr Tyr Pro Ala Asp Tyr
            20                  25                  30

Gln Lys Ile Val Asp Gly Ala Lys Glu Gly Lys Val Val Tyr
        35                  40                  45

Ser Ala Thr Asp Ile Lys Ala Ala Pro Leu Ile Lys Gly Phe Glu
    50                  55                  60

Ala Ala Tyr Pro Gly Ile Lys Val Glu Tyr Asn Asp Met Asn Ser Thr
65                  70                  75                  80

Glu Leu Tyr Asn Arg Tyr Ile Ser Glu Gln Ala Ser Gly Ser Thr Ser
                85                  90                  95

Gly Asp Val Val Trp Ser Ser Ser Met Asp Thr Ala Leu Lys Leu Ala
            100                 105                 110

Thr Asp Tyr Ala Leu Glu Tyr Leu Ser Pro Glu Gln Ala Glu Leu Pro
        115                 120                 125

Lys Trp Ala Ile Trp Lys Asn Lys Ala Tyr Gly Ser Thr Tyr Glu Pro
130                 135                 140

Val Val Phe Ile Tyr Asn Lys Arg Leu Ile Pro Gln Ala Asp Met Pro
145                 150                 155                 160

Asp Thr His Ile Ala Leu Ala Lys Leu Ile Val Ser Gln Pro Asp Lys
                165                 170                 175

Phe Lys Arg Lys Val Thr Thr Tyr Asp Ile Glu Lys Ser Gly Leu Gly
            180                 185                 190

Phe Met Leu Ser Val Gln Asp Phe Lys Ala Asp Pro Asn Tyr Phe Thr
        195                 200                 205

Thr Leu Ala Asn Ile Ala Lys Gly Gly Leu Thr Val Gln Ser Ser Thr
    210                 215                 220

Gly Thr Met Met Glu Arg Val Ser Ser Gly Glu Asn Leu Ile Gly Phe
225                 230                 235                 240

Asn Ile Leu Gly Ser Tyr Ala Glu Thr Arg Ala Lys Thr Asp Pro Ser
                245                 250                 255

Leu Gly Ile Ala Tyr Pro Lys Asp Tyr Thr Leu Val Leu Ser Arg Val
            260                 265                 270

Thr Phe Ile Ser Gln Lys Ala Pro His Gln Asn Ala Ala Lys Leu Trp
        275                 280                 285

Val Asp Tyr Leu Leu Ser Glu Lys Gly Gln Asn Ile Leu Ala Asn Gln
    290                 295                 300

Ser Asp Ile Pro Ser Ile Arg Lys Asp Ile Asp Gly Asn Asn Asp Ile
305                 310                 315                 320

Asp Gly Leu Thr Lys Lys Leu Gly Ser Ala Leu Arg Pro Ile Pro Val
                325                 330                 335

Asp Glu Ser Leu Leu Glu Tyr Met Glu Gln Ala Lys Arg Leu Asp Tyr
```

```
                340               345               350
Ile Lys Gln Trp Arg Thr Ala Ala Ala Lys
        355                 360

<210> SEQ ID NO 26
<211> LENGTH: 109
<212> TYPE: PRT
<213> ORGANISM: Yersinia pestis

<400> SEQUENCE: 26

Met Ser Tyr Lys Ser Leu Arg Asn Ile Ala Leu Thr Gly Leu Leu Leu
1               5                   10                  15

Ser Thr Ala Ala Thr Thr Phe Ala Ala Thr Pro Thr Gly Thr Thr Pro
            20                  25                  30

Ser Asp Met Thr Cys Lys Glu Phe Leu Asp Leu Asn Pro Lys Ser Phe
        35                  40                  45

Thr Pro Val Val Tyr Trp Val Leu Asn Asp Asp Thr Gln Tyr Lys Gln
    50                  55                  60

Gly Asp Tyr Val Asp Leu His Glu Thr Asp Thr Leu Val Thr Pro Lys
65                  70                  75                  80

Val Val Glu Val Cys Lys Lys Ala Pro Glu Ser Lys Leu Ser Glu Ile
                85                  90                  95

Lys Gln Asp Ile Leu Asn Phe Ala Lys Lys His Asn Met
            100                 105

<210> SEQ ID NO 27
<211> LENGTH: 305
<212> TYPE: PRT
<213> ORGANISM: Yersinia pestis

<400> SEQUENCE: 27

Met Gln Met Arg Lys Leu Ala Leu Val Leu Leu Leu Ala Gly Met Thr
1               5                   10                  15

Ser Ser Val Ala Gln Ala Glu Asp Ala Thr Ala Lys Ala Asp Thr Ala
            20                  25                  30

Ile Asp Thr Leu Gln Lys Val Lys Asn Asn Gly Val Ile Val Val Gly
        35                  40                  45

His Arg Glu Ser Ser Val Pro Phe Ser Tyr Tyr Asp Asn Gln Gln Lys
    50                  55                  60

Val Val Gly Tyr Ser Gln Asp Tyr Ser Asn Leu Ile Val Asp Ala Ile
65                  70                  75                  80

Arg Lys Glu Leu Asn Ala Pro Asn Leu Glu Val Lys Leu Ile Pro Ile
                85                  90                  95

Thr Ser Gln Asn Arg Ile Pro Leu Leu Gln Asn Gly Thr Phe Asp Phe
            100                 105                 110

Glu Cys Gly Ser Thr Thr Asn Asn Leu Glu Arg Gln Gln Gln Ala Ala
        115                 120                 125

Phe Ser Asn Thr Ile Phe Val Val Gly Thr Arg Leu Leu Thr Lys Lys
    130                 135                 140

Asp Ser Glu Val Lys Asp Phe Lys Asp Leu Ala Gly Lys Ala Val Val
145                 150                 155                 160

Val Thr Ser Gly Thr Thr Ser Glu Val Leu Leu Asn Lys Leu Asn Glu
                165                 170                 175

Lys Asp Asn Met Asn Met Arg Ile Ile Ser Ala Lys Asp His Gly Asp
            180                 185                 190

Ser Phe Arg Thr Leu Glu Ser Gly Arg Ala Val Ala Phe Met Met Asp
```

```
                 195                 200                 205
Asp Ala Leu Ala Gly Glu Arg Ala Lys Ala Lys Lys Pro Asp Glu
    210                 215                 220

Trp Ser Ile Val Gly Thr Pro Gln Ser Glu Glu Ala Tyr Gly Cys Met
225                 230                 235                 240

Met Arg Lys Asn Asp Pro Ala Phe Lys Ala Leu Leu Asp Lys Thr Ile
                245                 250                 255

Ala Thr Ala Gln Thr Thr Gly Val Ala Glu Lys Ser Phe Asp Arg Trp
            260                 265                 270

Phe Lys Asn Pro Ile Pro Pro Lys Asn Leu Asn Met Asn Phe Ala Leu
        275                 280                 285

Ser Asp Glu Met Lys Ala Leu Phe Lys Ala Pro Asn Asp Lys Ala Leu
    290                 295                 300

Asn
305

<210> SEQ ID NO 28
<211> LENGTH: 167
<212> TYPE: PRT
<213> ORGANISM: Yersinia pestis

<400> SEQUENCE: 28

Met Thr Gln Thr Val His Phe Gln Gly Asn Pro Val Ser Val Ala Gly
1               5                   10                  15

Lys Leu Pro Gln Ile Gly Asp Lys Ala Lys Asp Phe Thr Leu Val Ala
            20                  25                  30

Lys Asp Leu Ser Asp Val Ala Leu Ser Ser Phe Ala Gly Lys Arg Lys
        35                  40                  45

Val Leu Asn Ile Phe Pro Ser Ile Asp Thr Gly Val Cys Ala Ala Ser
    50                  55                  60

Val Arg Lys Phe Asn Gln Leu Ala Gly Glu Leu Glu Asn Thr Val Val
65                  70                  75                  80

Leu Cys Ile Ser Ser Asp Leu Pro Phe Ala Gln Ser Arg Phe Cys Gly
                85                  90                  95

Ala Glu Gly Leu Ser Asn Val Ile Thr Leu Ser Thr Leu Arg Gly Ala
            100                 105                 110

Asp Phe Lys Gln Ala Tyr Gly Val Ala Ile Thr Glu Gly Pro Leu Ala
        115                 120                 125

Gly Leu Thr Ala Arg Ala Val Val Leu Asp Gly Gln Asp Asn Val
    130                 135                 140

Ile Tyr Ser Glu Leu Val Asn Glu Ile Thr Thr Glu Pro Asn Tyr Asp
145                 150                 155                 160

Ala Ala Leu Ala Ala Leu Lys
                165

<210> SEQ ID NO 29
<211> LENGTH: 264
<212> TYPE: PRT
<213> ORGANISM: Yersinia pestis

<400> SEQUENCE: 29

Met Asn Lys Ser Leu Pro Leu Ile Leu Met Ala Ile Leu Ala Gly Cys
1               5                   10                  15

Gly Ala Lys Lys Asn Thr His Asn Pro Val Asp Ile Asp Ile Tyr Thr
            20                  25                  30

Ser Asn Arg Ile Asn Ser Ile Ile Glu Met Gln Val Lys Thr Ala Asp
```

```
                35                  40                  45
Gln Ser Asn Thr Gly Glu Ile Ile Ala Lys Val Ser Ala Glu Phe Leu
 50                  55                  60

Gly Thr Pro Tyr Lys Ala Asn Met Leu Ile Gly Ser Ser Thr Glu Pro
 65                  70                  75                  80

Glu Lys Leu Val Ile Asp Phe Arg Gly Leu Asp Cys Phe Thr Tyr Leu
                 85                  90                  95

Asp Tyr Val Glu Ser Leu Arg Lys Ser Lys Asn Lys Asn Asp Phe Ile
            100                 105                 110

Lys Gln Leu Val Gly Val Arg Tyr Ile Asp Gly Asp Ile Ser Tyr Gln
        115                 120                 125

His Arg Lys His Phe Phe Thr Asp Trp Ser Ser Arg Pro Pro Leu Asn
130                 135                 140

Ala Lys Asp Ile Thr Ala Glu Ile Ser Ala His Thr Leu Thr Val Thr
145                 150                 155                 160

Lys Tyr Leu Asn Gln Lys Ser Asp Gly Gly Glu Phe Ile Pro Thr Leu
                165                 170                 175

Gly Val Phe Lys Arg Asp Val Ser Tyr Ile Pro Ala Glu Phe Ile Asn
            180                 185                 190

Asp Ser Val Ile Asp Lys Leu Arg Thr Gly Asp Tyr Ile Gly Ile Tyr
        195                 200                 205

Thr His Ile Ala Gly Leu Asp Val Thr His Thr Gly Ile Phe Ile Met
210                 215                 220

Thr Lys Asn Gly Pro Val Leu Arg Asn Ala Ser Ser Leu Lys Val Asn
225                 230                 235                 240

Glu Lys Val Val Asp Ser Pro Phe Ile Glu Tyr Val Lys Lys Thr Pro
                245                 250                 255

Gly Ile Ile Val Leu Arg Ala Leu
            260

<210> SEQ ID NO 30
<211> LENGTH: 69
<212> TYPE: PRT
<213> ORGANISM: Yersinia pestis

<400> SEQUENCE: 30

Met Ala Lys Ile Lys Gly Gln Val Lys Trp Phe Asn Glu Ser Lys Gly
  1               5                  10                  15

Phe Gly Phe Ile Thr Pro Ala Asp Gly Ser Lys Asp Val Phe Val His
                 20                  25                  30

Phe Ser Ala Ile Gln Gly Asn Gly Phe Lys Thr Leu Ala Glu Gly Gln
             35                  40                  45

Asn Val Glu Phe Glu Ile Gln Asp Gly Gln Lys Gly Pro Ser Ala Val
         50                  55                  60

Asn Val Thr Ala Ile
 65

<210> SEQ ID NO 31
<211> LENGTH: 335
<212> TYPE: PRT
<213> ORGANISM: Yersinia pestis

<400> SEQUENCE: 31

Met Asn Lys Lys Val Phe Thr Leu Ala Ala Leu Val Thr Ser Met Met
  1               5                  10                  15

Val Thr Ser Met Met Val Gly Ala Tyr Ala Gln Ala Glu Thr Arg Ile
```

```
                    20                  25                  30
Gly Val Thr Ile Tyr Lys Tyr Asp Asp Asn Phe Met Ser Val Val Arg
            35                  40                  45
Lys Ala Ile Glu Lys Asp Ala Lys Ala Ser Pro Glu Ile Thr Leu Leu
        50                  55                  60
Met Asn Asp Ser Gln Asn Asp Gln Ser Lys Gln Asn Asp Gln Ile Asp
65                  70                  75                  80
Val Leu Leu Ala Lys Gly Val Lys Ala Leu Ala Ile Asn Leu Val Asp
                85                  90                  95
Pro Ala Ala Pro Val Val Ile Asp Lys Ala Arg Ser Asn Asp Ile
            100                 105                 110
Pro Ile Val Phe Tyr Asn Lys Glu Pro Ser Arg Lys Ala Leu Asp Ser
        115                 120                 125
Tyr Asp Lys Ala Tyr Tyr Val Gly Thr Asp Ser Lys Glu Ser Gly Val
        130                 135                 140
Ile Gln Gly Glu Leu Ile Ala Lys His Trp Gln Ala Asn Pro Glu Trp
145                 150                 155                 160
Asp Leu Asn Lys Asp Gly Lys Ile Gln Phe Val Leu Leu Lys Gly Glu
                165                 170                 175
Pro Gly His Pro Asp Ala Glu Ala Arg Thr Thr Tyr Val Ile Lys Thr
            180                 185                 190
Leu Asn Glu Lys Gly Leu Pro Thr Gln Gln Leu Gln Leu Asp Thr Ala
        195                 200                 205
Met Trp Asp Thr Ala Gln Ala Lys Asp Lys Met Asp Ala Trp Leu Ser
    210                 215                 220
Gly Pro Asn Ala Asn Lys Ile Glu Val Val Ile Ala Asn Asn Asp Ala
225                 230                 235                 240
Met Ala Met Gly Ala Val Glu Ala Leu Lys Ala His Asn Lys Thr Ser
                245                 250                 255
Val Pro Val Phe Gly Val Asp Ala Leu Pro Glu Ala Leu Ala Leu Val
            260                 265                 270
Lys Ser Gly Gln Met Ala Gly Thr Val Leu Asn Asp Ala Asn Asn Gln
        275                 280                 285
Ala Lys Ala Thr Phe Asp Leu Ala Lys Asn Leu Ala Ala Gly Lys Pro
    290                 295                 300
Ala Ala Glu Gly Thr Thr Trp Lys Ile Glu Asn Lys Ile Val Arg Ile
305                 310                 315                 320
Pro Tyr Val Gly Val Asp Lys Asp Asn Leu Ala Glu Phe Thr Lys
                325                 330                 335

<210> SEQ ID NO 32
<211> LENGTH: 353
<212> TYPE: PRT
<213> ORGANISM: Yersinia pestis

<400> SEQUENCE: 32

Met Lys Lys Thr Ala Ile Ala Leu Ala Val Ala Leu Val Gly Phe Ala
1               5                   10                  15
Thr Val Ala Gln Ala Ala Pro Lys Asp Asn Thr Trp Tyr Thr Gly Gly
            20                  25                  30
Lys Leu Gly Trp Ser Gln Tyr Gln Asp Thr Gly Ser Ile Ile Asn Asn
        35                  40                  45
Asp Gly Pro Thr His Lys Asp Gln Leu Gly Ala Gly Ala Phe Phe Gly
    50                  55                  60
```

-continued

```
Tyr Gln Ala Asn Gln Tyr Leu Gly Phe Glu Met Gly Tyr Asp Trp Leu
65                  70                  75                  80

Gly Arg Met Pro Tyr Lys Gly Asp Ile Asn Asn Gly Ala Phe Lys Ala
                85                  90                  95

Gln Gly Val Gln Leu Ala Ala Lys Leu Ser Tyr Pro Val Ala Gln Asp
            100                 105                 110

Leu Asp Val Tyr Thr Arg Leu Gly Gly Leu Val Trp Arg Ala Asp Ala
        115                 120                 125

Lys Gly Ser Phe Asp Gly Gly Leu Asp Arg Ala Ser Gly His Asp Thr
    130                 135                 140

Gly Val Ser Pro Leu Val Ala Leu Gly Ala Glu Tyr Ala Trp Thr Lys
145                 150                 155                 160

Asn Trp Ala Thr Arg Met Glu Tyr Gln Trp Val Asn Asn Ile Gly Asp
                165                 170                 175

Arg Glu Thr Val Gly Ala Arg Pro Asp Asn Gly Leu Leu Ser Val Gly
            180                 185                 190

Val Ser Tyr Arg Phe Gly Gln Glu Asp Ala Ala Ala Pro Ile Val Ala
        195                 200                 205

Pro Thr Pro Ala Pro Ala Pro Ile Val Asp Thr Lys Arg Phe Thr Leu
    210                 215                 220

Lys Ser Asp Val Leu Phe Gly Phe Asn Lys Ala Asn Leu Lys Pro Glu
225                 230                 235                 240

Gly Gln Gln Ala Leu Asp Gln Leu Tyr Ala Gln Leu Ser Ser Ile Asp
                245                 250                 255

Pro Lys Asp Gly Ser Val Val Val Leu Gly Phe Ala Asp Arg Ile Gly
            260                 265                 270

Gln Pro Ala Pro Asn Leu Ala Leu Ser Gln Arg Arg Ala Asp Ser Val
        275                 280                 285

Arg Asp Tyr Leu Val Ser Lys Gly Ile Pro Ala Asp Lys Ile Thr Ala
    290                 295                 300

Arg Gly Glu Gly Gln Ala Asn Pro Val Thr Gly Asn Thr Cys Asp Asn
305                 310                 315                 320

Val Lys Pro Arg Ala Ala Leu Ile Glu Cys Leu Ala Pro Asp Arg Arg
                325                 330                 335

Val Glu Ile Glu Val Lys Gly Tyr Lys Glu Val Val Thr Gln Pro Gln
            340                 345                 350

Ala
```

<210> SEQ ID NO 33
<211> LENGTH: 165
<212> TYPE: PRT
<213> ORGANISM: Yersinia pestis

<400> SEQUENCE: 33

```
Met Lys Lys Trp Leu Cys Ala Ala Ser Leu Gly Leu Ala Leu Ala Ala
1               5                   10                  15

Ser Ala Ser Val Gln Ala Ala Asp Lys Ile Ala Ile Val Asn Val Ser
            20                  25                  30

Ser Ile Phe Gln Gln Leu Pro Ala Arg Glu Ala Val Ala Lys Gln Leu
        35                  40                  45

Glu Asn Glu Phe Lys Gly Arg Ala Thr Glu Leu Gln Gly Met Glu Arg
    50                  55                  60

Asp Leu Gln Thr Lys Met Gln Lys Leu Gln Arg Asp Gly Ser Thr Met
65                  70                  75                  80
```

```
Lys Ala Ser Asp Arg Thr Lys Leu Glu Asn Glu Val Met Lys Gln Arg
                85                  90                  95

Glu Thr Phe Ser Thr Lys Ala Gln Ala Phe Glu Gln Asp Asn Arg Arg
            100                 105                 110

Arg Gln Ala Glu Glu Arg Asn Lys Ile Leu Ser Arg Ile Gln Asp Ala
        115                 120                 125

Val Lys Ser Val Ala Thr Lys Gly Gly Tyr Asp Val Val Ile Asp Ala
130                 135                 140

Asn Ala Val Ala Tyr Ala Asp Ser Ser Lys Asp Ile Thr Ala Asp Val
145                 150                 155                 160

Leu Lys Gln Val Lys
                165
```

<210> SEQ ID NO 34
<211> LENGTH: 251
<212> TYPE: PRT
<213> ORGANISM: Yersinia pestis

<400> SEQUENCE: 34

```
Met Ser Lys Ile Thr Asp Cys Cys Ser Glu Glu Asn His Pro Asn Ser
1               5                   10                  15

Arg Arg Ser Val Leu Lys Ala Ala Leu Gly Met Thr Ala Ala Gly Val
            20                  25                  30

Ile Gly Gly Ile Gly Leu Gly Leu Pro Gln Ile Ser Tyr Ala Ala Ala
        35                  40                  45

Leu Thr Gln Glu Glu Arg Asp Lys Leu Thr Pro Asp Gln Ile Val Glu
    50                  55                  60

Ser Leu Lys Gln Gly Asn Lys Arg Phe Thr Ser Gly Lys Ala Leu Gln
65                  70                  75                  80

His Asp Tyr Leu Ala Gln Lys Arg Ala Ser Ala Glu Gly Gln Phe Pro
                85                  90                  95

Ala Ala Val Ile Leu Ser Cys Ile Asp Ser Arg Ala Pro Ala Glu Ile
            100                 105                 110

Ile Leu Asp Thr Gly Ile Gly Glu Thr Phe Asn Ala Arg Val Ala Gly
        115                 120                 125

Asn Ile Ala Asn Asp Asp Leu Ile Gly Ser Leu Glu Phe Ala Ser Ala
130                 135                 140

Ala Ala Gly Ala Lys Val Ile Leu Val Met Gly His Thr Ala Cys Gly
145                 150                 155                 160

Ala Ile Lys Gly Ala Ile Asp Asn Val Glu Leu Gly Asn Leu Thr Gly
                165                 170                 175

Leu Leu Asn Arg Ile Lys Pro Ala Ile Glu Val Thr Gln Phe Asp Gly
            180                 185                 190

Glu Lys Ser Ser Lys Asn Glu Lys Tyr Val Asp Ala Val Ala Lys Thr
        195                 200                 205

Asn Val Lys Asn Thr Met Asp Glu Ile Arg Lys Asn Ser Glu Ile Ile
    210                 215                 220

Arg Lys Leu Glu Gln Glu Gly Lys Val Lys Ile Val Gly Ser Met Tyr
225                 230                 235                 240

Asn Leu Asn Asn Gly Glu Val Glu Phe Phe Met
                245                 250
```

<210> SEQ ID NO 35
<211> LENGTH: 101
<212> TYPE: PRT
<213> ORGANISM: Yersinia pestis

<400> SEQUENCE: 35

Met Pro Gln Asp Lys Thr Ser Glu His Leu Arg Ala Glu Leu Lys Ser
1               5                   10                  15

Leu Ala Asp Thr Leu Glu Glu Val Leu Gln Ser Ser Thr Asp Lys Pro
            20                  25                  30

Lys Ala Glu Leu Asp Lys Leu Arg Ala Lys Ala Glu Ser Ala Leu Lys
        35                  40                  45

Asp Thr Arg Val Arg Leu Ser Glu Thr Ser Asp Lys Ile Ala Ala Gln
    50                  55                  60

Thr Lys Glu Ile Ala Asp Lys Ala Asp Asn Tyr Val His Asp Asn Pro
65                  70                  75                  80

Trp Thr Gly Val Gly Ile Gly Ala Ala Val Gly Val Val Leu Gly Val
                85                  90                  95

Leu Leu Ser Arg Arg
            100

<210> SEQ ID NO 36
<211> LENGTH: 172
<212> TYPE: PRT
<213> ORGANISM: Yersinia pestis

<400> SEQUENCE: 36

Met Ala Ala Leu Val Asp Tyr Phe Leu His Ile Glu Gly Val Asp Gly
1               5                   10                  15

Glu Ser Pro Asp Gln Gln Tyr Asn Gly Trp Ile Gln Val Gln Ala Trp
            20                  25                  30

Gln Trp Ala Glu Glu Asn Ala Gly Arg Trp Gly Leu Gly Gly Gly Gly
        35                  40                  45

Gly Ser Gly Lys Val Glu Met Lys Asp Phe Glu Phe Arg Met Val Ser
    50                  55                  60

Asn Lys Ala Ser Pro Lys Leu Phe Leu Met Cys Ala Ile Gly Glu His
65                  70                  75                  80

Ile Pro Gln Ala Lys Leu Val Cys Arg Lys Ser Gly Gln Gly Gln Gln
                85                  90                  95

Asp Phe Leu Ile Val Thr Phe Ser Asn Cys Leu Val Ser Ser Phe Lys
            100                 105                 110

Thr Val Gly Asn Met Pro Leu Gly Lys Gly Asp Ala Val Phe Thr Asp
        115                 120                 125

Thr Val Leu Pro Thr Asp Ala Ile Ser Leu Asn Phe Ala Arg Ile Glu
    130                 135                 140

Val Glu Tyr Lys Glu Gln Gln Pro Asp Gly Ser Met Gly Ala Val Ile
145                 150                 155                 160

Lys Ala Gly Tyr Asp Leu Lys Leu Asn Ser Arg Ile
                165                 170

<210> SEQ ID NO 37
<211> LENGTH: 503
<212> TYPE: PRT
<213> ORGANISM: Yersinia pestis

<400> SEQUENCE: 37

Met Glu Asn Met Gln Lys Ala Gln Leu Asn Asp Thr Pro Asp Ile Asn
1               5                   10                  15

Val Asp Leu Ala Glu Asn Glu Leu Asp Asp Ile Leu Lys Arg Ser Phe
            20                  25                  30

-continued

```
Arg Pro Arg Thr Asp Glu Ala Ser Ala Thr Val Arg Arg Ala Ile Gly
         35                  40                  45

Thr Leu Ala Ala Tyr Ala Asn Lys Gly Gln Val Lys Val Asn Arg Asp
 50                  55                  60

Val Val Leu Thr Ile Glu Ser Leu Val Ala Glu Ile Asp Glu Lys Leu
 65                  70                  75                  80

Ser Asp Gln Met Asn Leu Ile Leu His His Lys Glu Phe Gln Lys Leu
                 85                  90                  95

Glu Ser Ala Trp Arg Gly Leu Ser Tyr Leu Val Asp Asn Thr Asp Ala
            100                 105                 110

Asn Glu Thr Leu Lys Ile Arg Val Leu Asn Ile Ser Gln Asp Glu Leu
        115                 120                 125

Gly Lys Thr Leu Arg Arg Tyr Arg Gly Ser Ala Trp Asp Gln Ser Pro
    130                 135                 140

Ile Phe Lys Gln Val Tyr Glu His Glu Tyr Gly Gln Phe Gly Gly Glu
145                 150                 155                 160

Pro Phe Gly Cys Met Ile Gly Asp Tyr Glu Phe Asp His Ser Pro Gln
                165                 170                 175

Ser Val Ala Leu Leu Thr Glu Leu Ala Lys Val Ala Ala Ala Ala His
            180                 185                 190

Cys Pro Phe Ile Thr Ser Ser Pro Ser Ile Met Gln Met Asn Asn
        195                 200                 205

Trp Arg Glu Leu Gly Asn Pro Arg Asp Ile Gly Lys Ile Phe Thr Thr
    210                 215                 220

Pro Glu Tyr Ala Pro Trp Arg Arg Leu Arg Glu Ser Asn Asp Ser Arg
225                 230                 235                 240

Tyr Leu Val Leu Thr Leu Pro Arg Phe Leu Ser Arg Leu Pro Tyr Gly
                245                 250                 255

Ala Lys Asn His Pro Ile Asp Asp Phe Ala Phe Glu Glu Val Val Ser
            260                 265                 270

Pro His Ala Ser Glu Asp Phe Thr Trp Ala Asn Ala Ala Tyr Ala Met
        275                 280                 285

Gly Val Asn Ile Asn Arg Ala Phe Asn Glu Tyr Gly Trp Cys Ser Arg
    290                 295                 300

Ile Arg Gly Ile Glu Ser Gly Gly Ser Val Glu Glu Leu Pro Ala Tyr
305                 310                 315                 320

Ala Phe Pro Ser Asp Glu Gly Gly Tyr Glu Leu Thr Cys Pro Thr Glu
                325                 330                 335

Leu Ala Ile Ser Asp Arg Arg Glu Asn Glu Leu Ser Asn Ala Gly Phe
            340                 345                 350

Leu Pro Leu Val Tyr Arg Lys Asn Ser Asp Phe Ala Ala Phe Ile Gly
        355                 360                 365

Ser Cys Thr Leu His Ala Pro Ala Asn Tyr Asp Asp Pro Asp Ala Thr
    370                 375                 380

Ala Asn Ala Arg Leu Ser Ala Arg Leu Pro Tyr Ile Phe Ala Thr Cys
385                 390                 395                 400

Arg Phe Ala His Tyr Leu Lys Cys Ile Val Arg Asp Lys Ile Gly Ser
                405                 410                 415

Phe Arg Ser Arg Asp Asp Met Gln Leu Trp Leu Asn Asp Trp Val Met
            420                 425                 430

Asn Tyr Val Asp Gly Asp Pro Ser Ile Ser Thr Glu Ala Thr Lys Ala
        435                 440                 445

Lys Arg Pro Leu Ala Ala Ala Glu Val Gln Val Glu Asp Val Glu Asp
```

```
                450                 455                 460
Asp Pro Gly Phe Tyr Arg Ala His Phe Tyr Leu Arg Pro His Tyr Gln
465                 470                 475                 480

Leu Glu Gly Met Thr Val Ser Leu Arg Leu Val Ser Lys Leu Pro Ser
                485                 490                 495

Asn Lys Glu Ser Glu Lys Lys
            500

<210> SEQ ID NO 38
<211> LENGTH: 636
<212> TYPE: PRT
<213> ORGANISM: Yersinia pestis

<400> SEQUENCE: 38

Met Gly Lys Ile Ile Gly Ile Asp Leu Gly Thr Thr Asn Ser Cys Val
1               5                   10                  15

Ala Ile Met Asp Gly Thr Lys Ala Arg Val Leu Glu Asn Ser Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Ala Gln Arg Asp Lys Asp Ile Met Pro Tyr Lys Ile Ile Ala Ala
                85                  90                  95

Asp Asn Gly Asp Ala Trp Leu Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Glu Val Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Met Asp Leu Arg Thr Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Gly Ser Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320
```

-continued

```
Lys Val Ala Leu Gln Asp Ala Gly Leu Ser Val Ser Asp Ile Gln Asp
                325                 330                 335

Val Ile Leu Val Gly Gly Gln Thr Arg Met Pro Met Val Gln Lys Lys
            340                 345                 350

Val Ala Asp Phe Phe Gly Lys Glu Pro Arg Lys Asp Val Asn Pro Asp
        355                 360                 365

Glu Ala Val Ala Ile Gly Ala Ala Val Gln Gly Gly Val Leu Ser Gly
    370                 375                 380

Glu Val Lys Asp Val Leu Leu Leu Asp Val Thr Pro Leu Ser Leu Gly
385                 390                 395                 400

Ile Glu Thr Met Gly Gly Val Met Thr Pro Leu Ile Thr Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Gln Asp Asn Lys Ser Leu Gly Gln Phe Asn Leu Asp Gly Ile Gln Pro
    450                 455                 460

Ala Pro Arg Gly Met Ala Gln Ile Glu Val Thr Phe Asp Ile Asp Ala
465                 470                 475                 480

Asp Gly Ile Leu His Val Ser Ala Lys Asp Lys Asn Thr Gly Arg Glu
                485                 490                 495

Gln Lys Ile Thr Ile Lys Ala Ser Ser Gly Leu Asn Glu Glu Glu Ile
            500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Ala Asp His Leu Ile His
    530                 535                 540

Gly Thr Arg Lys Gln Leu Glu Glu Ala Gly Asp Lys Leu Pro Ala Glu
545                 550                 555                 560

Asp Lys Thr Ala Ile Glu Glu Ala Met Lys Gly Leu Glu Ala Ala Leu
                565                 570                 575

Lys Gly Glu Asp Lys Ala Glu Ile Glu Ala Lys Thr Gln Ala Leu Val
            580                 585                 590

Gln Val Ser Gly Lys Leu Leu Glu Met Ala Gln Gln Gln Gln Ala Ala
        595                 600                 605

Ala Gly Gly Asp Ala Gly Asp Thr Ser Ala Lys Lys Glu Asp Asp Val
    610                 615                 620

Val Asp Ala Glu Phe Glu Glu Val Lys Asp Lys Lys
625                 630                 635
```

<210> SEQ ID NO 39
<211> LENGTH: 548
<212> TYPE: PRT
<213> ORGANISM: Yersinia pestis

<400> SEQUENCE: 39

```
Met Ala Ala Lys Asp Val Lys Phe Gly Asn Asp Ala Arg Ile Lys Met
1               5                   10                  15

Leu Arg Gly Val Asn Ile Leu Ala Asp Ala Val Lys Val Thr Leu Gly
            20                  25                  30

Pro Lys Gly Arg Asn Val Val Leu Asp Lys Ser Phe Gly Ser Pro Thr
        35                  40                  45

Ile Thr Lys Asp Gly Val Ser Val Ala Arg Glu Ile Glu Leu Glu Asp
    50                  55                  60
```

-continued

```
Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
             85                  90                  95

Gln Ser Ile Ile Thr Glu Gly Leu Lys Ala Val Ala Ala Gly Met Asn
            100                 105                 110

Pro Met Asp Leu Lys Arg Gly Ile Asp Lys Ala Val Ile Ala Ala Val
            115                 120                 125

Glu Glu Leu Lys Lys Leu Ser Val Pro Cys Ser Asp Ser Lys Ala Ile
        130                 135                 140

Ala Gln Val Gly Thr Ile Ser Ala Asn Ser Asp Ser Thr Val Gly Glu
145                 150                 155                 160

Leu Ile Ala Gln Ala Met Glu Lys Val Gly Lys Glu Gly Val Ile Thr
                165                 170                 175

Val Glu Glu Gly Ser Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ser Ile Glu Leu Glu Ser Pro Phe Ile Leu Leu Ala Asp
210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Ala Gly Thr Val Ile Ser Glu Glu
    290                 295                 300

Ile Gly Leu Glu Leu Glu Lys Thr Thr Leu Glu Asp Leu Gly Gln Ala
305                 310                 315                 320

Lys Arg Val Val Ile Asn Lys Asp Thr Thr Ile Ile Asp Gly Val
                325                 330                 335

Gly Asp Glu Ala Ala Ile Gln Gly Arg Val Ala Gln Ile Arg Gln Gln
            340                 345                 350

Ile Glu Asp Ala Thr Ser Asp Tyr Asp Lys Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Ala His Ala Ile Ala Gly Leu Lys Gly Asp
            420                 425                 430

Asn Glu Asp Gln Asn Val Gly Ile Lys Val Ala Leu Arg Ala Met Glu
        435                 440                 445

Ser Pro Leu Arg Gln Ile Val Asn Ala Gly Glu Glu Ala Ser Val
    450                 455                 460

Ile Ala Asn Lys Val Lys Ala Gly Glu Gly Ser Phe Gly Tyr Asn Ala
465                 470                 475                 480
```

-continued

Tyr Thr Glu Glu Tyr Gly Asp Met Ile Ala Met Gly Ile Leu Asp Pro
                485                 490                 495

Thr Lys Val Thr Arg Ser Ala Leu Gln Tyr Ala Ala Ser Ile Ala Gly
                500                 505                 510

Leu Met Ile Thr Thr Glu Cys Met Val Thr Asp Leu Pro Arg Asp Asp
                515                 520                 525

Lys Gly Ala Asp Met Gly Ala Gly Gly Met Gly Gly Met Gly Gly Met
                530                 535                 540

Gly Gly Met Met
545

<210> SEQ ID NO 40
<211> LENGTH: 206
<212> TYPE: PRT
<213> ORGANISM: Yersinia pestis

<400> SEQUENCE: 40

Met Ala Arg Tyr Leu Gly Pro Lys Leu Lys Leu Ser Arg Arg Glu Gly
1               5                   10                  15

Thr Asp Leu Phe Leu Lys Ser Gly Val Arg Ala Ile Asp Thr Lys Cys
                20                  25                  30

Lys Ile Glu Gln Pro Pro Gly Gln His Gly Ala Arg Lys Pro Arg Leu
            35                  40                  45

Ser Asp Tyr Gly Val Gln Leu Arg Glu Lys Gln Lys Val Arg Arg Ile
        50                  55                  60

Tyr Gly Val Leu Glu Arg Gln Phe Arg Asn Tyr Tyr Lys Glu Ala Ala
65                  70                  75                  80

Arg Leu Lys Gly Asn Thr Gly Ala Asn Leu Leu Gln Leu Leu Glu Gly
                85                  90                  95

Arg Leu Asp Asn Val Val Tyr Arg Met Gly Phe Gly Ala Thr Arg Ala
                100                 105                 110

Glu Ser Arg Gln Leu Val Ser His Lys Ala Ile Met Val Asn Gly Arg
            115                 120                 125

Val Val Asn Ile Ala Ser Tyr Gln Val Ser Pro Asn Asp Val Val Ser
        130                 135                 140

Ile Arg Glu Lys Ala Lys Lys Gln Ser Arg Val Lys Ala Ala Leu Glu
145                 150                 155                 160

Leu Ala Glu Gln Arg Glu Lys Pro Thr Trp Leu Glu Val Asp Ala Val
                165                 170                 175

Lys Met Glu Gly Val Phe Lys Arg Ile Pro Glu Arg Thr Asp Leu Ser
                180                 185                 190

Ala Asp Ile Asn Glu His Leu Ile Val Glu Leu Tyr Ser Lys
            195                 200                 205

<210> SEQ ID NO 41
<211> LENGTH: 232
<212> TYPE: PRT
<213> ORGANISM: Yersinia pestis

<400> SEQUENCE: 41

Met Gly Gln Lys Val His Pro Asn Gly Ile Arg Leu Gly Ile Val Lys
1               5                   10                  15

Ala Trp Asn Ser Thr Trp Tyr Ala Asn Thr Lys Glu Phe Ala Asp Asn
                20                  25                  30

Leu Asp Ser Asp Phe Lys Val Arg Gln Phe Leu Thr Lys Glu Leu Ala
            35                  40                  45

```
Lys Ala Ser Val Ser Arg Ile Val Ile Glu Arg Pro Ala Lys Ser Ile
            50                  55                  60

Arg Val Thr Ile His Thr Ala Arg Pro Gly Ile Val Ile Gly Lys Lys
 65                  70                  75                  80

Gly Glu Asp Val Glu Lys Leu Arg Lys Val Val Ala Asp Ile Ala Gly
                85                  90                  95

Val Pro Ala Gln Ile Asn Ile Ala Glu Val Arg Lys Pro Glu Leu Asp
               100                 105                 110

Ala Lys Leu Val Ala Asp Ser Ile Thr Ser Gln Leu Glu Arg Arg Val
           115                 120                 125

Met Phe Arg Arg Ala Met Lys Arg Ala Val Gln Asn Ala Met Arg Leu
           130                 135                 140

Gly Ala Lys Gly Ile Lys Val Glu Val Ser Gly Arg Leu Gly Gly Ala
145                 150                 155                 160

Glu Ile Ala Arg Thr Glu Trp Tyr Arg Glu Gly Arg Val Pro Leu His
                165                 170                 175

Thr Leu Arg Ala Asp Ile Asp Tyr Asn Thr Ser Glu Ala His Thr Thr
                180                 185                 190

Tyr Gly Val Ile Gly Val Lys Val Trp Ile Phe Lys Gly Glu Ile Leu
                195                 200                 205

Gly Gly Met Ala Ala Val Glu Gln Pro Glu Pro Ala Ala Gln Pro Lys
           210                 215                 220

Lys Gln Gln Arg Lys Gly Arg Lys
225                 230

<210> SEQ ID NO 42
<211> LENGTH: 394
<212> TYPE: PRT
<213> ORGANISM: Yersinia pestis

<400> SEQUENCE: 42

Met Ser Lys Glu Lys Phe Glu Arg Thr Lys Pro His Val Asn Val Gly
 1               5                  10                  15

Thr Ile Gly His Val Asp His Gly Lys Thr Thr Leu Thr Ala Ala Ile
                20                  25                  30

Thr Thr Val Leu Ala Lys Thr Tyr Gly Gly Ser Ala Arg Ala Phe Asp
            35                  40                  45

Gln Ile Asp Asn Ala Pro Glu Glu Lys Ala Arg Gly Ile Thr Ile Asn
        50                  55                  60

Thr Ser His Val Glu Tyr Asp Thr Pro Ala Arg His Tyr Ala His Val
 65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
               100                 105                 110

Met Pro Gln Thr Arg Glu His Ile Leu Leu Gly Arg Gln Val Gly Val
           115                 120                 125

Pro Tyr Ile Ile Val Phe Met Asn Lys Cys Asp Met Val Asp Asp Glu
           130                 135                 140

Glu Leu Leu Glu Leu Val Glu Met Glu Val Arg Glu Leu Leu Ser Ala
145                 150                 155                 160

Tyr Asp Phe Pro Gly Asp Asp Leu Pro Val Val Arg Gly Ser Ala Leu
                165                 170                 175

Lys Ala Leu Glu Gly Glu Ala Glu Trp Glu Ala Lys Ile Ile Glu Leu
            180                 185                 190
```

```
Ala Gly Tyr Leu Asp Ser Tyr Ile Pro Glu Pro Glu Arg Ala Ile Asp
            195                 200                 205

Lys Pro Phe Leu Leu Pro Ile Glu Asp Val Phe Ser Ile Ser Gly Arg
210                 215                 220

Gly Thr Val Val Thr Gly Arg Val Glu Arg Gly Ile Val Lys Val Gly
225                 230                 235                 240

Glu Glu Val Glu Ile Val Gly Ile Lys Asp Thr Val Lys Ser Thr Cys
            245                 250                 255

Thr Gly Val Glu Met Phe Arg Lys Leu Leu Asp Glu Gly Arg Ala Gly
            260                 265                 270

Glu Asn Val Gly Val Leu Leu Arg Gly Ile Lys Arg Glu Asp Ile Glu
            275                 280                 285

Arg Gly Gln Val Leu Ala Lys Pro Gly Ser Ile Lys Pro His Thr Thr
            290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
            325                 330                 335

Asp Val Thr Gly Thr Ile Glu Leu Pro Glu Gly Val Glu Met Val Met
            340                 345                 350

Pro Gly Asp Asn Ile Asn Met Ile Val Thr Leu Ile His Pro Ile Ala
            355                 360                 365

Met Asp Asp Gly Leu Arg Phe Ala Ile Arg Glu Gly Gly Arg Thr Val
            370                 375                 380

Gly Ala Gly Val Val Ala Lys Val Ile Ala
385                 390

<210> SEQ ID NO 43
<211> LENGTH: 266
<212> TYPE: PRT
<213> ORGANISM: Yersinia pestis

<400> SEQUENCE: 43

Met Lys Ser Leu Phe Lys Val Thr Leu Leu Ala Thr Ala Met Thr Leu
1               5                   10                  15

Thr Leu Asn Thr Ser Thr Val Phe Ala Ala Asp Ala Thr Ser Pro Val
            20                  25                  30

Val Thr Asn Ser Ala Phe Lys Asn Asn Asp Gln Gln Ser Ala Tyr Ala
            35                  40                  45

Leu Gly Ala Ser Leu Gly Arg Tyr Met Asp Asn Ser Leu Lys Glu Gln
        50                  55                  60

Glu Lys Leu Gly Ile Lys Leu Asp Lys Asp Gln Leu Ile Ala Gly Val
65                  70                  75                  80

Gln Asp Ala Phe Ala Asn Lys Ser Lys Leu Thr Asp Glu Glu Ile Glu
            85                  90                  95

Lys Thr Leu Gln Asn Phe Glu Ala Arg Val Lys Ala Ser Ala Gln Ala
            100                 105                 110

Lys Met Glu Gln Asp Ala Lys Glu Asn Ala Asp Lys Gly Ala Lys Tyr
        115                 120                 125

Arg Asp Thr Phe Ala Lys Glu Lys Gly Val Lys Thr Ala Ser Gly
130                 135                 140

Leu Leu Tyr Lys Val Glu Asn Ala Gly Thr Gly Asp Ala Pro Lys Asp
145                 150                 155                 160

Ser Asp Thr Val Val Val Asn Tyr Lys Gly Thr Leu Ala Asp Gly Thr
```

```
                    165                 170                 175
Glu Phe Asp Asn Ser Tyr Lys Arg Gly Glu Pro Leu Ser Phe Arg Leu
                180                 185                 190

Asp Gly Val Ile Pro Gly Trp Thr Glu Gly Leu Lys Gln Ile Lys Lys
            195                 200                 205

Gly Gly Lys Ile Thr Leu Val Ile Pro Pro Glu Leu Ala Tyr Gly Lys
        210                 215                 220

Ala Gly Val Pro Gly Ile Pro Ala Asn Ser Thr Leu Ile Phe Asp Val
225                 230                 235                 240

Glu Leu Leu Asp Val Lys Ala Ala Lys Ala Asp Ala Gln Glu Gln
                245                 250                 255

Gln Pro Ala Val Asp Thr Lys Ala Lys Lys
            260                 265

<210> SEQ ID NO 44
<211> LENGTH: 194
<212> TYPE: PRT
<213> ORGANISM: Yersinia pestis

<400> SEQUENCE: 44

Met Gln Arg Gly Cys Cys Phe Leu Arg Ser Thr Thr Thr Ala Gly Val
1               5                   10                  15

Ala Leu Ile Val Ala Met Thr Leu Ser Val Ser Ala Trp Ala Ile Ser
            20                  25                  30

Glu Gln Ala Lys Ser Glu Gln Ala Thr Thr Val Pro Asn Asn Asp Ile
        35                  40                  45

Val Cys His Val Ala His Leu Asn Ala Arg Phe Asp Asp Lys Glu Gly
    50                  55                  60

Leu Phe Glu Gly Ala Ser Gln Ser Gly Thr Leu Leu Ile Leu Arg Asn
65                  70                  75                  80

Ile Ser Ala Arg Ala Cys Gln Val Asn Ala Met Pro Val Ile Ser Phe
                85                  90                  95

Glu Gly Ala Val Gly Gln Gln Leu Ala Val Phe Arg Lys Val Pro Arg
            100                 105                 110

Gly Met Arg Gln Glu Pro Val Leu Ser Pro Val Thr Val Ala Ala Gly
        115                 120                 125

Ala Glu Val Ala Val Gln Leu Arg Trp Val Ala Ser Asp Ala Phe Asp
    130                 135                 140

Gly Asn Asn Cys Val Thr Pro Glu Lys Val Val Val Thr Leu Leu Gly
145                 150                 155                 160

Gly Thr Leu Arg Leu Pro Phe Gly Arg Gln Met Cys Ala Ala Ser Gly
                165                 170                 175

Asp Thr Glu Phe Phe Ser Gln Ala Pro Val Gly Pro Ala Thr Asn Glu
            180                 185                 190

Val Gln

<210> SEQ ID NO 45
<211> LENGTH: 158
<212> TYPE: PRT
<213> ORGANISM: Yersinia pestis

<400> SEQUENCE: 45

Met Ser Glu Gln Asn Asn Thr Glu Met Ala Phe Gln Ile Gln Arg Ile
1               5                   10                  15

Tyr Thr Lys Asp Ile Ser Phe Glu Ala Pro Asn Ala Pro Gln Val Phe
            20                  25                  30
```

```
Gln Gln Asp Trp Gln Pro Glu Val Lys Leu Asp Leu Asp Thr Ala Ser
            35                  40                  45

Ser Gln Leu Ala Glu Asp Val Tyr Glu Val Val Leu Arg Val Thr Val
 50                  55                  60

Thr Ala Ser Leu Gly Glu Thr Ala Phe Leu Cys Glu Val Gln Gln
 65                  70                  75                  80

Gly Gly Ile Phe Ser Val Ala Gly Ile Glu Gly Thr Gln Leu Ala His
                85                  90                  95

Cys Leu Gly Ala Tyr Cys Pro Asn Ile Leu Phe Pro Tyr Ala Arg Glu
                100                 105                 110

Cys Ile Thr Ser Leu Val Ser Arg Gly Thr Phe Pro Gln Leu Asn Leu
                115                 120                 125

Ala Pro Val Asn Phe Asp Ala Leu Phe Met Asn Tyr Leu Gln Gln Gln
            130                 135                 140

Ala Glu Gly Glu Val Glu Gly Val Glu Gln Arg Gln Asp Ala
145                 150                 155

<210> SEQ ID NO 46
<211> LENGTH: 207
<212> TYPE: PRT
<213> ORGANISM: Yersinia pestis

<400> SEQUENCE: 46

Met Lys Asn Val Trp Leu Ala Leu Val Gly Ile Val Met Ala Phe Ser
 1               5                  10                  15

Val Thr Ala Ala Gln Phe Thr Asp Gly Lys Gln Tyr Leu Thr Leu Asp
                20                  25                  30

Lys Pro Val Thr Gly Glu Pro Gln Val Leu Glu Phe Phe Ser Phe Tyr
                35                  40                  45

Cys Pro His Cys Tyr Gln Phe Glu Glu Val Tyr Gln Val Pro Lys Ala
 50                  55                  60

Val Lys Lys Ala Leu Pro Glu Gly Thr Lys Met Thr Arg Tyr His Val
 65                  70                  75                  80

Glu Phe Leu Gly Pro Leu Gly Lys Gln Leu Thr Gln Ala Trp Ala Val
                85                  90                  95

Ala Met Ala Leu Gly Val Glu Gly Lys Ile Thr Pro Leu Met Phe Glu
                100                 105                 110

Gly Val Gln Lys Thr Gln Thr Val Gln Thr Pro Gly Asp Ile Arg Asn
            115                 120                 125

Val Phe Ile Lys Ala Gly Ile Ser Gly Glu Asp Tyr Asp Ala Ala Leu
            130                 135                 140

Asn Ser Phe Val Val Lys Ser Leu Val Ala Gln Gln Gln Lys Ala Ala
145                 150                 155                 160

Glu Asp Leu Gln Leu Arg Gly Val Pro Ala Met Phe Val Asn Gly Lys
                165                 170                 175

Tyr Met Ile Lys Asn Asp Gly Met Asp Thr Ser Ser Met Asp Asn Tyr
                180                 185                 190

Val Lys Gln Tyr Ala Asp Val Val Thr Phe Leu Leu Thr Gln Lys
                195                 200                 205

<210> SEQ ID NO 47
<211> LENGTH: 284
<212> TYPE: PRT
<213> ORGANISM: Yersinia pestis

<400> SEQUENCE: 47
```

```
Met Lys Gln Asp Leu Ser Ile Lys Lys Ser Ala Ile Ala Leu Thr Leu
1               5                   10                  15

Leu Ala Gly Leu Ala Thr Leu Ser Gly Thr Ala Tyr Ala Asp Lys Leu
            20                  25                  30

Asp Asp Ile Lys Gln Ala Gly Val Val Arg Ile Ala Val Phe Asp Ser
                35                  40                  45

Asn Pro Pro Phe Gly Tyr Ile Asp Pro Gln Thr Lys Lys Leu Val Gly
            50                  55                  60

Tyr Asp Val Asp Val Ala Asn Ala Ile Ala Lys Asp Leu Gly Val Lys
65                  70                  75                  80

Val Glu Leu Arg Ala Thr Asn Pro Ala Asn Arg Ile Pro Leu Leu Ala
                85                  90                  95

Ser Lys Lys Val Asp Leu Ile Ala Ala Asn Phe Thr Ile Thr Asp Glu
                100                 105                 110

Arg Ala Lys Glu Val Asn Phe Ser Leu Pro Tyr Phe Ala Thr Gly Gln
                115                 120                 125

Lys Phe Ile Ala Arg Lys Gly Val Leu Lys Thr Pro Glu Asp Ile Gly
                130                 135                 140

Lys Leu Arg Ile Gly Ala Asp Lys Gly Thr Val Gln Glu Ile Thr Leu
145                 150                 155                 160

Arg Glu His Tyr Pro Thr Ala Lys Val Ile Ser Tyr Asp Asp Thr Pro
                165                 170                 175

Leu Ala Phe Thr Ala Leu Arg Asn Gly Asn Val Gln Ala Ile Thr Gln
                180                 185                 190

Asp Asp Ala Lys Leu Val Gly Leu Leu Gly Asn Ile Pro Glu Ala Gln
                195                 200                 205

Lys Ala Asp Phe Glu Ile Ser Pro Phe Ser Ile Thr Lys Glu Tyr Gln
                210                 215                 220

Gly Val Gly Ile Pro Lys Gly Glu Asp Arg Leu Thr Ala Val Val Asn
225                 230                 235                 240

Glu Thr Leu Ile Lys Leu Glu Lys Glu Gly Asp Ala Val Lys Ile Tyr
                245                 250                 255

Asp Arg Trp Phe Gly Pro Glu Thr Asn Ser Ala Gln Pro Arg Gly Glu
                260                 265                 270

Phe Lys Phe Ala Pro Leu Asp Gln Gln Pro Lys Ala
                275                 280

<210> SEQ ID NO 48
<211> LENGTH: 170
<212> TYPE: PRT
<213> ORGANISM: Yersinia pestis

<400> SEQUENCE: 48

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
            50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
```

-continued

```
                85                  90                  95
Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
            115                 120                 125

Val Gly Asp Asp Val Val Leu Ala Thr Gly Ser Gln Asp Phe Phe Val
            130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
            165                 170

<210> SEQ ID NO 49
<211> LENGTH: 326
<212> TYPE: PRT
<213> ORGANISM: Yersinia pestis

<400> SEQUENCE: 49

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285
```

```
Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
            325

<210> SEQ ID NO 50
<211> LENGTH: 312
<212> TYPE: PRT
<213> ORGANISM: Yersinia pestis

<400> SEQUENCE: 50

Met Lys Lys Ser Ser Ile Val Ala Thr Ile Thr Ile Leu Ser Gly
1               5                   10                  15

Ser Ala Asn Ala Ala Ser Ser Gln Leu Ile Pro Asn Ile Ser Pro Asp
                20                  25                  30

Ser Phe Thr Val Ala Ala Ser Thr Gly Met Leu Ser Gly Lys Ser His
            35                  40                  45

Glu Met Leu Tyr Asp Ala Glu Thr Gly Arg Lys Ile Ser Gln Leu Asp
    50                  55                  60

Trp Lys Ile Lys Asn Val Ala Ile Leu Lys Gly Asp Ile Ser Trp Asp
65                  70                  75                  80

Pro Tyr Ser Phe Leu Thr Leu Asn Ala Arg Gly Trp Thr Ser Leu Ala
                85                  90                  95

Ser Gly Ser Gly Asn Met Asp Asp Tyr Asp Trp Met Asn Glu Asn Gln
            100                 105                 110

Ser Glu Trp Thr Asp His Ser Ser His Pro Ala Thr Asn Val Asn His
        115                 120                 125

Ala Asn Glu Tyr Asp Leu Asn Val Lys Gly Trp Leu Leu Gln Asp Glu
    130                 135                 140

Asn Tyr Lys Ala Gly Ile Thr Ala Gly Tyr Gln Glu Thr Arg Phe Ser
145                 150                 155                 160

Trp Thr Ala Thr Gly Gly Ser Tyr Ser Tyr Asn Asn Gly Ala Tyr Thr
                165                 170                 175

Gly Asn Phe Pro Lys Gly Val Arg Val Ile Gly Tyr Asn Gln Arg Phe
            180                 185                 190

Ser Met Pro Tyr Ile Gly Leu Ala Gly Gln Tyr Arg Ile Asn Asp Phe
        195                 200                 205

Glu Leu Asn Ala Leu Phe Lys Phe Ser Asp Trp Val Arg Ala His Asp
    210                 215                 220

Asn Asp Glu His Tyr Met Arg Asp Leu Thr Phe Arg Glu Lys Thr Ser
225                 230                 235                 240

Gly Ser Arg Tyr Tyr Gly Thr Val Ile Asn Ala Gly Tyr Tyr Val Thr
                245                 250                 255

Pro Asn Ala Lys Val Phe Ala Glu Phe Thr Tyr Ser Lys Tyr Asp Glu
            260                 265                 270

Gly Lys Gly Gly Thr Gln Thr Ile Asp Lys Asn Ser Gly Asp Ser Val
        275                 280                 285

Ser Ile Gly Gly Asp Ala Ala Gly Ile Ser Asn Lys Asn Tyr Thr Val
    290                 295                 300

Thr Ala Gly Leu Gln Tyr Arg Phe
305                 310

<210> SEQ ID NO 51
```

```
<211> LENGTH: 795
<212> TYPE: PRT
<213> ORGANISM: Yersinia pestis

<400> SEQUENCE: 51
```

| | | | | | | | | | | | | | | |
|---|---|---|---|---|---|---|---|---|---|---|---|---|---|---|
| Met | Ala | Met | Lys | Lys | Leu | Leu | Ile | Ala | Ser | Leu | Leu | Phe | Gly | Ser | Ala |
| 1 | | | | 5 | | | | | 10 | | | | | 15 | |

Thr Val Tyr Gly Ala Asp Gly Phe Val Val Asn Asp Ile His Phe Glu
            20              25             30

Gly Leu Gln Arg Val Ala Val Gly Ala Ala Leu Leu Asn Met Pro Val
       35              40            45

Arg Val Gly Asp Thr Val Ser Asp Asp Ile Gly Lys Thr Ile Arg
50              55              60

Ala Leu Phe Ala Thr Gly Asn Phe Glu Asp Val Arg Val Leu Arg Asp
65             70             75           80

Gly Asn Thr Leu Ile Val Gln Val Lys Glu Arg Pro Thr Ile Ala Ser
             85            90            95

Ile Thr Phe Ser Gly Asn Lys Ala Val Lys Glu Asp Met Leu Lys Gln
          100            105           110

Asn Leu Glu Ala Ser Gly Val Arg Val Gly Ala Leu Asp Arg Thr
115            120            125

Thr Ile Ser Asn Ile Glu Lys Gly Leu Glu Asp Phe Tyr Tyr Ser Val
130             135            140

Gly Lys Tyr Ser Ala Ser Val Lys Ala Val Val Thr Pro Leu Pro Arg
145            150            155           160

Asn Arg Val Asp Leu Lys Leu Val Phe Thr Glu Gly Val Ser Ala Lys
          165            170           175

Ile Gln Gln Ile Asn Ile Val Gly Asn His Ser Phe Thr Thr Asp Glu
         180            185           190

Leu Ile Ser Arg Phe Gln Leu Arg Asp Glu Val Pro Trp Trp Asn Val
        195            200           205

Val Gly Asp Arg Lys Tyr Gln Lys Gln Lys Leu Ala Gly Asp Leu Glu
210            215            220

Thr Leu Arg Ser Phe Tyr Leu Asp Arg Gly Tyr Ala Arg Phe Asn Ile
225            230            235           240

Asp Ser Thr Gln Val Ser Leu Thr Pro Asp Lys Lys Gly Ile Tyr Val
          245            250           255

Thr Ile Asn Ile Thr Glu Gly Pro Gln Phe Lys Leu Asn Ser Val Ile
         260            265           270

Val Ser Gly Asn Leu Ala Gly His Gln Ser Glu Ala Glu Lys Leu Thr
        275            280           285

Lys Ile Glu Pro Gly Glu Leu Phe Asn Gly Ser Lys Val Thr Arg Met
290            295            300

Glu Asp Asp Ile Lys Lys Met Leu Gly Arg Tyr Gly Tyr Ala Tyr Pro
305            310            315           320

Arg Val Val Thr Gln Pro Glu Ile Asn Asp Asp Lys Thr Val Lys
          325            330           335

Leu His Ile Asn Val Asp Ala Gly Asn Arg Phe Tyr Val Arg His Ile
         340            345           350

Arg Phe Glu Gly Asn Asp Thr Ser Lys Asp Ser Val Leu Arg Arg Glu
        355            360           365

Met Arg Gln Met Glu Gly Ala Trp Leu Gly Asn Asp Gln Val Glu Ala
370            375            380

Gly Lys Glu Arg Leu Asn Arg Leu Gly Tyr Phe Glu Thr Val Asp Val

```
            385                 390                 395                 400
Glu Thr Gln Arg Val Pro Gly Ala Ala Asp Leu Val Asp Val Thr Tyr
                    405                 410                 415
Lys Val Lys Glu Arg Asn Thr Gly Ser Leu Asn Phe Gly Ile Gly Tyr
                420                 425                 430
Gly Thr Glu Ser Gly Val Ser Phe Gln Val Gly Val Gln Gln Asp Asn
                435                 440                 445
Trp Leu Gly Thr Gly Asn Thr Val Gly Ile Asn Gly Thr Lys Asn Asp
            450                 455                 460
Tyr Gln Thr Tyr Ala Glu Phe Thr Leu Met Asp Pro Tyr Phe Thr Val
465                 470                 475                 480
Asp Gly Val Ser Leu Gly Gly Arg Ile Phe Tyr Asn Asp Phe Lys Ala
                485                 490                 495
Asp Asn Ala Asp Leu Ser Gly Tyr Thr Asn Ser Ser Tyr Gly Ala Asp
                500                 505                 510
Gly Thr Leu Gly Phe Pro Ile Asn Glu Asn Asn Ser Leu Arg Val Gly
            515                 520                 525
Val Gly Tyr Val His Asn Asp Leu Ser Asp Met Leu Pro Gln Val Ala
        530                 535                 540
Met Trp Arg Tyr Leu Glu Ser Val Gly Glu Arg Pro Gly Tyr Asp Gly
545                 550                 555                 560
Arg Glu Gly Phe Thr Thr Asp Asp Phe Thr Leu Asn Leu Gly Trp Thr
                565                 570                 575
Tyr Asn Asn Leu Asp Arg Gly Phe Phe Pro Thr Ser Gly Val Lys Ser
            580                 585                 590
Ser Val Asn Thr Lys Ile Thr Val Pro Gly Ser Asp Asn Glu Phe Tyr
            595                 600                 605
Lys Val Thr Phe Asp Thr Ser Ala Tyr Gln Pro Leu Asn Glu Asp Arg
            610                 615                 620
Ser Trp Val Leu Leu Gly Arg Gly Arg Leu Tyr Gly Asp Gly Ile
625                 630                 635                 640
Gly Ser Lys Glu Met Pro Phe Tyr Glu Asn Phe Tyr Ala Gly Gly Ser
                645                 650                 655
Ser Thr Val Arg Gly Phe Arg Ser Asn Asn Ile Gly Pro Lys Ala Ala
                660                 665                 670
Tyr Tyr Ala Asn Gly Gly Ala Thr Val Thr Asn Ser Thr Asp Ala Val
            675                 680                 685
Gly Gly Asn Ala Met Ala Val Ala Ser Ile Glu Leu Ile Thr Pro Thr
            690                 695                 700
Pro Phe Ile Ser Glu Lys Tyr Ser Asn Ser Val Arg Thr Ser Ile Phe
705                 710                 715                 720
Ile Asp Ser Gly Thr Val Trp Asp Thr Asn Trp Glu Asn Thr Ala Lys
                725                 730                 735
Thr Arg Ala Ala Gly Ile Pro Asp Tyr Gly Lys Ala Ser Asn Ile Arg
                740                 745                 750
Val Ser Ala Gly Val Ala Leu Gln Trp Met Ser Pro Leu Gly Pro Leu
            755                 760                 765
Val Phe Ser Tyr Ala Lys Pro Val Lys Asp Tyr Glu Gly Asp Lys Ser
            770                 775                 780
Glu Gln Phe Gln Phe Asn Ile Gly Lys Thr Trp
785                 790                 795

<210> SEQ ID NO 52
```

```
<211> LENGTH: 241
<212> TYPE: PRT
<213> ORGANISM: Yersinia pestis

<400> SEQUENCE: 52

Met His Met Ile Phe Ala Leu Asn Thr Val Arg Asn Pro Arg Trp Leu
1               5                   10                  15

Ala Pro Leu Leu Ala Phe Leu Val Met Phe Leu Val Thr Ala Cys Gly
            20                  25                  30

Asp Lys Glu Leu Glu Gln Arg Lys Ala Phe Ile Asp Tyr Leu Gln Asn
        35                  40                  45

Thr Val Met Arg Ser Gly Met Lys Leu Pro Thr Leu Ser Glu Asp Gln
    50                  55                  60

Lys Gln Lys Phe Gly Pro Tyr Val Ser Asp Tyr Ala Ile Leu Val Thr
65                  70                  75                  80

Phe Ser Gln Gln Leu Ser Lys Ser Val Asp Ala Ser Leu Val Pro Ala
                85                  90                  95

Ile Glu Gln Ile Asn Gln Ile Arg Val Ala Gln Asp Tyr Leu Ser Lys
            100                 105                 110

Arg Asp Ala Leu Gln Gln Ser Ala Gly Ala Leu Asn Leu Leu Val Gln
        115                 120                 125

Gln Ile Arg Thr Ala Lys Ala Gln Ala Asp Ser Ala Gln Ala Ala Leu
    130                 135                 140

Lys Leu Pro Asp Asp Leu Lys Val Val Phe Asn Arg Ala Phe Asp Asn
145                 150                 155                 160

Ile Val Thr Gln Pro Ala Asn Val Leu Ile Pro Ala Val Pro Val Val
                165                 170                 175

Ser Ser Phe Val Gln Asp Leu Val Gln Val Gly Asp Phe Leu Gln Gln
            180                 185                 190

Gln Gly Thr Gln Val Thr Phe Asn Asn Gly Gly Ile Gln Phe Gln Thr
        195                 200                 205

Pro Gln Gln Ala Ala Gln Tyr Asn Thr Met Met Ser Asn Leu Val Ala
    210                 215                 220

Lys Tyr Pro Glu Met Met Ala Ala Gln Lys Arg Val Met Lys Val Met
225                 230                 235                 240

Gln

<210> SEQ ID NO 53
<211> LENGTH: 434
<212> TYPE: PRT
<213> ORGANISM: Yersinia pestis

<400> SEQUENCE: 53

Met Lys Asn Trp Arg Thr Leu Ile Leu Gly Leu Val Ile Cys Ala Asn
1               5                   10                  15

Thr Ala Phe Ala Ala Pro Gln Glu Val Asp Lys Val Ala Ala Val Val
            20                  25                  30

Asp Asn Gly Val Val Leu Gln Ser Asp Ile Asp Gly Leu Leu Gln Ser
        35                  40                  45

Val Lys Met Asn Ala Gln Gln Ser Gly Gln Gln Val Pro Asp Asp Ser
    50                  55                  60

Thr Leu Arg His Gln Ile Leu Glu Arg Leu Ile Met Asp Asn Ile Gln
65                  70                  75                  80

Leu Gln Met Ala Lys Lys Met Gly Ile Thr Ile Thr Asp Gln Ala Leu
                85                  90                  95
```

-continued

```
Asp Lys Ala Ile Ala Asp Ile Ala Ala Gln Asn Arg Met Thr Leu Ala
            100                 105                 110

Gln Met Arg Ser Arg Leu Ala Ala Asp Gly Leu Ser Tyr Asp Thr Tyr
        115                 120                 125

Arg Glu Gln Ile Arg Lys Glu Met Leu Thr Ser Glu Val Arg Asn Asn
    130                 135                 140

Glu Val Arg Arg Arg Ile Thr Ile Leu Pro Gln Glu Val Glu Ser Leu
145                 150                 155                 160

Ala Lys Gln Met Gly Asn Gln Val Ser Gly Asp Thr Glu Leu Asn Leu
                165                 170                 175

Ser His Ile Leu Ile Pro Leu Pro Glu Asn Pro Thr Gln Gln Gln Val
            180                 185                 190

Asp Gln Ala Glu Asp Leu Ala Asn Lys Leu Val Ala Asp Ile Lys Gly
        195                 200                 205

Gly Ala Asp Phe Gly Lys Leu Ala Ile Ala Asn Ser Ala Asp Ser Gln
    210                 215                 220

Ala Leu Lys Gly Gly Gln Met Gly Trp Gly Lys Leu Gln Glu Leu Pro
225                 230                 235                 240

Ser Leu Phe Ala Glu Arg Leu Gln Ser Ala His Lys Gly Glu Ile Val
                245                 250                 255

Gly Pro Ile Arg Ser Gly Val Gly Phe His Ile Leu Lys Val Asn Asp
            260                 265                 270

Met Arg Gly Ala Asp Gln Thr Ile Ser Val Thr Glu Val Asn Ala Arg
        275                 280                 285

His Ile Leu Leu Lys Pro Ser Pro Met Met Thr Asp Glu Gln Ala Arg
    290                 295                 300

Ala Lys Leu Glu Ala Ala Ala Ala Glu Ile Lys Ser Gly Lys Thr Ser
305                 310                 315                 320

Phe Ala Thr Ile Ala Lys Glu Ile Ser Gln Asp Pro Gly Ser Ala Met
                325                 330                 335

Gln Gly Gly Glu Leu Gly Trp Ala Ser Pro Asp Ile Tyr Asp Pro Ala
            340                 345                 350

Phe Arg Asp Ala Leu Met Lys Leu Lys Lys Gly Glu Ile Ser Ala Pro
        355                 360                 365

Val His Ser Ser Phe Gly Trp His Leu Ile Gln Leu Val Asp Thr Arg
    370                 375                 380

Gln Val Asp Lys Thr Asp Ala Ala Gln Lys Glu Arg Ala Tyr Arg Met
385                 390                 395                 400

Leu Phe Asn Arg Lys Phe Ala Glu Glu Ala Gln Thr Trp Met Gln Glu
                405                 410                 415

Gln Arg Ala Ala Ala Tyr Val Lys Ile Leu Asp Gly Ser Asn Ala Gln
            420                 425                 430

Pro Gln

<210> SEQ ID NO 54
<211> LENGTH: 467
<212> TYPE: PRT
<213> ORGANISM: Yersinia pestis

<400> SEQUENCE: 54

Met Gln Met Lys Lys Leu Leu Pro Leu Leu Ile Gly Leu Ser Leu Ala
1               5                   10                  15

Gly Phe Ser Thr Met Ser Gln Ala Glu Asn Leu Leu Gln Val Tyr Lys
            20                  25                  30
```

```
Gln Ala Arg Asp Ser Asn Pro Asp Leu Arg Lys Ala Ala Asp Arg
         35                  40                  45

Asp Ala Ala Tyr Glu Lys Ile Asn Glu Val Arg Ser Pro Leu Leu Pro
     50                  55                  60

Gln Leu Gly Leu Ser Ala Gly Tyr Thr His Ala Asn Gly Phe Arg Asp
 65                  70                  75                  80

Ala Ser Asn Ser Pro Asp Ser Asn Ala Thr Ser Gly Ser Leu Lys Leu
                 85                  90                  95

Thr Gln Thr Ile Phe Asp Met Ser Lys Trp Arg Ala Leu Thr Leu Gln
             100                 105                 110

Glu Lys Ala Ala Gly Ile Gln Asp Val Thr Phe Gln Thr Ser Glu Gln
         115                 120                 125

Gln Leu Ile Leu Asn Thr Ala Thr Ala Tyr Phe Asn Val Leu Arg Ala
     130                 135                 140

Ile Asp Ser Leu Ser Tyr Thr Glu Ala Gln Lys Gln Ser Val Tyr Arg
145                 150                 155                 160

Gln Leu Asp Gln Thr Thr Gln Arg Phe Asn Val Gly Leu Val Ala Ile
                 165                 170                 175

Thr Asp Val Gln Asn Ala Arg Ala Ser Tyr Asp Thr Val Leu Ala Ala
             180                 185                 190

Glu Val Ala Ala Arg Asn Asn Leu Asp Asn Ala Leu Glu Ser Leu Arg
         195                 200                 205

Gln Ile Thr Gly Val Tyr Tyr Pro Glu Leu Ala Ser Leu Asn Val Glu
     210                 215                 220

Arg Leu Lys Thr Gln Arg Pro Asp Ala Val Asn Asn Leu Leu Lys Glu
225                 230                 235                 240

Ala Glu Lys Arg Asn Leu Ser Leu Leu Ser Ala Arg Leu Ser Gln Asp
                 245                 250                 255

Leu Ala Arg Glu Gln Ile Lys Ser Ala Glu Thr Gly Tyr Met Pro Thr
             260                 265                 270

Val Asp Leu Thr Ala Ser Ser Ile Thr Asn Thr Arg Tyr Ser Gly
         275                 280                 285

Gly Thr Pro Ser Ser Gln Gln Val Asn Asn Asp Ser Gly Gln Asn Gln
     290                 295                 300

Ile Gly Val Gln Phe Ser Leu Pro Leu Tyr Ser Gly Gly Ala Thr Asn
305                 310                 315                 320

Ser Ala Val Lys Gln Ala Gln Tyr Asn Phe Val Gly Ala Ser Glu Leu
                 325                 330                 335

Leu Glu Ser Ala His Arg Asn Met Val Gln Thr Leu Arg Ser Ser Phe
             340                 345                 350

Asn Asn Ile Ser Ala Ser Ile Ser Ile Asn Ala Tyr Gln Gln Val
         355                 360                 365

Val Ile Ser Asn Gln Ser Ser Leu Asp Ala Met Glu Ala Gly Tyr Gln
     370                 375                 380

Val Gly Thr Arg Thr Ile Leu Asp Val Leu Thr Ala Thr Asn Leu
385                 390                 395                 400

Tyr Gln Ser Lys Gln Leu Ala Asp Ala Arg Tyr Asn Tyr Leu Ile
                 405                 410                 415

Asn Gln Leu Asn Ile Lys Ser Ala Leu Gly Thr Leu Asn Met Asn Asp
             420                 425                 430

Leu Met Ala Leu Asn Ala Val Leu Asp Lys Pro Val Pro Thr Ser Ala
         435                 440                 445

Ala Ala Leu Ala Pro Glu Asn Thr Thr Arg Gln Thr Val Thr Thr Pro
```

Arg Ala Gln
465

<210> SEQ ID NO 55
<211> LENGTH: 374
<212> TYPE: PRT
<213> ORGANISM: Yersinia pestis

<400> SEQUENCE: 55

Met Ile Thr Met Lys Leu Arg Val Leu Ser Phe Ile Ile Pro Ala Leu
1               5                   10                  15

Leu Val Ala Gly Ser Ala Ser Ala Ala Glu Ile Tyr Asn Lys Asp Gly
            20                  25                  30

Asn Lys Leu Asp Leu Tyr Gly Lys Ile Asp Gly Leu His Tyr Phe Ser
        35                  40                  45

Asp Asn Lys Asn Leu Asp Gly Asp Gln Ser Tyr Met Arg Phe Gly Leu
    50                  55                  60

Lys Gly Glu Thr Gln Ile Thr Asp Gln Leu Thr Gly Tyr Gly Gln Trp
65                  70                  75                  80

Glu Tyr Gln Val Asn Leu Asn Lys Ala Glu Asn Glu Asp Gly Asn His
                85                  90                  95

Asp Ser Phe Thr Arg Val Gly Phe Ala Gly Leu Lys Phe Ala Asp Tyr
            100                 105                 110

Gly Ser Leu Asp Tyr Gly Arg Asn Tyr Gly Val Leu Tyr Asp Val Thr
        115                 120                 125

Ser Trp Thr Asp Val Leu Pro Glu Phe Gly Gly Asp Thr Tyr Gly Ala
    130                 135                 140

Asp Asn Phe Leu Ser Gln Arg Gly Asn Gly Met Leu Thr Tyr Arg Asn
145                 150                 155                 160

Thr Asn Phe Phe Gly Leu Val Asp Gly Leu Asn Phe Ala Leu Gln Tyr
                165                 170                 175

Gln Gly Lys Asn Gly Ser Ser Ser Glu Thr Asn Asn Gly Arg Gly Val
            180                 185                 190

Ala Asp Gln Asn Gly Asp Gly Tyr Gly Met Ser Leu Ser Tyr Asp Leu
        195                 200                 205

Gly Trp Gly Val Ser Ala Ser Ala Ala Met Ala Ser Ser Leu Arg Thr
    210                 215                 220

Thr Ala Gln Asn Asp Leu Gln Tyr Gly Gln Gly Lys Arg Ala Asn Ala
225                 230                 235                 240

Tyr Thr Gly Gly Leu Lys Tyr Asp Ala Asn Asn Val Tyr Leu Ala Ala
                245                 250                 255

Asn Tyr Thr Gln Thr Tyr Asn Leu Thr Arg Phe Gly Asp Phe Ser Asn
            260                 265                 270

Arg Ser Ser Asp Ala Ala Phe Gly Phe Ala Asp Lys Ala His Asn Ile
        275                 280                 285

Glu Val Val Ala Gln Tyr Gln Phe Asp Phe Gly Leu Arg Pro Ser Val
    290                 295                 300

Ala Tyr Leu Gln Ser Lys Gly Lys Asp Ile Gly Ile Tyr Gly Asp Gln
305                 310                 315                 320

Asp Leu Leu Lys Tyr Val Asp Ile Gly Ala Thr Tyr Phe Phe Asn Lys
                325                 330                 335

Asn Met Ser Thr Tyr Val Asp Tyr Lys Ile Asn Leu Leu Asp Lys Asn
            340                 345                 350

Asp Phe Thr Lys Asn Ala Arg Ile Asn Thr Asp Asp Ile Val Ala Val
          355                 360                 365

Gly Met Val Tyr Gln Phe
        370

<210> SEQ ID NO 56
<211> LENGTH: 673
<212> TYPE: PRT
<213> ORGANISM: Yersinia pestis

<400> SEQUENCE: 56

Met Lys Met Thr Arg Leu Tyr Pro Leu Ala Leu Gly Gly Leu Leu Leu
1               5                   10                  15

Pro Ala Ile Ala Asn Ala Gln Thr Ser Gln Gln Asp Glu Ser Thr Leu
            20                  25                  30

Val Val Thr Ala Ser Lys Gln Ser Arg Ser Ala Ser Ala Asn Asn
            35                  40                  45

Val Ser Ser Thr Val Val Ser Ala Pro Glu Leu Ser Asp Ala Gly Val
    50                  55                  60

Thr Ala Ser Asp Lys Leu Pro Arg Val Leu Pro Gly Leu Asn Ile Glu
65                  70                  75                  80

Asn Ser Gly Asn Met Leu Phe Ser Thr Ile Ser Leu Arg Gly Val Ser
                85                  90                  95

Ser Ala Gln Asp Phe Tyr Asn Pro Ala Val Thr Leu Tyr Val Asp Gly
            100                 105                 110

Val Pro Gln Leu Ser Thr Asn Thr Ile Gln Ala Leu Thr Asp Val Gln
            115                 120                 125

Ser Val Glu Leu Leu Arg Gly Pro Gln Gly Thr Leu Tyr Gly Lys Ser
    130                 135                 140

Ala Gln Gly Gly Ile Ile Asn Ile Val Thr Gln Gln Pro Asp Ser Thr
145                 150                 155                 160

Pro Arg Gly Tyr Ile Glu Gly Gly Val Ser Ser Arg Asp Ser Tyr Arg
                165                 170                 175

Ser Lys Phe Asn Leu Ser Gly Pro Ile Gln Asp Gly Leu Leu Tyr Gly
            180                 185                 190

Ser Val Thr Leu Leu Arg Gln Val Asp Asp Gly Asp Met Ile Asn Pro
    195                 200                 205

Ala Thr Gly Ser Asp Asp Leu Gly Gly Thr Arg Ala Ser Ile Gly Asn
210                 215                 220

Val Lys Leu Arg Leu Ala Pro Asp Asp Gln Pro Trp Glu Met Gly Phe
225                 230                 235                 240

Ala Ala Ser Arg Glu Cys Thr Arg Ala Thr Gln Asp Ala Tyr Val Gly
                245                 250                 255

Trp Asn Asp Ile Lys Gly Arg Lys Leu Ser Ile Ser Asp Gly Ser Pro
            260                 265                 270

Asp Pro Tyr Met Arg Arg Cys Thr Asp Ser Gln Thr Leu Ser Gly Lys
    275                 280                 285

Tyr Thr Thr Asp Asp Trp Val Phe Asn Leu Ile Ser Ala Trp Gln Gln
290                 295                 300

Gln His Tyr Ser Arg Thr Phe Pro Ser Gly Ser Leu Ile Val Asn Met
305                 310                 315                 320

Pro Gln Arg Trp Asn Gln Asp Val Gln Glu Leu Arg Ala Ala Thr Leu
                325                 330                 335

Gly Asp Ala Arg Thr Val Asp Met Val Phe Gly Leu Tyr Arg Gln Asn
            340                 345                 350

```
Thr Arg Glu Lys Leu Asn Ser Ala Tyr Asp Met Pro Thr Met Pro Tyr
        355                 360                 365

Leu Ser Ser Thr Gly Tyr Thr Thr Ala Glu Thr Leu Ala Ala Tyr Ser
        370                 375                 380

Asp Leu Thr Trp His Leu Thr Asp Arg Phe Asp Ile Gly Gly Gly Val
385                 390                 395                 400

Arg Phe Ser His Asp Lys Ser Ser Thr Gln Tyr His Gly Ser Met Leu
                405                 410                 415

Gly Asn Pro Phe Gly Asp Gln Gly Lys Ser Asn Asp Asp Gln Val Leu
            420                 425                 430

Gly Gln Leu Ser Ala Gly Tyr Met Leu Thr Asp Asp Trp Arg Val Tyr
        435                 440                 445

Thr Arg Val Ala Gln Gly Tyr Lys Pro Ser Gly Tyr Asn Ile Val Pro
    450                 455                 460

Thr Ala Gly Leu Asp Ala Lys Pro Phe Val Ala Glu Lys Ser Ile Asn
465                 470                 475                 480

Tyr Glu Leu Gly Thr Arg Tyr Glu Thr Ala Asp Val Thr Leu Gln Ala
                485                 490                 495

Ala Thr Phe Tyr Thr His Thr Lys Asp Met Gln Leu Tyr Ser Gly Pro
            500                 505                 510

Val Arg Met Gln Thr Leu Ser Asn Ala Gly Lys Ala Asp Ala Thr Gly
        515                 520                 525

Val Glu Leu Glu Ala Lys Trp Arg Phe Ala Pro Gly Trp Ser Trp Asp
        530                 535                 540

Ile Asn Gly Asn Val Ile Arg Ser Glu Phe Thr Asn Asp Ser Glu Leu
545                 550                 555                 560

Tyr His Gly Asn Arg Val Pro Phe Val Pro Arg Tyr Gly Ala Gly Ser
                565                 570                 575

Ser Val Asn Gly Val Ile Asp Thr Arg Tyr Gly Ala Leu Met Pro Arg
            580                 585                 590

Leu Ala Val Asn Leu Val Gly Pro His Tyr Phe Asp Gly Asp Asn Gln
        595                 600                 605

Leu Arg Gln Gly Thr Tyr Ala Thr Leu Asp Ser Ser Leu Gly Trp Gln
    610                 615                 620

Ala Thr Glu Arg Met Asn Ile Ser Val Tyr Val Asp Asn Leu Phe Asp
625                 630                 635                 640

Arg Arg Tyr Arg Thr Tyr Gly Tyr Met Asn Gly Ser Ser Ala Val Ala
                645                 650                 655

Gln Val Asn Met Gly Arg Thr Val Gly Ile Asn Thr Arg Ile Asp Phe
            660                 665                 670

Phe

<210> SEQ ID NO 57
<211> LENGTH: 182
<212> TYPE: PRT
<213> ORGANISM: Yersinia pestis

<400> SEQUENCE: 57

Met Val Phe Met Asn Lys Thr Leu Leu Val Ser Ser Leu Ile Ala Cys
1               5                   10                  15

Leu Ser Ile Ala Ser Val Asn Val Tyr Ala Glu Gly Glu Ser Ser Ile
            20                  25                  30

Ser Ile Gly Tyr Ala Gln Ser Arg Val Lys Glu Asp Gly Tyr Lys Leu
        35                  40                  45
```

```
Asp Lys Asn Pro Arg Gly Phe Asn Leu Lys Tyr Arg Tyr Glu Phe Asn
    50                  55                  60

Asn Asp Trp Gly Val Ile Gly Ser Phe Ala Gln Thr Arg Arg Gly Phe
 65                  70                  75                  80

Glu Glu Ser Val Asp Gly Phe Lys Leu Ile Asp Gly Asp Phe Lys Tyr
                 85                  90                  95

Tyr Ser Val Thr Ala Gly Pro Val Phe Arg Ile Asn Glu Tyr Val Ser
                100                 105                 110

Leu Tyr Gly Leu Leu Gly Ala Gly His Gly Lys Ala Lys Phe Ser Ser
            115                 120                 125

Ile Phe Gly Gln Ser Glu Ser Arg Ser Lys Thr Ser Leu Ala Tyr Gly
    130                 135                 140

Ala Gly Leu Gln Phe Asn Pro His Pro Asn Phe Val Ile Asp Ala Ser
145                 150                 155                 160

Tyr Glu Tyr Ser Lys Leu Asp Asp Val Lys Val Gly Thr Trp Met Leu
                165                 170                 175

Gly Ala Gly Tyr Arg Phe
            180

<210> SEQ ID NO 58
<211> LENGTH: 201
<212> TYPE: PRT
<213> ORGANISM: Yersinia pestis

<400> SEQUENCE: 58

Met Lys Leu Ser Thr Leu Leu Pro Val Ile Leu Tyr Ser Ser Ala
 1               5                  10                  15

Thr Leu Ala Ala Asn Met Ala Gly Met Asn Asp Lys Ala Ser Met Asn
                20                  25                  30

Asp Lys Ala Ser Met Asn Asp Met Ala Ser Met Asn Gly Lys Ala Ser
            35                  40                  45

Met Thr Val Lys Ile Asn Glu Ser Leu Pro Gln Gly Asn Gly Lys Ala
 50                  55                  60

Leu Gly Thr Val Thr Val Thr Glu Thr Ala Tyr Gly Leu Leu Phe Thr
 65                  70                  75                  80

Pro His Leu Thr Gly Leu Ala Pro Gly Ile His Gly Phe His Leu His
                 85                  90                  95

Glu Lys Pro Ser Cys Ala Pro Gly Met Lys Asp Gly Lys Ala Val Pro
                100                 105                 110

Ala Leu Ala Ala Gly Gly His Leu Asp Pro Asn Lys Thr Gly Val His
            115                 120                 125

Leu Gly Pro Tyr Asn Asp Lys Gly His Leu Gly Asp Leu Pro Gly Leu
    130                 135                 140

Val Val Asn Ala Asp Gly Thr Ala Thr Tyr Pro Val Leu Ala Pro Arg
145                 150                 155                 160

Leu Lys Ser Leu Ser Glu Val Lys Gln His Ala Leu Met Ile His Ala
                165                 170                 175

Gly Gly Asp Asn Tyr Ser Asp His Pro Met Pro Leu Gly Gly Gly Gly
                180                 185                 190

Ala Arg Met Ala Cys Gly Val Ile Glu
            195                 200

<210> SEQ ID NO 59
<211> LENGTH: 340
<212> TYPE: PRT
```

<213> ORGANISM: Yersinia pestis

<400> SEQUENCE: 59

```
Met Phe Arg Cys Leu Ala Leu Thr Val Ser Leu Ala Phe Ile Leu Pro
1               5                   10                  15
Gly Ala Leu His Ala Ala Asp Thr Arg Glu Ser Ser Ser Ile Arg
            20                  25                  30
Asp Ile Asn Val Ile Thr Phe Gln Gly Gly Trp Asn Leu Pro Val Trp
            35                  40                  45
Val Ala Gln Glu Lys Gly Phe Phe Arg Lys Asn Gly Leu Asn Val Lys
    50                  55                  60
Met Asp Tyr Thr Pro Asn Ser Gly Gln Leu Val Arg Asn Leu Leu Asn
65                  70                  75                  80
Gly Lys Tyr Asn Ile Ala Val Ala Gly Ile Asp Asn Val Ile Ala Tyr
                85                  90                  95
Gln Glu Gly Gln Val Lys Glu Pro Val Val Asn Pro Asp Met Phe Ala
            100                 105                 110
Phe Tyr Gly Val Asp Asn Gly Leu Leu Ser Leu Val Ala Asn Pro Gln
        115                 120                 125
Ile Lys Asn Ile Ser Asp Leu Lys Gly Lys Gln Val Ser Val Asp Ala
130                 135                 140
Leu Thr Thr Gly Tyr Ala Phe Val Ile Arg Asn Tyr Leu Glu Lys Asn
145                 150                 155                 160
Gly Leu Thr Gln Asn Asp Val His Tyr Thr Ser Val Gly Ser Thr Asn
                165                 170                 175
Asp Arg Phe Asn Ala Leu Leu Ala Gly Lys Thr Asp Ala Thr Leu Leu
            180                 185                 190
Arg Thr Pro Leu Asn Leu Gln Ala Lys Glu Asn Gly Phe Lys Ile Leu
        195                 200                 205
Ala Ser Gly Ser Glu Leu Gly Asp Tyr Gln Gly Thr Thr Gly Ile Thr
210                 215                 220
Thr Arg Ser Trp Ala Ala Gln Asn Gly Asp Ile Leu Val Ser Tyr Ile
225                 230                 235                 240
Arg Ser Tyr Ile Asp Gly Leu Asn Trp Ile Tyr Asp Pro Arg Asn Gln
                245                 250                 255
Lys Glu Ala Glu Ile Leu Val Lys Lys Ala Pro Gly Met Thr Ala
            260                 265                 270
Glu Leu Ala Gly Pro Ala Leu Gln Glu Leu Leu Asn Asn Gly Leu Gln
        275                 280                 285
Arg Asp Ala Ala Ile Asn Ala Glu Gly Val Lys Asn Val Leu Leu Leu
290                 295                 300
Arg Ser Arg Leu Ala Lys Pro Glu Lys Asn Leu Thr Asp Thr His Lys
305                 310                 315                 320
Tyr Tyr Asp Thr Ser Tyr Tyr Gln Lys Ala Val Gly Leu Asn Lys Gln
                325                 330                 335
Glu Thr Gly Lys
            340
```

<210> SEQ ID NO 60
<211> LENGTH: 6
<212> TYPE: PRT
<213> ORGANISM: Artificial Sequence
<220> FEATURE:
<223> OTHER INFORMATION: Linker

<400> SEQUENCE: 60

-continued

Gly Ser Gly Gly Gly Gly
1               5

<210> SEQ ID NO 61
<211> LENGTH: 155
<212> TYPE: PRT
<213> ORGANISM: Yersinia pestis

<400> SEQUENCE: 61

Met Lys Lys Ser Trp Ile Phe Leu Gly Cys Leu Leu Ser Leu Gly Ala
1               5                   10                  15

Ile Thr Ala Gln Ala Glu Glu Ile Gly Ser Val Asp Thr Val Phe Lys
                20                  25                  30

Leu Leu Gly Pro Asp His Lys Ile Val Ile Glu Ala Phe Asp Asp Pro
            35                  40                  45

Asp Val Lys Asn Val Thr Cys Tyr Ile Ser Arg Ala Lys Thr Gly Gly
        50                  55                  60

Ile Lys Gly Gly Leu Gly Leu Ala Glu Asp Thr Ala Asp Ala Ala Ile
65                  70                  75                  80

Ser Cys Gln Gln Val Gly Pro Ile Glu Leu Ser Asp Lys Ile Lys Asn
                85                  90                  95

Lys Lys Ser Glu Gly Ala Val Val Phe Gln Lys Arg Thr Ser Leu Val
            100                 105                 110

Phe Lys Lys Leu Gln Val Val Arg Phe Tyr Asp Pro Lys Arg Asn Ser
        115                 120                 125

Leu Val Tyr Leu Thr Tyr Ser Asp Arg Ile Val Asp Gly Ser Pro Lys
    130                 135                 140

Asn Ala Ile Ser Ala Val Pro Ile Met Pro Trp
145                 150                 155

<210> SEQ ID NO 62
<211> LENGTH: 536
<212> TYPE: PRT
<213> ORGANISM: Yersinia pestis

<400> SEQUENCE: 62

Met Asn Glu Phe Glu Arg Gln Ile Arg Ala Ala Ile Ser Ala Ala Arg
1               5                   10                  15

Asn Gly Ala Lys His Ala Glu Gln Ser Leu Thr Thr Pro Met Trp Gln
                20                  25                  30

Ala Lys Ser Thr Val Ala Ser Leu Gly Gly Ile Val Pro Arg Ser Gly
            35                  40                  45

Ser Ser Ser Thr Ser Gln Ala Glu Asn Tyr Lys Glu Gly Leu Ala Asp
        50                  55                  60

Gln Ala Ala Ser Gly Asn Asn Met Ala Arg Thr Ser Ala Pro Pro Val
65                  70                  75                  80

Thr Leu Tyr Gln Gln Gln Pro Asn Ala Asn Asp Ser Tyr Pro Asn Gly
                85                  90                  95

Asn Asn Asn Asn Pro Asn Gly Asp Asn Asn Pro Asn Gly Ser Asn
            100                 105                 110

Asn Asn Ile Ala Arg Val Gln Arg Met Pro His Gly Ile Ser Arg Gly
        115                 120                 125

Leu Tyr Glu Arg Pro Gly Met Leu Leu Gly Ala Trp Asp Asn Ala Tyr
    130                 135                 140

Ile Ala Ala Ala Met Pro Leu Leu Leu Leu Val Glu Asn Ile Arg Ser
145                 150                 155                 160

Trp Pro Thr Arg Asn Ala Ala Glu Val Arg Pro Pro Ile Val Arg Glu
                165                 170                 175

Leu Gln Tyr Phe Gln Gln His Leu Gln Lys Lys Asn Tyr Pro Gln Glu
            180                 185                 190

Asp Ile Asn His Leu Ser Tyr Leu Cys Thr Tyr Ile Asp Gly Ile
        195                 200                 205

Phe Asn Gly Leu Gln Thr Pro Asp Ser Tyr Asn Gln Ser Leu Leu Val
    210                 215                 220

Glu Phe His Arg Asp Ala Trp Gly Glu Asp Cys Phe Glu His Leu
225                 230                 235                 240

Arg Val Tyr Met Asn Ser Pro Lys Gln Tyr Arg Glu Val Leu Glu Phe
                245                 250                 255

Tyr Asp Leu Ile Met Cys Leu Gly Phe Asp Gly Lys Tyr Gln Met Ile
            260                 265                 270

Glu His Gly Ala Val Leu Leu Met Asp Leu Arg Ser Arg Leu His Thr
        275                 280                 285

Gln Leu Tyr Gly Gln Asp Ala Thr Gln Ser Leu Ala Ile Ala Gln Ala
    290                 295                 300

Val Lys Gly Ser Pro Arg Arg Gln Tyr Ile Lys Ala Leu Lys Ile Phe
305                 310                 315                 320

Thr Tyr Gly Phe Ala Leu Cys Leu Cys Ala Tyr Gly Val Thr Ala Trp
                325                 330                 335

Tyr Leu His Gln Gln Ser Gln Gln Ile Arg Ser Asn Ile Leu Thr Trp
            340                 345                 350

Val Leu Pro Glu Pro Arg Lys Ile Asn Ile Met Glu Thr Leu Pro Asn
        355                 360                 365

Pro Leu Ser Asn Ile Leu Asn Glu Gly Trp Leu Glu Val Arg Lys Asp
    370                 375                 380

Pro Arg Gly Trp Leu Leu Ile Phe Thr Ser Asp Gly Ala Phe Arg Thr
385                 390                 395                 400

Gly Glu Ala Thr Leu Ser Glu Glu Phe Ile Asn Lys Lys Asn Ile Glu
                405                 410                 415

Arg Leu Gly Leu Ala Leu Ala Pro Trp Pro Gly Asp Ile Glu Val Ile
            420                 425                 430

Gly His Thr Asp Asn Lys Pro Phe Arg Ser Thr Ser Gly Asn Asn Asn
        435                 440                 445

Leu Lys Leu Ser Ala Ala Arg Ala Ser Val Val Ala Asp Lys Leu Arg
    450                 455                 460

Glu Ser Thr Gln Ile Asn Glu Thr His Gln Arg Glu Ile Ser Ala Ile
465                 470                 475                 480

Gly Arg Gly Glu Ser Asp Pro Leu Ala Asp Asn Ala Thr Glu Glu Gly
                485                 490                 495

Arg Lys Arg Asn Arg Arg Val Asp Ile Leu Trp Lys Ile Gly Gln Arg
            500                 505                 510

Asp Ala Asp Lys Ala Met Lys Gln Phe Leu Glu Asn Pro Thr Pro Glu
        515                 520                 525

Val Gln Gly Thr Asn Thr Gln Gln
    530                 535

<210> SEQ ID NO 63
<211> LENGTH: 288
<212> TYPE: PRT
<213> ORGANISM: Yersinia pestis -continued

<400> SEQUENCE: 63

Met Asn Arg Lys Phe Leu Ile Leu Phe Ser Leu Leu Ile Val Ala Ile
1 5 10 15

Gly Ile Ser Gly Ile Leu Leu Asn Pro Asp Lys Glu Ile Pro Glu Leu
20 25 30

Leu Thr Gln Thr Glu Lys Arg Lys Glu Arg Asn Ile Val Leu Ala Gln
35 40 45

Thr Arg His Asp Leu Thr Ala Gly Thr Leu Ile Ser Lys Glu Asp Tyr
50 55 60

Ser Leu Gln Asn Ile Thr Val Asp Glu Ser Ser Asp Leu Val Lys Asn
65 70 75 80

Asp Leu Ser His Gly His Arg Ile Asp Gly Asp Ser Ile Ala Asp Asp
85 90 95

Arg Thr His Asp His Lys Leu Asp Gly His Leu Leu Lys Asn Asn Ile
100 105 110

Leu Ala Gly Ser Tyr Ile Ile Asp Glu Met Leu Ile Ser Pro Asp Ser
115 120 125

Arg Glu Phe Ser Arg Leu Asn Leu Lys His Gly Glu Ile Ile Tyr Lys
130 135 140

Phe Tyr Ile Thr Glu Lys Asn Glu Tyr Leu Leu Asn Thr Leu Asn Pro
145 150 155 160

Gly Asp Phe Leu Ser Phe Gln Leu Leu Thr Leu Glu Thr Asn Lys Thr
165 170 175

Lys Gly Met Glu Asn Gly Ile Ala Ile Asp Ser Lys Ser Met Ser Ser
180 185 190

Lys Gln Arg Gln Lys Tyr Ser Leu Asn Asn Val Ile Pro Asp Met Pro
195 200 205

Ile Leu Ser Ile Lys Thr Tyr Ser Pro Glu Glu Leu Ser Val Lys Asn
210 215 220

Asn Lys Asn Asn Lys Thr Glu Glu Tyr Ser Leu Gly Tyr Ile Glu Val
225 230 235 240

Ile Met Lys Ile Gln Asp Leu Glu Phe Ile His Thr Val Glu Lys Ala
245 250 255

Gly Glu Val Phe Leu Thr Pro Lys Ser Gly Asp His Lys Arg Ile Asp
260 265 270

Leu Asp Asp Ile Ile Pro Thr Leu Gln Thr Ile Arg Glu Leu Arg Gly
275 280 285

<210> SEQ ID NO 64
<211> LENGTH: 101
<212> TYPE: PRT
<213> ORGANISM: Yersinia pestis

<400> SEQUENCE: 64

Met Pro Asn Ser Asn Ile Lys Leu Met Val Phe Phe Ala Pro Ile Leu
1 5 10 15

Phe Gly Cys Gln Ile Asn Ser Glu Glu Lys Lys Pro Asn Glu Glu Ile
20 25 30

Ile Asn Gln Leu Thr Ala Leu Thr Ala Gly Leu Arg Phe Leu Lys Glu
35 40 45

Asp Cys Asn Leu Lys Lys Ile Pro Asn Glu Gln Glu Ile Ile Asn Ser
50 55 60

Ala Ile Lys Ile Ala Asn Leu Lys Gly Glu Ile Met Thr Ser Lys His
65 70 75 80

-continued

Asn Asn Lys Ile Ile Lys Lys Ser Glu Ser Leu Tyr Gln Asp Ile Lys
85 90 95

Ile Ser Asn Gln Ile
100

<210> SEQ ID NO 65
<211> LENGTH: 131
<212> TYPE: PRT
<213> ORGANISM: Yersinia pestis

<400> SEQUENCE: 65

Met Met Asn Lys Phe Phe Lys Ile Ile Ser Ile Asn Leu Leu Ala Ile
1 5 10 15

Ser Leu Gly Gly Cys Gly Met Met Leu Asn Pro Leu Leu Met Lys Gln
20 25 30

Ala Glu Val Glu Pro Asn Asn Leu Pro Asp Gly Lys Leu Gly Gln Pro
35 40 45

Tyr Tyr Ala Lys Leu Arg Ile Thr Gly Gly Gly Gly Ala Ile Ala Ser
50 55 60

Phe Lys Gly Glu Ser Met Pro Val Gly Ser Gly Leu Val Leu Thr Ser
65 70 75 80

Asp Asn Pro Glu Arg Pro Pro Gly Arg Asp Glu Leu Val Ile Lys Gly
85 90 95

Ile Pro Val Ile Ser Gly Asp Ile Thr Phe Arg Val Ser Gly Ala Leu
100 105 110

Phe Ser Ser Ala Asp Lys Gly Tyr Phe Gly Lys Glu Tyr Lys Leu Lys
115 120 125

Ile Ala Glu
130

<210> SEQ ID NO 66
<211> LENGTH: 191
<212> TYPE: PRT
<213> ORGANISM: Yersinia pestis

<400> SEQUENCE: 66

Met Lys Lys Lys Asn Ile Ala Leu Ile Leu Pro Leu Ala Leu Leu Leu
1 5 10 15

Ser Ala Cys Ala Ser Asn Val Asn Pro Val Phe Glu Ala Thr Ser Ser
20 25 30

Arg Ser Ser Pro Cys Ile Glu Gly Gly Pro Asp Thr Val Ala Gln Lys
35 40 45

Phe Tyr Asp Leu Arg Ile Gln Gln Ile Gly Gly Gln Gln Gly Leu Pro
50 55 60

Asp Asp Asn Leu Ser Ala Gln Phe Arg Pro Tyr Leu Ser Gln Ser Leu
65 70 75 80

Tyr Asn Asp Ile Gln Ala Ala Arg Lys Gln Ala Ser Asn Arg Thr Pro
85 90 95

Ala Gln Val Asn Lys Thr Gln Met Ile Ser Gly Asp Ile Phe Thr Ser
100 105 110

Leu Arg Glu Gly Ser Thr Ser Ala Ser Val Ala Ser Ala Ser Thr Ile
115 120 125

Pro Asn Thr Asp Ala Arg Asn Ile Pro Leu Arg Val Asn Leu Ser His
130 135 140

Gln Met Ala Asp Gly Lys Ala Val Met Trp Gln Asp Glu Val Leu Met
145 150 155 160

```
Ile Arg Glu Gly Thr Cys Trp Val Val Asp Asp Ile Arg Phe Met Gly
            165                 170                 175

Val Ser Ala Pro Ala Ser Ser Leu Arg Gln Leu Leu Gly Asn His
            180                 185                 190

<210> SEQ ID NO 67
<211> LENGTH: 182
<212> TYPE: PRT
<213> ORGANISM: Yersinia pestis

<400> SEQUENCE: 67

Met Asp Lys Ile Asp Asn Asn Arg Arg Lys Trp Leu Thr Leu Gly Gly
1               5                   10                  15

Val Ala Leu Gly Met Ser Leu Leu Pro Gly Pro Val Phe Ala Thr Leu
            20                  25                  30

Ser Thr Pro Arg Pro Arg Ile Leu Thr Leu Asn Asn Leu Asn Thr Gly
            35                  40                  45

Glu Ser Ile Lys Ala Glu Phe Phe Asp Gly Arg Asn Tyr Asn Lys Asp
        50                  55                  60

Glu Leu Ser Arg Leu Asn His Ile Phe Arg Asp Tyr Arg Ala Asn Lys
65                  70                  75                  80

Val Lys Lys Ile Asp Pro Arg Leu Phe Asp Gln Leu Tyr Arg Leu Gln
            85                  90                  95

Val Leu Leu Glu Thr Thr Lys Pro Val Gln Leu Ile Ser Gly Tyr Arg
            100                 105                 110

Ser Leu Gly Thr Asn Asn Glu Leu Arg Glu His Ser Arg Gly Val Ala
            115                 120                 125

Lys Gln Ser Tyr His Thr Lys Gly Gln Ala Met Asp Phe His Ile Glu
        130                 135                 140

Gly Ile Gln Leu Ser Tyr Ile Arg Lys Ala Ala Leu Lys Met Arg Ala
145                 150                 155                 160

Gly Gly Val Gly Tyr Tyr Pro Arg Ser Asn Phe Val His Ile Asp Thr
            165                 170                 175

Gly Pro Thr Arg Ala Trp
            180

<210> SEQ ID NO 68
<211> LENGTH: 140
<212> TYPE: PRT
<213> ORGANISM: Yersinia pestis

<400> SEQUENCE: 68

Met Leu Ile Arg Ala Ser His Arg Val Leu Ile Leu Ala Thr Ser
1               5                   10                  15

Leu Leu Pro Leu Lys Ile Asn Ala Ala Ser Gly Ser Trp Val Ala Asp
            20                  25                  30

Asn Ile Gly Ile Thr Gln Gly Leu Arg Gly Val Val Thr Pro Ser Ser
            35                  40                  45

Pro Leu Gln Pro Pro Val Ala Leu Ala Gln Glu Asn Ala Arg Ile Val
        50                  55                  60

Ser Val Gly Trp Arg Tyr Gln Leu Met Ser Thr Ala Pro Asp Gly Leu
65                  70                  75                  80

Gln Val Lys Leu Cys Thr Pro Thr Arg Cys Ile Pro Leu Glu Gly Gly
            85                  90                  95

Ser Gly Gln Ser Val Gly Leu Ala Gly Glu Ala Val Asn Gln Leu
            100                 105                 110
```

```
Thr Phe Val Tyr Phe Ile Ala Gly Lys Gly Arg Val Asn Pro Pro Leu
            115                 120                 125

Gln Val Ile Ser Asn Gln Val Leu Val Asn Tyr Arg
    130                 135                 140
```

<210> SEQ ID NO 69
<211> LENGTH: 174
<212> TYPE: PRT
<213> ORGANISM: Yersinia pestis

<400> SEQUENCE: 69

```
Met Lys Lys Ile Ala Cys Leu Ser Ala Val Ala Cys Val Leu Ala
1               5                   10                  15

Val Thr Ala Gly Ser Ala Phe Ala Gly Gln Ser Thr Val Ser Gly Gly
            20                  25                  30

Tyr Ala Gln Ser Asp Tyr Gln Gly Val Ala Asn Lys Ser Ser Gly Phe
        35                  40                  45

Asn Leu Lys Tyr Arg Tyr Glu Trp Ser Asp Ser Gln Leu Gly Tyr Ile
    50                  55                  60

Thr Ser Phe Thr His Thr Glu Lys Ser Gly Phe Gly Asp Glu Ala Val
65                  70                  75                  80

Tyr Asn Lys Ala Gln Tyr Asn Ala Ile Thr Gly Gly Pro Ala Tyr Arg
                85                  90                  95

Ile Asn Asp Trp Ala Ser Ile Tyr Gly Leu Val Gly Val Gly His Gly
            100                 105                 110

Arg Phe Thr Gln Asn Glu Ser Ala Phe Val Gly Asp Lys His Ser Thr
        115                 120                 125

Ser Asp Tyr Gly Phe Thr Tyr Gly Ala Gly Leu Gln Phe Asn Pro Ala
    130                 135                 140

Glu Asn Val Ala Leu Asp Val Ser Tyr Glu Gln Ser Arg Ile Arg Asn
145                 150                 155                 160

Val Asp Val Gly Thr Trp Val Ala Gly Val Gly Tyr Thr Phe
                165                 170
```

<210> SEQ ID NO 70
<211> LENGTH: 318
<212> TYPE: PRT
<213> ORGANISM: Yersinia pestis

<400> SEQUENCE: 70

```
Met Lys Gln Leu Trp Phe Ser Val Cys Leu Met Thr Gly Ser Leu Phe
1               5                   10                  15

Met Ala Asn Ile Ala Ser Ala Glu Ser Thr Pro Ile Ala Met Leu Gln
            20                  25                  30

Glu Met Gly Ser Ala Ser Lys Ser Leu Asn Tyr Glu Leu Ser Tyr Ile
        35                  40                  45

Asn Val Asn Lys Gln Gly Ile Asp Ser Leu Arg Tyr Arg His Ala Ile
    50                  55                  60

Leu Asp Lys Lys Ser Leu Ala Gln Leu Arg Met Asp Gly Pro Arg
65                  70                  75                  80

Thr Glu Ile Leu Gln Arg Gly Asn Glu Ile Ser Tyr Phe Glu Pro Gly
                85                  90                  95

Phe Glu Ser Phe Thr Leu Ser Gly Glu His Ile Val Asp Ala Leu Pro
            100                 105                 110

Ser Ile Val Phe Ser Asn Phe Glu Lys Leu Ser Lys Thr Tyr Asn Tyr
        115                 120                 125
```

-continued

Ile Ala Leu Gly Arg Ala Arg Val Ala Asp Arg Pro Cys Gln Val Ile
130                 135                 140

Arg Val Val Ala Asn Asp Ser Thr Arg Tyr Ser Tyr Ile Ile Trp Leu
145                 150                 155                 160

Asp Glu Ala Thr Lys Leu Pro Met Arg Ile Asp Leu Leu Asp Arg Asp
                165                 170                 175

Gly Glu Thr Leu Glu Gln Phe Arg Val Ile Ser Phe Val Val Gly Glu
            180                 185                 190

Pro Ile Gln Gln Val Leu Gln Gly Met Leu Lys Leu Ala Leu Pro Pro
        195                 200                 205

Leu Leu Ser Leu Pro Ala Lys Thr Lys Val Asp Phe Thr Trp Ala Pro
210                 215                 220

Arg Trp Leu Pro Gln Gly Val Ala Glu Val Ser Arg Ser Arg Arg Thr
225                 230                 235                 240

Leu Pro Asn Met Asp Ala Pro Thr Glu Ser Arg Leu Tyr Thr Asp Gly
                245                 250                 255

Leu Phe Ser Phe Ser Val Asn Val Asn Pro Ala Gly Lys Glu Gly Thr
            260                 265                 270

Ser Glu Gln Ser Leu Arg Gln Gly Arg Arg Thr Val Gln Thr Glu Val
        275                 280                 285

Arg Asn Asn Val Glu Ile Thr Val Val Gly Glu Leu Pro Pro Ser Thr
290                 295                 300

Ala Lys Arg Ile Ala Asp Ser Val Val Leu Glu Ser Thr Lys
305                 310                 315

<210> SEQ ID NO 71
<211> LENGTH: 343
<212> TYPE: PRT
<213> ORGANISM: Yersinia pestis

<400> SEQUENCE: 71

Met Thr Arg Lys Leu Phe Ile Leu Val Phe Gly Ala Ala Ile Ser Gly
1               5                   10                  15

Gln Val Asn Ala Ser Cys Thr Leu His Leu Val Ser Asn Ser Glu Ser
            20                  25                  30

Val Ala Gly Val Met Pro Leu Thr Phe Pro Ile Ser Ser Phe Thr Phe
        35                  40                  45

Thr Ile Asp Ala Asp Ala Pro Asn Asp Ser Thr Val Pro Ile Leu Glu
    50                  55                  60

Lys Val Ala Gln Pro Gln Gly Leu Ala Val Ile Tyr Tyr Cys Thr Ser
65                  70                  75                  80

Val Asp Arg Tyr Gly Lys Asn Val Gly Pro Val Leu Gly Gln Asp Leu
                85                  90                  95

Gly Asn Gly Leu Phe Ala Thr Asn Ile Asp Gly Ile Ala Ile Lys Pro
            100                 105                 110

Ala Trp Asn Asn Gly Ala Ala Tyr Gly Tyr Phe Asn Ser Ser Gly Ile
        115                 120                 125

Met Pro Ala Phe Glu Arg Glu Gly Val Pro Thr Glu Glu Gly Phe Trp
    130                 135                 140

Thr Tyr Pro Ala Thr Ser His Phe Arg Phe Glu Leu Tyr Lys Ile Lys
145                 150                 155                 160

Asp Thr Leu Asn Leu Thr Asp Thr Asn Gly Glu Arg Val Leu Pro Gly
                165                 170                 175

Gly Thr Ile Ala Tyr Thr Trp Ala Thr Asn Asn Ser Leu Ala Asn Tyr
            180                 185                 190

```
Ala Gln Arg Leu Glu Ile Gly Glu Ile Lys Val Ile Ser Thr Pro Ser
            195                 200                 205

Cys Thr Phe Asp Gly Pro Gln Lys Val Asp Phe Gly Ile Val Thr Ser
    210                 215                 220

Ser Asn Leu Asn Asn Gly Gly Ile Glu Arg Asp Leu Asp Phe Asn Ile
225                 230                 235                 240

Thr Cys Lys Thr Asp Tyr Gly His Tyr Ser Ala Thr Ala Ile Phe
                245                 250                 255

Thr Gln Thr Ser Ser Ala Asp Asn Asn Tyr Ile Lys Val Lys Asp Ser
            260                 265                 270

Gln Asn Gln Glu Asp Arg Leu Leu Ile Lys Ile Ser Asp Thr Asn Gly
        275                 280                 285

Gln Gln Met Lys Val Asn Gly Ser Thr Thr Glu Gln Gln Val Asn Ile
        290                 295                 300

Ala Ser Gly Val Pro Ala Glu Phe Lys Trp Lys Ala Lys Leu Glu Ala
305                 310                 315                 320

Ala Pro Ala Ala Asn Lys Pro Ala Ile Gly Asn Phe Ser Ala Met Ala
                325                 330                 335

Glu Ile Ile Leu Gln Ile Lys
            340

<210> SEQ ID NO 72
<211> LENGTH: 203
<212> TYPE: PRT
<213> ORGANISM: Yersinia pestis

<400> SEQUENCE: 72

Met Asn Ile Arg Pro Arg Leu Ser Gly Val Arg Leu Leu Leu Leu Ser
1               5                   10                  15

Ala Pro Leu Leu Leu Ala Gly Cys Ser Thr Val Ser Gly Phe Ser Trp
            20                  25                  30

Ser Ser Leu Ser Pro Leu Asn Trp Phe Ser Gly Ser Arg Ser Met Gln
        35                  40                  45

Val Thr Glu Gln Gly Val Gly Gly Ile Thr Ala Ser Thr Leu Leu Thr
50                  55                  60

Glu Ser Asp Ile Asn Ala Gly Leu Gln Gly Asp Tyr Arg Leu Arg Ser
65                  70                  75                  80

Gly Met Ala Thr Asn Asp Gly Lys Leu Val Ser Phe Tyr Gln Ala Leu
                85                  90                  95

Lys Glu Asp Gln Ile Lys Leu Val Ile Ser Gly Gln Pro Lys Gly Gln
            100                 105                 110

Val Glu Arg Ile Asp Val Met Asp Lys Gly Ile Pro Ser Gln Trp Gly
        115                 120                 125

Val Thr Ile Gly Thr Pro Phe Ser Asp Leu Tyr Lys Lys Ala Phe Gly
130                 135                 140

Ala Cys His Lys Gly Arg Gly Asp Asp Val Asn Gln Val Glu Cys Val
145                 150                 155                 160

Ala Pro Glu Ser Lys His Val Ser Tyr Leu Phe Asn Gly Asn Trp His
                165                 170                 175

Gly Pro Glu Glu Leu Met Pro Ser Asp Asp Ala Leu Gln Ser Trp Thr
            180                 185                 190

Val Ser Lys Ile Ile Trp Arg Ala Lys Ser Glu
        195                 200
```

<210> SEQ ID NO 73
<211> LENGTH: 475
<212> TYPE: PRT
<213> ORGANISM: Yersinia pestis

<400> SEQUENCE: 73

Met Met Ser Thr Glu Ile Lys Thr Gln Val Val Leu Gly Ala Gly
1               5                   10                  15

Pro Ala Gly Tyr Ser Ala Ala Phe Arg Cys Ala Asp Leu Gly Leu Glu
                20                  25                  30

Thr Ile Leu Val Glu Arg Tyr Ser Thr Leu Gly Gly Val Cys Leu Asn
            35                  40                  45

Val Gly Cys Ile Pro Ser Lys Ala Leu Leu His Val Ala Lys Val Ile
50                  55                  60

Glu Glu Ala Lys Ala Leu Ala Glu His Gly Ile Val Phe Gly Glu Pro
65                  70                  75                  80

Lys Thr Asp Ile Asp Lys Val Arg Val Trp Lys Asp Lys Val Ile Asn
                85                  90                  95

Gln Leu Thr Gly Gly Leu Ala Gly Met Ala Lys Gly Arg Lys Val Lys
            100                 105                 110

Val Val Thr Gly Phe Gly Lys Phe Thr Gly Ala Asn Thr Leu Val Val
        115                 120                 125

Asp Gly Glu Asn Gly Pro Thr Thr Ile Asn Phe Asp Asn Ala Ile Ile
130                 135                 140

Ala Ala Gly Ser Arg Pro Ile Gln Leu Pro Phe Ile Pro His Glu Asp
145                 150                 155                 160

Ser Arg Ile Trp Asp Ser Thr Asp Ala Leu Ala Leu Arg Thr Val Pro
                165                 170                 175

Glu Arg Leu Leu Val Met Gly Gly Gly Ile Ile Gly Leu Glu Met Gly
            180                 185                 190

Thr Val Tyr His Ala Leu Gly Ser Lys Ile Asp Val Val Glu Met Leu
        195                 200                 205

Asp Gln Val Ile Pro Ala Ala Asp Lys Asp Val Val Lys Val Phe Thr
210                 215                 220

Lys Arg Ile Ser Lys Gln Phe Asn Leu Met Leu Glu Thr Lys Val Thr
225                 230                 235                 240

Ala Val Glu Ala Lys Glu Asp Gly Ile Tyr Val Thr Met Glu Gly Lys
                245                 250                 255

Lys Ala Pro Ala Glu Pro Gln Arg Tyr Asp Ala Val Leu Val Ala Ile
            260                 265                 270

Gly Arg Val Pro Asn Gly Lys Leu Leu Asp Ala Gly Gln Ala Gly Val
        275                 280                 285

Glu Val Asp Asp Arg Gly Phe Ile His Val Asp Lys Gln Leu Arg Thr
290                 295                 300

Asn Val Pro His Ile Phe Ala Ile Gly Asp Ile Val Gly Gln Pro Met
305                 310                 315                 320

Leu Ala His Lys Gly Val His Glu Gly His Val Ala Ala Glu Val Ile
                325                 330                 335

Ala Gly Met Lys His Tyr Phe Asp Pro Lys Val Ile Pro Ser Ile Ala
            340                 345                 350

Tyr Thr Glu Pro Glu Val Ala Trp Val Gly Leu Thr Glu Lys Glu Ala
        355                 360                 365

Lys Glu Lys Gly Ile Ser Tyr Glu Thr Ser Thr Phe Pro Trp Ala Ala
370                 375                 380

```
Ser Gly Arg Ala Ile Ala Ser Asp Cys Ala Asp Gly Met Thr Lys Leu
385                 390                 395                 400

Ile Phe Asp Lys Glu Thr His Arg Ile Ile Gly Gly Ala Ile Val Gly
                405                 410                 415

Thr Asn Gly Gly Glu Leu Leu Gly Glu Ile Gly Leu Ala Ile Glu Met
            420                 425                 430

Gly Cys Asp Ala Glu Asp Ile Ala Leu Thr Ile His Ala His Pro Thr
        435                 440                 445

Leu His Glu Ser Val Gly Leu Ala Ala Glu Ile Tyr Glu Gly Ser Ile
    450                 455                 460

Thr Asp Leu Pro Asn Pro Lys Ala Lys Lys Lys
465                 470                 475
```

<210> SEQ ID NO 74
<211> LENGTH: 191
<212> TYPE: PRT
<213> ORGANISM: Yersinia pestis

<400> SEQUENCE: 74

```
Met Lys Val Gly Tyr Ile Phe Ala Met Leu Phe Ser Thr Leu Leu Leu
1               5                   10                  15

Gln Gly Cys Val Gly Ala Val Val Gly Ser Ala Ala Val Ala Thr
            20                  25                  30

Lys Thr Ala Thr Asp Pro Arg Thr Ile Gly Thr Gln Val Asp Asp Gly
        35                  40                  45

Thr Leu Glu Ala Arg Val Val Asn Ala Leu Ser Lys Asp Lys Glu Ile
50                  55                  60

Lys Ser Gln Thr Arg Phe Val Val Thr Ala Tyr Gln Gly Lys Val Leu
65                  70                  75                  80

Leu Thr Gly Gln Thr Pro Ser Ala Glu Leu Ser Asn Arg Ala Lys Gln
            85                  90                  95

Ile Ala Ser Gly Val Asp Gly Val Thr Glu Val Tyr Asn Glu Met Arg
        100                 105                 110

Leu Gly Lys Pro Val Asp Leu Ser Thr Ala Ser Met Asp Thr Trp Ile
    115                 120                 125

Thr Thr Lys Val Arg Ser Gln Leu Leu Thr Ser Asp Ser Val Lys Ser
130                 135                 140

Ser Asn Val Lys Val Thr Thr Glu Asn Gly Glu Val Phe Leu Leu Gly
145                 150                 155                 160

Leu Val Thr Gln Gln Glu Ala Gln Ser Ala Ala Gln Ile Ala Ser Lys
            165                 170                 175

Val Ser Gly Val Lys His Val Thr Thr Ala Phe Thr Ile Val Lys
        180                 185                 190
```

<210> SEQ ID NO 75
<211> LENGTH: 155
<212> TYPE: PRT
<213> ORGANISM: Yersinia pestis

<400> SEQUENCE: 75

```
Met Asn Lys Leu Ala Ile Ala Val Ala Leu Ala Ala Thr Val Leu Ser
1               5                   10                  15

Gly Cys Ala Asn Asn Thr Ala Ser Gly Asp Thr Phe Thr Ala Ser Gln
            20                  25                  30

Ala Arg Gln Val Gln Thr Val Thr Tyr Gly Ser Ile Val Ser Ala Arg
        35                  40                  45
```

Pro Val Thr Ile Gln Gly Gly Asn Asn Asn Val Ala Gly Ala Ile
    50                  55                  60

Gly Gly Ala Val Val Gly Gly Phe Leu Gly Asn Thr Ile Gly Gly Gly
65                  70                  75                  80

Arg Gly Asn Ser Leu Ala Thr Ala Gly Gly Ala Val Ala Gly Gly Val
                85                  90                  95

Ala Gly Gln Gly Ile Gln Ser Ala Met Asn Arg Ser Glu Gly Val Gln
            100                 105                 110

Leu Glu Ile Arg Arg Asp Asp Gly Ser Asn Ile Val Val Gln Ala
            115                 120                 125

Gln Gly Pro Thr Arg Phe Ser Ala Gly Gln Arg Val Ile Ile Ala Ser
    130                 135                 140

Asp Arg Ser Gly Thr Val Thr Val Ser Pro Arg
145                 150                 155

<210> SEQ ID NO 76
<211> LENGTH: 165
<212> TYPE: PRT
<213> ORGANISM: Yersinia pestis

<400> SEQUENCE: 76

Met Leu Lys Thr Lys Tyr Asn Ile Leu Phe Gly Val Val Thr Ile Gly
1               5                   10                  15

Ile Leu Tyr Ser Ala Trp Glu Ile Ala Arg Pro Val Glu Ile Val Asp
                20                  25                  30

Val His Ile Asn Asn Ser Ser Glu Gly Tyr Tyr Ser Asn Tyr Ile Leu
            35                  40                  45

Val Asn Asn Phe Pro Ile Thr Asp Arg Gly Arg Ile Ala Trp Trp Glu
        50                  55                  60

Asn Asn Lys Ser Met Leu Lys Glu Lys Tyr Asn Ile Pro Lys His His
65                  70                  75                  80

Leu Asp Asp Arg Phe Ser Val Ser Val Trp Asp Phe Gly Asp Gly Tyr
                85                  90                  95

Lys Lys Leu Pro Thr Gly Asp Val Arg Leu Ser Leu Glu Ser Ser Asp
            100                 105                 110

Leu Leu Cys Phe Asp Asp Met Lys Val Val Glu Asn Cys Ile Glu Lys
        115                 120                 125

Lys Ser Leu Leu Phe Ile Arg Lys Tyr Asp Asp Arg Tyr Val Phe Ser
130                 135                 140

Met Gly Arg Ser Ser Tyr Arg Gln Ser Val Glu Gly Gly Glu Ile Thr
145                 150                 155                 160

Lys Asp Val Glu Asp
                165

<210> SEQ ID NO 77
<211> LENGTH: 144
<212> TYPE: PRT
<213> ORGANISM: Yersinia pestis

<400> SEQUENCE: 77

Met Leu Gln Glu Ile Met Gln Phe Ile Ser Gln His Pro Ile Leu Ser
1               5                   10                  15

Leu Ala Trp Val Leu Leu Phe Gly Ala Val Val Phe Thr Ser Phe Lys
                20                  25                  30

Asn Ser Leu Ser Lys Val Lys Glu Val Thr Arg Gly Glu Ala Thr Arg
            35                  40                  45

-continued

```
Leu Ile Asn Lys Glu Asp Ala Val Val Val Asp Ile Arg Thr Arg Glu
    50                  55                  60

Asp Tyr Arg Lys Gly His Ile Ala Asn Ser Ile Asn Leu Ile Pro Ser
65                  70                  75                  80

Asp Ile Lys Asn Gly Asn Leu Gly Glu Leu Glu Lys His Lys Thr Gln
                85                  90                  95

Pro Ile Ile Val Val Cys Ala Met Gly Thr Thr Ser Arg Ala Ser Ala
            100                 105                 110

Asp Met Leu Ser Lys Ala Gly Phe Glu Arg Val Phe Thr Leu Lys Glu
        115                 120                 125

Gly Ile Ser Gly Trp Ser Gly Glu Asn Leu Pro Leu Ala Arg Gly Lys
    130                 135                 140

<210> SEQ ID NO 78
<211> LENGTH: 337
<212> TYPE: PRT
<213> ORGANISM: Yersinia pestis

<400> SEQUENCE: 78

Met Ile Leu Lys Arg Met Asp Asn Asn Met Ser Asp Ile Phe Pro Gln
1               5                   10                  15

Ala Leu Phe Gly Val Glu Tyr Asp Pro Ala Tyr Gly Glu Ile Glu Ser
            20                  25                  30

Ile Leu Ser Gln Leu Asp Glu Ser Ala Asp Pro Leu Ser Arg Pro His
        35                  40                  45

Glu Pro Pro Gln Ile Asn Trp His His Ile Ser Glu Gln Ala Asn Lys
    50                  55                  60

Leu Leu Glu Gln Cys Phe Asp Leu Arg Val Met Leu Trp Phe Ile Arg
65                  70                  75                  80

Ala Asn Ile His Ile Lys Gly Ile Ser Ala Leu Tyr Asp Gly Phe Met
                85                  90                  95

Arg Ile Asn Ala Gln Thr Gln Asp Thr Asp Val Val Ile Tyr Pro Gln
            100                 105                 110

Ser Glu Glu Pro Pro Leu Asn Ser Gly His Ala Ala Ala Leu Gly Trp
        115                 120                 125

Leu Ser Thr Ala Gln Cys Ile Ala Glu Leu Lys Thr Ala Arg Leu Thr
    130                 135                 140

Glu Glu His Pro Tyr Ile Leu Gln Asp Leu Ile Thr Thr Glu Ala Leu
145                 150                 155                 160

Pro Asn Gly Gln Glu Arg Tyr Phe Val Thr Ser Ser Thr Leu Phe Leu
                165                 170                 175

Thr Val Asn Asn Tyr Phe Gln Gln Asn Gly Leu Pro Asp Leu Lys Asp
            180                 185                 190

Gln Leu Thr Lys Val Asp Met Leu Leu Glu Gln Ile Glu Ser Tyr Ala
        195                 200                 205

Asn Gln Ser Thr Glu Ser Tyr Gln Leu His Cys Glu Gln Leu Arg Ile
    210                 215                 220

Phe Leu Lys Asn Asn Ile Ser Gln Leu Ala Gln Leu Asn Ala Pro Glu
225                 230                 235                 240

His Asp Asp Pro Glu Thr Val Tyr Gln Lys Ile Asp Ser His Glu Ser
                245                 250                 255

Leu Asp Thr Gln Ser Phe Asn Ser Asn Asp Lys Ser Ile Arg Ser Arg
            260                 265                 270

Gln Glu Ile Ile Met Met Leu Asp Arg Ile Leu Glu Tyr Phe Gln His
        275                 280                 285
```

```
Tyr Glu Pro Ser His Pro Ala Pro Ile Phe Ile Arg Arg Thr Lys Glu
    290                 295                 300
Met Ile Gly Met Asp Phe Tyr Ser Ile Val Glu Glu Ile Leu Pro Glu
305                 310                 315                 320
Ala Val Ile Thr Leu Lys Gln Phe Thr Gly Lys Thr Asn Leu Pro Phe
                325                 330                 335
Arg

<210> SEQ ID NO 79
<211> LENGTH: 327
<212> TYPE: PRT
<213> ORGANISM: Yersinia pestis

<400> SEQUENCE: 79

Met Ala Ser Leu Gln Thr Leu Lys Asn Thr Phe Leu Pro Gly Ile Ser
1               5                   10                  15
Ala Ser Gln Asp Phe Phe Glu Leu Leu Arg Arg Ile Glu Arg Ala Thr
                20                  25                  30
Pro Glu Gln Gly Arg Leu Gly Thr Gln Arg Asp Arg Ser His Leu Arg
            35                  40                  45
Leu Arg Ile Ile Gln Pro Ala Asp Met Gly Phe Ala Pro Arg Glu Val
        50                  55                  60
Ser Asp Ile Arg Gln Thr Leu Asn Thr His Gln His Leu Ala Glu Ile
65                  70                  75                  80
Thr Ile Phe Cys Arg His Phe Gly Leu Phe Ala Pro Tyr Gly Pro Leu
                85                  90                  95
Pro Ile His Val Thr Glu His Ala Arg Asn Glu Ala Leu Ala Lys Arg
            100                 105                 110
Asn Gln Ala Phe Glu His Phe Ala Gly Ile Leu Ser Gln Arg Met Ala
        115                 120                 125
Ile Leu His Tyr Arg Ser Trp Ala Gln Met His Val Ala Val Gly His
    130                 135                 140
Asp Arg Ala Ser Ala Asn Pro Phe Met Asn His Val Arg Gln Ile Ala
145                 150                 155                 160
Gly Leu Thr Pro Gln Gln Ala Leu Asn Ser His Val Asp Arg Val Arg
                165                 170                 175
Arg Cys Phe Pro Gly Val Tyr Leu Pro Gly Arg Gly Ser Leu Arg Lys
            180                 185                 190
Leu Gln Glu Ile Leu Ser Leu Tyr Phe Ser Val Pro Ile Arg Val Glu
        195                 200                 205
Ala Arg Lys Gly Leu Trp Ile Asp Asp Ser Arg Asn Ile Glu Ser Gln
    210                 215                 220
Arg Met Gly Arg Leu Gly Asn Thr Arg Ile Gly Ser Arg Phe Phe Asp
225                 230                 235                 240
Val Gln His Ser Leu Val Leu Ser Ile Gly Pro Val Ser Asp Pro Gln
                245                 250                 255
Tyr Leu Asp Phe Gln Arg Asn Ser Lys Arg Ile Asn Thr Leu Val Gln
            260                 265                 270
Ile Cys His Asp Phe Val Arg His Arg Met Val Leu Asp Val Gln Leu
        275                 280                 285
Ile Ile Gln Thr Ser Pro Asn Met Ala Cys Arg Leu Gly Gly Gly Thr
    290                 295                 300
Leu Ser Arg His Ser Trp Leu Lys Pro Gly Ser Ala Leu Ser Ile Gln
305                 310                 315                 320
```

```
Pro Ile Tyr Arg Thr Val Thr
            325

<210> SEQ ID NO 80
<211> LENGTH: 186
<212> TYPE: PRT
<213> ORGANISM: Yersinia pestis

<400> SEQUENCE: 80

Met Ala Lys Asp Ala Ser Ser Gln Lys Phe Ile Gly Arg Asn Asn Ala
1               5                   10                  15

Pro Arg Val Gln Ile Glu Tyr Asp Val Glu Ile Tyr Gly Ser Asn Lys
            20                  25                  30

Lys Val Glu Leu Pro Phe Val Thr Gly Val Met Ala Asp Leu Ser Gly
        35                  40                  45

His Arg Ala Lys Pro Leu Pro Ala Val Glu Asp Arg Lys Phe Leu Thr
    50                  55                  60

Phe Asp Gln Asp Asn Phe Asp Ala Arg Met Arg Ala Ile Lys Pro Arg
65                  70                  75                  80

Leu Lys Phe Tyr Val Asp Asn Thr Leu Ser Glu Asp Asn Glu Leu Leu
                85                  90                  95

Asp Ile Glu Leu Asp Phe Glu Ser Met Asp Asp Phe Ser Pro Gly Ser
            100                 105                 110

Leu Ala Arg Arg Ile Pro Gln Met Glu Lys Leu Leu Glu Ala Arg Thr
        115                 120                 125

His Leu Ala Glu Leu Ile Thr Tyr Met Asp Gly Lys Thr Ser Ala Glu
    130                 135                 140

Glu Val Val Lys Gln Leu Leu Glu Gln Pro Asp Phe Leu Gln Asn Leu
145                 150                 155                 160

Ala Thr Asp Ala Gln Gly Thr Ile Ser Lys Leu Ser Gln Asp Asp
                165                 170                 175

Val Leu Val Glu Asp Asp Gly Glu Lys
            180                 185

<210> SEQ ID NO 81
<211> LENGTH: 147
<212> TYPE: PRT
<213> ORGANISM: Yersinia pestis

<400> SEQUENCE: 81

Met Asp Ile Ser Ala Pro Ile Leu Phe Asp Lys Leu Ser Leu Arg His
1               5                   10                  15

Glu His Val Arg Leu Pro His Trp Arg Glu Val Ile Val Arg Asp Ile
            20                  25                  30

Glu Ser Leu Leu Asn Asp Ser Ala His Ser Ala Arg Leu Lys Leu Lys
        35                  40                  45

Lys Tyr Pro His Cys Glu Ala Ser Val Leu Asn Tyr Gly Leu Pro Ser
    50                  55                  60

Leu Ser Gln Gln Val Pro Val Ile Thr Asp Leu Leu Glu Leu Ala Arg
65                  70                  75                  80

His Ile Gln Arg Ile Ile Ala Thr Phe Glu Ser Arg Leu Asp Pro Arg
                85                  90                  95

Ser Ile Lys Val Val Pro Leu Ile Asn Lys Gly Glu Thr Trp Val Leu
            100                 105                 110

Ala Ile Leu Phe Asp Ile His Ala Arg Cys Asn Leu Pro Gly Glu Glu
        115                 120                 125
```

His Leu Val Asn Leu Arg Ile Ala Leu Asp Tyr Ser Tyr Gly Met Val
        130                 135                 140

Arg Val Leu
145

<210> SEQ ID NO 82
<211> LENGTH: 867
<212> TYPE: PRT
<213> ORGANISM: Yersinia pestis

<400> SEQUENCE: 82

Met Gly Ala Ile Thr Val Tyr Gln Arg Glu Arg Leu Phe Asn Arg Leu
1               5                   10                  15

Gly Thr Phe Ala Tyr Lys Thr Phe Val Glu Ala Thr Arg Leu Cys Arg
            20                  25                  30

Ser Tyr Arg His Glu Tyr Val Glu Leu Glu His Trp Leu Lys Ile Leu
        35                  40                  45

Met Asp Gln Gln Arg Gly Asp Ile Pro Ala Leu Leu Thr His Tyr Gly
    50                  55                  60

Leu Ser Gln Thr Val Ile Ser Thr Gln Leu Asp Arg Ile Ile Gln His
65                  70                  75                  80

Met Pro Val Thr Lys Ala Ser Val Gln Asp Leu Ser Ser Arg Leu Glu
                85                  90                  95

Ser Val Val Glu Gly Gly Leu Val Leu Ser Gln Leu Met Ala Ser Pro
            100                 105                 110

Ser Pro Ile Arg Thr Ser His Ile Leu Leu Ala Leu Leu Gln Asp Thr
        115                 120                 125

Gln His Gln Arg Trp Leu Tyr Arg Leu Cys Asp Glu Phe Lys Lys Leu
    130                 135                 140

Pro Val Pro Gln Val Ala Glu Glu Tyr Glu Gly Leu Leu Val Asn Ser
145                 150                 155                 160

Ile Glu Gln Thr Ser Glu Val Gln Arg Gly Asp Ala Leu Val Thr Glu
                165                 170                 175

Thr Asp Ser Ser Ser Lys Glu Ala His Ala Ala Leu Asn Lys Trp
            180                 185                 190

Cys Asn Asp Leu Thr Gln Gln Ala Arg Asp Gly Glu Ile Asp Pro Val
        195                 200                 205

Ile Gly Arg Glu Ala Glu Leu Arg Gln Val Ile Asp Ile Leu Leu Arg
    210                 215                 220

Arg Arg Gln Asn Asn Pro Ile Leu Val Gly Glu Ala Gly Val Gly Lys
225                 230                 235                 240

Thr Ala Val Val Glu Ala Leu Ala Arg Lys Leu Ala Ser Gly Asp Val
                245                 250                 255

Pro Pro Leu Leu Gln Gly Ala Arg Leu Leu Ser Leu Asp Leu Gly Arg
            260                 265                 270

Met Gln Ala Gly Ala Ser Met Arg Gly Glu Phe Glu Ser Arg Leu Lys
        275                 280                 285

Ser Leu Ile Asp Gly Ile Ser Gln Ser Asp Thr Pro Val Ile Leu Phe
    290                 295                 300

Cys Asp Glu Ala His Thr Leu Val Gly Ala Gly Gln Ala Gly Thr
305                 310                 315                 320

Gly Asp Ala Val Asn Leu Leu Lys Pro Met Leu Ala Arg Gly Ala Leu
                325                 330                 335

Arg Met Ile Ala Ala Thr Thr Trp Ser Glu Tyr Lys Gln Phe Ile Glu

-continued

```
                340                 345                 350
Pro Asp Ala Ala Leu Thr Arg Arg Phe Gln Arg Val Leu Ile Gly Glu
            355                 360                 365
Pro Asn Glu Ser Thr Ala Val Asp Met Leu Arg Ala Ile Ala Pro His
        370                 375                 380
Phe Ala Gln His His Asn Val Thr Ile Arg Asp Gly Ala Ile His Ala
385                 390                 395                 400
Ala Val Arg Leu Ser Leu Arg Asn Leu Pro Ser Arg Gln Leu Pro Asp
                405                 410                 415
Lys Ala Ile Ser Leu Leu Asp Thr Ala Cys Ala Arg Val Ala Leu Ser
            420                 425                 430
Gln Tyr Ala Gln Pro Gln Ala Ile Glu Gln Leu Ser Ala Gln Leu Asp
        435                 440                 445
Val Leu Lys Thr Glu His Gln Tyr Leu Val Arg Glu Lys Gln Leu Gly
    450                 455                 460
Glu Ala Val Asp Gln Arg Leu Asp Asp Val Gln Thr Gln Ile Gln Ala
465                 470                 475                 480
Phe Glu His Glu Leu Thr Ala Leu Gln Ser Arg His Leu His Glu Gln
                485                 490                 495
Gln Leu Val Arg Glu Val Leu Pro Glu Gly Glu Gly Ser Gly Met Met
            500                 505                 510
Thr Glu Asn Ala Arg Trp Gly Glu Leu Met Ala Leu Gln Glu Ala Ser
        515                 520                 525
Pro Leu Val Tyr Pro Trp Val Asp Glu Gln Ser Ile Ala Ala Val Leu
    530                 535                 540
Ser Asp Trp Thr Gly Ile Pro Ser Gly Lys Met Leu Gln Asp Asp Ile
545                 550                 555                 560
Glu Cys Val Leu Asn Leu Glu Gln Arg Leu Gly Asp His Ile Phe Gly
                565                 570                 575
Gln Arg Asn Ala Ile Lys Glu Ile Ser Gln Ala Ile Arg Ile Ala Arg
            580                 585                 590
Ala Gly Ile Gln Ser Gln Glu Arg Pro Leu Gly Ile Phe Leu Leu Ala
        595                 600                 605
Gly Ser Thr Gly Thr Gly Lys Thr Glu Thr Ala Asn Val Leu Val Glu
    610                 615                 620
Thr Leu Tyr Gly Gly Ala His Asn Leu Ile Thr Phe Asn Met Ser Glu
625                 630                 635                 640
Phe Gln Glu Ala His Thr Leu Ser Thr Leu Lys Gly Ala Pro Pro Gly
                645                 650                 655
Tyr Val Gly Tyr Gly Lys Gly Gly Lys Leu Thr Glu Ala Val Arg Arg
            660                 665                 670
Lys Pro Tyr Ser Val Ile Leu Leu Asp Glu Phe Asp Lys Ala His Ala
        675                 680                 685
Asp Ile Gln Asp Ala Phe Tyr Gln Val Phe Asp Lys Gly Trp Met Glu
    690                 695                 700
Asp Ala Glu Gly Arg Arg Val Ser Phe Arg Gln Cys Phe Ile Leu Leu
705                 710                 715                 720
Thr Cys Asn Gln Gly Ala Glu Glu Ile Glu Gln Ala Tyr Leu Thr Ala
                725                 730                 735
Asn Asp Ile Lys Pro Gly Ala Leu Lys Pro Leu Val Tyr Asp Ala Leu
            740                 745                 750
Leu Arg Arg Phe Ala Pro Ala Leu Leu Ala Arg Val Asn Ile Ile Pro
        755                 760                 765
```

```
Tyr Ile Pro Leu Asp Gln Asp Ala Leu Ala Gln Ile Ala Ser His His
        770                 775                 780

Leu Ala Arg Leu Gln Thr Arg Leu Trp Asp Glu Ile Gly Ala Thr Leu
785                 790                 795                 800

Val Thr Glu Gly Asp Ile Pro Gly Trp Ile Ala Ser Arg Val Cys Ser
                805                 810                 815

His Pro Asn His Gly Arg Ala Val Glu Glu Leu Leu Arg Gln Thr Leu
            820                 825                 830

Leu Pro Ala Val Gly Asn Glu Val Leu Lys Arg Arg His Glu Ala Glu
        835                 840                 845

Pro Leu Arg Glu Ile Arg Leu Ile Val Glu Glu Thr Glu Leu Ser Ile
850                 855                 860

Glu Phe Ala
865

<210> SEQ ID NO 83
<211> LENGTH: 190
<212> TYPE: PRT
<213> ORGANISM: Yersinia pestis

<400> SEQUENCE: 83

Met Arg Ile Ile Arg Pro Gln Gln Leu Val Val Leu Lys Ser Ser Tyr
1               5                   10                  15

Gln Ile Gly His Glu Ser His Met Gly Ile Ser Val Val Ala Gly Cys
            20                  25                  30

Tyr Leu Ser Lys Pro Glu His Met Val Thr Glu Ser Gln Ile Trp Gln
        35                  40                  45

Ala Trp Lys Ala Ala Pro Leu Ser Phe Arg Met Leu Asp Ser Ala Glu
    50                  55                  60

Pro Lys Pro Phe Ala Glu Phe Leu Leu Ala Gly His Ala Gly Ile Gly
65                  70                  75                  80

Glu Glu Val Thr Ser Leu Ser Ala Glu Val Ser Val Gly Ser Leu Thr
                85                  90                  95

Arg Arg Trp Cys Ile Glu Gly Glu Ser Asn Lys Thr Gly Leu Val Ile
            100                 105                 110

Lys Pro Phe Leu Arg Met Ser Met Asp His Thr Gln Ser Trp Gly Gly
        115                 120                 125

Lys Gly Cys Lys Glu Asn Pro Leu Gly Arg Gly Tyr Asn Asp Glu Arg
    130                 135                 140

Lys Pro Thr Ile Met Ser Leu Gly Leu Asp Gly Ser Ala Ile Val Arg
145                 150                 155                 160

Ser Pro Leu Ala Ser Pro Ser Pro Val Pro His Asp Phe Gln Leu Arg
                165                 170                 175

Lys Val His Ile Asn Glu Val Ala Ser Thr Met Thr Asp Pro
            180                 185                 190

<210> SEQ ID NO 84
<211> LENGTH: 540
<212> TYPE: PRT
<213> ORGANISM: Yersinia pestis

<400> SEQUENCE: 84

Met Pro Pro Gln Ile Asp Arg Arg Tyr Phe Gln Met Ala Pro Pro Gly
1               5                   10                  15

Gln Trp Leu Lys Lys Ser Ala Trp Pro Asp Ser Val Pro Phe Lys Leu
            20                  25                  30
```

-continued

```
Ile Gly Phe Arg Pro Asp Asn Glu Glu Ile Ser Gly Ala Phe Pro Ala
        35                  40                  45
Val Ser Ala Arg Ala Phe Val Trp Asp Asn Pro Ser Ala Pro Pro Ser
    50                  55                  60
Glu Val Thr Leu Leu Arg Lys Thr Leu Trp Leu Pro Asp Asn Asp
65                  70                  75                  80
Met Gly Leu Met Val Phe Thr Gly Ser Val Pro Leu Thr His Leu Phe
                85                  90                  95
Asp Glu Pro Ile Asp Thr Leu Leu Val Gly Leu Asp Asp Ser His Ser
            100                 105                 110
Leu Arg Glu Leu Glu Tyr Tyr Gln Gln Val Tyr Lys Ser Arg Ser Val
        115                 120                 125
Glu Gly Ala Ala Ser Phe Glu Phe Leu Lys Asp Pro Glu Leu Met Pro
    130                 135                 140
Glu Gly Met Pro Leu Asn Val Ile Arg Asp Leu Ala Asp His Pro Asp
145                 150                 155                 160
Ser Leu Arg Tyr Ser Ala Ser Ala Met Ser Glu Ala Glu Ser Glu Arg
                165                 170                 175
Phe Tyr Gln Asp Val Gln Asp Ala Ile Asp Arg Gln Glu Gln Gln Lys
            180                 185                 190
Ser Glu Glu Gln Glu Thr Leu Gly Asp Leu Asn Val Pro Ala Ala Gly
        195                 200                 205
Lys Glu Glu Ala Gly Thr Gln Trp Leu Glu Ser Lys Glu Asp Thr Ala
    210                 215                 220
Thr Asn Val Thr Phe Leu Gly Thr Asp Phe Ser Gly Met Thr Leu Asp
225                 230                 235                 240
Asn Lys Gln Phe Arg Tyr Cys Met Phe Thr Gly Cys His Phe Asp Lys
                245                 250                 255
Ala Thr Phe Lys Asp Cys Thr Phe Glu His Cys Gln Phe Thr Gln Ser
            260                 265                 270
Asp Phe Glu Asn Ser Arg Trp Asn Asn Val His Leu Ser Gly Cys Leu
        275                 280                 285
Phe Lys Gln Ala Glu Trp Gln Lys Ala Ala Phe Thr His Cys Lys Trp
    290                 295                 300
Glu Lys Ser Thr Phe Glu Tyr Gly Val Phe Lys His Ala Gln Phe Thr
305                 310                 315                 320
Asp Asn Ala Leu Asp Asn Cys Leu Ile Asn His Ser Asp Phe Ser Leu
                325                 330                 335
Gly Thr Phe Asp His Cys Thr Leu Asn Gly Cys Phe Phe Ser Glu Thr
            340                 345                 350
His Cys Asp Gln Thr Gln Phe Asn Gln Val Ile Ile Thr Ser Cys Ile
        355                 360                 365
Phe Glu Lys Cys Asp Gly Pro Lys Ala Cys Phe Thr Glu Ser Thr Ile
    370                 375                 380
Glu Lys Thr Ser Phe Ile Ser Ser Ser Trp Val Gly Gly Arg Leu Ser
385                 390                 395                 400
His Cys Tyr Leu Asn Ser Leu Thr Thr Gly Leu Asn Thr Asn Leu Ser
                405                 410                 415
Glu Ser His Phe Glu Gln Cys Ser Leu Asn Lys Met Gly Phe Leu Lys
            420                 425                 430
Val Asn Leu Gln Ser Ser Thr Phe Ile Asn Cys Ser Met Leu Glu Ser
        435                 440                 445
```

Cys Cys Asp Lys Ala Asp Phe Ser Gln Ala Thr Leu Ile Ala Cys Asp
            450                 455                 460

Met Thr Ala Val Arg Leu Lys Asp Ala Asn Leu Val His Ser His Trp
465                 470                 475                 480

Gln Asn Thr Ser Leu Gln Gln Ser Met Phe Tyr Asn Ala Asp Leu Arg
                485                 490                 495

Asp Ala Thr Phe Gln Arg Cys Asn Leu Ala Gly Ala Asn Leu Ala Met
            500                 505                 510

Ile Ser Gln Asn Met Asp Thr Arg Phe Glu His Cys Leu Thr Glu Lys
            515                 520                 525

Thr His Trp Ile Pro Arg Arg Tyr Thr Val Pro Ala
            530                 535                 540

<210> SEQ ID NO 85
<211> LENGTH: 187
<212> TYPE: PRT
<213> ORGANISM: Yersinia pestis

<400> SEQUENCE: 85

Met Ser Lys Thr Arg Arg Trp Ile Thr Leu Val Leu Ala Leu Ile Ala
1               5                   10                  15

Leu Ala Leu Ile Gly Trp Asn Met Ser Gly Phe Asn Gln Gln Gly Ala
            20                  25                  30

Pro Val Val Ala Asp Asp Asn Glu Pro Ser Gln Ser Gln His Thr
        35                  40                  45

Val Thr Thr Val Phe Asn Pro Val Gly Gln Leu Asn Tyr Lys Leu Val
    50                  55                  60

Ala Glu Glu Val Gln Asn Phe Ser Ala Lys Glu Leu Thr Trp Phe Thr
65                  70                  75                  80

Lys Pro Val Met Thr Leu Phe Gly Asp Asn Ala Val Ala Thr Trp Thr
                85                  90                  95

Val Arg Ala Asp Arg Ala Lys Leu Thr Asp Asp Lys Met Leu Tyr Leu
            100                 105                 110

Tyr Gly His Val Glu Val Asp Ser Leu Thr Ala Asp Ala Gln Leu Lys
        115                 120                 125

Lys Ile Arg Thr Asp Asn Ala Gln Val Asn Leu Ile Thr Gln Asp Val
    130                 135                 140

Ala Ser Asp Asp Glu Val Thr Leu Phe Gly Ile Gly Phe Thr Ser Glu
145                 150                 155                 160

Gly Met Arg Ile Arg Gly Asn Leu Arg Asp Lys Thr Ala Glu Leu Ile
                165                 170                 175

Glu Lys Val Lys Thr Ser Tyr Glu Ile Gln Lys
            180                 185

<210> SEQ ID NO 86
<211> LENGTH: 328
<212> TYPE: PRT
<213> ORGANISM: Yersinia pestis

<400> SEQUENCE: 86

Met Met Gln Thr Ile Leu Asn Lys Ile Gly Arg Ile Gly Gly Cys Ile
1               5                   10                  15

Ala Leu Ser Phe Val Ala Met Leu Leu Ser Gln Ala Ala Tyr Ala Leu
            20                  25                  30

Asp Cys Val Glu Lys Gly Thr Asn Val Val Asn Lys Pro Gly Ile Pro
        35                  40                  45

```
Ile Gly Gln Leu Ala Ile Pro Ser Asn Ile Ala Pro Gly Thr Lys Ile
 50                  55                  60

Trp Glu Ser Arg Asp Ile Thr Val Thr Ala Tyr Cys Asp Asn Val Leu
 65                  70                  75                  80

Gly Ser Val Tyr Asp Gln Val Trp Phe Tyr Phe Asn Pro Leu Gly Gln
                 85                  90                  95

Ser Leu Gly Pro Gly Leu Gln Leu Gly Val Asn Tyr Leu Gly Gln Asp
            100                 105                 110

Leu Gln Ala Asn Ala Ala Arg Leu Asn Thr Asn Thr Ser Pro Ile Thr
        115                 120                 125

Ser Gly Gln Asn Val Thr Val Thr Val Thr Phe Arg Leu Tyr Ile Lys
    130                 135                 140

Val Thr Asn Asp Leu Pro Ser Ser Gly Asn Tyr Ile Gly Thr Asp Ser
145                 150                 155                 160

Phe Thr Val Phe Gln Leu Asp Gly Ser Gly Gly Ile Asn Val Thr Ala
                165                 170                 175

Gly Ala Lys Asn Leu Lys Tyr Thr Leu Ser Gly Leu Ser Ile Val Arg
            180                 185                 190

Phe Ile Pro Cys Gly Ala Asp Leu Val Ile Ser Pro Ala Ser Gln Val
        195                 200                 205

Val Asn Phe Gly Ser Phe Asn Gln Ala Arg Leu Leu Ser Ser Asn Asn
    210                 215                 220

Asn Leu Ser Arg Pro Phe Ser Ile Thr Ala Ile Lys Gln Gly Cys Leu
225                 230                 235                 240

Ala Asn Phe Ser Ile Gln Ala Gln Phe Leu Thr Ala Asn Pro Leu Val
                245                 250                 255

Gly Asp Asn Ala Ile Asp Leu Gln Asn Gly Ile Lys Leu Thr Ile Tyr
            260                 265                 270

Asp Asp Lys Asn Gln Ala Ile Val Tyr Asn Arg Tyr Ala Asp Phe Ala
        275                 280                 285

Gln Leu Asn Asn Ile Thr Gln Val Thr Arg Asn Tyr Thr Ala Arg Leu
    290                 295                 300

Asn Ala Ile Glu Gly Gln Pro Ile Lys Leu Gly Gln Phe Asp Ala Thr
305                 310                 315                 320

Ala Ile Ile Lys Ile Asn Tyr Tyr
                325

<210> SEQ ID NO 87
<211> LENGTH: 277
<212> TYPE: PRT
<213> ORGANISM: Yersinia pestis

<400> SEQUENCE: 87

Met Arg Tyr Trp Gly Lys Leu Leu Gly Leu Val Leu Gly Val Met Tyr
 1               5                  10                  15

Ala Pro Gly Val Val Gly Ala Leu Leu Gly Leu Leu Val Gly His Met
                 20                  25                  30

Val Asp Arg Ala Leu Gly Ala Lys Arg Arg Gly Phe Phe Ala Asp Gln
             35                  40                  45

Gln Thr Arg Gln Ser Leu Phe Phe Arg Thr Thr Phe Gln Val Met Gly
         50                  55                  60

His Leu Thr Lys Ala Lys Gly Arg Val Thr Glu Val Asp Ile Gln Leu
 65                  70                  75                  80

Ala Ser Gln Leu Met Asp Arg Met Gln Leu His Gly Ala Ala Arg Thr
                 85                  90                  95
```

```
Ala Ala Gln Gln Ala Phe Arg Glu Gly Lys Glu Ser His Phe Pro Leu
            100                 105                 110

Arg Lys Ala Leu Gln Glu Phe Arg Arg Val Cys Phe Gly Arg Phe Asp
        115                 120                 125

Leu Ile Arg Ile Phe Leu Glu Ile Gln Leu Gln Ala Ala Phe Ala Asp
    130                 135                 140

Gly Ser Leu His Pro Asn Glu Arg Gln Val Leu Tyr Val Ile Ala Glu
145                 150                 155                 160

Glu Leu Gly Ile Ser Arg Gly Gln Phe Asp Gln Phe Leu Arg Met Phe
                165                 170                 175

Asp Gly Gly Arg Gln Phe Gly Gly His Gly Gly Trp Gln Gly Gln Gln
            180                 185                 190

Gly Gly Tyr Ser Gln Ser Gly Tyr Gln Arg Ala Ser Gln Gly Pro Thr
        195                 200                 205

Leu Glu Asp Ala Cys Lys Val Leu Gly Val Asn Ser Ser Asp Asp Ser
    210                 215                 220

Val Ala Ile Lys Arg Ala Tyr Arg Lys Leu Met Gly Glu His His Pro
225                 230                 235                 240

Asp Lys Leu Val Ala Lys Gly Leu Pro Pro Glu Met Met Glu Met Ala
                245                 250                 255

Lys Gln Lys Ala Gln Glu Ile Gln Ala Ala Tyr Asp Leu Ile Lys Arg
            260                 265                 270

Glu Lys Gly Phe Lys
        275

<210> SEQ ID NO 88
<211> LENGTH: 388
<212> TYPE: PRT
<213> ORGANISM: Yersinia pestis

<400> SEQUENCE: 88

Met Asp Lys Arg Leu Leu Lys Arg Leu Ser Ala Pro Leu Leu Ala Ala
1               5                   10                  15

Ala Leu Trp Thr Ile Pro Leu His Ser His Ala Asp Thr Gln Pro Leu
            20                  25                  30

Thr Ser Gln Asp Thr Lys Leu Leu Thr Ser Gln Ile Val Asp Gln Tyr
        35                  40                  45

Ala Glu His Ile Phe Tyr Asn Ser Gly Ala Val Gly Met Ala Leu Val
    50                  55                  60

Val Ile Asp Asn Asn Gln Val Val Asn Arg Ser Phe Gly Glu Thr Gln
65                  70                  75                  80

Pro Gly Asn Asn Ile Arg Pro Arg Pro Asp Ser Leu Ile Arg Ile Ala
                85                  90                  95

Ser Ile Thr Lys Leu Met Thr Ser Glu Ile Met Val Lys Leu Ala Asp
            100                 105                 110

Asp Gly Ile Val Lys Leu Thr Asp Pro Leu Lys Lys Tyr Ala Pro Lys
        115                 120                 125

Gly Val Asn Val Pro Ser Tyr Ser Ala Lys Gln Pro Ile Arg Leu Leu
    130                 135                 140

His Leu Ala Ser His Thr Ser Gly Leu Pro Arg Glu Gln Pro Gly Gly
145                 150                 155                 160

Pro Gln Lys Arg Pro Val Phe Thr Trp Pro Thr Lys Asp Asn Arg Trp
                165                 170                 175

Gln Trp Leu Lys Leu Ala Lys Val Thr Val Pro Pro Gly Val Lys Ala
```

```
                180               185               190
Ala Tyr Ser Asn Leu Ala Tyr Asp Leu Leu Ala Asp Ala Leu Ser Arg
                    195               200               205

Ala Ala Gly Lys Pro Tyr Ala His Leu Leu Arg Asp Lys Ile Thr Ala
        210               215               220

Pro Leu Gly Met Lys Asn Thr Thr Leu Thr Pro Thr Ala Glu Gln Cys
225             230               235               240

Lys Arg Leu Met Ile Gly Val Gly Ser Ser Arg Cys Gly Asn Thr Val
                245               250               255

Ala Ala Ala Gly Ser Gly Gly Ile Tyr Ser Thr Pro Glu Asp Met Gln
            260               265               270

His Trp Met Gln Gln Phe Leu Ala Ser Asp Asn Ser Ala Pro Lys Arg
        275               280               285

Ser Ala Lys Arg Glu Gln Ala Leu Tyr Phe Gln Arg Gly Asp Leu Val
    290               295               300

Ser Leu Lys Gly Met Asp Val Ala Gly Gln Ala Asp Ala Leu Gly Leu
305             310               315               320

Gly Trp Val Tyr Met Ala Pro Lys Ala Asp Leu Pro Gly Ile Met Gln
                325               330               335

Lys Thr Gly Gly Gly Gly Phe Ile Thr Tyr Met Ala Met Val Pro
            340               345               350

Glu Lys Asn Ile Gly Val Phe Val Val Thr Arg Ser Gln Leu Thr
        355               360               365

Lys Phe Ser Asn Met Ser Asp Gly Val Asn Gln Leu Val Ala Glu Leu
    370               375               380

Val Lys Asn His
385

<210> SEQ ID NO 89
<211> LENGTH: 217
<212> TYPE: PRT
<213> ORGANISM: Yersinia pestis

<400> SEQUENCE: 89

Met Lys Thr Val Gly Val Val Leu Ser Gly Cys Gly Val Leu Asp Gly
1               5                   10                  15

Ala Glu Ile His Glu Ser Val Leu Thr Met Leu Ala Leu Asp Arg Ala
                20                  25                  30

Gly Ala Glu Val Leu Phe Phe Ala Pro Asp Lys Pro Gln Leu His Val
            35                  40                  45

Ile Asn His Ile Thr Gly Glu Ile Val Ala Glu Glu Arg Asn Val Leu
        50                  55                  60

Val Glu Ser Ala Arg Ile Ala Arg Gly Leu Ile Thr Pro Leu Ser Ala
65                  70                  75                  80

Ala Asp Pro Glu Val Leu Asp Ala Leu Ile Val Pro Gly Gly Phe Gly
                85                  90                  95

Ala Ala Lys Asn Leu Cys Asp Phe Ala Ile Lys Gly Gly Glu Cys Ser
            100                 105                 110

Val Glu Pro Asp Leu Tyr Lys Leu Ile Gln Leu Met His Lys Ser Gly
        115                 120                 125

Lys Pro Ile Gly Leu Met Cys Ile Ser Pro Val Met Leu Pro Lys Leu
    130                 135                 140

Leu Gly Lys Pro Ile Arg Leu Thr Ile Gly Asn Asp Pro Asp Thr Ile
145                 150                 155                 160
```

```
Asp Ala Ile Glu Ile Met Gly Gly Glu His Val Ile Cys Pro Ala Asp
            165                 170                 175

Asp Val Val Ile Asp Leu Glu Asn Lys Val Val Thr Thr Pro Ala Tyr
            180                 185                 190

Met Leu Ala Gly Ser Ile Ser Glu Ala Ala Lys Gly Ile Asp Lys Leu
            195                 200                 205

Val Thr Lys Val Leu Asp Leu Thr Glu
            210                 215

<210> SEQ ID NO 90
<211> LENGTH: 740
<212> TYPE: PRT
<213> ORGANISM: Yersinia pestis

<400> SEQUENCE: 90

Met Thr Arg Thr Gly Lys Val Leu Val Gly Ala Ser Gly Phe Ile Leu
1               5                   10                  15

Leu Ser Leu Val Ala Val Val Ile Phe Val Ser Ser Phe Asp Trp Asn
                20                  25                  30

Arg Leu Lys Pro Thr Ile Asn Gln Lys Val Ser Ala Glu Leu Gln Arg
            35                  40                  45

Pro Phe Ala Ile Arg Gly Asn Leu Ser Val Asp Trp Ser Arg Glu Gly
        50                  55                  60

Glu Gly Pro Gly Trp Arg Gly Trp Ile Pro Trp Pro His Ile His Ala
65              70                  75                  80

Glu Asp Leu Val Leu Gly Asn Pro Thr Thr Leu Ile Ser Thr Gln Glu
                85                  90                  95

Ser Arg Asp Ala Gln Ser Ala Gln Gly Thr Pro Leu Ser Asp Ala Phe
            100                 105                 110

Pro Thr Gly Glu Met Val Thr Leu Lys Arg Ile Asp Ala Ser Leu Ala
        115                 120                 125

Pro Leu Ser Leu Leu Ser Lys Glu Val Arg Ile Pro Arg Leu Trp Leu
    130                 135                 140

Thr Gln Pro Asp Ile His Leu Gln Arg Leu Ala Asn Gly Asn Asn Asn
145                 150                 155                 160

Trp Thr Phe Asn Leu Thr Asn Thr Ser Thr Asp Ser Ala Ser Trp Ser
                165                 170                 175

Val Asp Ile Gly Asp Ile Ile Phe Asp Arg Gly Glu Ile Thr Leu Lys
            180                 185                 190

Asp Ala Ile Leu Gln Ala Asp Leu Leu Ala Val Ile Asp Pro Leu Ala
        195                 200                 205

Lys Ala Leu Pro Phe Ala Gln Val Thr Gly Val Arg Arg Gly Ala Ser
    210                 215                 220

Ile Asn Ser Val Thr Ser Thr His Ser Val Asn Thr Thr Pro Val
225                 230                 235                 240

Asn Thr Thr Thr Ala Thr Ala Thr Asn Pro Val Thr Glu Thr Val
                245                 250                 255

Lys Ser Thr Thr Pro Asp Tyr Leu Phe Gly Trp Lys Val Asp Gly Gln
            260                 265                 270

Tyr Gln Gly Gln Pro Leu Ala Gly Ser Gly Lys Ile Gly Gly Met Ile
        275                 280                 285

Ser Met Asn Asp Ala Asn Val Pro Phe Pro Leu Gln Ala Asp Met Arg
    290                 295                 300

Tyr Gly Ser Thr Leu Val Ala Val Val Gly Thr Leu Thr Asp Pro Gly
305                 310                 315                 320
```

-continued

Asn Leu Ala Gly Leu Asp Leu Gln Leu Val Leu Ser Gly Thr Ser Leu
                325                 330                 335

Asp Asn Leu Tyr Pro Leu Leu Asp Val Val Leu Pro Ala Thr Pro Pro
            340                 345                 350

Tyr Gln Thr Glu Gly His Leu Ser Ala Arg Leu Lys Gln Ala Gly Gly
        355                 360                 365

Ala Val Tyr His Tyr Glu Asn Phe Asn Gly Lys Ile Gly Asp Ser Asp
    370                 375                 380

Ile His Gly Asp Leu Thr Tyr Thr Asp Ser Gln Pro Arg Pro Lys Leu
385                 390                 395                 400

Ala Gly Gln Val Asp Ser Glu Lys Leu Arg Phe Thr Asp Leu Ala Pro
                405                 410                 415

Leu Ile Gly Ala Asp Ser Asn Gln Glu Lys Ala Leu Arg Gly Glu Arg
            420                 425                 430

Asn Arg Gln Pro Gly Asn Lys Val Leu Pro Thr Glu Thr Phe Asp Thr
        435                 440                 445

Lys Ser Trp Gly Val Met Asp Ala Asp Val Thr Tyr Thr Ala Lys Arg
    450                 455                 460

Ile Glu Arg Asp Lys Ser Leu Pro Leu Ser Asp Leu Tyr Thr His Val
465                 470                 475                 480

Val Leu Lys Glu Gly Met Leu Leu Leu Asp Pro Leu Arg Phe Gly Met
                485                 490                 495

Ala Gly Gly Asp Leu Ala Ala Thr Leu Arg Leu Asp Ser His Gln Ile
            500                 505                 510

Pro Met Asn Gly Lys Val Asp Leu His Val Arg Arg Ile Gln Leu Lys
        515                 520                 525

Ala Leu Leu Pro Gln Val Gln Ala Met Arg Ser Ser Leu Gly Arg Leu
    530                 535                 540

Ser Gly Asp Ala Ser Phe Ile Ala Ala Gly Asn Ser Val Ala Gly Leu
545                 550                 555                 560

Leu Ala Thr Ser Asn Gly Asn Val Arg Leu Leu Ser Gln Gly Gln
                565                 570                 575

Ile Ser Arg Ser Leu Met Glu Leu Leu Gly Leu Asn Val Gly Asn Tyr
            580                 585                 590

Leu Val Ala Lys Leu Phe Gly Asp Asp Thr Val Lys Ile Asn Cys Ala
        595                 600                 605

Val Ala Asp Ile Thr Leu Arg Asn Gly Val Ala Thr Pro Asn Val Phe
    610                 615                 620

Val Phe Asp Thr Glu Asn Ala Ile Ile Asn Ile Thr Gly Asn Ala Asn
625                 630                 635                 640

Phe Ala Thr Glu Arg Leu Asn Leu Ser Ile Asp Pro Glu Ser Lys Gly
                645                 650                 655

Leu Arg Ile Leu Thr Leu Arg Ser Pro Leu Tyr Val Lys Gly Thr Phe
            660                 665                 670

Lys Arg Pro Asp Val Gly Val Lys Thr Gly Ala Leu Ile Ala Arg Gly
        675                 680                 685

Ala Val Ala Ala Ala Leu Gly Val Ala Leu Thr Pro Ala Ala Ala Leu
    690                 695                 700

Leu Ala Leu Ile Ser Pro Val Lys Val Lys Val Lys Arg Ile Ser Ala
705                 710                 715                 720

Pro Arg Tyr Cys Glu Lys Tyr Ser Lys Arg Asn Asn Val Leu Leu His
                725                 730                 735

```
-continued

Arg Glu Val Arg
            740

<210> SEQ ID NO 91
<211> LENGTH: 179
<212> TYPE: PRT
<213> ORGANISM: Yersinia pestis

<400> SEQUENCE: 91

Met Lys Trp Ile Thr Thr Leu Ala Pro Leu Ser Leu Ala Leu Ser Leu
1               5                   10                  15

Gly Ile Ser Val Ala Asn Ala Ala Ser Asp Ala Ser Asn Thr Val Ser
            20                  25                  30

Phe Gly Tyr Ala Gln Ser Thr Leu Lys Ile Asp Gly Glu Lys Ile Gly
        35                  40                  45

Lys Asp Asn Lys Gly Phe Asn Leu Lys Tyr Arg His Glu Leu Asp Ser
    50                  55                  60

Val Leu Gly Ile Val Ala Ser Phe Thr His Thr Lys Gln Asn Tyr Gly
65                  70                  75                  80

Met Pro Gly Asp Ser Asp Gly Lys Arg Lys Val Glu Tyr Tyr Ser Leu
                85                  90                  95

Met Val Gly Pro Ser Trp Arg Phe Asn Glu Phe Val Ser Ala Tyr Ala
                100                 105                 110

Leu Ile Gly Ala Thr Gln Gly Lys Ser Thr His Thr Lys Pro Arg Met
            115                 120                 125

Val Ser Asn Thr Val Ser Lys Thr Ser Met Gly Tyr Gly Ala Gly Leu
        130                 135                 140

Gln Phe Asn Pro Val Lys His Val Ala Ile Asp Thr Ala Tyr Glu Tyr
145                 150                 155                 160

Ala Lys Ile Glu Asp Val Lys Ile Gly Thr Trp Ile Val Gly Val Gly
                165                 170                 175

Tyr Arg Phe
```

COMPOSITIONS COMPRISING *YERSINIA PESTIS* ANTIGENS

GOVERNMENT SUPPORT

The invention was supported, in whole or in part, by Grant No. 1U01 AI56513-01 from the US National Institute of Allergy and Infectious Diseases. The US Government may have certain rights in the invention.

All documents cited herein are incorporated by reference in their entirety.

TECHNICAL FIELD

This invention is in the fields of immunology and vaccinology. In particular, it relates to antigens derived from *Yersinia pestis* and their use in immunisation.

BACKGROUND ART

There are three recognised forms of plague in man: bubonic, septicaemic and pneumonic. All are caused by the *Yersinia pestis* bacterium, which has also been known as *Pasteurella pestis*, *Bacterium pestis* and *Pestisella pestis*. *Y. pestis* is endemic on every continent in the world except Australia [1], and results in around 1700 cases of plague a year. It is a Gram-negative non-motile aerobic *bacillus*.

Bubonic plague is the most common form of disease and arises following a bite from a flea which has fed previously on an infected animal. From the initial site of infection the bacteria are disseminated to the draining lymph nodes, which become swollen and tender to form buboes.

Septicaemic plague occurs when there is bacteremia without the development of buboes and is characterised by an elevated temperature, chills, headache, malaise and gastrointestinal disturbances. Because of the generalised nature of these symptoms a diagnosis of plague is often delayed, and even with medical intervention 50% of patients die, probably as a result of the induction of the systemic inflammatory response syndrome.

The most feared form of plague arises when there is colonisation of the alveolar spaces leading to a pneumonia, causing the pneumonic plague. Pneumonic plague is transmitted by airborne droplets containing bacteria, generated by coughing, which can be inhaled by susceptible individuals. The pneumonic form of the disease is feared because of the rapidity with which the disease develops (1-3 days), the high mortality rate in infected individuals (about 100%) and the rapid spread of disease from man to man.

Due to the high infectivity and mortality of pneumonic plague, *Y. pestis* is considered to be a likely biological threat agent [2].

The only plague vaccine licensed in the United States is the 'USP vaccine', a preparation of formaldehyde-killed *Y. pestis*, but it is no longer produced. This vaccine relies on the F1 capsular protein as the main immunogen. While it has been shown to be effective against subcutaneous challenge, it is not effective against aerosol challenge [3], and unpleasant side effects have been reported. The vaccine also fails to protect against the F1⁻ variants of *Y. pestis*, which are equally virulent in rodents [4, 5] and which have been isolated from at least one fatal human case [6].

More recent studies have focused on recombinant subunit vaccines. Purified or recombinant F1 antigen may confer protection against both bubonic and pneumonic plague [7], as may the V antigen [8]. The V antigen is found on the cell surface and is involved in induction of IL-10 synthesis, which contributes to the block of macrophage activation necessary for successful *Y. pestis* virulence [1]. Recombinant V antigen has been shown to confer protection against parenteral and aerosol challenge by both F1$^+$ and F1$^-$ strains [8]. A fully-recombinant subunit vaccine containing both the F1 and V antigens has been formulated either with cholera toxin for transcutaneous and intradermal immunisation [9]. Three immunisations with this vaccine protected animals from a low dose injected challenge with virulent *Y. pestis*. The same F1/V combination has been adjuvanted with aluminium hydroxide, and confers good protection against aerosol challenge in mouse strains of different genetic background [10]. Importantly, protection was achieved after a single dose of this vaccine although the dose required was high and protective antibody titers against the V antigen required more than two months to develop [11]. For safe use in humans, reference 12 suggests that the V antigen should be altered to delete amino acid residues 271 to 300 in order to reduce immune-modulatory properties.

These studies indicate that development of an efficacious subunit vaccine based on recombinant *Y. pestis* proteins for use in man is feasible.

While the F1 and V antigens are promising candidates for inclusion in a prophylactic vaccine, these are the only known protective antigens against this pathogen and it is unclear if these antigens alone will afford sufficient protection in humans, or whether they would be useful in immunotherapeutic vaccines. Indeed, variability in the response to F1 in humans has been reported [13]. Reference 14 suggests that an optimal vaccine against plague should include essential virulence factors as immunogens in addition to F1. Furthermore, naturally occurring F1$^-$ strains appear to be equally virulent and with current technology it is straightforward to engineer such a strain [5], thereby bypassing any F1-based immunity. In addition, substitution of the LcrV gene in *Y. pestis* with that of *Y. pseudotuberculosis* or *Y. enterocoliticus* is a worry, as there is little cross protection between these different species [15]. A bivalent F1/V vaccine is therefore inadequate for use against bioterrorism.

Thus there remains a need to identify alternatives to the F1 and V antigens for use in immunising against *Yersinia*, and in particular for developing of a broadly-protective multivalent vaccine against all potential variant and engineered strains [2].

DISCLOSURE OF THE INVENTION

The inventors believe that an effective *Y. pestis* vaccine will require several antigenic components, and that these components may or may not include the F1 or V antigens.

With this in mind, they have identified various surface-exposed *Y. pestis* antigens that are particularly suitable for immunisation purposes, particularly when used in combinations. Although the existence of these proteins has been postulated, based on the publication of genome sequences in references 16 (virulent strain CO92), 17 (virulent strain KIM) and 18 (avirulent strain 91001), their immunogenic use has not been disclosed. The antigens are exposed on the bacterial surface and have been identified using "surface shaving" techniques or by detecting proteins that were labelled in situ on the cell surface *Y. pestis* proteins (e.g., by biotinylation).

Thus the invention provides a composition comprising a combination of *Y. pestis* antigens, said combination comprising two or more (i.e. 2, or all 3) *Y. pestis* antigens selected from the group consisting of: (1) a YPO0512 antigen; (2) a YPO0563 antigen; and (3) a YPO3489 antigen. These three antigens form the "first antigen group".

The invention also provides a composition comprising a combination of *Y. pestis* antigens, said combination comprising two or more (i.e. 2, 3, 4 or all 5) *Y. pestis* antigens selected from the group consisting of: (1) a YPO0512 antigen; (2) a YPO0563 antigen; (3) a YPO3489 antigen; (4) a YPO4003 antigen; and (5) a YPO1604 antigen. These five antigens form the "second antigen group", which includes the three antigens of the first antigen group.

The invention also provides a composition comprising a combination of *Y. pestis* antigens, said combination comprising one or more (i.e. 1, 2, 3, 4, 5, 6, 7, 8, 9, 10, 11, 12, 13, 14, 15, 16, 17, 18, 19, 20, or all 21) *Y. pestis* antigens from the group consisting of: (1) a YPO0512 antigen; (2) a YPO0563 antigen; (3) a YPO3489 antigen; (4) a YPO4003 antigen; (5) a YPO1604 antigen; (6) a YPO3061 antigen; (7) a YPO3559 antigen; (8) a YPO3382 antigen; (9) a YPO0860 antigen; (10) a YPO0086 antigen; (11) a YPO3631 antigen; (12) a YPO2881 antigen; (13) a YPO3343 antigen; (14) a YPO3361 antigen; (15) a YPO3430 antigen; (16) a YPO1411 antigen; (17) a YPO3935 antigen; (18) a YPO0809 antigen; (19) a YPO1123 antigen; (20) a YPO3065 antigen; and (21) a YPO1070 antigen. These 21 antigens form the "third antigen group", which includes the five antigens from the second antigen group.

The invention also provides a composition comprising a combination of *Y. pestis* antigens, said combination comprising one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens from the group consisting of: (1) a YPO0102 antigen; (2) a YPO0570 antigen; (3) a YPO1053 antigen; (4) a YPO1435 antigen; (5) a YPO2674 antigen; (6) a YPO2292 antigen; (7) a YPO3050 antigen; (8) a YPO2615 antigen; (9) a YPO1507 antigen; (10) a YPO4111 antigen; (11) a YPO0015 antigen; (12) a YPO0195 antigen; (13) a YPO2342 antigen; (14) a YPO0501 antigen; (15) a YPO0502 antigen; (16) a YPO0819 antigen; (17) a YPO3644 antigen; (18) a YPO1746 antigen; (19) a YPO0351 antigen; (20) a YPO0468 antigen; (21) a YPO0203 antigen; (22) a YPO0216 antigen; (23) a YPO3536 antigen; (24) a YPO0233 antigen; (25) a YPO0067 antigen; (26) a YPO3643 antigen; (27) a YPO3375 antigen; (28) a YPO0494 antigen; (29) a YPO1052 antigen; (30) a YPO1906 antigen; (31) a YPO0663 antigen; (32) a YPO1222 antigen; (33) a YPO2905 antigen; (34) a YPO4070 antigen; (35) a YPPCP1.07 antigen; and (36) a YPMT1.42 antigen. These 36 antigens form the "fourth antigen group", which does not overlap with the first, second or third antigen groups.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group) and one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens of the fourth antigen group.

The immunogenicity of other *Y. pestis* antigens of known and unknown biological function may be improved by combination with one or more *Y. pestis* antigens from either the first antigen group and/or the second and/or the third antigen group and/or the fourth antigen group. Such other *Y. pestis* antigens of known and unknown biological function include a F1 antigen and/or a V antigen. These two antigens form the "fifth antigen group".

Thus the invention provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group) and one or two *Y. pestis* antigens from the fifth antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens selected from the fourth antigen group and one or two *Y. pestis* antigens from the fifth antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group), one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens selected from the fourth antigen group, and one or two *Y. pestis* antigens from the fifth antigen group.

The invention also provides a composition comprising a combination of *Y. pestis* antigens, said combination comprising one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens from the group consisting of: (1) a YPO0457 antigen; (2) a YPO0514 antigen; (3) a YPO0694 antigen; (4) a YPO0805 antigen; (5) a YPO0982 antigen; (6) a YPO1354 antigen; (7) a YPO1408 antigen; (8) a YPO1792 antigen; (9) a YPO2506 antigen; (10) a YPO2713 antigen; (11) a YPO2950 antigen; (12) a YPO3026 antigen; (13) a YPO3417 antigen; (14) a YPO3551 antigen; (15) a YPO3646 antigen; (16) a YPO3982 antigen; (17) a YPO0065 antigen; (18) a YPO0499 antigen; (19) a YPO0505 antigen; (20) a YPO0500 antigen; (21) a YPO0503 antigen; (22) a YPO0506 antigen; (23) a YPO0508 antigen; (24) a YPO0509 antigen; (25) a YPO3579 antigen and (26) a YPO4040 antigen. These 26 antigens form the "sixth antigen group", which does not overlap with the first, second, third, fourth or fifth antigen groups.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21) *Y. pestis* antigens selected from the third antigen group (preferably comprising an antigen from the second group, and more preferably from the first antigen group) and one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens of the sixth antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens of the fourth antigen group and one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens of the sixth antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens selected from the sixth antigen group and one or two *Y. pestis* antigens from the fifth antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group), one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens selected from the fourth antigen group, one or two *Y. pestis* antigens from the fifth antigen group, and one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens selected from the sixth antigen group.

The invention also provides a composition comprising a combination of *Y. pestis* antigens, said combination comprising one or more (i.e. 1, 2, 3, 4 or all 5) *Y. pestis* antigens from the group consisting of: (1) a YPO0496 antigen; (2) a YPO1224 antigen; (3) a YPO3553 antigen; (4) a YPO3987 antigen; and (5) a YPO2190 antigen. These 5 antigens form the "seventh antigen group", which does not overlap with the first, second, third, fourth, fifth or sixth antigen groups.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group) and one or more (i.e. 1, 2, 3, 4 or all 5) *Y. pestis* antigens of the seventh antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens selected from the fourth antigen group and one or more (i.e. 1, 2, 3, 4 or all 5) *Y. pestis* antigens of the seventh antigen group.

The invention also provides a composition comprising a combination of *Y. pestis* antigens, said combination including one or two *Y. pestis* antigens selected from the fifth antigen group and one or more (i.e. 1, 2, 3, 4 or all 5) *Y. pestis* antigens of the seventh antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens selected from the sixth antigen group and one or more (i.e. 1, 2, 3, 4 or all 5) *Y. pestis* antigens of the seventh antigen group.

The invention also provides a composition comprising a combination of *Y. pestis* antigens, said combination including one or more (i.e. 1, 2, 3, 4, 5, 6, 7, 8, 9, 10, 11, 12, 13, 14, 15, 16, 17, 18, 19, 20, or all 21) *Y. pestis* antigens selected from the third antigen group (preferably comprising an antigen from the second group, and more preferably from the first antigen group), one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36) *Y. pestis* antigens selected from the fourth antigen group, one or two *Y. pestis* antigens from the fifth antigen group, one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Y. pestis* antigens selected from the sixth antigen group and one or more (i.e. 1, 2, 3, 4 or all 5) *Y. pestis* antigens of the seventh antigen group. The invention also provides a composition comprising a combination of *Y. pestis* antigens, said combination comprising a antigens from the third antigen group, b antigens from the fourth antigen group, and c antigens from the fifth antigen group, wherein: a is selected from 0, 1, 2, 3, 4, 5, 6, 7, 8, 9, 10, 11, 12, 13, 14, 15, 16, 17, 18, 19, 20 or 21; b is selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36; and c is selected from 0, 1 or 2; provided that a+b+c is at least 2 (e.g. 2, 3, 4, 5, 6, 7, 8, 9, 10, or more). Preferably a is not 0. Preferably c is not 0.

Such a composition may optionally comprise d antigens from the sixth antigen group, wherein d is selected from 0, 1, 2, 3, 4, 5, 6, 7, 8, 9, 10, 11, 12, 13, 14, 15, 16, 17, 18, 19, 20, 21, 22, 23, 24, 25 or 26; provided that a+b+c+d is at least 2 (e.g. 2, 3, 4, 5, 6, 7, 8, 9, 10, or more). Preferably a is not 0. Preferably c is not 0.

Such compositions may optionally comprise e antigens from the seventh antigen group, wherein e is selected from 0, 1, 2, 3, 4 or 5; provided that a+b+c+d+e is at least 2 (e.g. 2, 3, 4, 5, 6, 7, 8, 9, 10, or more). Preferably a is not 0. Preferably c is not 0.

The above compositions may also include further *Y. pestis* antigens that are not members of any of the first, second, third, fourth, fifth or sixth antigen groups. For example, the compositions may include a pesticin (YPPCP1.05c), a W antigen, a pH 6 antigen (YPO1303), a Fe or Mn superoxide dismutase (Fe YPO2386; Mn YPO4061), a YOP antigen (e.g. YPCD1.34c), an iron regulated membrane protein (e.g. YPO1313), a murine toxin (YPMT1.74), a hemin storage protein (e.g. YPO0281), etc. Preferably, a composition according to the invention may further comprise an OppA antigen (YPO2182) as described in reference 19.

There is an upper limit to the number of *Y. pestis* antigens which will be found in compositions of the invention. Preferably, the number of *Y. pestis* antigens in a composition of the invention is less than 20 (e.g. less than 19, less than 18, less than 17, less than 16, less than 15, less than 14, less than 13, less than 12, less than 11, less than 10, less than 9, less than 8, less than 7, less than 6, less than 5, less than 4, or less than 3). In particular, the number of *Y. pestis* antigens in a composition of the invention is preferably less than 6, less than 5, or less than 4.

Preferred antigens selected from the third antigen group are those in the second antigen group, and preferred antigens selected from the second antigen group are those in the first antigen group.

Preferred compositions according to the invention may comprise one or more (i.e. 1, 2, 3 or all 4) of a YPO0499 antigen, a YPO1604 antigen, a YPO3489 antigen and a YPO4003 antigen.

Further preferred compositions according to the invention may comprise one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or all 31) of a YPO0065 antigen, a YPO0086 antigen, a YPO0496 antigen, a YPO0499 antigen, a YPO0501 antigen, a YPO0502 antigen, a YPO0505 antigen, a YPO0809 antigen, a YPO0860 antigen, a YPO1070 antigen, a YPO1123 antigen, a YPO1224 antigen, a YPO1411 antigen, a YPO1604 antigen, a YPO2506 antigen, a YPO2881 antigen, a YPO3935 antigen, a YPO3061 antigen, a YPO3065 antigen, a YPO3382 antigen, a YPO3489 antigen, a YPO3551 antigen, a YPO3553 antigen, a YPO3579 antigen, a YPO3631 antigen, a YPO3982 antigen, a YPO4003 antigen, a YPO3987 antigen, a YPO1354 antigen, a YPO2190 antigen and a YPO3417 antigen.

Further preferred compositions according to the invention may comprise one or more of a YPO0468 antigen (DnaK), a YPO0351 antigen (GroEL), a YPO0203 antigen (EF-Tu) and a YPO1222 antigen (OmpC). Compositions may also optionally comprise a YPO1792 antigen (FlhE).

First Antigen Group (1) YPO0512

The 'YPO0512' sequence was annotated in reference 16 as 'putative lipoprotein' (see GI:16120843). For reference purposes, the amino acid sequence of full-length YPO0512 as found in the *Y. pestis* CO92 strain is given as SEQ ID NO:1 herein. Furthermore, it is postulated that YPO0512 forms part of a Type Three Secretion System (TTSS).

Preferred YPO0512 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:1; and/or (b) that is a fragment of at least n consecutive amino acids of SEQ ID NO:1, wherein n is 7 or more (e.g. 8, 10, 12, 14, 16, 18, 20, 25, 30, 35, 40, 50, 60, 70, 80, 90, 100, 150, 200, 250 or more). These YPO0512 proteins include variants of SEQ ID NO:1. Preferred fragments of (b) comprise an epitope from SEQ ID NO:1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1. Other fragments omit one or more protein domains.

(2) YPO0563

The 'YPO0563' sequence was annotated in reference 16 as 'hypothetical protein' (see GI:16120891). For reference purposes, the amino acid sequence of full-length YPO0563 as found in the *Y. pestis* CO92 strain is given as SEQ ID NO:3 herein. This protein is postulated herein to be a putative exported protein and furthermore to be a Secretion Monitor Precursor (SecM) protein.

Preferred YPO0563 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:3; and/or (b) that is a fragment of at least n consecutive amino acids of SEQ ID NO:3, wherein n is 7 or more (e.g. 8, 10, 12, 14, 16, 18, 20, 25, 30, 35, 40, 50, 60, 70, 80, 90, 100, 150, 200, 250 or more). These YPO0563 proteins include variants of SEQ ID NO:3. Preferred fragments of (b) comprise an epitope from SEQ ID NO:3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:3. Other fragments omit one or more protein domains.

(3) YPO3489

The 'YPO3489' sequence was annotated in reference 16 as 'lipoprotein NlpI' (see GI:16123635). For reference purposes, the amino acid sequence of full-length YPO3489 as found in the *Y. pestis* CO92 strain is given as SEQ ID NO:17 herein.

Preferred YPO3489 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:17; and/or (b) that is a fragment of at least n consecutive amino acids of SEQ ID NO:17, wherein n is 7 or more (e.g. 8, 10, 12, 14, 16, 18, 20, 25, 30, 35, 40, 50, 60, 70, 80, 90, 100, 150, 200, 250 or more). These YPO3489 proteins include variants of SEQ ID NO:17. Preferred fragments of (b) comprise an epitope from SEQ ID NO:17. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:17. Other fragments omit one or more protein domains.

Second Antigen Group (4) YPO4003

The 'YPO4003' sequence was annotated in reference 16 as 'periplasmic dipeptide transport protein' (see GI:16124128), also known as dppA. For reference purposes, the amino acid sequence of full-length YPO4003 as found in the *Y. pestis* CO92 strain is given as SEQ ID NO:21 herein.

Preferred YPO4003 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:21; and/or (b) that is a fragment of at least n consecutive amino acids of SEQ ID NO:21, wherein n is 7 or more (e.g. 8, 10, 12, 14, 16, 18, 20, 25, 30, 35, 40, 50, 60, 70, 80, 90, 100, 150, 200, 250 or more). These YPO4003 proteins include variants of SEQ ID NO:21. Preferred fragments of (b) comprise an epitope from SEQ ID NO:21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:21. Other fragments omit one or more protein domains.

(5) YPO1604

The 'YPO1604' sequence was annotated in reference 16 as 'hypothetical protein' (see GI:16121872). For reference purposes, the amino acid sequence of full-length YPO1604 as found in the *Y. pestis* CO92 strain is given as SEQ ID NO:9 herein. This protein is postulated herein to be a putative exported protein.

Preferred YPO1604 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:9; and/or (b) that is a fragment of at least n consecutive amino acids of SEQ ID NO:9, wherein n is 7 or more (e.g. 8, 10, 12, 14, 16, 18, 20, 25, 30, 35, 40, 50, 60, 70, 80, 90, 100, 150, 200, 250 or more). These YPO1604 proteins include variants of SEQ ID NO:9. Preferred fragments of (b) comprise an epitope from SEQ ID NO:9. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:9. Other fragments omit one or more protein domains.

Third Antigen Group (6) YPO3061

The 'YPO3061' sequence was annotated in reference 16 as 'lipoprotein' (see GI:16123238), also known as nlpB. For reference purposes, the amino acid sequence of full-length YPO3061 as found in the *Y. pestis* CO92 strain is given as SEQ ID NO:11 herein.

Preferred YPO3061 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:11; and/or (b) that is a fragment of at least n consecutive amino acids of SEQ ID NO:11, wherein n is 7 or more (e.g. 8, 10, 12, 14, 16, 18, 20, 25, 30, 35, 40, 50, 60, 70, 80, 90, 100, 150, 200, 250 or more). These YPO3061 proteins include variants of SEQ ID NO:11. Preferred fragments of (b) comprise an epitope from SEQ ID NO:11. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:11. Other fragments omit one or more protein domains.

(7) YPO3559

The 'YPO3559' sequence was annotated in reference 16 as 'hypothetical protein' (see GI:16123703). For reference purposes, the amino acid sequence of full-length YPO3559 as found in the *Y. pestis* CO92 strain is given as SEQ ID NO:18 herein.

Preferred YPO3559 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:18; and/or (b) that is a fragment of at least n consecutive amino acids of SEQ ID NO:18, wherein n is 7 or more (e.g. 8, 10, 12, 14, 16, 18, 20, 25, 30, 35, 40, 50, 60, 70, 80, 90, 100, 150, 200, 250 or more). These YPO3559 proteins include variants of SEQ ID NO:18. Preferred fragments of (b) comprise an epitope from SEQ ID NO:18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:18. Other fragments omit one or more protein domains.

(8) YPO3382

The 'YPO3382' sequence was annotated in reference 16 as 'global stress requirement protein GsrA' (see GI:16123531), also known as htrA or degP. For reference purposes, the amino acid sequence of full-length YPO3382 as found in the *Y. pestis* CO92 strain is given as SEQ ID NO:15 herein.

Preferred YPO3382 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:15; and/or (b) that is a fragment of at least n consecutive amino acids of SEQ ID NO:15, wherein n is 7 or more (e.g. 8, 10, 12, 14, 16, 18, 20, 25, 30, 35, 40, 50, 60, 70, 80, 90, 100, 150, 200, 250 or more). These YPO3382 proteins include variants of SEQ ID NO:15. Preferred fragments of (b) comprise an epitope from SEQ ID NO:15. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:15. Other fragments omit one or more protein domains.

(9) YPO0860

The 'YPO0860' sequence was annotated in reference 16 as 'sugar-binding periplasmic protein' (see GI:16121168). For reference purposes, the amino acid sequence of full-length YPO0860 as found in the *Y. pestis* CO92 strain is given as SEQ ID NO:5 herein.

Preferred YPO0860 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:5; and/or (b) that is a fragment of at least n consecutive amino acids of SEQ ID NO:5, wherein n is 7 or more (e.g. 8, 10, 12, 14, 16, 18, 20, 25, 30, 35, 40, 50, 60, 70, 80, 90, 100, 150, 200, 250 or more). These YPO0860 proteins include variants of SEQ ID NO:5. Preferred fragments of (b) comprise an epitope from SEQ ID NO:5. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:5. Other fragments omit one or more protein domains.

(10) YPO0086

The 'YPO0086' sequence was annotated in reference 16 as 'hypothetical protein' (see GI:16120437). For reference purposes, the amino acid sequence of full-length YPO0086 as found in the *Y. pestis* CO92 strain is given as SEQ ID NO:2 herein. This protein is postulated herein to be a putative exported protein.

Preferred YPO0086 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:2; and/or (b) that is a fragment of at least n consecutive amino acids of SEQ ID NO:2, wherein n is 7 or more (e.g. 8, 10, 12, 14, 16, 18, 20, 25, 30, 35, 40, 50, 60, 70, 80, 90, 100, 150, 200, 250 or more). These YPO0086 proteins include variants of SEQ ID NO:2. Preferred fragments of (b) comprise an epitope from SEQ ID NO:2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:2. Other fragments omit one or more protein domains.

(11) YPO3631

The 'YPO3631' sequence was annotated in reference 16 as 'hypothetical protein' (see GI:16123773). For reference purposes, the amino acid sequence of full-length YPO3631 as found in the *Y. pestis* CO92 strain is given as SEQ ID NO:19 herein. This protein is postulated herein to be a putative exported protein.

Preferred YPO3631 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:19; and/or (b) that is a fragment of at least n consecutive amino acids of SEQ ID NO:19, wherein n is 7 or more (e.g. 8, 10, 12, 14, 16, 18, 20, 25, 30, 35, 40, 50, 60, 70, 80, 90, 100, 150, 200, 250 or more). These YPO3631 proteins include variants of SEQ ID NO:19. Preferred fragments of (b) comprise an epitope from SEQ ID NO:19. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:19. Other fragments omit one or more protein domains.

(12) YPO2881

The 'YPO2881' sequence was annotated in reference 16 as 'putative fimbrial biogenesis protein' (see GI:16123073). For reference purposes, the amino acid sequence of full-length YPO2881 as found in the *Y. pestis* CO92 strain is given as SEQ ID NO:10 herein.

Preferred YPO2881 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:10; and/or (b) that is a fragment of at least n consecutive amino acids of SEQ ID NO:10, wherein n is 7 or more (e.g. 8, 10, 12, 14, 16, 18, 20, 25, 30, 35, 40, 50, 60, 70, 80, 90, 100, 150, 200, 250 or more). These YPO2881 proteins include variants of SEQ ID NO:10. Preferred fragments of (b) comprise an epitope from SEQ ID NO:10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:10. Other fragments omit one or more protein domains.

(13) YPO3343

The 'YPO3343' sequence was annotated in reference 16 as 'probable extracellular solute-binding protein' (see GI:16123493). For reference purposes, the amino acid sequence of full-length YPO3343 as found in the *Y. pestis* CO92 strain is given as SEQ ID NO:13 herein.

Preferred YPO3343 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:13; and/or (b) that is a fragment of at least n consecutive amino acids of SEQ ID NO:13, wherein n is 7 or more (e.g. 8, 10, 12, 14, 16, 18, 20, 25, 30, 35, 40, 50, 60, 70, 80, 90, 100, 150, 200, 250 or more). These YPO3343 proteins include variants of SEQ ID NO: 13. Preferred fragments of (b) comprise an epitope from SEQ ID NO:13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13. Other fragments omit one or more protein domains.

(14) YPO3361

The 'YPO3361' sequence was annotated in reference 16 as '4-diphosphocytidyl-2C-methyl-D-erythritol synthase' (see GI:16123511). For reference purposes, the amino acid sequence of full-length YPO3361 as found in the *Y. pestis* CO92 strain is given as SEQ ID NO:14 herein.

Preferred YPO3361 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:14; and/or (b) that is a fragment of at least n consecutive amino acids of SEQ ID NO:14, wherein n is 7 or more (e.g. 8, 10, 12, 14, 16, 18, 20, 25, 30, 35, 40, 50, 60, 70, 80, 90, 100, 150, 200, 250 or more). These YPO3361 proteins include variants of SEQ ID NO:14. Preferred fragments of (b) comprise an epitope from SEQ ID NO:14. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:14. Other fragments omit one or more protein domains.

(15) YPO3430

The 'YPO3430' sequence was annotated in reference 16 as 'hypothetical protein' (see GI:16123579). For reference purposes, the amino acid sequence of full-length YPO3430 as found in the *Y. pestis* CO92 strain is given as SEQ ID NO:16 herein.

Preferred YPO3430 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:16; and/or (b) that is a fragment of at least n consecutive amino acids of SEQ ID NO:16, wherein n is 7 or more (e.g. 8, 10, 12, 14, 16, 18, 20, 25, 30, 35, 40, 50, 60, 70, 80, 90, 100, 150, 200, 250 or more). These YPO3430 proteins include variants of SEQ ID NO:16. Preferred fragments of (b) comprise an epitope from SEQ ID NO:16. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:16. Other fragments omit one or more protein domains.

(16) YPO1411

The 'YPO1411' sequence was annotated in reference 16 as 'putative outer membrane porin C protein' (see GI:16121691). For reference purposes, the amino acid sequence of full-length YPO1411 as found in the *Y. pestis* CO92 strain is given as SEQ ID NO:8 herein.

Preferred YPO1411 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:8; and/or (b) that is a fragment of at least n consecutive amino acids of SEQ ID NO:8, wherein n is 7 or more (e.g. 8, 10, 12, 14, 16, 18, 20, 25, 30, 35, 40, 50, 60, 70, 80, 90, 100, 150, 200, 250 or more). These YPO1411 proteins include variants of SEQ ID NO:8. Preferred fragments of (b) comprise an epitope from SEQ ID NO:8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:8. Other fragments omit one or more protein domains.

(17) YPO3935

The 'YPO3935' sequence was annotated in reference 16 as 'membrane protein' (see GI:16124063). For reference purposes, the amino acid sequence of full-length YPO3935 as found in the *Y. pestis* CO92 strain is given as SEQ ID NO:20 herein.

Preferred YPO3935 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:20; and/or (b) that is a fragment of at least n consecutive amino acids of SEQ ID NO:20, wherein n is 7 or more (e.g. 8, 10, 12, 14, 16, 18, 20, 25, 30, 35, 40, 50, 60, 70, 80, 90, 100, 150, 200, 250 or more). These YPO3935 proteins include variants of SEQ ID NO:20. Preferred fragments of (b) comprise an epitope from SEQ ID NO:20. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:20. Other fragments omit one or more protein domains.

(18) YPO0809

The 'YPO0809' sequence was annotated in reference 16 as 'general secretion pathway protein K' (see GI:16121121). For reference purposes, the amino acid sequence of full-length YPO0809 as found in the *Y. pestis* CO92 strain is given as SEQ ID NO:4 herein.

Preferred YPO0809 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:4; and/or (b) that is a fragment of at least n consecutive amino acids of SEQ ID NO:4, wherein n is 7 or more (e.g. 8, 10, 12, 14, 16, 18, 20, 25, 30, 35, 40, 50, 60, 70, 80, 90, 100, 150, 200, 250 or more). These YPO0809 proteins include variants of SEQ ID NO:4. Preferred fragments of (b) comprise an epitope from SEQ ID NO:4. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:4. Other fragments omit one or more protein domains.

(19) YPO1123

The 'YPO1123' sequence was annotated in reference 16 as 'TolA colicin import membrane protein' (see GI:16121423). For reference purposes, the amino acid sequence of full-length YPO1123 as found in the *Y. pestis* CO92 strain is given as SEQ ID NO:7 herein.

Preferred YPO1123 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:7; and/or (b) that is a fragment of at least n consecutive amino acids of SEQ ID NO:7, wherein n is 7 or more (e.g. 8, 10, 12, 14, 16, 18, 20, 25, 30, 35, 40, 50, 60, 70, 80, 90, 100, 150, 200, 250 or more). These YPO1123 proteins include variants of SEQ ID NO:7. Preferred fragments of (b) comprise an epitope from SEQ ID NO:7. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:7. Other fragments omit one or more protein domains.

(20) YPO3065

The 'YPO3065' sequence was annotated in reference 16 as 'hypothetical protein' (see GI:16123242). For reference purposes, the amino acid sequence of full-length YPO3065 as found in the *Y. pestis* CO92 strain is given as SEQ ID NO:12 herein.

Preferred YPO3065 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:12; and/or (b) that is a fragment of at least n consecutive amino acids of SEQ ID NO:12, wherein n is 7 or more (e.g. 8, 10, 12, 14, 16, 18, 20, 25, 30, 35, 40, 50, 60, 70, 80, 90, 100, 150, 200, 250 or more). These YPO3065 proteins include variants of SEQ ID NO:12. Preferred fragments of (b) comprise an epitope from SEQ ID NO:12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:12. Other fragments omit one or more protein domains.

(21) YPO1070

The 'YPO1070' sequence was annotated in reference 16 as 'putative lipoprotein' (see GI:16121371), also known as rcsF. For reference purposes, the amino acid sequence of full-length YPO1070 as found in the *Y. pestis* CO92 strain is given as SEQ ID NO:6 herein.

Preferred YPO1070 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:6; and/or (b) that is a fragment of at least n consecutive amino acids of SEQ ID NO:6, wherein n is 7 or more (e.g. 8, 10, 12, 14, 16, 18, 20, 25, 30, 35, 40, 50, 60, 70, 80, 90, 100, 150, 200, 250 or more). These YPO1070 proteins include variants of SEQ ID NO:6. Preferred fragments of (b) comprise an epitope from SEQ ID NO:6. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:6. Other fragments omit one or more protein domains.

Fourth Antigen Group

(1) YPO0102

The 'YPO0102' sequence was annotated in reference 16 as 'hypothetical protein' (see GI:16120449). For reference purposes, the amino acid sequence of full-length YPO0102 as found in the *Y. pestis* CO92 strain is given as SEQ ID NO:44 herein.

Preferred YPO0102 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:44; and/or (b) that is a fragment of at least n consecutive amino acids of SEQ ID NO:44, wherein n is 7 or more (e.g. 8, 10, 12, 14, 16, 18, 20, 25, 30, 35, 40, 50, 60, 70, 80, 90, 100, 150, 200, 250 or more). These YPO0102 proteins include variants of SEQ ID NO:44. Preferred fragments of (b) comprise an epitope from SEQ ID NO:44. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:44. Other fragments omit one or more protein domains.

(2) YPO0570

The 'YPO0570' sequence was annotated in reference 16 as 'putative membrane protein' (see GI:16120899). For reference purposes, the amino acid sequence of full-length YPO0570 as found in the *Y. pestis* CO92 strain is given as SEQ ID NO:35 herein.

Preferred YPO0570 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:35; and/or (b) that is a fragment of at least n consecutive amino acids of SEQ ID NO:35, wherein n is 7 or more (e.g. 8, 10, 12, 14, 16, 18, 20, 25, 30, 35, 40, 50, 60, 70, 80, 90, 100, 150, 200, 250 or more). These YPO0570 proteins include variants of SEQ ID NO:35. Preferred fragments of (b) comprise an epitope from SEQ ID NO:35. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:35. Other fragments omit one or more protein domains.

(3) YPO1053

The 'YPO1053' sequence was annotated in reference 16 as 'cationic 19 kDa outer membrane protein precursor' (see GI:16121353). For reference purposes, the amino acid sequence of full-length YPO1053 as found in the *Y. pestis* CO92 strain is given as SEQ ID NO:33 herein. This protein is postulated herein to be a member of the OmpH family of proteins.

Preferred YPO1053 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:33; and/or (b) that is a fragment of at least n consecutive amino acids of SEQ ID NO:33, wherein n is 7 or more (e.g. 8, 10, 12, 14, 16, 18, 20, 25, 30, 35, 40, 50, 60, 70, 80, 90, 100, 150, 200, 250 or more). These YPO1053 proteins include variants of SEQ ID NO:33. Preferred fragments of (b) comprise an epitope from SEQ ID NO:33. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:33. Other fragments omit one or more protein domains.

(4) YPO1435

The 'YPO1435' sequence was annotated in reference 16 as 'putative outer membrane porin A protein' (see GI:16121713). For reference purposes, the amino acid sequence of full-length YPO1435 as found in the *Y. pestis* CO92 strain is given as SEQ ID NO:32 herein.

Preferred YPO1435 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:32; and/or (b) that is a fragment of at least n consecutive amino acids of SEQ ID NO:32, wherein n is 7 or more (e.g. 8, 10, 12, 14, 16, 18, 20, 25, 30, 35, 40, 50, 60, 70, 80, 90, 100, 150, 200, 250 or more). These YPO1435 proteins include variants of SEQ ID NO:32. Preferred fragments of (b) comprise an epitope from SEQ ID NO:32. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:32. Other fragments omit one or more protein domains.

(5) YPO2674

The 'YPO2674' sequence was annotated in reference 16 as 'hypothetical protein' (see GI:16122879). For reference purposes, the amino acid sequence of full-length YPO2674 as found in the *Y. pestis* CO92 strain is given as SEQ ID NO:26 herein.

Preferred YPO2674 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:26; and/or (b) that is a fragment of at least n consecutive amino acids of SEQ ID NO:26, wherein n is 7 or more (e.g. 8, 10, 12, 14, 16, 18, 20, 25, 30, 35, 40, 50, 60, 70, 80, 90, 100, 150, 200, 250 or more). These YPO2674 proteins include variants of SEQ ID NO:26. Preferred fragments of (b) comprise an epitope from SEQ ID NO:26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:26. Other fragments omit one or more protein domains.

(6) YPO2292

The 'YPO2292' sequence was annotated in reference 16 as 'putative lipoprotein' (see GI:16122516). For reference purposes, the amino acid sequence of full-length YPO2292 as found in the *Y. pestis* CO92 strain is given as SEQ ID NO:29 herein.

Preferred YPO2292 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:29; and/or (b) that is a fragment of at least n consecutive amino acids of SEQ ID NO:29, wherein n is 7 or more (e.g. 8, 10, 12, 14, 16, 18, 20, 25, 30, 35, 40, 50, 60, 70, 80, 90, 100, 150, 200, 250 or more). These YPO2292 proteins include variants of SEQ ID NO:29. Preferred fragments of (b) comprise an epitope from SEQ ID NO:29. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:29. Other fragments omit one or more protein domains.

(7) YPO3050

The 'YPO3050' sequence was annotated in reference 16 as 'hypothetical protein' (see GI:16123227). For reference purposes, the amino acid sequence of full-length YPO3050 as found in the *Y. pestis* CO92 strain is given as SEQ ID NO:25 herein.

Preferred YPO3050 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:25; and/or (b) that is a fragment of at least n consecutive amino acids of SEQ ID NO:25, wherein n is 7 or more (e.g. 8, 10, 12, 14, 16, 18, 20, 25, 30, 35, 40, 50, 60, 70, 80, 90, 100, 150, 200, 250 or more). These YPO3050 proteins include variants of SEQ ID NO:25. Preferred fragments of (b) comprise an epitope from SEQ ID NO:25. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:25. Other fragments omit one or more protein domains.

(8) YPO2615

The 'YPO2615' sequence was annotated in reference 16 as 'putative amino acid-binding protein precursor' (see GI:16122828). For reference purposes, the amino acid sequence of full-length YPO2615 as found in the *Y. pestis* CO92 strain is given as SEQ ID NO:27 herein.

Preferred YPO2615 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:27; and/or (b) that is a fragment of at least n consecutive amino acids of SEQ ID NO:27, wherein n is 7 or more (e.g. 8, 10, 12, 14, 16, 18, 20, 25, 30, 35, 40, 50, 60, 70, 80, 90, 100, 150, 200, 250 or more). These YPO2615 proteins include variants of SEQ ID NO:27. Preferred fragments of (b) comprise an epitope from SEQ ID NO:27. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:27. Other fragments omit one or more protein domains.

(9) YPO1507

The 'YPO1507' sequence was annotated in reference 16 as 'galactose-binding protein' (see GI:16121780). For reference purposes, the amino acid sequence of full-length YPO1507 as found in the *Y. pestis* CO92 strain is given as SEQ ID NO:31 herein.

Preferred YPO1507 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:31; and/or (b) that is a fragment of at least n consecutive amino acids of SEQ ID NO:31, wherein n is 7 or more (e.g. 8, 10, 12, 14, 16, 18, 20, 25, 30, 35, 40, 50, 60, 70, 80, 90, 100, 150, 200, 250 or more). These YPO1507 proteins include variants of SEQ ID NO:31. Preferred fragments of (b) comprise an epitope from SEQ ID NO:31. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:31. Other fragments omit one or more protein domains.

(10) YPO4111

The 'YPO4111' sequence was annotated in reference 16 as 'putative periplasmic solute-binding protein' (see GI:16124219). For reference purposes, the amino acid sequence of full-length YPO4111 as found in the *Y. pestis* CO92 strain is given as SEQ ID NO:47 herein.

Preferred YPO4111 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:47; and/or (b) that is a fragment of at least n consecutive amino acids of SEQ ID NO:47, wherein n is 7 or more (e.g. 8, 10, 12, 14, 16, 18, 20, 25, 30, 35, 40, 50, 60, 70, 80, 90, 100, 150, 200, 250 or more). These YPO4111 proteins include variants of SEQ ID NO:47. Preferred fragments of (b) comprise an epitope from SEQ ID NO:47. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:47. Other fragments omit one or more protein domains.

(11) YPO0015

The 'YPO0015' sequence was annotated in reference 16 as 'secreted thiol:disulfide interchange protein DsbA' (see GI:16120369). For reference purposes, the amino acid sequence of full-length YPO0015 as found in the *Y. pestis* CO92 strain is given as SEQ ID NO:46 herein.

Preferred YPO0015 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:46; and/or (b) that is a fragment of at least n consecutive amino acids of SEQ ID NO:46, wherein n is 7 or more (e.g. 8, 10, 12, 14, 16, 18, 20, 25, 30, 35, 40, 50, 60, 70, 80, 90, 100, 150, 200, 250 or more). These YPO0015 proteins include variants of SEQ ID NO:46. Preferred fragments of (b) comprise an epitope from SEQ ID NO:46. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:46. Other fragments omit one or more protein domains.

(12) YPO0195

The 'YPO0195' sequence was annotated in reference 16 as 'peptidyl-prolyl cis-trans isomerase' (see GI:16120534). For reference purposes, the amino acid sequence of full-length YPO0195 as found in the *Y. pestis* CO92 strain is given as SEQ ID NO:43 herein.

Preferred YPO0195 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:43; and/or (b) that is a fragment of at least n consecutive amino acids of SEQ ID NO:43, wherein n is 7 or more (e.g. 8, 10, 12, 14, 16, 18, 20, 25, 30, 35, 40, 50, 60, 70, 80, 90, 100, 150, 200, 250 or more). These YPO0195 proteins include variants of SEQ ID NO:43. Preferred fragments of (b) comprise an epitope from SEQ ID NO:43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:43. Other fragments omit one or more protein domains.

(13) YPO2342

The 'YPO2342' sequence was annotated in reference 16 as 'thiol peroxidase' (see GI:16122566). For reference purposes, the amino acid sequence of full-length YPO2342 as found in the *Y. pestis* CO92 strain is given as SEQ ID NO:28 herein.

Preferred YPO2342 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:28; and/or (b) that is a fragment of at least n consecutive amino acids of SEQ ID NO:28, wherein n is 7 or more (e.g. 8, 10, 12, 14, 16, 18, 20, 25, 30, 35, 40, 50, 60, 70, 80, 90, 100, 150, 200, 250 or more). These YPO2342 proteins include variants of SEQ ID NO:28. Preferred fragments of (b) comprise an epitope from SEQ ID NO:28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:28. Other fragments omit one or more protein domains.

(14) YPO0501

The 'YPO0501' sequence was annotated in reference 16 as 'hypothetical protein' (see GI:16120831). For reference purposes, the amino acid sequence of full-length YPO0501 as found in the *Y. pestis* CO92 strain is given as SEQ ID NO:37 herein. However, it is postulated herein that YPO0501 forms part of a Type Three Secretion System (TTSS).

Preferred YPO0501 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:37; and/or (b) that is a fragment of at least n consecutive amino acids of SEQ ID NO:37, wherein n is 7 or more (e.g. 8, 10, 12, 14, 16, 18, 20, 25, 30, 35, 40, 50, 60, 70, 80, 90, 100, 150, 200, 250 or more). These YPO0501 proteins include variants of SEQ ID NO:37. Preferred fragments of (b) comprise an epitope from SEQ ID NO:37. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:37. Other fragments omit one or more protein domains.

(15) YPO0502

The 'YPO0502' sequence was annotated in reference 16 as 'hypothetical protein' (see GI:16120832). For reference purposes, the amino acid sequence of full-length YPO0502 as found in the *Y. pestis* CO92 strain is given as SEQ ID NO:36 herein. However, it is postulated herein that YPO0502 forms part of a Type Three Secretion System (TTSS).

Preferred YPO0502 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:36; and/or (b) that is a fragment of at least n consecutive amino acids of SEQ ID NO:36, wherein n is 7 or more (e.g. 8, 10, 12, 14, 16, 18, 20, 25, 30, 35, 40, 50, 60, 70, 80, 90, 100, 150, 200, 250 or more). These YPO0502 proteins include variants of SEQ ID NO:36. Preferred fragments of (b) comprise an epitope from SEQ ID NO:36. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:36. Other fragments omit one or more protein domains.

(16) YPO0819

The 'YPO0819' sequence was annotated in reference 16 as 'putative carbonic anhydrase' (see GI:16121130). For reference purposes, the amino acid sequence of full-length YPO0819 as found in the *Y. pestis* CO92 strain is given as SEQ ID NO:34 herein.

Preferred YPO0819 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:34; and/or (b) that is a fragment of at least n consecutive amino acids of SEQ ID NO:34, wherein n is 7 or more (e.g. 8, 10, 12, 14, 16, 18, 20, 25, 30, 35, 40, 50, 60, 70, 80, 90, 100, 150, 200, 250 or more). These YPO0819 proteins include variants of SEQ ID NO:34. Preferred fragments of (b) comprise an epitope from SEQ ID NO:34. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:34. Other fragments omit one or more protein domains.

(17) YPO3644

The 'YPO3644' sequence was annotated in reference 16 as 'major cold shock protein Cspa1' (see GI:16123786). For reference purposes, the amino acid sequence of full-length YPO3644 as found in the *Y. pestis* CO92 strain is given as SEQ ID NO:22 herein.

Preferred YPO3644 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:22; and/or (b) that is a fragment of at least n consecutive amino acids of SEQ ID NO:22, wherein n is 7 or more (e.g. 8, 10, 12, 14, 16, 18, 20, 25, 30, 35, 40, 50, 60, 70, 80, 90, 100, 150, 200, 250 or more). These YPO3644 proteins include variants of SEQ ID NO:22. Preferred fragments of (b) comprise an epitope from SEQ ID NO:22. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:22. Other fragments omit one or more protein domains.

(18) YPO1746

The 'YPO1746' sequence was annotated in reference 16 as 'cold shock protein' (see GI:16122003). For reference purposes, the amino acid sequence of full-length YPO1746 as found in the *Y. pestis* CO92 strain is given as SEQ ID NO:30 herein.

Preferred YPO1746 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:30; and/or (b) that is a fragment of at least n consecutive amino acids of SEQ ID NO:30, wherein n is 7 or more (e.g. 8, 10, 12, 14, 16, 18, 20, 25, 30, 35, 40, 50, 60, 70, 80, 90, 100, 150, 200, 250 or more). These YPO1746 proteins include variants of SEQ ID NO:30. Preferred fragments of (b) comprise an epitope from SEQ ID NO:30. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:30. Other fragments omit one or more protein domains.

(19) YPO0351

The 'YPO0351' sequence was annotated in reference 16 as '60 kDa chaperonin' (see GI:16120686). For reference purposes, the amino acid sequence of full-length YPO0351 as found in the *Y. pestis* CO92 strain is given as SEQ ID NO:39 herein.

Preferred YPO0351 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:39; and/or (b) that is a fragment of at least n consecutive amino acids of SEQ ID NO:39, wherein n is 7 or more (e.g. 8, 10, 12, 14, 16, 18, 20, 25, 30, 35, 40, 50, 60, 70, 80, 90, 100, 150, 200, 250 or more). These YPO0351 proteins include variants of SEQ ID NO:39. Preferred fragments of (b) comprise an epitope from SEQ ID NO:39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:39. Other fragments omit one or more protein domains. A YPO0351 antigen has been shown to be an outer membrane protein suitable for use as an antigenic protein in reference 20.

(20) YPO0468

The 'YPO0468' sequence was annotated in reference 16 as 'chaperone protein DnaK' (see GI:16120797). For reference purposes, the amino acid sequence of full-length YPO0468 as found in the *Y. pestis* CO92 strain is given as SEQ ID NO:38 herein.

Preferred YPO0468 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:38; and/or (b) that is a fragment of at least n consecutive amino acids of SEQ ID NO:38, wherein n is 7 or more (e.g. 8, 10, 12, 14, 16, 18, 20, 25, 30, 35, 40, 50, 60, 70, 80, 90, 100, 150, 200, 250 or more). These YPO0468 proteins include variants of SEQ ID NO:38. Preferred fragments of (b) comprise an epitope from SEQ ID NO:38. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:38. Other fragments omit one or more protein domains. A YPO0468 antigen has been shown to be an outer membrane protein suitable for use as an antigenic protein in reference 20.

(21) YPO0203

The 'YPO0203' sequence was annotated in reference 16 as 'elongation factor Tu' (see GI:16120542). For reference purposes, the amino acid sequence of full-length YPO0203 as found in the *Y. pestis* CO92 strain is given as SEQ ID NO:42 herein.

Preferred YPO0203 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:42; and/or (b) that is a fragment of at least n consecutive amino acids of SEQ ID NO:42, wherein n is 7 or more (e.g. 8, 10, 12, 14, 16, 18, 20, 25, 30, 35, 40, 50, 60, 70, 80, 90, 100, 150, 200, 250 or more). These YPO0203 proteins include variants of SEQ ID NO:42. Preferred fragments of (b) comprise an epitope from SEQ ID NO:42. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:42. Other fragments omit one or more protein domains. A YPO0203 antigen has been shown to be an outer membrane protein suitable for use as an antigenic protein in reference 20.

(22) YPO0216

The 'YPO0216' sequence was annotated in reference 16 as '30S ribosomal protein S3' (see GI:16120553). For reference purposes, the amino acid sequence of full-length YPO0216 as found in the *Y. pestis* CO92 strain is given as SEQ ID NO:41 herein.

Preferred YPO0216 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:41; and/or (b) that is a fragment of at least n consecutive amino acids of SEQ ID NO:41, wherein n is 7 or more (e.g. 8, 10, 12, 14, 16, 18, 20, 25, 30, 35, 40, 50, 60, 70, 80, 90, 100, 150, 200, 250 or more). These YPO0216 proteins include variants of SEQ ID NO:41. Preferred fragments of (b) comprise an epitope from SEQ ID NO:41. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:41. Other fragments omit one or more protein domains.

(23) YPO3536

The 'YPO3536' sequence was annotated in reference 16 as '50S ribosomal protein L9' (see GI:16123682). For reference purposes, the amino acid sequence of full-length YPO3536 as found in the *Y. pestis* CO92 strain is given as SEQ ID NO:24 herein.

Preferred YPO3536 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:24; and/or (b) that is a fragment of at least n consecutive amino acids of SEQ ID NO:24, wherein n is 7 or more (e.g. 8, 10, 12, 14, 16, 18, 20, 25, 30, 35, 40, 50, 60, 70, 80, 90, 100, 150, 200, 250 or more). These YPO3536 proteins include variants of SEQ ID NO:24. Preferred fragments of (b) comprise an epitope from SEQ ID NO:24. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:24. Other fragments omit one or more protein domains.

(24) YPO0233

The 'YPO0233' sequence was annotated in reference 16 as '30S ribosomal protein S4' (see GI:16120571). For reference purposes, the amino acid sequence of full-length YPO0233 as found in the *Y. pestis* CO92 strain is given as SEQ ID NO:40 herein.

Preferred YPO0233 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:40; and/or (b) that is a fragment of at least n consecutive amino acids of SEQ ID NO:40, wherein n is 7 or more (e.g. 8, 10, 12, 14, 16, 18, 20, 25, 30, 35, 40, 50, 60, 70, 80, 90, 100, 150, 200, 250 or more). These YPO0233 proteins include variants of SEQ ID NO:40. Preferred fragments of (b) comprise an epitope from SEQ ID NO:40. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:40. Other fragments omit one or more protein domains.

(25) YPO0067

The 'YPO0067' sequence was annotated in reference 16 as 'protein-export protein' (see GI:16120418). For reference purposes, the amino acid sequence of full-length YPO0067 as found in the *Y. pestis* CO92 strain is given as SEQ ID NO:45 herein.

Preferred YPO0067 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:45; and/or (b) that is a fragment of at least n consecutive amino acids of SEQ ID NO:45, wherein n is 7 or more (e.g. 8, 10, 12, 14, 16, 18, 20, 25, 30, 35, 40, 50, 60, 70, 80, 90, 100, 150, 200, 250 or more). These YPO0067 proteins include variants of SEQ ID NO:45. Preferred fragments of (b) comprise an epitope from SEQ ID NO:45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:45. Other fragments omit one or more protein domains.

(26) YPO03643

The 'YPO3643' sequence was annotated in reference 16 as 'major cold shock protein Cspa2' (see GI:16123785). For reference purposes, the amino acid sequence of full-length YPO3643 as found in the *Y. pestis* CO92 strain is given as SEQ ID NO:23 herein.

Preferred YPO3643 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:23; and/or (b) that is a fragment of at least n consecutive amino acids of SEQ ID NO:23, wherein n is 7 or more (e.g. 8, 10, 12, 14, 16, 18, 20, 25, 30, 35, 40, 50, 60, 70, 80, 90, 100, 150, 200, 250 or more). These YPO3643 proteins include variants of SEQ ID NO:23. Preferred fragments of (b) comprise an epitope from SEQ ID NO:23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:23. Other fragments omit one or more protein domains.

(27) YPO3375

The 'YPO3375' sequence was annotated in reference 16 as 'superoxide dismutase [Cu—Zn] precursor' (see GI:16123524). For reference purposes, the amino acid sequence of full-length YPO3375 as found in the *Y. pestis* CO92 strain is given as SEQ ID NO:58 herein.

Preferred YPO3375 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:58; and/or (b) that is a fragment of at least n consecutive amino acids of SEQ ID NO:58, wherein n is 7 or more (e.g. 8, 10, 12, 14, 16, 18, 20, 25, 30, 35, 40, 50, 60, 70, 80, 90, 100, 150, 200, 250 or more). These YPO3375 proteins include variants of SEQ ID NO:58. Preferred fragments of (b) comprise an epitope from SEQ ID NO:58. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:58. Other fragments omit one or more protein domains.

(28) YPO0494

The 'YPO0494' sequence was annotated in reference 16 as 'survival protein SurA precursor (peptidyl-prolyl cis-trans isomerase' (see GI:16120824). For reference purposes, the amino acid sequence of full-length YPO0494 as found in the *Y. pestis* CO92 strain is given as SEQ ID NO:53 herein.

Preferred YPO0494 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:53; and/or (b) that is a fragment of at least n consecutive amino acids of SEQ ID NO:53, wherein n is 7 or more (e.g. 8, 10, 12, 14, 16, 18, 20, 25, 30, 35, 40, 50, 60, 70, 80, 90, 100, 150, 200, 250 or more). These YPO0494 proteins include variants of SEQ ID NO:53. Preferred fragments of (b) comprise an epitope from SEQ ID NO:53. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:53. Other fragments omit one or more protein domains.

(29) YPO1052

The 'YPO1052' sequence was annotated in reference 16 as 'putative surface antigen' (see GI:16121352). For reference purposes, the amino acid sequence of full-length YPO1052 as found in the *Y. pestis* CO92 strain is given as SEQ ID NO:51 herein.

Preferred YPO1052 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:51; and/or (b) that is a fragment of at least n consecutive amino acids of SEQ ID NO:51, wherein n is 7 or more (e.g. 8, 10, 12, 14, 16, 18, 20, 25, 30, 35, 40, 50, 60, 70, 80, 90, 100, 150, 200, 250 or more). These YPO1052 proteins include variants of SEQ ID NO:51. Preferred fragments of (b) comprise an epitope from SEQ ID NO:51. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:51. Other fragments omit one or more protein domains.

(30) YPO1906

The 'YPO1906' sequence was annotated in reference 16 as 'pesticin/yersiniabactin receptor protein' (see GI:16122154). For reference purposes, the amino acid sequence of full-length YPO1906 as found in the *Y. pestis* CO92 strain is given as SEQ ID NO:56 herein.

Preferred YPO1906 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:56; and/or (b) that is a fragment of at least n consecutive amino acids of SEQ ID NO:56, wherein n is 7 or more (e.g. 8, 10, 12, 14, 16, 18, 20, 25, 30, 35, 40, 50, 60, 70, 80, 90, 100, 150, 200, 250 or more). These YPO1906 proteins include variants of SEQ ID NO:56. Preferred fragments of (b) comprise an epitope from SEQ ID NO:56. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:56. Other fragments omit one or more protein domains.

(31) YPO0663

The 'YPO0663' sequence was annotated in reference 16 as 'ABC-transporter outer membrane component' (see GI:16120988). For reference purposes, the amino acid sequence of full-length YPO0663 as found in the *Y. pestis* CO92 strain is given as SEQ ID NO:54 herein.

Preferred YPO0663 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:54; and/or (b) that is a fragment of at least n consecutive amino acids of SEQ ID NO:54, wherein n is 7 or more (e.g. 8, 10, 12, 14, 16, 18, 20, 25, 30, 35, 40, 50, 60, 70, 80, 90, 100, 150, 200, 250 or more). These YPO0663 proteins include variants of SEQ ID NO:54. Preferred fragments of (b) comprise an epitope from SEQ ID NO:54. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:54. Other fragments omit one or more protein domains.

(32) YPO1222

The 'YPO1222' sequence was annotated in reference 16 as 'outer membrane protein C, porin' (see GI:16121511). For reference purposes, the amino acid sequence of full-length YPO1222 as found in the *Y. pestis* CO92 strain is given as SEQ ID NO:55 herein.

Preferred YPO1222 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:55; and/or (b) that is a fragment of at least n consecutive amino acids of SEQ ID NO:55, wherein n is 7 or more (e.g. 8, 10, 12, 14, 16, 18, 20, 25, 30, 35, 40, 50, 60, 70, 80, 90, 100, 150, 200, 250 or more). These YPO1222 proteins include variants of SEQ ID NO:55. Preferred fragments of (b) comprise an epitope from SEQ ID NO:55. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:55. Other fragments omit one or more protein domains. A YPO1222 antigen has been shown to be an outer membrane protein suitable for use as an antigenic protein in reference 20.

(33) YPO2905

The 'YPO2905' sequence was annotated in reference 16 as 'attachment invasion locus protein' (see GI:16123096). For reference purposes, the amino acid sequence of full-length YPO2905 as found in the *Y. pestis* CO92 strain is given as SEQ ID NO:57 herein.

Preferred YPO2905 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:57; and/or (b) that is a fragment of at least n consecutive amino acids of SEQ ID NO:57, wherein n is 7 or more (e.g. 8, 10, 12, 14, 16, 18, 20, 25, 30, 35, 40, 50, 60, 70, 80, 90, 100, 150, 200, 250 or more). These YPO2905 proteins include variants of SEQ ID NO:57. Preferred fragments of (b) comprise an epitope from SEQ ID NO:57. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:57. Other fragments omit one or more protein domains.

(34) YPO4070

The 'YPO4070' sequence was annotated in reference 16 as 'hypothetical protein' (see GI:16124183). For reference purposes, the amino acid sequence of full-length YPO4070 as found in the *Y. pestis* CO92 strain is given as SEQ ID NO:52 herein.

Preferred YPO4070 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:52; and/or (b) that is a fragment of at least n consecutive amino acids of SEQ ID NO:52, wherein n is 7 or more (e.g. 8, 10, 12, 14, 16, 18, 20, 25, 30, 35, 40, 50, 60, 70, 80, 90, 100, 150, 200, 250 or more). These YPO4070 proteins include variants of SEQ ID NO:52. Preferred fragments of (b) comprise an epitope from SEQ ID NO:52. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:52. Other fragments omit one or more protein domains.

(35) YPPCP1.07

The 'YPPCP1.07' sequence was annotated in reference 16 as 'plasminogen activator protease precursor' (see GI:16082686). For reference purposes, the amino acid sequence of full-length YPPCP1.07 as found in the *Y. pestis* CO92 strain is given as SEQ ID NO:50 herein.

Preferred YPPCP1.07 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:50; and/or (b) that is a fragment of at least n consecutive amino acids of SEQ ID NO:50, wherein n is 7 or more (e.g. 8, 10, 12, 14, 16, 18, 20, 25, 30, 35, 40, 50, 60, 70, 80, 90, 100, 150, 200, 250 or more). These YPPCP1.07 proteins include variants (e.g. allelic variants, polymorphic forms, homologs, orthologs, paralogs, mutants, etc.) of SEQ ID NO:50. Preferred fragments of (b) comprise an epitope from SEQ ID NO:50. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:50. Other fragments omit one or more protein domains.

(36) YPMT1.42

The 'YPMT1.42' sequence was annotated in reference 16 as 'putative periplasmic protein' (see GI:16082828). For reference purposes, the amino acid sequence of full-length YPMT1.42 as found in the *Y. pestis* CO92 strain is given as SEQ ID NO:59 herein.

Preferred YPMT1.42 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:59; and/or (b) that is a fragment of at least n consecutive amino acids of SEQ ID NO:59, wherein n is 7 or more (e.g. 8, 10, 12, 14, 16, 18, 20, 25, 30, 35, 40, 50, 60, 70, 80, 90, 100, 150, 200, 250 or more). These YPMT1.42 proteins include variants (e.g. allelic variants, polymorphic forms, homologs, orthologs, paralogs, mutants, etc.) of SEQ ID NO:59. Preferred fragments of (b) comprise an epitope from SEQ ID NO:59. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:59. Other fragments omit one or more protein domains.

Fifth Antigen Group (1) F1 Antigen

The 'F1' antigen is the envelope or capsular protein of *Y. pestis*, and derives its name from fraction 1'. It is also known as 'caf1', and is encoded on a plasmid. Cloning and sequencing of the F1 gene was reported in 1990 in reference 21 (GI:115437). In reference 16, the F1 antigen is referred to as 'YPMT1.84' (see GI:16082876). For reference purposes, the amino acid sequence of full-length F1 from the *Y. pestis* CO92 strain is given as SEQ ID NO:48 herein.

Preferred F1 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:48; and/or (b) that is a fragment of at least n consecutive amino acids of SEQ ID NO:48, wherein n is 7 or more (e.g. 8, 10, 12, 14, 16, 18, 20, 25, 30, 35, 40, 50, 60, 70, 80, 90, 100, 150, 200, 250 or more). These F1 proteins include variants of SEQ ID NO:48. Preferred fragments of (b) comprise an epitope from SEQ ID NO:48, and reference 21 suggests that the region located between amino acids 100 and 150 contains such epitopes. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:48. Other fragments omit one or more protein domains. For example, reference 103 discloses F1 proteins in which the 21-mer N-terminus signal peptide has been removed.

(2) V Antigen

The V antigen is recognised as a major virulence factor of *Y. pestis*. In reference 16, the F1 antigen is referred to as 'YPCD1.31c', encoding the 'antihost protein/regulator' (see GI:5832451). It is also known as 'lcrV' for 'low-calcium-response V'. For reference purposes, the amino acid sequence of full-length V antigen from the *Y. pestis* CO92 strain is given as SEQ ID NO:49 herein. Reference 22 reports V antigen sequences for 22 diverse strains of *Y. pestis*, with all but two being identical.

Preferred V antigens for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:49; and/or (b) that is a fragment of at least n consecutive amino acids of SEQ ID NO:49, wherein n is 7 or more (e.g. 8, 10, 12, 14, 16, 18, 20, 25, 30, 35, 40, 50, 60, 70, 80, 90, 100, 150, 200, 250 or more). These proteins include variants of SEQ ID NO:49. For example, GI:17380409 reports on sequence variants (K18N, K72R, I135V, C273S, and a mutant where $^{324}$SGK$^{326}$ is replaced by R). Preferred fragments of (b) comprise an epitope from SEQ ID NO:49. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:49. Other fragments omit one or more protein domains.

Sixth Antigen Group (1) YPO0457

The 'YPO0457' sequence was annotated in reference 16 as 'hypothetical protein' (see GI: 16120786). For reference purposes, the amino acid sequence of full-length YPO0457 as found in the *Y. pestis* CO92 strain is given as SEQ ID NO:61 herein. This protein is postulated herein to be a putative outer membrane protein.

Preferred YPO0457 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:61; and/or (b) that is a fragment of at least n consecutive amino acids of SEQ ID NO:61, wherein n is 7 or more (e.g. 8, 10, 12, 14, 16, 18, 20, 25, 30, 35, 40, 50, 60, 70, 80, 90, 100, 150, 200, 250 or more). These YPO0457 proteins include variants of SEQ ID NO:61. Preferred fragments of (b) comprise an epitope from SEQ ID NO:61. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:61. Other fragments omit one or more protein domains.

(2) YPO0514

The 'YPO0514' sequence was annotated in reference 16 as 'hypothetical protein' (see GI: 16120845). For reference purposes, the amino acid sequence of full-length YPO0514 as found in the *Y. pestis* CO92 strain is given as SEQ ID NO:62 herein. However, it is postulated herein that YPO0514 forms part of a Type Three Secretion System (TTSS) and is an OmpA-family member protein.

Preferred YPO0514 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:62; and/or (b) that is a fragment of at least n consecutive amino acids of SEQ ID NO:62, wherein n is 7 or more (e.g. 8, 10, 12, 14, 16, 18, 20, 25, 30, 35, 40, 50, 60, 70, 80, 90, 100, 150, 200, 250 or more). These YPO0514 proteins include variants of SEQ ID NO:62. Preferred fragments of (b) comprise an epitope from SEQ ID NO:62. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:62. Other fragments omit one or more protein domains.

(3) YPO0694

The 'YPO0694' sequence was annotated in reference 16 as 'hypothetical protein' (see GI: 16121015). For reference purposes, the amino acid sequence of full-length YPO0694 as found in the *Y. pestis* CO92 strain is given as SEQ ID NO:63 herein. This protein is postulated herein to be a putative membrane protein and furthermore, a fimbrial component.

Preferred YPO0694 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:63; and/or (b) that is a fragment of at least n consecutive amino acids of SEQ ID NO:63, wherein n is 7 or more (e.g. 8, 10, 12, 14, 16, 18, 20, 25, 30, 35, 40, 50, 60, 70, 80, 90, 100, 150, 200, 250 or more). These YPO0694 proteins include variants of SEQ ID NO:63. Preferred fragments of (b) comprise an epitope from SEQ ID NO:63. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:63. Other fragments omit one or more protein domains.

(4) YPO0805

The 'YPO0805' sequence was annotated in reference 16 as 'putative lipoprotein' (see GI: 16121117). For reference purposes, the amino acid sequence of full-length YPO0805 as found in the *Y. pestis* CO92 strain is given as SEQ ID NO:64 herein. This protein is postulated herein to be a member of a virulence-associated secretion apparatus.

Preferred YPO0805 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:64; and/or (b) that is a fragment of at least n consecutive amino acids of SEQ ID NO:64, wherein n is 7 or more (e.g. 8, 10, 12, 14, 16, 18, 20, 25, 30, 35, 40, 50, 60, 70, 80, 90, 100, 150, 200, 250 or more). These YPO0805 proteins include variants of SEQ ID NO:64. Preferred fragments of (b) comprise an epitope from SEQ ID NO:64. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:64. Other fragments omit one or more protein domains.

(5) YPO0982

The 'YPO0982' sequence was annotated in reference 16 as 'putative lipoprotein' (see GI: 16121286). For reference purposes, the amino acid sequence of full-length YPO0982 as found in the *Y. pestis* CO92 strain is given as SEQ ID NO:65 herein.

Preferred YPO0982 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:65; and/or (b) that is a fragment of at least n consecutive amino acids of SEQ ID NO:65, wherein n is 7 or more (e.g. 8, 10, 12, 14, 16, 18, 20, 25, 30, 35, 40, 50, 60, 70, 80, 90, 100, 150, 200, 250 or more). These YPO0982 proteins include variants of SEQ ID NO:65. Preferred fragments of (b) comprise an epitope from SEQ ID NO:65. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:65. Other fragments omit one or more protein domains.

(6) YPO1354

The 'YPO1354' sequence was annotated in reference 16 as 'putative lipoprotein' (see GI: 16121634). For reference purposes, the amino acid sequence of full-length YPO1354 as found in the *Y. pestis* CO92 strain is given as SEQ ID NO:66 herein.

Preferred YPO1354 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:66; and/or (b) that is a fragment of at least n consecutive amino acids of SEQ ID NO:66, wherein n is 7 or more (e.g. 8, 10, 12, 14, 16, 18, 20, 25, 30, 35, 40, 50, 60, 70, 80, 90, 100, 150, 200, 250 or more). These YPO1354 proteins include variants of SEQ ID NO:66. Preferred fragments of (b) comprise an epitope from SEQ ID NO:66. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:66. Other fragments omit one or more protein domains.

(7) YPO1408

The 'YPO1408' sequence was annotated in reference 16 as 'hypothetical protein' (see GI: 16121688). For reference purposes, the amino acid sequence of full-length YPO1408 as found in the *Y. pestis* CO92 strain is given as SEQ ID NO:67 herein. This protein is postulated herein to be a putative exported protein and a member of a type IV secretion system.

Preferred YPO1408 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:67; and/or (b) that is a fragment of at least 17 consecutive amino acids of SEQ ID NO:67, wherein n is 7 or more (e.g. 8, 10, 12, 14, 16, 18, 20, 25, 30, 35, 40, 50, 60, 70, 80, 90, 100, 150, 200, 250 or more). These YPO1408 proteins include variants of SEQ ID NO:67. Preferred fragments of (b) comprise an epitope from SEQ ID NO:67. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:67. Other fragments omit one or more protein domains.

(8) YPO1792

The 'YPO1792' sequence was annotated in reference 16 as 'flagellar protein FlhE precursor' (see GI: 16122046). For reference purposes, the amino acid sequence of full-length YPO1792 as found in the *Y. pestis* CO92 strain is given as SEQ ID NO:68 herein.

Preferred YPO1792 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:68; and/or (b) that is a fragment of at least n consecutive amino acids of SEQ ID NO:68, wherein n is 7 or more (e.g. 8, 10, 12, 14, 16, 18, 20, 25, 30, 35, 40, 50, 60, 70, 80, 90, 100, 150, 200, 250 or more). These YPO1792 proteins include variants of SEQ ID NO:68. Preferred fragments of (b) comprise an epitope from SEQ ID NO:68. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:68. Other fragments omit one or more protein domains. A YPO1792 antigen has been shown to be an effective antigen for immunisation against lethal respiratory challenge with *Y. pestis* [23].

(9) YPO2506

The 'YPO2506' sequence was annotated in reference 16 as 'outer membrane protein X' (see GI: 16122727). For reference purposes, the amino acid sequence of full-length YPO2506 as found in the *Y. pestis* CO92 strain is given as SEQ ID NO:69 herein.

Preferred YPO2506 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:69; and/or (b) that is a fragment of at least n consecutive amino acids of SEQ ID NO:69, wherein n is 7 or more (e.g. 8, 10, 12, 14, 16, 18, 20, 25, 30, 35, 40, 50, 60, 70, 80, 90, 100, 150, 200, 250 or more). These YPO2506 proteins include variants of SEQ ID NO:69. Preferred fragments of (b) comprise an epitope from SEQ ID NO:69. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:69. Other fragments omit one or more protein domains.

(10) YPO2713

The 'YPO2713' sequence was annotated in reference 16 as 'periplasmic negative regulator of sigmaE' (see GI: 16122917). For reference purposes, the amino acid sequence of full-length YPO2713 as found in the *Y. pestis* CO92 strain is given as SEQ ID NO:70 herein.

Preferred YPO2713 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:70; and/or (b) that is a fragment of at least n consecutive amino acids of SEQ ID NO:70, wherein n is 7 or more (e.g. 8, 10, 12, 14, 16, 18, 20, 25, 30, 35, 40, 50, 60, 70, 80, 90, 100, 150, 200, 250 or more). These YPO2713 proteins include variants of SEQ ID NO:70. Preferred fragments of (b) comprise an epitope from SEQ ID NO:70. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:70. Other fragments omit one or more protein domains.

(11) YPO2950

The 'YPO2950' sequence was annotated in reference 16 as 'putative fimbrial protein' (see GI: 16123133). For reference purposes, the amino acid sequence of full-length YPO2950 as found in the *Y. pestis* CO92 strain is given as SEQ ID NO:71 herein.

Preferred YPO2950 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:71; and/or (b) that is a fragment of at least n consecutive amino acids of SEQ ID NO:71, wherein n is 7 or more (e.g. 8, 10, 12, 14, 16, 18, 20, 25, 30, 35, 40, 50, 60, 70, 80, 90, 100, 150, 200, 250 or more). These YPO2950 proteins include variants of SEQ ID NO:71. Preferred fragments of (b) comprise an epitope from SEQ ID NO:71. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:71. Other fragments omit one or more protein domains.

(12) YPO3026

The 'YPO3026' sequence was annotated in reference 16 as 'putative lipoprotein' (see GI: 16123203). For reference purposes, the amino acid sequence of full-length YPO3026 as found in the *Y. pestis* CO92 strain is given as SEQ ID NO:72 herein. This protein is postulated herein to be a pilin component.

Preferred YPO3026 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:72; and/or (b) that is a fragment of at least n consecutive amino acids of SEQ ID NO:72, wherein n is 7 or more (e.g. 8, 10, 12, 14, 16, 18, 20, 25, 30, 35, 40, 50, 60, 70, 80, 90, 100, 150, 200, 250 or more). These YPO3026 proteins include variants of SEQ ID NO:72. Preferred fragments of (b) comprise an epitope from SEQ ID NO:72. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:72. Other fragments omit one or more protein domains.

(13) YPO3417

The 'YPO3417' sequence was annotated in reference 16 as 'dihydrolipoamide dehydrogenase' (see GI: 16123566). For reference purposes, the amino acid sequence of full-length YPO3417 as found in the *Y. pestis* CO92 strain is given as SEQ ID NO:73 herein.

Preferred YPO3417 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:73; and/or (b) that is a fragment of at least n consecutive amino acids of SEQ ID NO:73, wherein n is 7 or more (e.g. 8, 10, 12, 14, 16, 18, 20, 25, 30, 35, 40, 50, 60, 70, 80, 90, 100, 150, 200, 250 or more). These YPO3417 proteins include variants of SEQ ID NO:73. Preferred fragments of (b) comprise an epitope from SEQ ID NO:73. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:73. Other fragments omit one or more protein domains.

(14) YPO3551

The 'YPO3551' sequence was annotated in reference 16 as 'hypothetical protein' (see GI: 16123695). For reference purposes, the amino acid sequence of full-length YPO3551 as found in the *Y. pestis* CO92 strain is given as SEQ ID NO:74 herein. This protein is postulated herein to be a putative exported protein.

Preferred YPO3551 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:74; and/or (b) that is a fragment of at least n consecutive amino acids of SEQ ID NO:74, wherein n is 7 or more (e.g. 8, 10, 12, 14, 16, 18, 20, 25, 30, 35, 40, 50, 60, 70, 80, 90, 100, 150, 200, 250 or more). These YPO3551 proteins include variants of SEQ ID NO:74. Preferred fragments of (b) comprise an epitope from SEQ ID NO:74. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:74. Other fragments omit one or more protein domains.

(15) YPO3646

The 'YPO3646' sequence was annotated in reference 16 as 'outer membrane lipoprotein' (see GI: 16123788). For reference purposes, the amino acid sequence of full-length YPO3646 as found in the *Y. pestis* CO92 strain is given as SEQ ID NO:75 herein. This protein is postulated herein to play a role in membrane integrity.

Preferred YPO3646 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:75; and/or (b) that is a fragment of at least n consecutive amino acids of SEQ ID NO:75, wherein n is 7 or more (e.g. 8, 10, 12, 14, 16, 18, 20, 25, 30, 35, 40, 50, 60, 70, 80, 90, 100, 150, 200, 250 or more). These YPO3646 proteins include variants of SEQ ID NO:75. Preferred fragments of (b) comprise an epitope from SEQ ID NO:75. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:75. Other fragments omit one or more protein domains.

(16) YPO3982

The 'YPO3982' sequence was annotated in reference 16 as 'hypothetical protein' (see GI: 16124109). For reference purposes, the amino acid sequence of full-length YPO3982 as found in the *Y. pestis* CO92 strain is given as SEQ ID NO:76 herein.

Preferred YPO3982 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:76; and/or (b) that is a fragment of at least n consecutive amino acids of SEQ ID NO:76, wherein n is 7 or more (e.g. 8, 10, 12, 14, 16, 18, 20, 25, 30, 35, 40, 50, 60, 70, 80, 90, 100, 150, 200, 250 or more). These YPO3982 proteins include variants of SEQ ID NO:76. Preferred fragments of (b) comprise an epitope from SEQ ID NO:76. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:76. Other fragments omit one or more protein domains.

(17) YPO0065

The 'YPO0065' sequence was annotated in reference 16 as 'hypothetical protein' (see GI: 16120416). For reference purposes, the amino acid sequence of full-length YPO0065 as found in the *Y. pestis* CO92 strain is given as SEQ ID NO:77 herein. This protein is postulated herein to be a putative membrane protein.

Preferred YPO0065 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:77; and/or (b) that is a fragment of at least n consecutive amino acids of SEQ ID NO:77, wherein n is 7 or more (e.g. 8, 10, 12, 14, 16, 18, 20, 25, 30, 35, 40, 50, 60, 70, 80, 90, 100, 150, 200, 250 or more). These YPO0065 proteins include variants of SEQ ID NO:77. Preferred fragments of (b) comprise an epitope from SEQ ID NO:77. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:77. Other fragments omit one or more protein domains.

(18) YPO0499

The 'YPO0499' sequence was annotated in reference 16 as 'hypothetical protein' (see GI: 16120829). For reference purposes, the amino acid sequence of full-length YPO0499 as found in the *Y. pestis* CO92 strain is given as SEQ ID NO:78 herein. However, it is postulated herein that YPO0499 forms part of a Type Three Secretion System (TTSS).

Preferred YPO0499 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:78; and/or (b) that is a fragment of at least n consecutive amino acids of SEQ ID NO:78, wherein n is 7 or more (e.g. 8, 10, 12, 14, 16, 18, 20, 25, 30, 35, 40, 50, 60, 70, 80, 90, 100, 150, 200, 250 or more). These YPO0499 proteins include variants of SEQ ID NO:78. Preferred fragments of (b) comprise an epitope from SEQ ID NO:78. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:78. Other fragments omit one or more protein domains.

(19) YPO0505

The 'YPO0505' sequence was annotated in reference 16 as 'hypothetical protein' (see GI: 16120835). For reference purposes, the amino acid sequence of full-length YPO0505 as found in the *Y. pestis* CO92 strain is given as SEQ ID NO:79 herein. However, it is postulated herein that YPO0505 forms part of a Type Three Secretion System (TTSS).

Preferred YPO0505 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:79; and/or (b) that is a fragment of at least n consecutive amino acids of SEQ ID NO:79, wherein n is 7 or more (e.g. 8, 10, 12, 14, 16, 18, 20, 25, 30, 35, 40, 50, 60, 70, 80, 90, 100, 150, 200, 250 or more). These YPO0505 proteins include variants of SEQ ID NO:79. Preferred fragments of (b) comprise an epitope from SEQ ID NO:79. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:79. Other fragments omit one or more protein domains.

(20) YPO0500

The 'YPO0500' sequence was annotated in reference 16 as 'hypothetical protein' (see GI: 16120830). For reference purposes, the amino acid sequence of full-length YPO0500 as found in the *Y. pestis* CO92 strain is given as SEQ ID NO:80 herein. However, it is postulated herein that YPO0500 forms part of a Type Three Secretion System (TTSS).

Preferred YPO0500 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:80; and/or (b) that is a fragment of at least n consecutive amino acids of SEQ ID NO:80, wherein 77 is 7 or more (e.g. 8, 10, 12, 14, 16, 18, 20, 25, 30, 35, 40, 50, 60, 70, 80, 90, 100, 150, 200, 250 or more). These YPO0500 proteins include variants of SEQ ID NO:80. Preferred fragments of (b) comprise an epitope from SEQ ID NO:80. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:80. Other fragments omit one or more protein domains.

(21) YPO0503

The 'YPO0503' sequence was annotated in reference 16 as 'hypothetical protein' (see GI: 16120833). For reference purposes, the amino acid sequence of full-length YPO0503 as found in the *Y. pestis* CO92 strain is given as SEQ ID NO:81 herein. However, it is postulated herein that YPO0503 forms part of a Type Three Secretion System (TTSS).

Preferred YPO0503 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:81; and/or (b) that is a fragment of at least n consecutive amino acids of SEQ ID NO:81, wherein n is 7 or more (e.g. 8, 10, 12, 14, 16, 18, 20, 25, 30, 35, 40, 50, 60, 70, 80, 90, 100, 150, 200, 250 or more). These YPO0503 proteins include variants of SEQ ID NO:81. Preferred fragments of (b) comprise an epitope from SEQ ID NO:81. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 81. Other fragments omit one or more protein domains.

(22) YPO0506

The 'YPO0506' sequence was annotated in reference 16 as 'putative Clp ATPase' (see GI: 16120836). For reference purposes, the amino acid sequence of full-length YPO0506 as found in the *Y. pestis* CO92 strain is given as SEQ ID NO:82 herein. However, it is postulated herein that YPO0506 forms part of a Type Three Secretion System (TTSS).

Preferred YPO0506 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:82; and/or (b) that is a fragment of at least n consecutive amino acids of SEQ ID NO:82, wherein n is 7 or more (e.g. 8, 10, 12, 14, 16, 18, 20, 25, 30, 35, 40, 50, 60, 70, 80, 90, 100, 150, 200, 250 or more). These YPO0506 proteins include variants of SEQ ID NO:82. Preferred fragments of (b) comprise an epitope from SEQ ID NO:82. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:82. Other fragments omit one or more protein domains.

(23) YPO0508

The 'YPO0508' sequence was annotated in reference 16 as 'hypothetical protein' (see GI: 16120838). For reference purposes, the amino acid sequence of full-length YPO0508 as found in the *Y. pestis* CO92 strain is given as SEQ ID NO:83 herein. However, it is postulated herein that YPO0508 forms part of a Type Three Secretion System (TTSS).

Preferred YPO0508 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:83; and/or (b) that is a fragment of at least n consecutive amino acids of SEQ ID NO:83, wherein n is 7 or more (e.g. 8, 10, 12, 14, 16, 18, 20, 25, 30, 35, 40, 50, 60, 70, 80, 90, 100, 150, 200, 250 or more). These YPO0508 proteins include variants of SEQ ID NO:83. Preferred fragments of (b) comprise an epitope from SEQ ID NO:83. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:83. Other fragments omit one or more protein domains.

(24) YPO0509

The 'YPO0509' sequence was annotated in reference 16 as 'hypothetical protein' (see GI: 16120839). For reference purposes, the amino acid sequence of full-length YPO0509 as found in the *Y. pestis* CO92 strain is given as SEQ ID NO:84 herein. However, it is postulated herein that YPO0509 forms part of a Type Three Secretion System (TTSS).

Preferred YPO0509 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:84; and/or (b) that is a fragment of at least n consecutive amino acids of SEQ ID NO:84, wherein n is 7 or more (e.g. 8, 10, 12, 14, 16, 18, 20, 25, 30, 35, 40, 50, 60, 70, 80, 90, 100, 150, 200, 250 or more). These YPO0509 proteins include variants of SEQ ID NO:84. Preferred fragments of (b) comprise an epitope from SEQ ID NO:84. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 84. Other fragments omit one or more protein domains.

(25) YPO3579

The 'YPO3579' sequence was annotated in reference 16 as 'hypothetical protein' (see GI: 16123723). For reference purposes, the amino acid sequence of full-length YPO3579 as found in the *Y. pestis* CO92 strain is given as SEQ ID NO:85 herein. This protein is postulated herein to be a putative exported protein.

Preferred YPO3579 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:85; and/or (b) that is a fragment of at least n consecutive amino acids of SEQ ID NO:85, wherein n is 7 or more (e.g. 8, 10, 12, 14, 16, 18, 20, 25, 30, 35, 40, 50, 60, 70, 80, 90, 100, 150, 200, 250 or more). These YPO3579 proteins include variants of SEQ ID NO:85. Preferred fragments of (b) comprise an epitope from SEQ ID NO:85. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:85. Other fragments omit one or more protein domains.

(26) YPO4040

The 'YPO4040' sequence was annotated in reference 16 as 'hypothetical protein' (see GI: 16124160). For reference purposes, the amino acid sequence of full-length YPO4040 as found in the *Y. pestis* CO92 strain is given as SEQ ID NO:86 herein. This protein is postulated herein to be a putative exported protein and furthermore to be a fimbrial component.

Preferred YPO4040 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:86; and/or (b) that is a fragment of at least n consecutive amino acids of SEQ ID NO:86, wherein n is 7 or more (e.g. 8, 10, 12, 14, 16, 18, 20, 25, 30, 35, 40, 50, 60, 70, 80, 90, 100, 150, 200, 250 or more). These YPO4040 proteins include variants of SEQ ID NO:86. Preferred fragments of (b) comprise an epitope from SEQ ID NO:86. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:86. Other fragments omit one or more protein domains.

Seventh Antigen Group (1) YPO0496

The 'YPO0496' sequence was annotated in reference 16 as 'hypothetical protein' (see GI: 16120826). For reference purposes, the amino acid sequence of full-length YPO0496 as found in the *Y. pestis* CO92 strain is given as SEQ ID NO: 87 herein.

Preferred YPO0496 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:87; and/or (b) that is a fragment of at least n consecutive amino acids of SEQ ID NO:87, wherein n is 7 or more (e.g. 8, 10, 12, 14, 16, 18, 20, 25, 30, 35, 40, 50, 60, 70, 80, 90, 100, 150, 200, 250 or more). These YPO0496 proteins include variants of SEQ ID NO:87. Preferred fragments of (b) comprise an epitope from SEQ ID NO:87. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:87. Other fragments omit one or more protein domains.

(2) YPO1224

The 'YPO1224' sequence was annotated in reference 16 as 'putative penicillin-bindin protein' (see GI: 16121513). For reference purposes, the amino acid sequence of full-length YPO1224 as found in the *Y. pestis* CO92 strain is given as SEQ ID NO: 88 herein.

Preferred YPO1224 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:88; and/or (b) that is a fragment of at least n consecutive amino acids of SEQ ID NO:88, wherein n is 7 or more (e.g. 8, 10, 12, 14, 16, 18, 20, 25, 30, 35, 40, 50, 60, 70, 80, 90, 100, 150, 200, 250 or more). These YPO1224 proteins include variants of SEQ ID NO:88. Preferred fragments of (b) comprise an epitope from SEQ ID NO:88. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:88. Other fragments omit one or more protein domains.

(3) YPO3553

The 'YPO3553' sequence was annotated in reference 16 as 'enhancing lycopene biosynthesis protein 2' (see GI: 16123697). For reference purposes, the amino acid sequence of full-length YPO3553 as found in the *Y. pestis* CO92 strain is given as SEQ ID NO: 89 herein.

Preferred YPO3553 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:89; and/or (b) that is a fragment of at least n consecutive amino acids of SEQ ID NO:89, wherein n is 7 or more (e.g. 8, 10, 12, 14, 16, 18, 20, 25, 30, 35, 40, 50, 60, 70, 80, 90, 100, 150, 200, 250 or more). These YPO3553 proteins include variants of SEQ ID NO:89. Preferred fragments of (b) comprise an epitope from SEQ ID NO:89. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:89. Other fragments omit one or more protein domains.

(4) YPO3987

The 'YPO3987' sequence was annotated in reference 16 as 'hypothetical protein' (see GI: 16124114). For reference purposes, the amino acid sequence of full-length YPO3987 as found in the *Y. pestis* CO92 strain is given as SEQ ID NO: 90 herein. It has been suggested that this protein is an exported protein.

Preferred YPO3987 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:90; and/or (b) that is a fragment of at least n consecutive amino acids of SEQ ID NO:90, wherein n is 7 or more (e.g. 8, 10, 12, 14, 16, 18, 20, 25, 30, 35, 40, 50, 60, 70, 80, 90, 100, 150, 200, 250 or more). These YPO3987 proteins include variants of SEQ ID NO:90. Preferred fragments of (b) comprise an epitope from SEQ ID NO:90. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:90. Other fragments omit one or more protein domains.

(5) YPO2190

The 'YPO2190' sequence was annotated in reference 16 as 'attachment invasion locus protein precursor' (see GI: 16122420). For reference purposes, the amino acid sequence of full-length YPO2190 as found in the *Y. pestis* CO92 strain is given as SEQ ID NO: 91 herein.

Preferred YPO2190 proteins for use with the invention comprise an amino acid sequence: (a) that has 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:91; and/or (b) that is a fragment of at least n consecutive amino acids of SEQ ID NO:91, wherein n is 7 or more (e.g. 8, 10, 12, 14, 16, 18, 20, 25, 30, 35, 40, 50, 60, 70, 80, 90, 100, 150, 200, 250 or more). These YPO2190 proteins include variants of SEQ ID NO:91. Preferred fragments of (b) comprise an epitope from SEQ ID NO:91. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:91. Other fragments omit one or more protein domains.

Type Three Secretion System

The *Y. pestis* proteins YPO0499, YPO0500, YPO0501, YPO0502, YPO0503, YPO0504, YPO0505, YPO0506, YPO0507, YPO0508, YPO0509, YPO0510, YPO0511, YPO0512, YPO0513, YPO0514, YPO0515 and YPO0516 are postulated herein to form part of a Type Three Secretion System (TTSS). Analysis reveals sequence similarity between these proteins and those of the Icm/Dot secretion system, also known as the IcmF-associated homologous protein (IAHP) gene cluster of *Legionella pneumophila* [24-28]. Furthermore, YPO0499-YPO0506 have sequence similarity with proteins of the EVP cluster, which forms a secretion system in *Edwardsiella tarda* [29]. A further Type Three Secretion System has recently been described in *Vibrio cholerae*. Elements of this *Vibrio* system share identity with proteins of the system share identity with proteins of the *Y. pestis* cluster YPO0499-YPO0516.

Of these proteins, YPO0499, YPO0500, YPO0501, YPO0502, YPO0503, YPO0505, YPO0506, YPO0508, YPO0509, YPO0512 and YPO0514 are considered to be surface exposed and therefore useful as immunising antigens.

Thus, particularly preferred compositions of the invention comprise one or more (i.e. 1, 2, 3, 4, 5, 6, 7, 8, 9, 10 or all 11) of YPO0499, YPO0500, YPO0501, YPO0502, YPO0503, YPO0505, YPO0506, YPO0508, YPO0509, YPO0512 and/or YPO0514.

Fusion and Hybrid Polypeptides

The *Y. pestis* antigens used in the invention may be present in the composition as individual separate polypeptides. Where more than one antigen is used, however, they do not have to be present as separate polypeptides. Instead, at least two (e.g. 2, 3, 4, 5, or more) antigens can be expressed as a single polypeptide chain (a 'hybrid' polypeptide). Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful. The F1 and V antigens, for instance, can be expressed as a hybrid [30].

The hybrid polypeptide may comprise two or more polypeptide sequences from the first antigen group. The hybrid polypeptide may comprise one or more polypeptide sequences from the first antigen group and one or more polypeptide sequences from the second antigen group. The hybrid polypeptide may comprise one or more polypeptide sequences from the first antigen group and one or more polypeptide sequences from the third antigen group. The hybrid polypeptide may comprise one or more polypeptide sequences from the second antigen group and one or more polypeptide sequences from the third antigen group. The hybrid polypeptide may comprise one or more polypeptide sequences from the first, second and/or third antigen group and one or more polypeptide sequences from the fourth antigen group. The hybrid polypeptide may comprise one or more polypeptide sequences from the first, second and/or third antigen group and one or more polypeptide sequences from the fifth antigen group. The hybrid polypeptide may comprise one or more polypeptide sequences from the first, second and/or third antigen group and one or more polypeptide sequences from the sixth antigen group. The hybrid polypeptide may comprise one or more polypeptide sequences from the first, second and/or third antigen group and one or more polypeptide sequences from the seventh antigen group.

Hybrids for use in the present invention may also comprise combinations of antigens selected from the second, third, fourth, fifth, sixth and seventh antigen groups.

Hybrids consisting of amino acid sequences from two, three, four, five, six, seven, eight, nine, or ten *Y. pestis* antigens are preferred. In particular, hybrids consisting of amino acid sequences from two, three, four, or five *Y. pestis* antigens are preferred. Particularly preferred are hybrids consisting of amino acid sequences from two or three *Y. pestis* antigens.

Different hybrid polypeptides may be mixed together in a single formulation. Within such combinations, a *Y. pestis* antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-$\{$-X-L-$\}_n$-B—COOH, wherein: X is an amino acid sequence of a *Y. pestis* antigen, as described above; L is an optional linker amino acid sequence; A is an optional N-terminal amino acid sequence; B is an optional C-terminal amino acid sequence; n is an integer of 2 or more (e.g. 2, 3, 4, 5, 6, 7, 8, 9, 10, 11, 12, 13, 14 or 15). Most preferably, n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of $\{$—X-L-$\}$, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$, where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO:60), with the Gly-Ser dipeptide being formed from a BamHI restriction site, thus aiding cloning and manipulation, and the (Gly)$_4$ tetrapeptide being a typical poly-glycine linker.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$, where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance protein stability. Other suitable C-terminal amino acid sequences will be apparent to those skilled in the art.

Preferred fusion protein compositions of the invention comprise one or more (i.e. 1, 2, 3, 4, 5, 6, 7, 8, 9, 10 or more) of 0809_GST, 0809_His, 0499_GST, 0499_His, 1070_GST, 1070_His, 3489_GST, 3489_His, 1354_GST, 1354_His, 3631_GST, 3631_His, 1604_GST, 1604_His, 4003_GST, 4003_His, 0500_His, 0501_His, 0502_His, 0502_GST, 0503_His, 0503_GST, 0505_His, 0505GST, 0506_His, 0508_GST and/or 0509_GST. According to this nomenclature, each antigen may have a N-terminal GST tag or a C-terminal his tag. Therefore, for example, 3489_His is YPO3489 with a C-terminal his tag and 0809_GST is YPO0809 with a N-terminal GST tag.

Particularly preferred combinations comprise (1) 0809_GST and 0499_GST, (2) 1070_GST and 3489_His, (3) 1354_His and 3631_His, and/or (4) 1604_His and 4003_His. Such preferred combinations may be found in an immunogenic composition further comprising alum and/or CpG.

The invention also provides nucleic acid encoding hybrid polypeptides of the invention. The term "nucleic acid" includes DNA and RNA, and also their analogues, such as those containing modified backbones (e.g. phosphorothioates, etc.), and also peptide nucleic acids (PNA), etc.

Polypeptides Used with the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). F1, for instance, is known to exist in various forms, including a multimeric glycoprotein form. Lipoproteins are particularly preferred for use as immunogens.

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other Yersinia or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

Polypeptides used with the invention are preferably Y. pestis polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Fusion proteins of F1 are known, for instance, from reference 103, where a heterologous anchor domain is attached to allow cell-surface display of a protein that would normally be secreted. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Polypeptides used with the invention may be prepared as a GST-fusion protein and/or a His-tagged fusion protein.

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

Strains

Polypeptides of the invention may comprise an amino acid sequence found in a *Y. pestis* of biovar Antiqua, Mediaevalis, Orientalis and/or Microtus, with biovar orientalis being preferred [31].

Polypeptides of the invention may comprise an amino acid sequence found in a *Y. pestis* of ribotypes A, B, C, Q, R, and/or T.

Preferred polypeptides of the invention comprise an amino acid sequence found in *Y. pestis* strains CO92 [16], KIM [17], 91001 [18], 685, etc., including the strains listed in references 31 and 100. The sequence may also be found in other *Yersinia* species, such as a *Y. pseudotuberculosis* (full genome sequence available as GI: 51587641 [32]) or a *Y. enterocolitica*.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Heterologous Hosts Whilst expression of the polypeptides of the invention may take place in *Yersinia*, the invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Immunogenic Compositions and Medicaments

Compositions of the invention are preferably immunogenic compositions, such as vaccine compositions. The pH of the composition is preferably between 6 and 8, preferably about 7. The pH may be maintained by the use of a buffer. A phosphate buffer is typical. The composition may be sterile and/or pyrogen-free. The composition may be gluten-free. The composition may be substantially free from formaldehyde, phenol, beef-heart extract, yeast extract, and/or agar. The composition may be free from *Y. pestis* DNA. The composition may be isotonic with respect to humans.

Vaccines according to the invention may either be prophylactic (i.e. to prevent infection) or therapeutic (i.e. to treat infection), but will typically be prophylactic. Accordingly, the invention includes a method for the therapeutic or prophylactic treatment of *Y. pestis* infection in an animal susceptible to *Yersinia* infection comprising administering to said animal a therapeutic or prophylactic amount of the immunogenic compositions of the invention.

Compositions may include a preservative, particularly if packaged in a multiple dose format.

Compositions may comprise detergent e.g. a Tween (polysorbate), such as Tween 80. Detergents are generally present at low levels e.g. <0.01%.

Compositions may include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material.

The immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

A. Mineral-containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 33], or mixtures of different mineral compounds, with the compounds taking any suitable form (e.g. gel, crystalline, amorphous, etc.), and with adsorption being preferred. The mineral containing compositions may also be formulated as a particle of metal salt [34].

Aluminium phosphates are particularly preferred, particularly in compositions which include a *H. influenzae* saccharide antigen, and a typical adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 33; see also ref. 35] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. *Saponin* Formulations [Chapter 22 of Ref. 33]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 36. Saponin formulations may also comprise a sterol, such as cholesterol [37].

Combinations of saponins and cholesterols can be used to form unique particles called immunostimulating complexs (ISCOMs) [chapter 23 of ref. 33]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 37-39. Optionally, the ISCOMS may be devoid of additional detergent [40].

A review of the development of saponin based adjuvants can be found in refs. 41 & 42.

D. Virosomes and Virus-like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 43-48. Virosomes are discussed further in, for example, ref. 49

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 50. Such "small particles" of 3dMPL are small enough to be sterile filtered through a 0.22 μm membrane [50]. Other non-toxic LPS derivatives include monophosphoryl lipid A mimics, such as aminoalkyl glucosaminide phosphate derivatives e.g. RC-529 [51,52]. Lipid A derivatives include derivatives of lipid A from *Escherichia coli* such as OM-174. OM-174 is described for example in refs. 53 & 54.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 55, 56 and 57 disclose possible analog substitutions e.g. replacement of guanosine with 2'-deoxy-7-deazaguanosine. The adjuvant effect of CpG oligonucleotides is further discussed in refs. 58-63.

The CpG sequence may be directed to TLR9, such as the motif GTCGTT or TTCGTT [64]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 65-67. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 64 & 68-70.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 71 and as parenteral adjuvants in ref. 72. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 73-80. Numerical reference for amino acid substitutions is preferably based on the alignments of the A and B subunits of ADP-ribosylating toxins set forth in ref. 81, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [82], etc.) [83], interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [84] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [85].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 33)

Examples of liposome formulations suitable for use as adjuvants are described in refs. 86-88.

J. Polyoxyethylene Ether and Polyoxyethylene Ester Formulations

Adjuvants suitable for use in the invention include polyoxyethylene ethers and polyoxyethylene esters [89]. Such formulations further include polyoxyethylene sorbitan ester surfactants in combination with an octoxynol [90] as well as polyoxyethylene allyl ethers or ester surfactants in combination with at least one additional non-ionic surfactant such as an octoxynol [91]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 92 and 93.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 94 and 95.

The invention may also comprise combinations of aspects of one or more of the adjuvants identified above. For example, the following adjuvant compositions may be used in the invention: (1) a saponin and an oil-in-water emulsion [96]; (2) a saponin (e.g. QS21)+a non-toxic LPS derivative (e.g. 3dMPL) [97]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [98]; (5) combinations of 3dMPL with, for example, QS21 and/or oil-in-water emulsions [99]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 33.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum.

Use of the combination of a mineral salt, such as an aluminium salt, and an oligonucleotide containing a CpG motif provide for an enhanced immune response. The invention therefore provides a composition comprising an oligonucleotide containing a CpG motif, a mineral salt such as an aluminium salt, and one or more Y. pestis antigens as defined above. The invention also provides a composition comprising an ADP ribosylating toxin (such as a detoxified ADP ribosylating toxin), an oligonucleotide containing a CpG motif, and one or more Y. pestis antigens as defined above.

The compositions of the invention will preferably elicit both a cell mediated immune response as well as a humoral immune response in order to effectively address a Yersinia intracellular infection. This immune response will preferably induce long lasting (e.g. neutralising) antibodies and a cell mediated immunity that can quickly respond upon exposure to Yersinia.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment and Medical Uses

The invention provides one or more of (1) a YPO0512 antigen; (2) a YPO0563 antigen; (3) a YPO3489 antigen; (4) a YPO4003 antigen; (5) a YPO1604 antigen; (6) a YPO3061 antigen; (7) a YPO3559 antigen; (8) a YPO3382 antigen; (9) a YPO0860 antigen; (10) a YPO0086 antigen; (11) a YPO3631 antigen; (12) a YPO2881 antigen; (13) a YPO3343 antigen; (14) a YPO3361 antigen; (15) a YPO3430 antigen; (16) a YPO1411 antigen; (17) a YPO3935 antigen; (18) a YPO0809 antigen; (19) a YPO1123 antigen; (20) a YPO3065 antigen; and/or (21) a YPO1070 antigen, for use (i) as an immunogen, (ii) in therapy, and/or (iii) in the manufacture of a medicament for raising an immune response in a mammal.

The invention also provides the use of one or more of (1) a YPO0512 antigen; (2) a YPO0563 antigen; (3) a YPO3489 antigen; (4) a YPO4003 antigen; (5) a YPO1604 antigen; (6) a YPO3061 antigen; (7) a YPO3559 antigen; (8) a YPO3382 antigen; (9) a YPO0860 antigen; (10) a YPO0086 antigen; (11) a YPO3631 antigen; (12) a YPO2881 antigen; (13) a YPO3343 antigen; (14) a YPO3361 antigen; (15) a YPO3430 antigen; (16) a YPO1411 antigen; (17) a YPO3935 antigen; (18) a YPO0809 antigen; (19) a YPO1123 antigen; (20) a YPO3065 antigen; and/or (21) a YPO1070 antigen, in the manufacture of a medicament for raising an immune response in a mammal.

The invention provides one or more of (1) a YPO0102 antigen; (2) a YPO0570 antigen; (3) a YPO1053 antigen; (4) a YPO1435 antigen; (5) a YPO2674 antigen; (6) a YPO2292 antigen; (7) a YPO3050 antigen; (8) a YPO2615 antigen; (9) a YPO1507 antigen; (10) a YPO4111 antigen; (11) a YPO0015 antigen; (12) a YPO0195 antigen; (13) a YPO2342 antigen; (14) a YPO0501 antigen; (15) a YPO0502 antigen; (16) a YPO0819 antigen; (17) a YPO3644 antigen; (18) a YPO1746 antigen; (19) a YPO0351 antigen; (20) a YPO0468 antigen; (21) a YPO0203 antigen; (22) a YPO0216 antigen; (23) a YPO3536 antigen; (24) a YPO0233 antigen; (25) a YPO0067 antigen; (26) a YPO3643 antigen; (27) a YPO3375 antigen; (28) a YPO0494 antigen; (29) a YPO1052 antigen; (30) a YPO1906 antigen; (31) a YPO0663 antigen; (32) a YPO1222 antigen; (33) a YPO2905 antigen; (34) a YPO4070 antigen; (35) a YPPCP1.07 antigen; and/or (36) a YPMT1.42 antigen, for use (i) as an immunogen, (ii) in therapy, and/or (iii) in the manufacture of a medicament for raising an immune response in a mammal.

The invention also provides the use of one or more of (1) a YPO0102 antigen; (2) a YPO0570 antigen; (3) a YPO1053 antigen; (4) a YPO1435 antigen; (5) a YPO2674 antigen; (6) a YPO2292 antigen; (7) a YPO3050 antigen; (8) a YPO2615 antigen; (9) a YPO1507 antigen; (10) a YPO4111 antigen; (11) a YPO0015 antigen; (12) a YPO0195 antigen; (13) a YPO2342 antigen; (14) a YPO0501 antigen; (15) a YPO0502 antigen; (16) a YPO0819 antigen; (17) a YPO3644 antigen; (18) a YPO1746 antigen; (19) a YPO0351 antigen; (20) a YPO0468 antigen; (21) a YPO0203 antigen; (22) a YPO0216 antigen; (23) a YPO3536 antigen; (24) a YPO0233 antigen; (25) a YPO0067 antigen; (26) a YPO3643 antigen; (27) a YPO3375 antigen; (28) a YPO0494 antigen; (29) a YPO1052 antigen; (30) a YPO1906 antigen; (31) a YPO0663 antigen; (32) a YPO1222 antigen; (33) a YPO2905 antigen; (34) a YPO4070 antigen; (35) a YPPCP1.07 antigen; and/or (36) a YPMT1.42 antigen, in the manufacture of a medicament for raising an immune response in a mammal.

The invention provides one or more of (1) a YPO0457 antigen; (2) a YPO0514 antigen; (3) a YPO0694 antigen; (4) a YPO0805 antigen; (5) a YPO0982 antigen; (6) a YPO1354 antigen; (7) a YPO1408 antigen; (8) a YPO1792 antigen; (9) a YPO2506 antigen; (10) a YPO2713 antigen; (11) a YPO2950 antigen; (12) a YPO3026 antigen; (13) a YPO3417 antigen; (14) a YPO3551 antigen; (15) a YPO3646 antigen; (16) a YPO3982 antigen; (17) a YPO0065 antigen; (18) a YPO0499 antigen; (19) a YPO0505 antigen, (20) a YPO0500 antigen; (21) a YPO0503 antigen; (22) a YPO0506 antigen; (23) a YPO0508 antigen; (24) a YPO0509 antigen; (25) a YPO3579 antigen and/or (26) a YPO4040 antigen, for use (i) as an immunogen, (ii) in therapy, and/or (iii) in the manufacture of a medicament for raising an immune response in a mammal.

The invention provides the use of one or more of (1) a YPO0457 antigen; (2) a YPO0514 antigen; (3) a YPO0694 antigen; (4) a YPO0805 antigen; (5) a YPO0982 antigen; (6) a YPO1354 antigen; (7) a YPO1408 antigen; (8) a YPO1792 antigen; (9) a YPO2506 antigen; (10) a YPO2713 antigen; (11) a YPO2950 antigen; (12) a YPO3026 antigen; (13) a YPO3417 antigen; (14) a YPO3551 antigen; (15) a YPO3646 antigen; (16) a YPO3982 antigen; (17) a YPO0065 antigen; (18) a YPO0499 antigen; (19) a YPO0505 antigen, (20) a YPO0500 antigen; (21) a YPO0503 antigen; (22) a YPO0506 antigen; (23) a YPO0508 antigen; (24) a YPO0509 antigen; (25) a YPO3579 antigen and/or (26) a YPO4040 antigen in the manufacture of a medicament for raising an immune response in a mammal.

The invention provides one or more of (1) a YPO0496 antigen; (2) a YPO1224 antigen; (3) a YPO3553 antigen; (4) a YPO3987 antigen and/or (5) a YPO2190 antigen, for use (i) as an immunogen, (ii) in therapy, and/or (iii) in the manufacture of a medicament for raising an immune response in a mammal.

The invention provides the use of one or more of (1) a YPO0496 antigen; (2) a YPO1224 antigen; (3) a YPO3553 antigen; (4) a YPO3987 antigen and/or (5) a YPO2190 antigen in the manufacture of a medicament for raising an immune response in a mammal.

These medicaments are preferably vaccines.

The invention also provides a method for raising an immune response in a mammal comprising the step of administering an effective amount of a composition of the invention. The immune response is preferably protective and preferably involves antibodies and/or cell-mediated immunity. The method may raise a booster response.

By raising an immune response in the mammal by these uses and methods, the mammal can be protected against *Y. pestis* infection. More particularly, the mammal may be protected against a plague, including bubonic plague, septicemic plague and/or pneumonic plague. Other related diseases include cellulocutaneous plague and plague meningitis. The medicament is preferably for protecting a mammal against pneumonic plague.

Compositions of the invention can preferably protect against *Y. pestis* ribotypes [100,101] including one or more of A, B, C, Q, R, and/or T.

Compositions of the invention can preferably protect against *Y. pestis* biovars including one or more of antiqua, mediaevalis, orientalis and/or microtus [102].

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

One way of checking efficacy of therapeutic treatment involves monitoring *Y. pestis* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the *Y. pestis* antigens in the compositions of the invention after administration of the composition. Typically, serum *Yersinia* specific antibody responses are determined post-immunisation but pre-challenge whereas mucosal *Yersinia* specific antibody body responses are determined post-immunisation and post-challenge. The protective effect of a composition can be tested in standard animal models, including the murine aerosol challenge model of reference 8.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The vaccine compositions of the present invention can be evaluated in in vitro and in vivo animal models prior to host, e.g., human, administration. For example, in vitro neutralization is suitable for testing vaccine compositions directed toward *Y. pestis*.

The efficacy of vaccine compositions can also be determined in vivo by challenging animal models of *Y. pestis* infection, e.g., guinea pigs or mice, with the vaccine compositions. For example, reference 103 describes the immunisation of mice against *Y. pestis* and then challenging with F1 antigen. The administered compositions may or may not be derived from the same strains as the challenge strains. Preferably the compositions are derived from the same strains as the challenge strains. In vivo efficacy models include but are not limited to: (i) murine infection models using *Y. pestis* strains that are infectious to humans; (ii) murine disease models which use mouse-adapted *Y. pestis* strains, such as strains which are particularly virulent in mice; and (iii) primate models using human strains.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (see e.g. reference 104) or transcutaneous (see e.g. references 9, 105 and 106), intranasal (see e.g. reference 107), ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc.

*Yersinia* infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Further Components of the Composition

*Yersinia* antigens of the invention can be combined with pharmaceutically acceptable carriers. Such carriers include any carrier that does not itself induce the production of antibodies harmful to the individual receiving the composition. Such carriers are well known to those of ordinary skill in the art. The compositions may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 108.

The invention further provides a method for preparing a pharmaceutical product, comprising the steps of: (a) preparing *Yersinia* antigens as described above; (b) mixing the antigens with one or more pharmaceutically acceptable carriers; and (c) packaging the antigen/carrier mixture into a container, such as a vial or a syringe, to give a pharmaceutical product. Insertion into a syringe may be performed in a factory or in a surgery.

The compositions can also include non-*Yersinia* immunogens. Thus the compositions may include one or more of: an immunogen from *Bacillus anthracis* for protecting against anthrax infection (e.g. a PA antigen [109], a spore antigen, etc.); an immunogen from a bacterium in the *Francisella* genus, such as *F. tularensis* for protecting against tularemia; an immunogen from a bacterium in the *Pasteurella* genus; an immunogen from a bacterium in the *Brucella* genus for protecting against brucellosis, such as *B. abortus, B. melitensis*, or *B. suis*; an immunogen from a bacterium in the *Burkholderia* genus, such as *B. mallei* for protecting against glanders or *B. pseudomallei* for protecting against melioidosis; an immunogen from a bacterium in the *Chlamydia* genus, such as *Chlamydia psittaci* for protecting against psittacosis; an immunogen from a bacterium in the *Clostridium* genus, such as *C. botulinum* for protecting against botulism or *C. perfringens* for protecting against Epsilon toxin); an immunogen from a bacterium in the *Francisella* genus, such as *F. tularensis* for protecting against tularemia; an immunogen from a *Vibrio cholerae* bacterium for protecting against cholera; an immunogen from a *Coxiella burnetii* bacterium for protecting against Q fever; an immunogen from an Ebola virus and/or a Marburg virus and/or a Lassa virus and/or a Machupo virus, for protecting against hemorrhagic fever; an immunogen from a bacterium in the *Rickettsia* genus, such as *R. prowazekii* bacterium for protecting against typhus fever, or from *R. rickettsii*; an immunogen from a fungus in the *Coccidioides* genus, such as *C. immitis* or *C. posadasii*; etc.

Chromosomal Antigens and Epitopes for Use in Immunisation

As mentioned above, the F1 and V antigens have been used for immunisation. These two antigens are encoded by *Y. pestis* plasmids. Thus, more generally, the invention provides an immunogenic composition comprising one or more chromosomal *Y. pestis* proteins. It also provides a chromosomal *Y. pestis* protein for use as an immunogen. It also provides the use of a chromosomal *Y. pestis* protein in the manufacture of a medicament, as described above.

The chromosomal protein may be, for example, a ribosomal protein, such as a 50S or 30S ribosomal protein. The chromosomal protein may be a lipoprotein. The chromosomal protein may be a periplasmic protein. The chromosomal protein may be a membrane protein. The chromosomal protein may be a heat-shock or cold-shock protein. The chromosomal protein may be an enzyme. The chromosomal protein may be a chaperone or chaperonin.

The composition may include the chromosomal protein in the form of a full-length protein as encoded by the chromosome, a hybrid protein (as described above), or a fragment of the chromosomal protein (as described above).

Nucleic Acid Immunisation

The immunogenic compositions described above include polypeptide antigens from *Y. pestis*. In all cases, however, the polypeptide antigens can be replaced by nucleic acids (typically DNA) encoding those polypeptides, to give compositions, methods and uses based on nucleic acid immunisation. Nucleic acid immunisation is now a developed field (e.g. see references 103 and 110 to 117 etc.), and has been applied to *Y. pestis* vaccines [118-123].

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter.

Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in, for example, references 124 to 129. Therapeutic compositions containing a nucleic acid are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 130 to 133).

Viral-based vectors for delivery of a desired nucleic acid and expression in a desired cell are well known in the art. Exemplary viral-based vehicles include, but are not limited to, recombinant retroviruses (e.g. references 134 to 144), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 145 to 150). Administration of DNA linked to killed adenovirus [151] can also be employed.

Non-viral delivery vehicles and methods can also be employed, including, but not limited to, polycationic condensed DNA linked or unlinked to killed adenovirus alone [e.g. 151], ligand-linked DNA [152], eukaryotic cell delivery vehicles cells [e.g. refs. 153 to 157] and nucleic charge neutralization or fusion with cell membranes. Naked DNA can also be employed. Exemplary naked DNA introduction methods are described in refs. 158 and 159. Liposomes (e.g. immunoliposomes) that can act as gene delivery vehicles are described in refs. 160 to 164. Additional approaches are described in references 165 & 166.

Further non-viral delivery suitable for use includes mechanical delivery systems such as the approach described in ref. 166. Moreover, the coding sequence and the product of expression of such can be delivered through deposition of photopolymerized hydrogel materials or use of ionizing radiation [e.g. refs. 167 & 168]. Other conventional methods for gene delivery that can be used for delivery of the coding sequence include, for example, use of hand-held gene transfer particle gun [169] or use of ionizing radiation for activating transferred genes [167 & 170].

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Antibodies

Antibodies against *Y. pestis* antigens can be used for passive immunisation [171]. Thus the invention provides an antibody that is specific for an antigen in the first, second, third or fourth antigen groups. The invention also provides the use of such antibodies in therapy. The invention also provides the use of such antibodies in the manufacture of a medicament. The invention also provides a method for treating a mammal comprising the step of administering an effective amount of a antibody of the invention. As described above for immunogenic compositions, these methods and uses allow a mammal to be protected against *Y. pestis* infection.

The term "antibody" includes intact immunoglobulin molecules, as well as fragments thereof which are capable of binding an antigen. These include hybrid (chimeric) antibody molecules [172, 173]; F(ab')2 and F(ab) fragments and Fv molecules; non-covalent heterodimers [174, 175]; single-chain Fv molecules (sFv) [176]; dimeric and trimeric antibody fragment constructs; minibodies [177, 178]; humanized antibody molecules [179-181]; and any functional fragments obtained from such molecules, as well as antibodies obtained through non-conventional processes such as phage display.

Preferably, the antibodies are monoclonal antibodies. Methods of obtaining monoclonal antibodies are well known in the art.

Humanised or fully-human antibodies are preferred.

Knockout Mutants

The invention also provides a *Yersinia* bacterium in which expression of one or more of the genes encoding an antigen in the third or fourth antigen groups has been knocked out.

The bacterium may be any *Yersinia* species, including *Y. pestis, Y. pseudotuberculosis* or *Y. enterocoliticus*. Preferably, however, it is *Y. pestis*. The homologous non-pestis genes that correspond to the genes encoding the *pestis* antigens of the third and fourth antigen groups can readily be identified based on sequence similarity and/or chromosomal location.

Techniques for gene knockout in bacteria are well known, and *Yersinia* knockout mutants have been reported previously (e.g. refs. 182-186, etc.).

The knockout is preferably achieved using isogenic deletion of the coding region, but any other suitable technique may be used e.g. deletion or mutation of the promoter, deletion or mutation of the start codon, antisense inhibition, inhibitory RNA, etc. In the resulting bacterium, however, mRNA encoding the antigen of interest will be absent and/or its translation will be inhibited (e.g. to less than 1% of wild-type levels).

The bacterium may contain a marker gene in place of the knocked out gene e.g. an antibiotic resistance marker.

As well as knocking out the *Yersinia* antigens of the third and fourth groups, knockout of YPO1025 is also possible, as is knockout of YPO0154, and knockout of one or more genes in the operon including YPO1121, YPO1122, YPO1123, YPO1124 and YPO1125. Again, the homologous genes in *Y. pseudotuberculosis* or *Y. enterocoliticus* can readily be identified.

The invention also provides a protein vesicle obtainable from said knockout bacteria. These vesicles may be spontaneously released into culture medium during bacterial growth. The vesicles contain lipids and proteins, and are useful as immunogens. A composition containing the vesicles preferably does not comprise any living and/or whole bacteria.

The vesicles preferably include (e.g. in a surface-exposed form) an antigen from the third antigen group and/or the fourth antigen group and/or the fifth antigen group.

Animal Model

For preliminary screening of antigens for protective efficacy, a simple animal model is useful. For example, reference 8 discloses a murine aerosol challenge model. The invention provides a new animal model that is useful for quickly assessing the protective efficacy of an antigen, or of a new formulation (e.g. new adjuvant, or new combination) of an antigen.

The invention provides a method for assessing the protective efficacy of a composition that comprises a *Y. pestis* antigen (e.g. a composition of the invention), wherein the method comprises the steps of: immunising an animal with the composition; collecting antiserum from the animal; incubating the antiserum with a *Y. pseudotuberculosis* or *Y. enterocolitica* bacterium in the presence of complement; and assessing bacterial growth.

The invention also provides a method for assessing the protective efficacy of a composition that comprises a *Y. pestis* antigen (e.g. a composition of the invention), wherein the method comprises the steps of: incubating an antiserum with a *Yersinia* bacterium, other than *Y. pestis*, in the presence of complement, wherein the antiserum has been taken from an animal that was immunised with the composition; and assessing bacterial growth.

The animal is preferably a rodent, such as a mouse, and preferably an inbred laboratory mouse strain.

The *Yersinia* bacterium is preferably *Y. pseudotuberculosis* or *Y. enterocolitica*.

The complement is preferably rabbit complement.

In the assessment of bacterial growth, there will usually be a comparison with a negative control or reference sample in which bacteria are grown either in the absence of any antiserum or in the presence of a negative control antiserum. The degree of inhibition of growth (or of bacterial killing) relative to the negative control indicates the degree of protective efficacy of the composition. Similarly, there may be a comparison with a positive control or reference sample in which bacteria are grown either in the presence of an agent (e.g. an antiserum) that is known to be protective.

The control growths may be performed in parallel with the method of the invention, or may be performed separately.

Antisera may be tested at different dilutions, and the result of the assay may be given as the dilution at which growth inhibition does not occur. The degree of dilution required before loss of bactericidal activity indicates the degree of protective efficacy of the composition.

The bacterial growth step may occur at below 37° C. e.g. between 25-32° C., or about 28° C.

General

Antigens are defined above by reference to "YPO" (or, in one case, "YPPCP") nomenclature. This nomenclature refers to the numbering used in reference 16 for unique identification of open reading frames in the CO92 strain of *Y. pestis*. The basic reference sequence for any "YPO" or "YPPCP" number can easily be found in public gene databases. For instance, accession number NC_003143 (GI:16120353) is the complete CO92 genome sequence (4,653,728 bp), and the individual YPO sequences are given as "locus_tag" entries in the genome sequence's "features" section. Similarly, NC_003132 (GI:16082679) is the complete sequence of the pPCP1 plasmid, and the "locus_tag" field gives the YPPCP number. Thus the nucleotide and amino acid sequences for any given YPO or YPPCP number can be established unambiguously.

"GI" numbering is also used above. A GI number, or "GenInfo Identifier", is a series of digits assigned consecutively to each sequence record processed by NCBI when sequences are added to its databases. The GI number bears no resemblance to the Accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN [187,188] or similar methods), or they can be predicted (e.g. using the Jameson-Wolf antigenic index [189], matrix-based approaches [190], TEPITOPE [191,192], neural networks [193], OptiMer & EpiMer [194, 195], ADEPT [196], Tsites [197], hydrophilicity [198], antigenic index [199] or the methods disclosed in reference 200, etc.). Epitopes are the parts of an antigen that are recognised by and bind to the antigen binding sites of antibodies or T-cell receptors, and they may also be referred to as "antigenic determinants".

Variants of SEQ ID NOs include allelic variants, polymorphic forms, homologs, orthologs, paralogs, mutants, etc.

Polypeptides of the invention may, compared to the CO92 reference sequence, include one or more (e.g. 1, 2, 3, 4, 5, 6, 7, 8, 9, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the CO92 sequences. The polypeptides may also include one or more (e.g. 1, 2, 3, 4, 5, 6, 7, 8, 9, etc.) insertions (e.g. each of 1, 2, 3, 4 or 5 amino acids) relative to the CO92 sequences.

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x means, for example, x±10%.

If desired, antigens can be conjugated to a carrier protein in order to enhance immunogenicity.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 201. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 202.

BRIEF DESCRIPTION OF DRAWINGS

In FIG. 5, black bars are data on pLCR- strains and grey bars are data on pgm-pst- strains.

MODES FOR CARRYING OUT THE INVENTION

Antigen Identification

Figure 1:
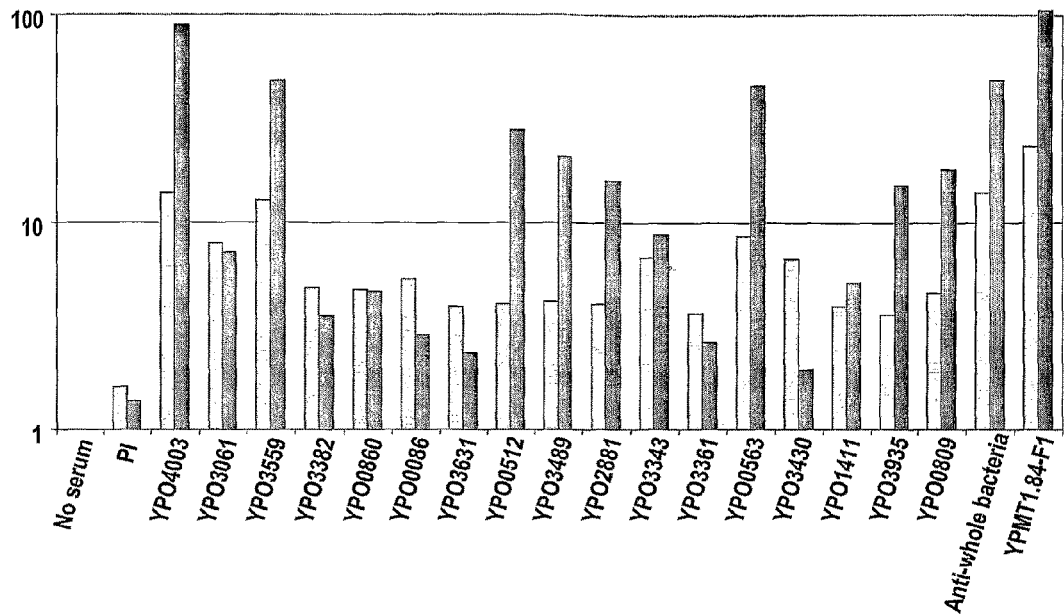
FIGS. 1 and 2 show the results of opsonophagocytosis assays. Two bars are shown for each assay: the left is with active complement and the right is with inactive complement. The Y-axis shows the fold increase in phagocytosis, and the X-axis shows the antigen used to elicit the antiserum.
Figure 2:
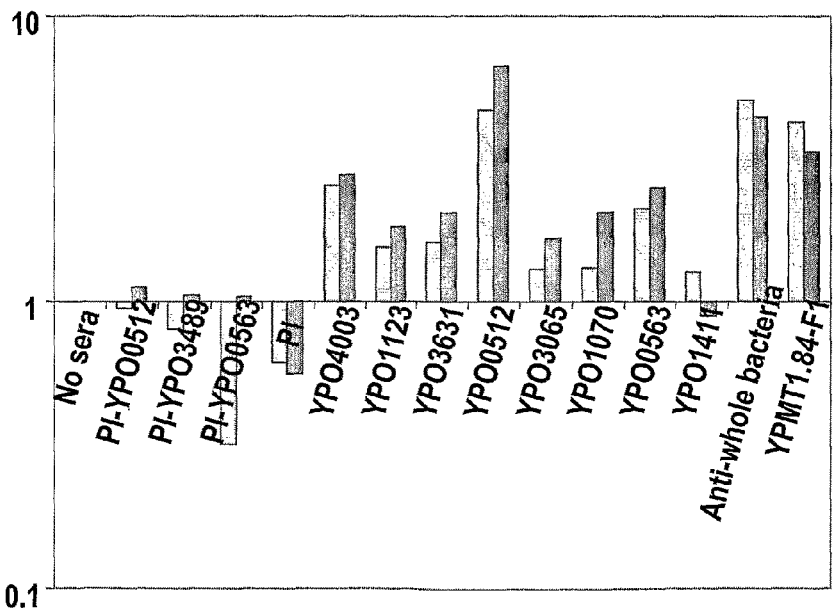

The *Y. pestis* genome includes more than 4000 open reading frames, and its annotation includes little information useful for the identification of useful immunogens. To identify useful immunogens from within these 4000 possibilities, four approaches were utilised. Firstly, computational analysis of the genome was used to identify useful immunogens. Second, transcriptional profiling was used to identify highly-expressed genes under in vitro and in vivo growth conditions, and in particular after a temperature shift from 28° C. to 37° C., which mimics the natural host change from flea to mammal. Third, comparative genomic hybridization (CGH) was used to identify genes that are conserved in a variety of *Y. pestis* clinical isolates representative of major biovars [203]. Fourth, surface shaving and labelling were used to identify surface-exposed proteins (cf. reference 204).

The first three approaches eliminated about 90% of the ORFs. The remaining ~400 ORFs were selected for cloning, purification and immunisation tests, together with (a) screening in in vitro and in vivo models in order to identify antigens that can induce a bactericidal immune response, and (b) FACS analysis and western blots to confirm cellular localization. Antigens were typically expressed in *E. coli* as N-terminal GST fusions, or as C-terminal or N-terminal hex-His fusions, and the amplified coding sequences usually omitted signal peptides, to give intracellular expression. Expression without GST or His fusion partners is also possible, though. 360 ORFs were successfully cloned and expressed in at least one of the two fusion forms. Each recombinant protein was used to immunize groups of 4 CD1 mice.

FACS

Sera from the mice were recovered two weeks after the final immunization and were tested by immunoblot analysis on both purified recombinant proteins and *Y. pestis* total extracts. In general, all sera specifically recognized the corresponding recombinant protein used for immunization and a protein species with the expected molecular weight in the total cell extract. Having confirmed the specificity of the polyclonal antibodies, the sera were used for flow cytometry analysis (FACS) on whole bacteria to define which of the 360 expressed antigens were sufficiently accessible to interact with their specific antibodies. As CO92 pLCR- strain carries the pMT1 plasmid and expresses the F1 capsular antigen, anti-F1 antigen antibodies were used as positive control in each experiment. Antisera raised against bulk *E. coli* contaminants of the GST-tagged proteins and His-tagged proteins were obtained and used to define the experimental cut-off of the FACS positive antigens.

Approximately 150 of the 360 sera analyzed gave fluorescence value higher than negative control sera, indicating that the corresponding antigens are exposed on the *Y. pestis* surface. These 150 antigens were further analyzed for protective activities against *Y. pestis.*

Proteolysis of the *Yersinia* Surface and Analysis of Resultant Peptides.

Infectious forms of *Y. pestis* were grown in cell cultures and purified by gradient centrifugation as described in the literature. Approximately, $10^7$ IFU in transport buffer were digested ("shaved") with trypsin. Limited digestion was carried out with 20 μg trypsin (Promega, Madison, Wis., USA) for 30 min at 37° C.

The digestion mixture was centrifuged in an Expender centrifuge at 14,000 g for 30 min at 4° C., in order to separate the *Yersinia* cells from the peptides released by the surface proteolysis. The supernatant, containing the peptides released by trypsin digestion, was filtered from residual cells by centrifugation at 4° C. in Centric on tubes. The filtrate was treated with formic acid (0.1% formic acid final concentration) and submitted to proteomic analysis for the identification of the released peptides and consequent identification of the proteins which were exposed on the *Yersinia* surface.

Two different experimental platforms were used for the chromatographic separation of peptides and further identification was performed by tandem mass spectrometry (MS/MS).

In the first platform, prior to analysis salts were removed by off-line HPLC, with a 7-min gradient of 2-80% acetonitrile (ACN) in 0.1% formic acid. Peptide fractions were concentrated with a Speed-van centrifuge (Savant, Holbrook, N.Y.), and kept at −20° C. until further analysis. Peptides were separated by two-dimensional (2-D) nana-liquid chromatography (Dionne, Amsterdam, The Netherlands). In the first dimension, peptides were loaded on a strong cation exchange (SCX) column (10 cm×320 μm i.d.) and eluted by 5 salt concentrations (0.01, 0.05, 0.1, 0.5 and 1 M NaCl). In the second dimension, peptides were separated by a reversed phase C18 analytical column (15 cm×75 μm i.d., C18 Pep- Map 100™, 3 µm, 100 Å) via a C18 trap column (PepMap™ C18 µl-precolumn, 300 µm i.d.×1 mm, Dionne). Peptides were eluted with a 45-min gradient from 5 to 50% of 80% ACN in 0.1% formic acid. The flow rate was 300 nl/min. Eluates were continuously spotted onto an Anchor-Chip™ MALDI target, prepared with a thin layer of a saturated solution of α-cyano-4-hydroxycynnamic acid in acetone, every 60 s using a Proteineer FC robot. After fraction collection, spots were recrystallyzed with 0.6 µl of ethanol/acetone/0.1% trifluoroacetic acid (6:3:1). Mass spectrometry analysis was performed automatically with an Ultraflex MALDI TOF-TOF instrument, under the control of the WARP LC software.

In the second platform, peptides were separated by nana-LC on a CapLC HPLC system connected to a Q-ToF Micro ESI mass spectrometer equipped with a nanospray source. Samples were loaded onto an Atlantis C18 NanoEase column (100 µm i.d.×100 mm), via a C18 trap column (300 µm i.d.×5 mm). Peptides were eluted with a 50-min gradient from 2% to 60% of 95% ACN, 0.1% formic acid at a flow of 400 nl/min. The eluted peptides were subjected to an automated data-dependent acquisition program, using the MassLynx software. For both platforms, searching and identification of peptides were performed in batch mode with a licensed version of MASCOT, in a local database.

Shaving identified the following antigens: YPO1507, YPO2674, YPO4111, YPO1435, YPO0015, YPO2292, YPO3375, YPO3050 and YPO0494. In addition, YPO0501 and YPO0502 were identified as surface components which lack a canonical signal peptide and so could not be predicted using in silico analysis.

Biotinylation of Bacterial Surface

Surface proteins were obtained by biotinylating the bacterial surface, fragmenting the bacteria and then isolating the biotinylated proteins. These proteins were then separated on a gel excised, and exposed to tryptic digestion. Peptide mass fingerprinting was then used to identify the protein fragments. This technique identified the following antigens: YPO1052, YPO1906, YPO0663, YPO1435, YPO1222, YPO1411, YPO2905, YPO4905, YPO4070 and YPPCP1.07.

ORFs Selected for Immunogenic Use

These various analyses led to the identification of YPO0015, YPO0067, YPO0086, YPO0102, YPO0195, YPO0203, YPO0216, YPO0233, YPO0351, YPO0468, YPO0501, YPO0502, YPO0512, YPO0563, YPO0570, YPO0809, YPO0819, YPO0860, YPO1053, YPO1070, YPO1123, YPO1411, YPO1435, YPO1507, YPO1604, YPO1746, YPO2292, YPO2342, YPO2615, YPO2674, YPO2881, YPO3050, YPO3061, YPO3065, YPO3343, YPO3361, YPO3382, YPO3430, YPO3489, YPO3536, YPO3559, YPO3631, YPO3643, YPO3644, YPO3935, YPO4003, and YPO4111. These 47 antigens were further characterised using a variety of techniques.

Functional Studies

Various antigens were tested in an opsonophagocytosis assay using human monocytes against CO92 pLCR- cells. The assay was performed using both active complement and inactive complement. It measures the capacity of antibodies to increase Y. pestis phagocytosis by IFNγ-activated monocytes. The rationale of using this assay is that antisera against the V antigen have been shown to promote bacterial phagocytosis by macrophages [205,206]. Thus opsonophagocytosis appears to be an important mechanism of protection against *Y. pestis* infection.

According to the assay, *Y. pestis* pLCR- bacteria were incubated with each of the sera raised against the test proteins and subsequently incubated with the Monomac 6 cell line (previously stimulated for two days with 50 U/ml IFN-γ). After 1 h incubation, bacteria adhering to the surface of monocytes were killed by antibiotic treatment and the number of internalized bacteria was determined by colony counting after cell lysis with 1% saponin.

Briefly, the protocol for this assay is as follows: mix bacteria with different sera in 96 well plate (160 μl bacteria with 5.5 μl undiluted serum) and incubate in agitation (120 rpm) at 37° C. for 30 minutes; after opsonization, bacteria are added directly to cells (i.e. without washing step); add 20 μl of each sample to the plate containing the monocytes (resuspended in 60 μl medium); add 20 μl complement; incubate for 1 hour at 37° C. and 20 hours at 37° C. in the incubator with 5% $CO_2$; evaluate total bacteria by adding 100 μl of 2% saponin (diluted in RPMI without kan) and leave 15 minutes at 37° C., then plate at $10^{-2}$ and $10^{-3}$; evaluate internalisation by transferring entire volume (100 μl) in 96 well plate with "u-bottom", resuspend pellets with 100 μl gentamycin 200 μg/ml and incubate for 1 hour at 37° C., 1 wash with 20 μl medium per well, add 100 μl of 1% saponin (diluted in RPMI without kan) and leave 10-15 minutes at 37° C., then mix.

When *Y. pestis* pLCR- bacteria were opsonized with sera against whole bacteria and F1 protein (positive controls) a 40-fold and 100-fold increase of the Monomac 6 cell line phagocytic capacity with respect to pre-immune sera was observed, respectively. Thus the OPA assay was used to screen antisera specific for FACS-positive antigens, in search for sera able to increase bacterial uptake by phagocytic cells.

Results from a first set of experiments, with 3 hours of growth at 37° C., are shown in FIG. 1, expressed as phagocytosis (fold increase) against antiserum used. Results from a second set of experiments, with overnight growth at 37° C., are shown in FIG. 2. Many of the antigens were able to induce a serum response that led to increased phagocytosis. Antisera raised against the following 21 antigens gave the best results: YPO4003, YPO3061, YPO3559, YPO3382, YPO0860, YPO0086, YPO3631, YPO0512, YPO3489, YPO2881, YPO3343, YPO3361, YPO0563, YPO3430, YPO1411, YPO3935, YPO0809, YPMT1.84, YPO1123, YPO3065, and YPO1070. The inclusion of YPMT1.84 in this group (i.e. the F1 antigen) is a useful confirmatory positive control.

Phagocytosis-positive sera were tested for their ability to induce bacterial killing by blood cells, using blood from three donors against $pLCR^-$ strain CO92. In this assay bacterial cells were incubated with antigen-specific antisera for 30 minutes and subsequently exposed to human blood from four different healthy donors (age ranging from 26 to 65 years). The capacity of sera to induce bacterial killing was evaluated at 37° C. at different time points over a 3 hour period. Under these experimental conditions, while incubation with pre-immune sera did not prevent bacteria from growing in blood, incubation with anti-F1 protein serum caused over 1 log 10 reduction of viable bacteria after a 3 hour incubation in 3 out of the 4 blood samples.

Briefly, the protocol for this assay is as follows: incubate 10 μl (approximately 1000 CFU) *Y. pestis* CO92 $LCR^-$ $pgm^-$ bacteria with 10 μl sera (decomplemented for 30 min at 56° C.) for 30 min 37° C. (the 'no sera' control sample used 10 μl RPMI, 10% FCS, no antibiotic); add 80 μl blood with heparin (200 μl heparin "liquemil"/10 ml blood); in a microtitre plate at time zero, dilute 20 μl in 20 μl RPMI-10% FCS-gln-no antibiotic (1:2) and plate (20 μl) $10^0$, $10^{-1}$, $10^{-2}$, $10^{-3}$ dilutions; on a 37° C. rocking platform, mix after 1 hour by pipette; remove 20 μl for plating, and incubation on the rocking platform continued; after 2 hrs, mix again and continue incubation on the rocking platform; plate after 1 hr and 3 hrs; dilute as before (1:2) and plate $10^0$, $10^{-1}$ dilutions (20 µl)

Figure 3:
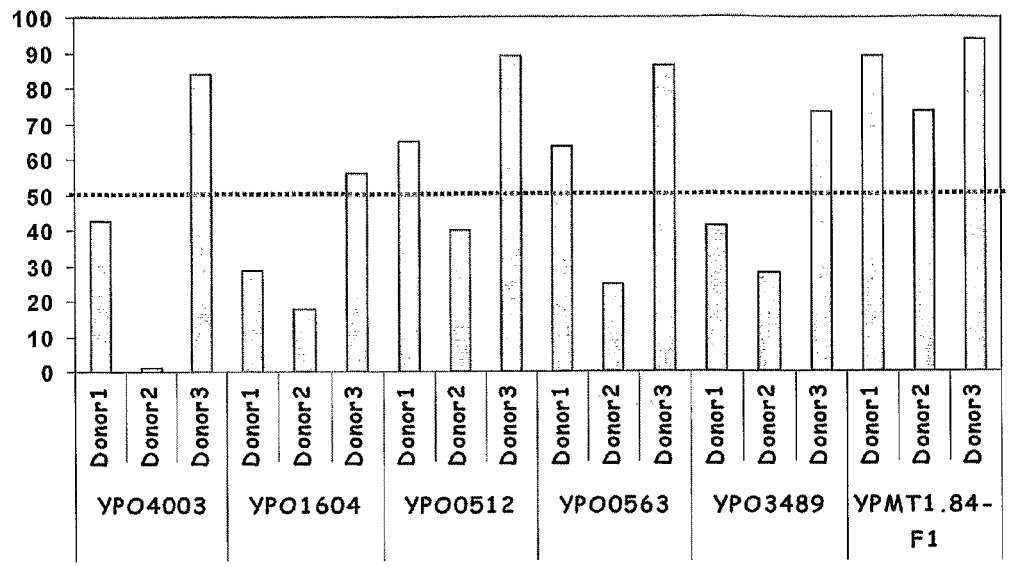
FIGS. 3 to 5 show the results of bactericidal assays. Bacterial killing is indicated at the difference between colony forming units (cfu) at time zero and at time 3 hours.
Figure 4:
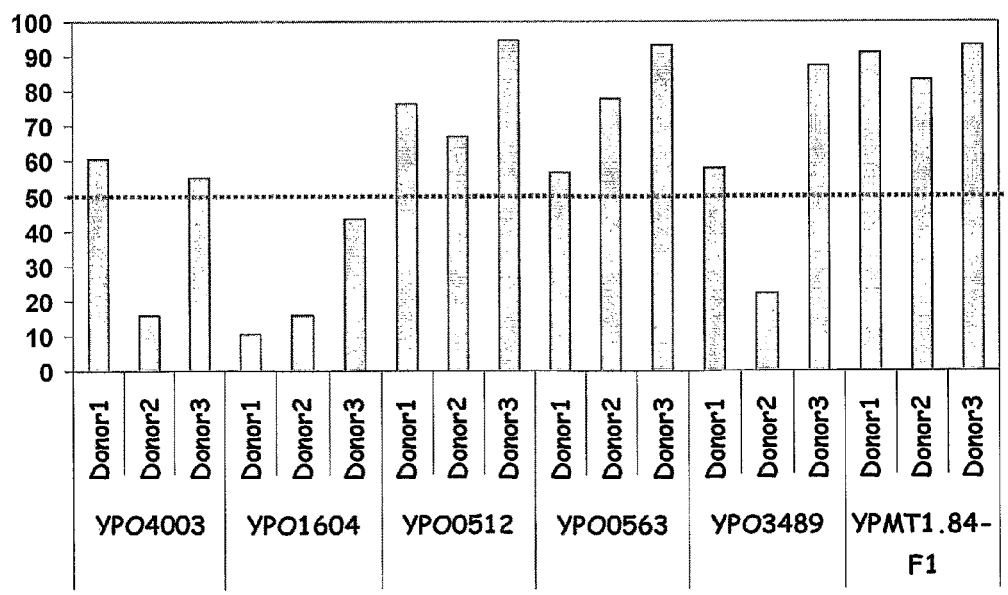

Results are shown in FIGS. 3 (1 hour assay) and 4 (3 hour assay) as the percentage of killed bacteria relative to pre-immune sera. The best results were seen with YPO4003, YPO1604, YPO0512, YPO0563 and YPO3489.

Figure 5:
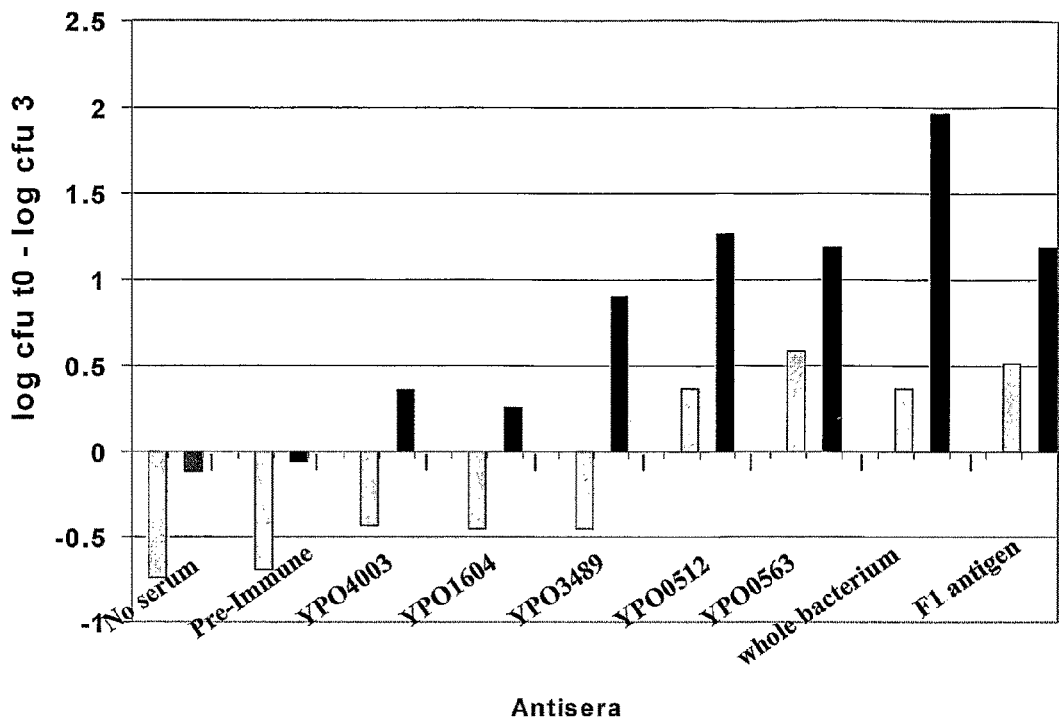

Killing was compared between CO92 pgm⁻ and pLCR⁻ strains with human blood. Results are shown in FIG. 5. The best results were seen with YPO0512, YPO0563 and YPO3489. Sera raised against these antigens promoted bacterial killing in all three blood samples at levels comparable to that observed with the anti-F1 antiserum. In particular, sera against proteins YPO0512 and YPO0563 killed *Y. pestis* in all four blood samples tested, thus performing even better then the F1 antigen. Remarkably, these two sera were also capable of killing the less attenuated CO92 pgm– pst– strain (a CO92-derived mutant lacking the 102 kb pigmentation locus) when tested in the blood of one of the human donors.

In conclusion, these functional studies revealed a number of antigens, in addition to F1, that are able to elicit antibodies that promote phagocytosis in vitro. Considering that the sera against two known protective antigens (the V [206] and F1 antigens) also have phagocytic properties, the identified antigens are very attractive candidates for inclusion in anti-*Y. pestis* vaccines. Moreover, five antigens (in particular YPO4003, YPO1604 and YPO3489) elicit sera that, in addition to stimulating phagocytosis, also promote substantial bacterial killing in the presence of human blood.

Further studies revealed a 55-fold and 70-fold increase of the Monomac 6 cell line phgocytic capacity with respect to pre-immune sera, when *Y. pestis* pLCR-bacteria were opsonised with sera against whole bacteria and F1 protein (positive controls), respectively.

Figure 11:
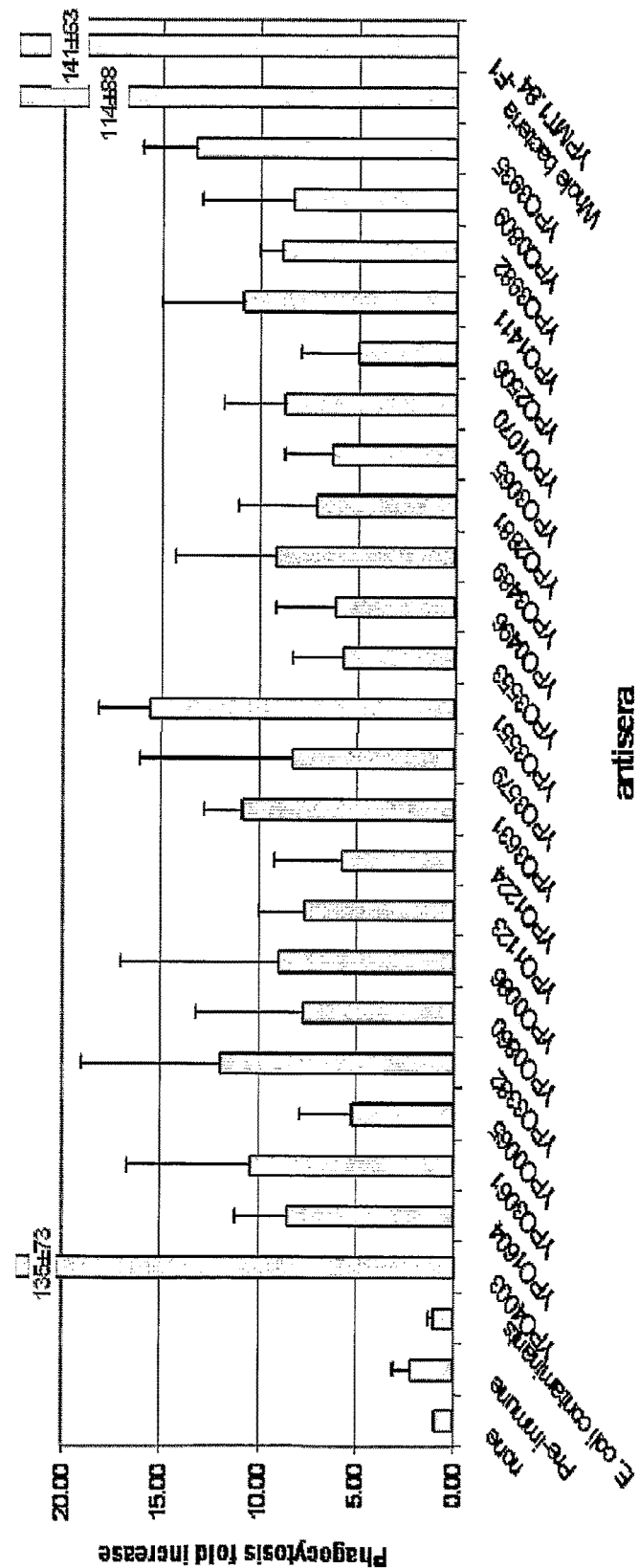
FIG. 11 shows the opsophagocytosis assay with the human pro-myelomonocytic Monomac 6 cell line. Monomac 6 cells were sub-cultured in RPMI-10% FCS at 37° C., 6% $CO_2$, stimulated for two days with 50 U/ml IFN-γ and distributed in 96 w plates ($4 \times 10^5$ cells/well). For the infection, bacteria grown at 37° C. in BHI until OD600=0.4. Bacteria were opsonized with specific (at 1:30 dilution) for 30' at 37° C. and added to the cells at a Molteplicity of Infection (MOI) of one bacterium per cell. Non opsonized bacteria and bacteria opsonized with Pre-Immune sera and sera against Antisera against *E. coli* contaminant proteins obtained from IMAC-purification were included as negative controls of the assay. After 1 h incubation at 37° C., non adhering bacteria were removed by extensive washing and externot determinedly associated bacteria were killed by 1 h incubation with 200 ug/ml gentamycin. Intracellular bacteria were measured after cell lysis with 1% saponin by viable counting. All samples were in triplicates. For each samples % phagocytosis was evaluated as compared to non-opsonized bacteria.

Further experiments revealed that the following 23 antigens induced a particularly good serum response that led to increased phagocytosis: YPO4003, YPO1604, YPO3061, YPO0065, YPO3382, YPO0860, YPO0086, YPO1123, YPO1224, YPO3631, YPO3579, YPO3551, YPO3553, YPO0496, YPO3489, YPO2881, YPO3065, YPO1070, YPO2506, YPO1411, YPO3982, YPO0809 and YPO3935 (see FIG. 11). As mentioned above, the inclusion of YPMT1.84 (the F1 antigen) is as a confirmatory positive control.

Figure 6:
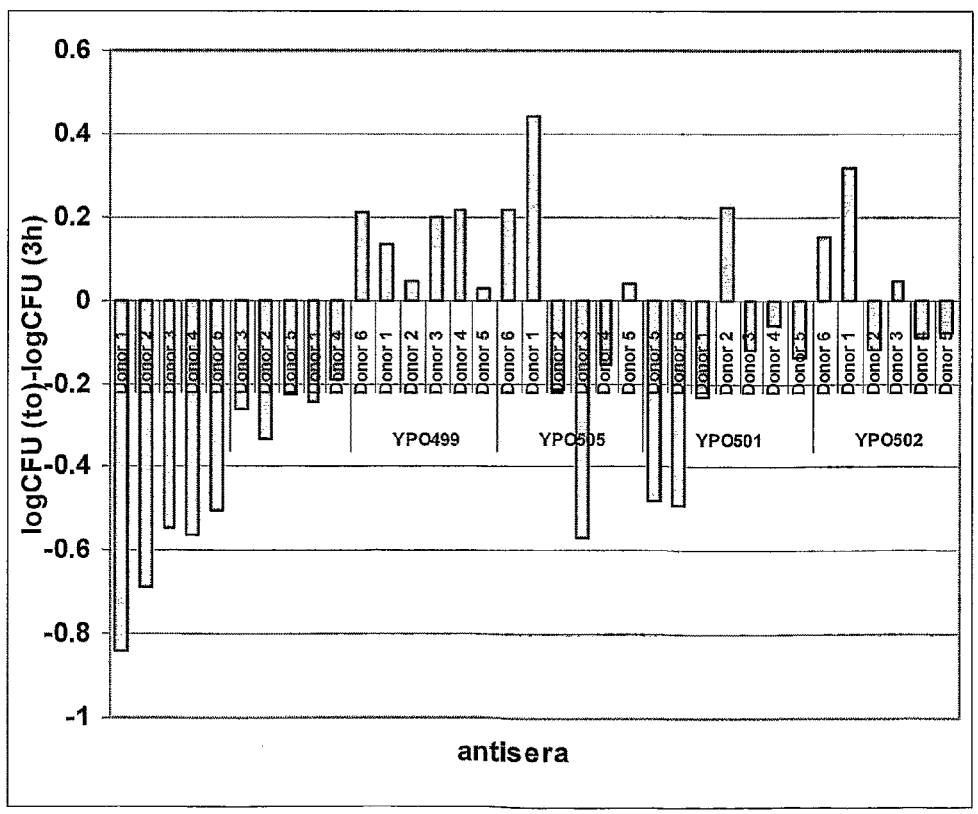
FIG. 6 shows serum bactericidal assay with human blood. *Y. pestis* CO92 pLCR- Bacteria were re-inoculated from ON cultures grown at 37° C. in BHI and incubated at 37° C. for about 4 h, until $OD_{600}$=0.4. Bacteria were opsonized for 30' at 37° C. with mouse antisera (10 µl) specific for *Y. pestis* antigens (reported in the table) and subsequently incubated with blood (80 µl) of 5 different healthy donors at 37° C. 6% $CO_2$. Colony counting was performed at time 0 and after 3 h incubation with blood. All samples were in duplicates. Bacterial killing was evaluated by determining the difference between the colony forming units (cfu), expressed as $log_{10}$, at time 0 and at 3 h.
Figure 10:
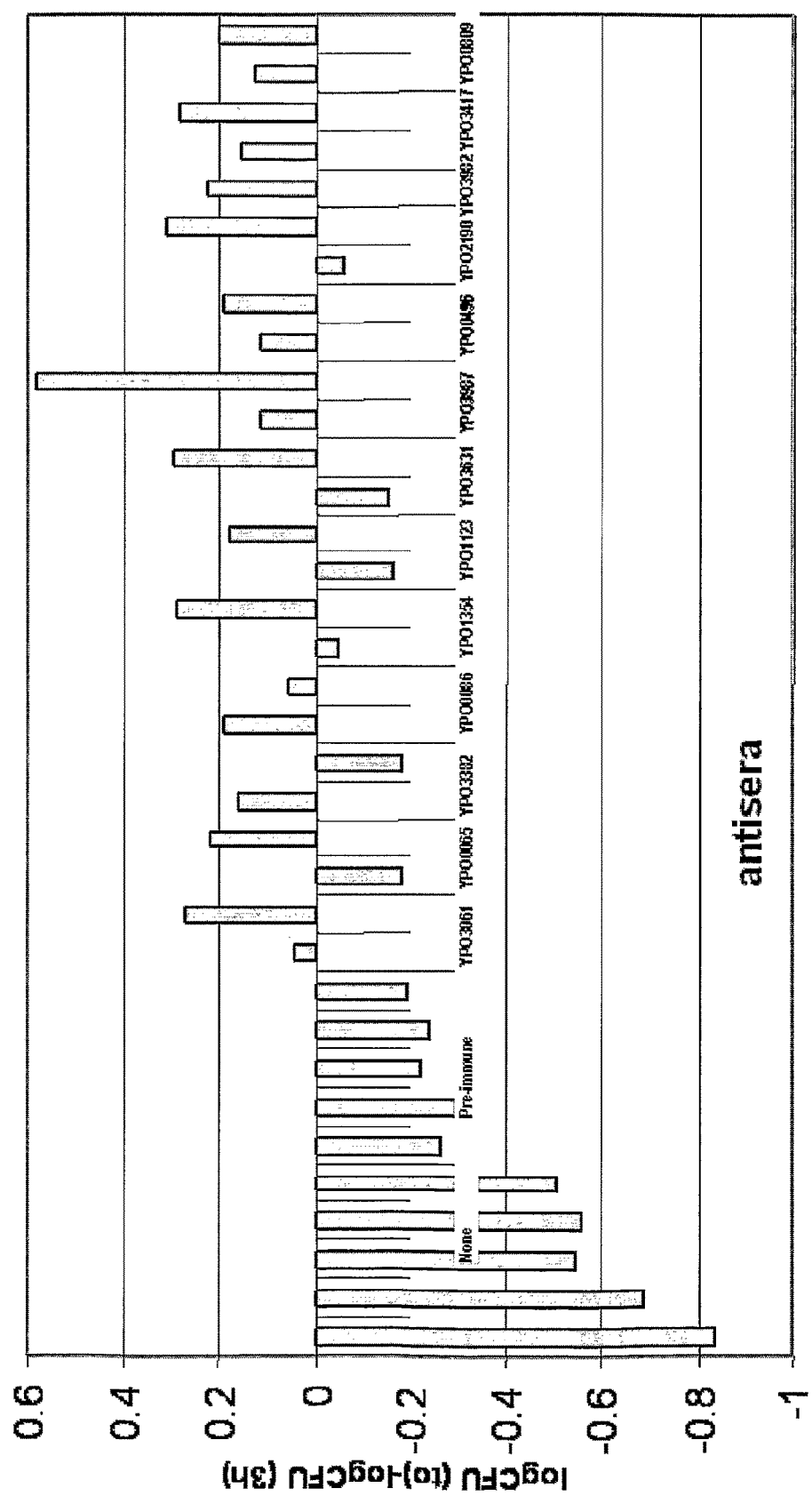
FIG. 10 shows serum bactericidal assay with human blood. (same protocol as FIG. 6)
Figure 12:
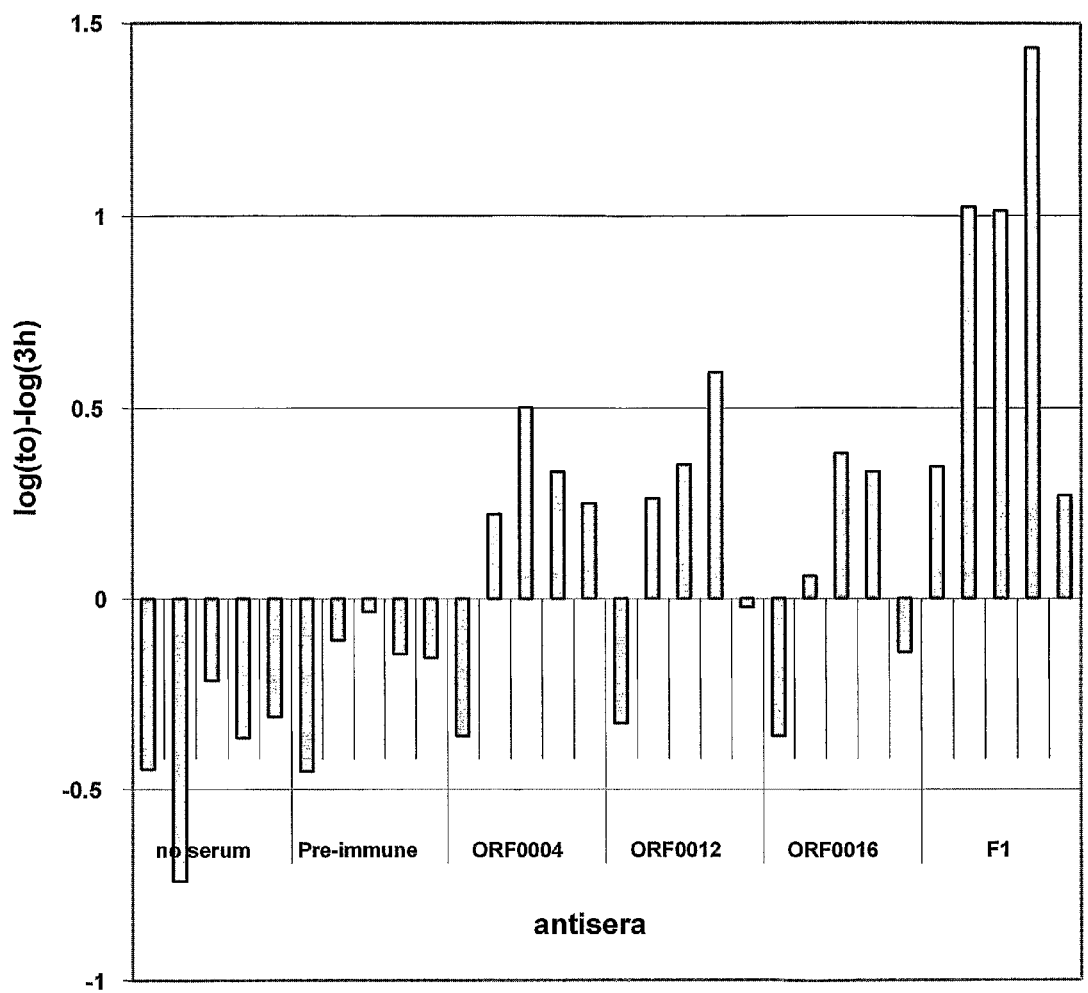
FIG. 12 shows serum bactericidal assay with human blood. (same protocol as FIG. 6)

FACS-positive sera were tested for their ability to induce bacterial killing. Bacterial cells were incubated with antigen specific sera and then exposed to human blood from five different healthy donors. While incubation with pre-immune sera did not prevent bacteria from growing in blood, incubation with anti-F1 protein serum caused over 1 log 10 reduction of viable bacteria in three of the five blood samples tested. The results are shown in FIGS. 12, 6 and 10 as the percentage of killed bacteria relative to pre-immune sera (protocol as described above). The best results were seen with YPO4003, YPO1604 and YPO3489.

Further Studies

To confirm the specificity of an antigen's in vitro protective activity, the gene coding for that antigen is deleted from a *Y. pestis* strain and the opsonophagocytic and/or killing assays are repeated on the knockout strains. It is expected that the knockout strains will be insensitive to the opsonophagocytic/killing activity of the sera. *Y. pestis* mutants will be generated essentially as previously described [186]. Briefly, *Y. pestis* CO92 pLCR- attenuated strain is transformed with a plasmid carrying the λ phageRed recombinase [207] under the control of the ara inducible promoter, and the trimethoprim (tp) resistance cassette. The plasmid-carrying derivative, which has an increased recombination frequency due to the presence of the arabinose-inducible Red recombinase, is used as recipient of gene mutants. For mutant construction, the 500 bp upstream and downstream regions of the gene to be deleted are amplified from *Y. pestis* CO92 genomic DNA and fused on either side of a kanamycin resistance cassette by PCR. The resulting PCR product is used to transform tp-resistant *Y. pestis* competent cells and positive clones are identified on BHI plates containing km and tp. Gene deletions are confirmed by PCR on the genomic DNA of resulting tpr-kmr clones. Finally mutants are cured of the plasmid encoding the λ phageRed recombinase by repeated passages on BHI plates in the absence of Tp. The absence of expression of the proteins corresponding to the deleted genes is confirmed by Western blot and/or by FACS analysis.

The knockout mutants are also useful for elucidating the biological role of the knocked out genes.

In addition to the analysis of their in vitro functional activity, antigens are tested for their protective activity in vivo using the mouse model of aerosol challenge in a BL4 facility.

Immunisation Studies

Antigens are selected for combining to give a composition of the invention. BALB/c mice are divided into nine groups and immunized as follows:

| Group | Immunizing Composition | Route of Delivery |
|---|---|---|
| 1 | Mixture of antigens (10-20 µg protein/each) + CFA (Complete Freund's Adjuvant) | Intra-peritoneal or intra-nasal or subcutaneous |
| 2 | Mixture of antigens (5 µg/each) + Al-hydroxide (200 µg) | Intra-peritoneal or intra-nasal or subcutaneous |
| 3 | Mixture of antigens (10-20 µg protein/each) + CpG (10 ug) | Intra-peritoneal or intra-nasal or subcutaneous |
| 4 | Mixture of antigens (10-20 µg protein/each) + Al-hydroxide (200 µg) + CpG (10 µg) | Intra-peritoneal or intra-nasal or subcutaneous |
| 5 | CFA | Intra-peritoneal or intra-nasal or subcutaneous |
| 6 | Mixture of antigens (10-20 µg protein/each) + LTK63 (5 µg) | Intra-peritoneal or Intra-nasal or subcutaneous |
| 7 | Al-hydroxide (200 µg) + CpG (10 µg) | Intra-peritoneal or intra-nasal or subcutaneous |
| 8 | CpG (10 µg) | Intra-peritoneal or intra-nasal or subcutaneous |
| 9 | LTK63 (5 µg) | Intra-peritoneal or intra-nasal or subcutaneous |

Mice are immunized at two week intervals. Two to three weeks after the last immunization, all mice are challenged with the appropriate *Y. pestis* strain. When mucosal immunization (e.g. intranasal) is used, the animal model is also challenged mucosally to test the protective effect of the mucosal immunogen. Immediately prior to challenge, mice are bled to determine antibody titre to the antigens that were administered.

Total IgG and IgG1/IgG2A subtypes can be measured in mouse sera resulting from the different immunization regimens by using an ELISA assay on whole bacteria and on purified recombinant proteins. Furthermore, assessment of antigen-specific CD4+ and CD8+Th-cells in spleen cells and/or PBMC isolated from immunized mice can be carried out by multi-parametric FACS analysis, to evaluate the cytokine expression profiles of antigen-specific T-cells. In particular production of IFN-γ and IL-5 can be measured after in vitro stimulation of T cells with purified antigens and/or whole *Y.*

*pestis* cells. In addition, splenocytes and/or PBMC from mice immunized with each antigen/vaccine formulation may be collected 10-12 days after the last immunization dose and stimulated with whole *Y. pestis* bacteria. After 4 hours of stimulation, Brefeldin A is added to the cells for the following 12 hours, to block cytokines secretion. Afterwards cells are fixed and stained with antibodies to detect *Y. pestis*-specific T cells expressing IFN-γ and IL-5.

For the mouse challenge, virulent bacteria will be grown at 30° C. in heart infusion broth (HIB) containing 0.2% xylose. Bacteria are harvested by centrifugation, re-suspended, and serially diluted in HIB for the challenge inoculum. BALD/c mice are challenged using a 1 μm-generating Collision nebulizer contained within a Class III biocabinet. Mice are exposed in a temperature- and humidity-controlled whole-body exposure chamber. The aerosol is continuously sampled by an all glass impinger (AGI) containing HIB. The inhaled dose is determined from serial dilution and culture of AGI samples according to the formula determined by Guyton [208]. Mice are observed daily for 30 days post-exposure. For these initial studies, the virulent strain CO92 at a dose of 100 $LD_{50}$ units is used for challenges.

Outer Membrane Vesicles

Outer membrane vesicles are produced by a wide variety of gram-negative bacteria during growth in liquid cultures. Although the mechanism by which OMVs are generated has not been fully elucidated, they appear to represent spontaneous release of bacterial membranes which tend to form vesicles. In general the amount of OMVs released is very low. However, defects in proteins involved in membrane and cell wall assembling have been reported to favour OMVs production. In particular, in *E. coli* mutations of the major lipoprotein (Lpp) and any of the five proteins of the Tol-Pal system promote accumulation of OMVs in the culture supernatant. In *Salmonella enterica*, DNA adenine methylase (Dam) mutants present a reduction in the amount of Pal, TolB, OmpA and Lpp and, as a result of the absence of Dam methylation, release OMVs into the culture medium. Deletion of the *N. meningitidis* gna33 gene, which encodes a lytic transglycosylase homologous to *E. coli* mltA, produces large amounts of vesicles. Vesicles derived from the Δgna33 *N. meningitidis* mutant elicit a strong antibody-mediated protective activity.

In line with this meningococcal work, the *Y. pestis* genes encoding the Tol-Pal system homolog (the YPO1121-1125 operon), the DNA adenine methylase homolog (YPO0154), and the GNA33 homolog (YPO01025) are knocked out, and the mutants are tested for their capacity to release vesicles. The vesicles are then tested for their capacity to protect mice against *Y. pestis* infection.

Type Three Secretion System

It is postulated herein that the *Y. pestis* gene cluster YPO0499-YPO0516 are part of a Type Three Secretion System due to homology with similar systems in other organisms. A number of these proteins are also surface exposed and therefore useful for raising immune responses.

With the exception of YPO0510 and YPO0514, all of the genes in this cluster have been cloned and purified. Antisera have also been raised against most of these proteins. The antisera produced were tested by Western blot on total protein extract of *Y. pestis* grown overnight (O/N) at 28° C., O/N at 37° C. and O/N at 28° C. followed by 2 h at 37° C. Western blot analysis was also carried out in the presence or absence of the human J774.1 macrophage cell line to evaluate whether interaction with human cells influence the protein expression level. As shown in Table 1, in agreement with microarray data (see Table 2), in general the proteins showed highest expression at 28° C. rather than 37° C. In some cases the protein was highly expressed at both temperatures (YPO0499, YPO0502, YPO0505, YPO0508 and YPO0509).

Figure 7:
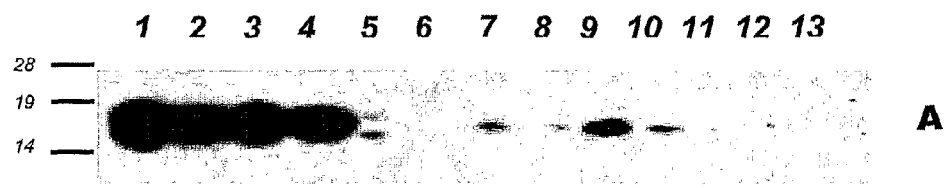
FIG. 7 shows a Western blot indicating the secretion of YPO0502. A: Serum anti-YPO0502 (19 KDa), B: Serum anti-YPO0503 (17 KDa) and C: Serum anti-YPO0213 (30 KDa). Lanes 1-13 are as follows: (1) Bacteria extract, 28° C.; (2) Cells lysate, 28° C.; (3) Bacteria extract, switch 28-37° C.; (4) Cells lysate, switch 28-37° C.; (5) Bacteria extract, 37° C.; (6) Cells lysate, 37° C.; (7) Supernatant bacteria, 28° C.; (8) Supernatant cells, 28° C.; (9) Supernatant bacteria, switch 28-37° C.; (10) Supernatant cells, switch 28-37° C.; (11) Supernatant bacteria, 28° C.; (12) Supernatant cells, 28° C.; and (13) Supernatant cells.
Figure 7:
Figure 7:
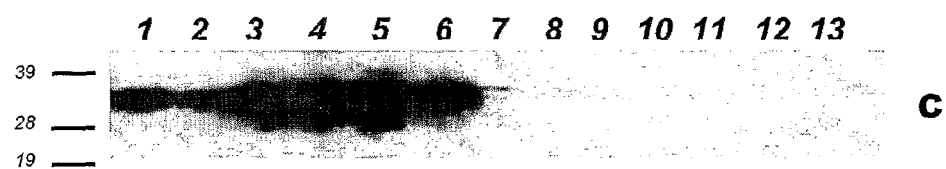

Western blot analysis was then carried out to verify whether the interaction of *Y. pestis* CO92 with a murine macrophage cell line can induce secretion of a component of the cluster. Bacteria grown over night at 28° C. or 37° C. in BHI medium were diluted 1:20 the day after and grown at the same temperature or switched from 28° C. to 37° C. until an $O.D._{600}=0.4$ (=logarithmic phase) was reached. Bacteria were harvested by centrifugation at 3,500 g for 10 min, washed once in DMEM high glucose+2% FCS and resuspended in the same cell medium. Bacteria were then added to the murine macrophages cell line J774.1 plated at a density of $1 \times 10^6$ cells/well, with a M.O.I. of 10:1 (bacteria:cells), in 6 wells plates. Bacteria incubated in plates not containing cells were also prepared in parallel. The plates, after a centrifugation of 5 min at 250 g, were incubated for 30 min at 37° C., 5% $CO_2$. Bacteria were harvested by centrifugation and lysed in LSB1X; the supernatant separated from bacteria were TCA precipitated. Cells monolayers were lysed in PBS+0.1% triton X. Samples were tested in western blot with the anti-sera against 7 proteins belonging to the cluster (=YPO0499-0500-0501-0502-0503-0505-0506) and a negative lysis control (=YPO0213, ribosomal protein). The only protein detected in the supernatant was YPO0502 (see FIG. 7).

Figure 8:
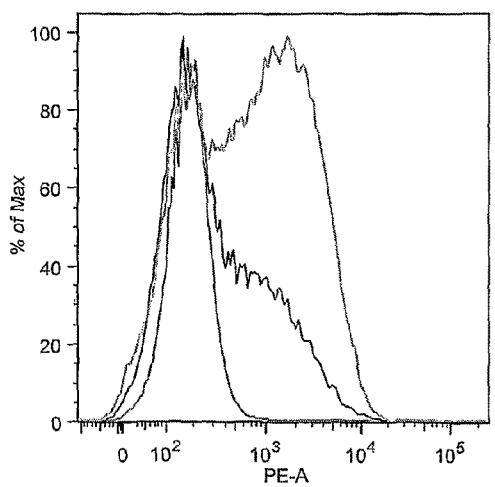
FIG. 8 shows the binding of 0502_His (A) and 2634_His (B) with J774 cells. Cells were incubated for 1 h with 0 µg/ml, 5 µg/ml or 12 µg/ml recombinant 0502_His or 2634_His as negative control. Binding and internalisation was quantified by direct immunofluorescence using anti-mouse sera raised against each respective protein.
Figure 8:
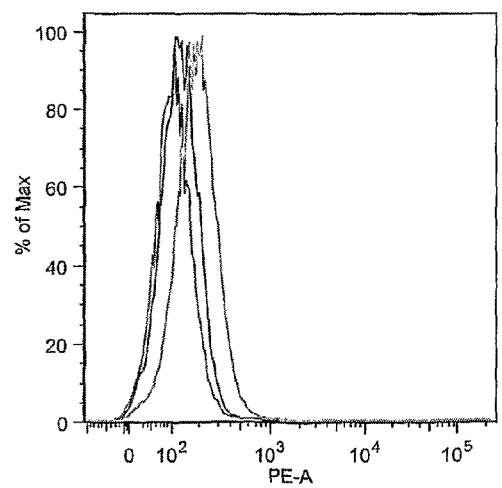

According to the structure prediction of YPO0502, it was hypothesized that the protein could have a role in altering the permeability of host cells. The fact that the protein is secreted in the bacterial supernatant reinforces this hypothesis. In order to confirm this, the ability of the protein to interact with eukaryotic cells was evaluated. To this purpose, the purified recombinant protein was incubated in the presence of J774.1 cells at different concentrations. The ability of YPO0502 to bind J774.1 surface was evaluated by intracellular staining using the specific antisera. As negative control, an irrelevant protein was included in the assay (2634_His). The following method was used. J774 cells were seeded into 12 well plates at a concentration of $2 \times 10^6$ cells/well and incubated at 37° C. 5% $CO_2$. After 24 hrs incubation purified preparations of recombinant 0502_His and 2634_His were added to the cells at a final concentration of 0, 5 or 12 μg/ml and incubated for a further hour. As a control for 0 μg/ml 0502_His, cells were incubated with 12 μg/ml 2634_His (and inversely the 0 μg/ml 2634_His cells incubated with 12 μg/ml 0502_His). The cells were then washed with PBS, and fixed with 2% paraformaldehyde (15 min at room temperature). The cells were then permeabilized (20 min at room temperature) with permeabilizing solution (PS; PBS containing 1% bovine serum albumin and 0.5% saponin). After permeabilization the cells were washed with PS and incubated for 10 min at room temperature with 20% rabbit serum in PS followed by 30 min at room temperature with anti-mouse sera raised against either 0502_His or 2634_His (1:200) in PS. The cells were then washed in PS, followed by incubation with second antibody (1:300) R-Phycoerthythrin-conjugated AffiniPure F(ab')2 Fragment Goat Anti-Mouse IgG (Jackson ImmunoResearch Laboratories, Inc. #115-116-072) for 30 min at room temperature. After a washing with PBS containing 1% BSA, the samples were analyzed using a FACSCanto machine (Becton Dickinson). This analysis revealed that YPO0502 is able to bind J774.1 cells (see FIG. 8).

Figure 9:
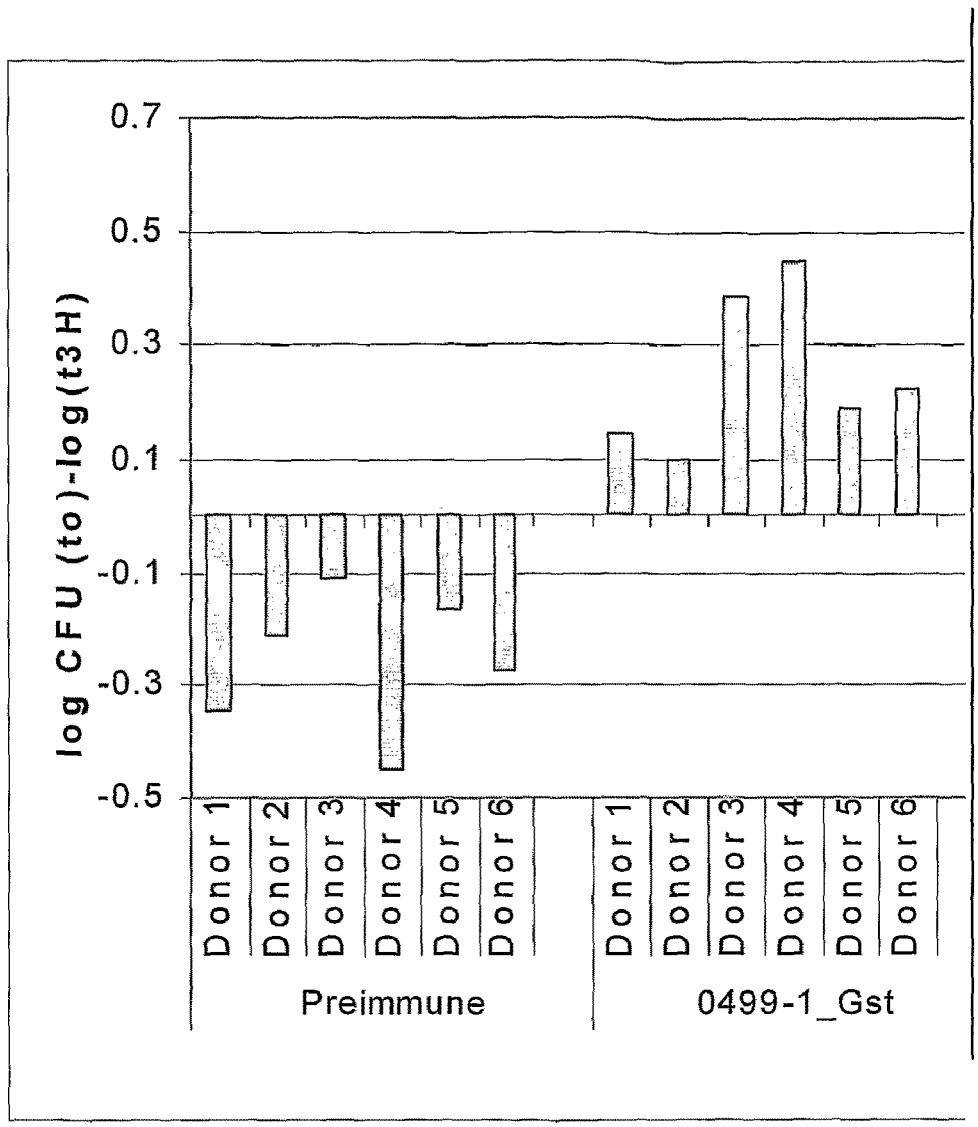
FIG. 9 shows the ability of sera raised against 0499_GST to induce bacterial killing.

Various proteins of the cluster were tested for their antigenic abilities. Antisera specific for the different antigens of the cluster were tested using the in vitro bactericidal assay with human blood. This analysis revealed that YPO0499 natiserum was capable of killing *Y. pestis* in the presence of blood from different donors (see FIG. 9). Furthermore, YPO0505, YPO0502 and YPO0501 were also able to induce functional antibodies (data not shown).

It will be understood that the invention has been described by way of example only and modifications may be made whilst remaining within the scope and spirit of the invention.

BRIEF DESCRIPTION OF SEQUENCE LISTING

| SEQ ID NO: | Name | GI |
|---|---|---|
| 1 | YPO0512 | 16120843 |
| 2 | YPO0086 | 16120437 |
| 3 | YPO0563 | 16120891 |
| 4 | YPO0809 | 16121121 |
| 5 | YPO0860 | 16121168 |
| 6 | YPO1070 | 16121371 |
| 7 | YPO1123 | 16121423 |
| 8 | YPO1411 | 16121691 |
| 9 | YPO1604 | 16121872 |
| 10 | YPO2881 | 16123073 |
| 11 | YPO3061 | 16123238 |
| 12 | YPO3065 | 16123242 |
| 13 | YPO3343 | 16123493 |
| 14 | YPO3361 | 16123511 |
| 15 | YPO3382 | 16123531 |
| 16 | YPO3430 | 16123579 |
| 17 | YPO3489 | 16123635 |
| 18 | YPO3559 | 16123703 |
| 19 | YPO3631 | 16123773 |
| 20 | YPO3935 | 16124063 |
| 21 | YPO4003 | 16124128 |
| 22 | YPO3644 | 16123786 |
| 23 | YPO3643 | 16123785 |
| 24 | YPO3536 | 16123682 |
| 25 | YPO3050 | 16123227 |
| 26 | YPO2674 | 16122879 |
| 27 | YPO2615 | 16122828 |
| 28 | YPO2342 | 16122566 |
| 29 | YPO2292 | 16122516 |
| 30 | YPO1746 | 16122003 |
| 31 | YPO1507 | 16121780 |
| 32 | YPO1435 | 16121713 |
| 33 | YPO1053 | 16121353 |
| 34 | YPO0819 | 16121130 |
| 35 | YPO0570 | 16120899 |
| 36 | YPO0502 | 16120832 |
| 37 | YPO0501 | 16120831 |
| 38 | YPO0468 | 16120797 |
| 39 | YPO0351 | 16120686 |
| 40 | YPO0233 | 16120571 |
| 41 | YPO0216 | 16120553 |
| 42 | YPO0203 | 16120542 |
| 43 | YPO0195 | 16120534 |
| 44 | YPO1002 | 16120449 |
| 45 | YPO0067 | 16120418 |
| 46 | YPO0015 | 16120369 |
| 47 | YPO4111 | 16124219 |
| 48 | YPMT1.84 | 16082876 |
| 49 | YPCD1.31c | 5832451 |
| 50 | YPPCP1.07 | 16082686 |
| 51 | YPO1052 | 16121352 |
| 52 | YPO4070 | 16124183 |
| 53 | YPO0494 | 16120824 |
| 54 | YPO0663 | 16120988 |
| 55 | YPO1222 | 16121511 |
| 56 | YPO1906 | 16122154 |
| 57 | YPO2905 | 16123096 |
| 58 | YPO3375 | 16123524 |
| 59 | YPMT1.42 | 16082828 |
| 60 | Linker | — |
| 61 | YPO0457 | 16120786 |
| 62 | YPO0514 | 16120845 |
| 63 | YPO0694 | 16121015 |
| 64 | YPO0805 | 16121117 |
| 65 | YPO0982 | 16121286 |
| 66 | YPO1354 | 16121634 |
| 67 | YPO1408 | 16121688 |
| 68 | YPO1792 | 16122046 |
| 69 | YPO2506 | 16122727 |
| 70 | YPO2713 | 16122917 |
| 71 | YPO2950 | 16123133 |
| 72 | YPO3026 | 16123203 |
| 73 | YPO3417 | 16123566 |
| 74 | YPO3551 | 16123695 |
| 75 | YPO3646 | 16123788 |
| 76 | YPO3982 | 16124109 |
| 77 | YPO0065 | 16120416 |
| 78 | YPO0499 | 16120829 |
| 79 | YPO0505 | 16120835 |
| 80 | YPO0500 | 16120830 |
| 81 | YPO0503 | 16120833 |
| 82 | YPO0506 | 16120836 |
| 83 | YPO0508 | 16120838 |
| 84 | YPO0509 | 16120839 |
| 85 | YPO3579 | 16123723 |
| 86 | YPO4040 | 16124160 |
| 87 | YPO0496 | 16120826 |
| 88 | YPO1224 | 16121513 |
| 89 | YPO3553 | 16123697 |
| 90 | YPO3987 | 16124114 |
| 91 | YPO2190 | 16122420 |

TABLE 1

The surface expression of various proteins following growth overnight at 37° C., growth overnight at 28° C. or growth overnight at 28° C. followed by 2 h at 37° C.

| Protein | Fusion type | Growth 37° C. overnight | | Growth 28° C. overnight followed by 37° C. for 2 hrs | | Growth 28° C. overnight | |
|---|---|---|---|---|---|---|---|
| | | ΔMean value[a] | Fluorescence immune/ preimmune | ΔMean value[a] | Fluorescence immune/ preimmune | ΔMean value[a] | Fluorescence immune/ preimmune |
| YPO0499 | HIS[b] | 6.6 | 1.7 | 18.8 | 4.8 | 19.0 | 4.1 |
| YPO0499 | GST | 62.0 | 6.5 | 42.0 | 6.2 | 52.3 | 5.9 |
| YPO0500 | HIS[b] | 4.6 | 1.4 | 23.8 | 3.7 | 26.1 | 3.7 |
| YPO0501 | HIS[b] | 3.9 | 1.3 | 25.8 | 4.3 | 25.4 | 3.6 |
| YPO0502 | HIS[b] | 1.0 | 1.0 | 26.1 | 3.7 | 30.6 | 4.2 |
| YPO0502 | GST | 50.2 | 11.4 | 42.4 | 6.3 | 51.0 | 5.8 |
| YPO0503 | HIS[b] | −3.7 | 0.8 | 11.8 | 1.7 | 10.9 | 1.5 |
| YPO0503 | GST[b] | 23.1 | 6.5 | 29.0 | 6.9 | 39.5 | 6.7 |
| YPO0505 | HIS[b] | 24.6 | 2.7 | 38.8 | 3.4 | 31.4 | 2.4 |

TABLE 1-continued

The surface expression of various proteins following growth overnight at 37° C., growth overnight at 28° C. or growth overnight at 28° C. followed by 2 h at 37° C.

| Protein | Fusion type | Growth 37° C. overnight | | Growth 28° C. overnight followed by 37° C. for 2 hrs | | Growth 28° C. overnight | |
|---|---|---|---|---|---|---|---|
| | | ΔMean value[a] | Fluorescence immune/ preimmune | ΔMean value[a] | Fluorescence immune/ preimmune | ΔMean value[a] | Fluorescence immune/ preimmune |
| YPO0505 | GST[b] | 65.2 | 12.3 | 65.6 | 11.3 | 118.7 | 12.7 |
| YPO0506 | HIS[b] | 12.1 | 1.6 | 29.1 | 2.7 | 28.1 | 2.3 |
| YPO508 | GST | 131.2 | 8.4 | 50.1 | 11.4 | 58.2 | 9.3 |
| YPO509 | GST[b] | 31.8 | 6.8 | 35.7 | 7.3 | 51.1 | 6.5 |
| GST[c] | — | 13.1 | 2.5 | 10.4 | 3.3 | 24.4 | 4.1 |

[a]Δmean value is the difference between the immune and preimmune sera;
[b]Sera raised against an insoluble preparation of the purified protein; and
[c]GST was used as a negative control for the soluble GST fusions.

TABLE 2

The results of microarray experiments to determine the expression profile of various proteins at different temperatures.

| Gene | pval | ratio 28° C. vs 37° C. | Annotation |
|---|---|---|---|
| YPO0495 | 4.01E−05 | 2.10 | YPO0495, organic solvent tolerance protein precursor |
| YPO0498 | 2.06E−09 | 39.20 | YPO0498, hYPothetical protein |
| YPO0499 | 2.04E−07 | 39.26 | YPO0499, hYPothetical protein |
| YPO0500 | 1.08E−06 | 27.68 | YPO0500, conserved hYPothetical protein |
| YPO0501 | 2.37E−07 | 30.97 | YPO0501, conserved hYPothetical protein |
| YPO0502 | 3.01E−07 | 32.73 | YPO0502, conserved hYPothetical protein |
| YPO0503 | 1.86E−07 | 36.30 | YPO0503, conserved hYPothetical protein |
| YPO0504 | 7.88E−07 | 46.94 | YPO0504, conserved hYPothetical protein |
| YPO0505 | 2.40E−06 | 40.05 | YPO0505, conserved hYPothetical protein |
| YPO0506 | 1.87E−06 | 21.88 | YPO0506, putative Clp ATPase |
| YPO0507 | 1.43E−07 | 24.88 | YPO0507, conserved hYPothetical protein |
| YPO0508 | 1.20E−07 | 28.36 | YPO0508, hYPothetical protein |
| YPO0510 | 6.32E−05 | 3.12 | YPO0510, hYPothetical protein |
| YPO0511 | 5.45E−07 | 3.20 | YPO0511, hYPothetical protein |
| YPO0511a | 2.03E−04 | 6.98 | YPO0511a, hYPothetical protein |
| YPO0513 | 7.06E−04 | 15.09 | YPO0513, conserved hYPothetical protein |
| YPO0513_2 | 5.71E−05 | 3.41 | |
| YPO0514 | 7.31E−05 | 2.65 | YPO0514, putative OmpA-family membrane protein |

REFERENCES

The Contents of which are Hereby Incorporated in Full

[1] Perry & Fetherstone 1997 *Clin Microbiol Rev* 10:35-66.
[2] Inglesby et al. 2001 *Jama* 283:2281-90.
[3] Titball & Williamson 2001 *Vaccine* 19:4175-84.
[4] Drozdov et al. 1995 *J Med Microbiol* 42:264-268.
[5] Worsham et al. 1995 *Contrib. Microbiol Immunol* 13:325-328.
[6] Winter 1960 *Bull W.H.O.* 23:408-409.
[7] Miller et al. 1998 *FEMS Immunol Med Microbiol* 21:213-221.
[8] Anderson et al. 1996 *Infect Immunol* 64:4580-4585.
[9] Eyes et al. 2004 *Vaccine* 22:4365-73.
[10] Jones et al. 2000 *Vaccine* 19:358-366.
[11] Williamson et al. 2000 *Vaccine* 19:566-571.
[12] Overheat et al. 2005 *Infect Immune* 73:5152-9.
[13] Marshall et al. 1974 *J Infect Dis* 129:S26-29.
[14] Friedlander et al. (1995) *Clin Infect Dis* 21 Suppl 2:S178-81.
[15] Roggenkamp et al. 1997 *Lancet* 353:51-56.
[16] Parkhill et al. 2001 *Nature* 413:523-7.
[17] Deng et al. 2002 *J Bacteriol.* 184(16):4601-11.
[18] Song et al. (2004) *DNA Res.* 11:179-97.
[19] Tanabe et al. (2006) *Infect. J Immun.* 74(6):3687-3691.
[20] Smither et al. (2006) *J. Microbiol Methods* E-publication 17/07/06.
[21] Galyov et al. (1990) *FEBS Lett* 277(1-2):230-2.
[22] Adair et al. 2000 *J Clin Microbiol* 38:1516-1519.
[23] Honko et al. (2006) *Infect. Immune* 74(2):1113-1120.
[24] Segal et al. 2005 *FEMS Microbiol Rev* 29(1):65-81.
[25] Das et al. 2003 *In Silico Biol.* 3:287-300.
[26] Brand et al. 1994 *Mol Microbiol* 14(4):797-808.
[27] VanRheenen et al. 2004 *Infect Immune* 72(10):5972-82.
[28] Sexton et al. 2004 *Infect Immune* 72(10):5983-92.
[29] Zheng et al. 2005 *Infect Immune* 73(7):4127-37.
[30] Powell et al. (2005) *Biotechnol Prog* 21(5):1490-510.
[31] Drancourt et al. (2004) *Emerg Infect Dis* 10:1585-92.
[32] Chain et al. (2004) *PNAS USA* 101(38): 13826-13831.
[33] *Vaccine Design* . . . (1995) eds. Powell & Newman. ISBN: 030644867X. Plenum.
[34] WO00/23105.
[35] WO90/14837.
[36] U.S. Pat. No. 5,057,540.
[37] WO96/33739.
[38] EP-A-0109942.

[39] WO96/11711.
[40] WO00/07621.
[41] Barr et al. (1998) *Advanced Drug Delivery Reviews* 32:247-271.
[42] Sjolanderet et al. (1998) *Advanced Drug Delivery Reviews* 32:321-338.
[43] Niikura et al. (2002) *Virology* 293:273-280.
[44] Lenz et al. (2001) *J Immunol* 166:5346-5355.
[45] Pinto et al. (2003) *J Infect Dis* 188:327-338.
[46] Gerber et al. (2001) *J Virol* 75:4752-4760.
[47] WO03/024480
[48] WO03/024481
[49] Gluck et al. (2002) *Vaccine* 20:B10-B16.
[50] EP-A-0689454.
[51] Johnson et al. (1999) *Bioorg Med Chem Lett* 9:2273-2278.
[52] Evans et al. (2003) *Expert Rev Vaccines* 2:219-229.
[53] Meraldi et al. (2003) *Vaccine* 21:2485-2491.
[54] Pajak et al. (2003) *Vaccine* 21:836-842.
[55] Kandimalla et al. (2003) *Nucleic Acids Research* 31:2393-2400.
[56] WO02/26757.
[57] WO99/62923.
[58] Krieg (2003) *Nature Medicine* 9:831-835.
[59] McCluskie et al. (2002) *FEMS Immunology and Medical Microbiology* 32:179-185.
[60] WO98/40100.
[61] U.S. Pat. No. 6,207,646.
[62] U.S. Pat. No. 6,239,116.
[63] U.S. Pat. No. 6,429,199.
[64] Kandimalla et al. (2003) *Biochemical Society Transactions* 31 (part 3):654-658.
[65] Blackwell et al. (2003) *J Immunol* 170:4061-4068.
[66] Krieg (2002) *Trends Immunol* 23:64-65.
[67] WO01/95935.
[68] Kandimalla et al. (2003) *BBRC* 306:948-953.
[69] Bhagat et al. (2003) *BBRC* 300:853-861.
[70] WO03/035836.
[71] WO95/17211.
[72] WO98/42375.
[73] Beignon et al. (2002) *Infect Immune* 70:3012-3019.
[74] Pizza et al. (2001) *Vaccine* 19:2534-2541.
[75] Pizza et al. (2000) *Int J Med Microbiol* 290:455-461.
[76] Scharton-Kersten et al. (2000) *Infect Immune* 68:5306-5313.
[77] Ryan et al. (1999) *Infect Immune* 67:6270-6280.
[78] Partidos et al. (1999) *Immunol Lett* 67:209-216.
[79] Peppoloni et al. (2003) *Expert Rev Vaccines* 2:285-293.
[80] Pine et al. (2002) *J Control Release* 85:263-270.
[81] Domenighini et al. (1995) *Mol Microbiol* 15:1165-1167.
[82] WO99/40936.
[83] WO99/44636.
[84] Singh et al] (2001) *J Cont Release* 70:267-276.
[85] WO99/27960.
[86] U.S. Pat. No. 6,090,406
[87] U.S. Pat. No. 5,916,588
[88] EP-A-0626169.
[89] WO99/52549.
[90] WO01/21207.
[91] WO01/21152.
[92] Andrianov et al. (1998) *Biomaterials* 19:109-115.
[93] Payne et al. (1998) *Adv Drug Delivery Review* 31:185-196.
[94] Stanley (2002) *Clin Exp Dermatol* 27:571-577.
[95] Jones (2003) *Curr Opin Investig Drugs* 4:214-218.
[96] WO99/11241.
[97] WO94/00153.
[98] WO98/57659.
[99] European patent applications 0835318, 0735898 and 0761231.
[100] Huang et al. (2002) *J Clin Microbiol.* 40(4):1164-73.
[101] Grif et al. (2003) *Diagn Microbiol Infect Dis* 47(1):313-20.
[102] Zhou et al. (2004) *Bacteriol* 186(15):5147-52.
[103] WO98/24912
[104] WO99/27961
[105] WO02/074244
[106] WO02/064162
[107] WO03/028760
[108] Gennaro (2000) *Remnington: The Science and Practice of Pharmacy.* 20th edition, ISBN: 0683306472.
[109] Williamson et al. (2005) *Infect Immune* 73(9):5978-87.
[110] Donnelly et al. (1997) *Annu Rev Immunol* 15:617-648.
[111] Strugnell et al. (1997) *Immunol Cell Biol* 75(4):364-369.
[112] Cui (2005) *Adv Genet.* 54:257-89.
[113] Robinson & Torres (1997) *Seminars in Immunol* 9:271-283.
[114] Brunham et al. (2000) *J Infect Dis* 181 Suppl 3:S538-43.
[115] Svanholm et al. (2000) *Scand J Immunol* 51(4):345-53.
[116] *DNA Vaccination—Genetic Vaccination* (1998) eds. Koprowski et al. (ISBN 3540633928).
[117] *Gene Vaccination: Theory and Practice* (1998) ed. Raz (ISBN 3540644288).
[118] Wang et al. (2004) *Vaccine* 22:3348-57.
[119] Titball & Williamson (2004) *Expert Opin Biol Ther* 4:965-73.
[120] Garmory et al. (2004) *Vaccine* 22:947-57.
[121] Grosfeld et al. (2003) *Infect Immune* 71(1):374-83.
[122] Williamson et al. (2002) *Vaccine* 20:2933-41.
[123] Bennett et al. (1999) *Vaccine* 18(7-8):588-96.
[124] Findeis et al., *Trends Biotechnol.* (1993) 11:202
[125] Chiou et al. (1994) *Gene Therapeutics: Methods And Applications Of Direct Gene Transfer.* ed. Wolff
[126] Wu et al., *J. Biol. Chem.* (1988) 263:621
[127] Wu et al., *J. Biol. Chem.* (1994) 269:542
[128] Zenke et al., *Proc. Natl. Acad. Sci.* (USA) (1990) 87:3655
[129] Wu et al., *J. Biol. Chem.* (1991) 266:338
[130] Jolly, *Cancer Gene Therapy* (1994) 1:51
[131] Kimura, *Human Gene Therapy* (1994) 5:845
[132] Connelly, *Human Gene Therapy* (1995) 1:185
[133] Kaplitt, *Nature Genetics* (1994) 6:148
[134] WO 90/07936
[135] WO 94/03622
[136] WO 93/25698
[137] WO 93/25234
[138] U.S. Pat. No. 5,219,740
[139] WO 93/11230
[140] WO 93/10218
[141] U.S. Pat. No. 4,777,127
[142] GB Patent No. 2,200,651
[143] EP-A-0 345 242
[144] WO 91/02805
[145] WO 94/12649
[146] WO 93/03769
[147] WO 93/19191
[148] WO 94/28938
[149] WO 95/11984
[150] WO 95/00655
[151] Curiel, *Hum. Gene Ther.* (1992) 3:147
[152] Wu, *J. Biol. Chem.* (1989) 264:16985
[153] U.S. Pat. No. 5,814,482

[154] WO 95/07994
[155] WO 96/17072
[156] WO 95/30763
[157] WO 97/42338
[158] WO 90/11092
[159] U.S. Pat. No. 5,580,859
[160] U.S. Pat. No. 5,422,120
[161] WO 95/13796
[162] WO 94/23697
[163] WO 91/14445
[164] EP 0524968
[165] Philip, *Mol. Cell. Biol.* (1994) 14:2411
[166] Woffendin, *Proc. Natl. Acad. Sci.* (1994) 91:11581
[167] U.S. Pat. No. 5,206,152
[168] WO 92/11033
[169] U.S. Pat. No. 5,149,655
[170] WO 92/11033
[171] WO2005/047309.
[172] Winter et al., (1991) *Nature* 349:293-99
[173] U.S. Pat. No. 4,816,567
[174] Inbar et al., (1972) *Proc. Natl. Acad. Sci. U.S.A.* 69:2659-62.
[175] Ehrlich et al., (1980) *Biochem* 19:4091-96.
[176] Huston et al., (1988) *Proc. Natl. Acad. Sci. U.S.A.* 85:5897-83.
[177] Pack et al., (1992) *Biochem* 31, 1579-84.
[178] Cumber et al., (1992) *J. Immunology* 149B, 120-26.
[179] Riechmann et al., (1988) *Nature* 332, 323-27.
[180] Verhoeyan et al., (1988) *Science* 239, 1534-36.
[181] GB 2,276,169
[182] Ruckdeschel et al. (2001) *Infect Immune* 69(12):7652-62.
[183] Goure et al. (2005) *J Infect Dis* 192(2):218-25.
[184] Elvin & Williamson (2004) *Microb Pathog.* 37(4):177-84.
[185] Sauvonnet et al. (2002) *J Biol Chem.* 277(28):25133-42.
[186] Conchas & Carniel (1990) *Gene* 87:133-137.
[187] Geysen et al. (1984) *PNAS USA* 81:3998-4002.
[188] Carter (1994) *Methods Mol Biol* 36:207-23.
[189] Jameson, B A et al. 1988, *CABIOS* 4(1):181-186.
[190] Raddrizzani & Hammer (2000) *Brief Bioinform* 1(2):179-89.
[191] De Lalla et al. (1999) *J. Immunol.* 163:1725-29.
[192] Kwok et al. (2001) *Trends Immunol* 22:583-88.
[193] Brusic et al. (1998) *Bioinformatics* 14(2):121-30
[194] Meister et al. (1995) *Vaccine* 13(6):581-91.
[195] Roberts et al. (1996) *AIDS Res Hum Retroviruses* 12(7):593-610.
[196] Maksyutov & Zagrebelnaya (1993) *Comput Appl Biosci* 9(3):291-7.
[197] Feller & de la Cruz (1991) *Nature* 349(6311):720-1.
[198] Hopp (1993) *Peptide Research* 6:183-190.
[199] Welling et al. (1985) *FEBS Lett.* 188:215-218.
[200] Davenport et al. (1995) *Immunogenetics* 42:392-297.
[201] *Current Protocols in Molecular Biology* (F. M. Ausubel et al., eds., 1987) Supplement 30
[202] Smith & Waterman (1981) *Adv. Appl. Math.* 2: 482-489.
[203] Hinchliffe et al. (2003) *Genome Res* 13:2018-2029.
[204] Montigiani et al. (2002) *Infect Immune* 70(1):368-79.
[205] Weeks et al. (2002) *Microb. Pathog* 32:227-237.
[206] Cowan et al. (2005) *Infect. Immun.* 73: 6127-6137.
[207] Datsenko & Wanner (2000) *PNAS USA* 97:6640-6645.
[208] Guyton (1947) *Am. J. Physiol.* 150:70-77.

The invention claimed is:

1. An immunogenic composition comprising a combination of isolated *Y. pestis* (YP) antigens, said combination comprising two or more isolated antigens selected form the group consisting of: a YPO4003 antigen set forth as SEQ ID NO: 21, a YPO1604 antigen set forth as SEQ ID NO: 9, a YPO3489 antigen set forth as SEQ ID NO: 17 and a YPO0499 antigen set forth as SEQ ID NO: 78.

2. The immunogenic composition of claim 1, wherein at least one of the antigens is a fusion protein.

3. The immunogenic composition of claim 1, wherein at least two of the antigens are expressed as a single chain.

4. The immunogenic composition of claim 1, wherein the composition includes one or more immunoregulatory elements.

5. A method for raising an immune response in a mammal comprising the step of administering an effective amount of a composition of claim 1.

* * * * *